(12) United States Patent
Muneoka et al.

(10) Patent No.: US 9,833,481 B2
(45) Date of Patent: Dec. 5, 2017

(54) METHOD FOR ARTICULAR CARTILAGE AND JOINT FORMATION

(71) Applicants: Ken Muneoka, New Orleans, LA (US); Minqan Yan, New Orleans, LA (US); Ling Yan, New Orleans, LA (US)

(72) Inventors: Ken Muneoka, New Orleans, LA (US); Minqan Yan, New Orleans, LA (US); Ling Yan, New Orleans, LA (US)

( * ) Notice: Subject to any disclaimer, the term of this patent is extended or adjusted under 35 U.S.C. 154(b) by 0 days.

(21) Appl. No.: 14/016,071

(22) Filed: Aug. 31, 2013

(65) Prior Publication Data
US 2015/0065428 A1 Mar. 5, 2015

Related U.S. Application Data

(60) Provisional application No. 61/696,145, filed on Sep. 1, 2012.

(51) Int. Cl.
| | | |
|---|---|---|
| *A61K 38/16* | (2006.01) | |
| *A61K 38/17* | (2006.01) | |
| *A61K 38/18* | (2006.01) | |
| *A61K 35/32* | (2015.01) | |

(52) U.S. Cl.
CPC .......... *A61K 35/32* (2013.01); *A61K 38/1875* (2013.01)

(58) Field of Classification Search
None
See application file for complete search history.

(56) References Cited

U.S. PATENT DOCUMENTS

| 5,661,007 A | * | 8/1997 | Wozney | C07K 14/51 435/252.3 |
|---|---|---|---|---|
| 5,902,785 A | * | 5/1999 | Hattersley et al. | 514/8.8 |
| 6,034,061 A | * | 3/2000 | Rosen | A61K 38/1875 424/423 |
| 6,287,816 B1 | * | 9/2001 | Rosen | A61K 38/1875 424/423 |

OTHER PUBLICATIONS

Structure of a Joint, http://www.rci.rutgers.edu/~uzwiak/AnatPhys/APFallLect11_files/image006.jpg, accessed Sep. 27, 2014.*
Ide (2012, Developmental Dynamics 241:435-441).*

* cited by examiner

*Primary Examiner* — Elizabeth C Kemmerer
(74) *Attorney, Agent, or Firm* — William C. Yarbrough; Bibby, McWilliams & Kearney, PLLC

(57) ABSTRACT

The invention is a method of applying a joint inducing protein preferably BMP-9 or BMP-3 to an ossification center in order to create a joint, articular cartilage, or an endochondral cap. The ossification center may be one that occurs naturally such as in the case of amputation, wound healing or fracture, or, it may be artificially induced by the application of an ossification center inducing protein, which may include other BMP family proteins such as BMP-2, BMP-4 or BMP-7. Further, this invention is a method of producing joints, or joint-like structures in vitro by application of BMP-9 to cells derived from tissue regions capable of producing ossification centers, such as digit-derived fibroblasts.

7 Claims, 31 Drawing Sheets

```
┌─────────────────────────────────────────────────────────────────────┐
│  a person identifies a joint molecule induction substrate for application of the joint  │
│       induction molecules to said joint molecule induction substrate    509             │
│   ┌─────────────────────────────────────────────────────────────┐   │
│   │  a person identifies the joint molecule induction substrate as the apical  │   │
│   │                    end of an amputated limb                  │   │
│   └─────────────────────────────────────────────────────────────┘   │
│                                                                   510
│   ┌─────────────────────────────────────────────────────────────┐   │
│   │   a person identifies the joint induction molecule substrate as   │   │
│   │            damaged articular cartilage in a joint region       │   │
│   └─────────────────────────────────────────────────────────────┘   │
│                                                                   511
│   ┌─────────────────────────────────────────────────────────────┐   │
│   │   a person identifies the joint molecule induction substrate as ligament  │   │
│   │                            tissue                              │   │
│   └─────────────────────────────────────────────────────────────┘   │
│                                                                   512     502
│   ┌─────────────────────────────────────────────────────────────┐   │
│   │   a person identifies the joint molecule induction substrate as tendon    │   │
│   │                            tissue                              │   │
│   └─────────────────────────────────────────────────────────────┘   │
│                                                                   513
│   ┌─────────────────────────────────────────────────────────────┐   │
│   │   a person identifies the joint molecule induction substrate as a limb to │   │
│   │                          be amputated                         │   │
│   └─────────────────────────────────────────────────────────────┘   │
│                                                                   514
│   ┌─────────────────────────────────────────────────────────────┐   │
│   │   a person identifies the joint molecule induction substrate as   │   │
│   │           dissociated progenitor cells in a cell culture       │   │
│   └─────────────────────────────────────────────────────────────┘   │
│                                                                   515
│   ┌─────────────────────────────────────────────────────────────┐   │
│   │   a person identifies the joint molecule induction substrate as   │   │
│   │           dissociated digit fibroblasts in a cell culture      │   │
│   └─────────────────────────────────────────────────────────────┘   │
│                                                                   516
│   ┌─────────────────────────────────────────────────────────────┐   │
│   │ a person identifies the joint molecule induction substrate as dissociated │   │
│   │         digit fibroblasts seeded on a scaffold in a bioreactor │   │
│   └─────────────────────────────────────────────────────────────┘   │
└─────────────────────────────────────────────────────────────────────┘
```

FIG 23

METHOD FOR ARTICULAR CARTILAGE AND JOINT FORMATION

CROSS-REFERENCE TO RELATED APPLICATIONS

This application claims priority of U.S. provisional application 61/696,145 filed on Sep. 1, 2012

STATEMENT REGARDING FEDERALLY SPONSORED RESEARCH AND DEVELOPMENT

This invention was made with government support under MURI grant number is W911NF-09-1-0305; proposal number is 56157-LS-MUR and DARPA grant number is W911NF-06-0161; proposal number is 50547-LS-DRP.) awarded by the MURI—Multidisciplinary University Research Initiative—Program funded by the US Army Research Laboratory (ARL) and the Defense Advanced Research Projects Agency. The government has certain rights in the invention.

REFERENCE TO A "SEQUENCE LISTING APPENDIX"

Included in this application is a sequence listing provided on a compact disc which is hereby incorporated by reference.

BACKGROUND OF INVENTION

Field of the Invention/Technical Field

The present invention is in the technical field of drug, bio-affecting and body treating compositions: More particularly, the present invention is in the technical field of growth factor or derivative affecting or utilizing: bone morphogenic protein (BMP) or derivative.

Description of Related Art/Background Art

It is of great interest in regenerative medicine to repair, restore/regenerate bone, cartilage, joints, tendons and ligaments. These tissue types are necessary for locomotion and under normal usage have significant mechanical forces applied to them in order to to accomplish normal ambulatory movement and there are unique phenotypic characteristics of the tissue and cells that allow the implementation and mediation of physical forces, also present an engineering challenge when theses tissue types are injured or missing. When there is an injury to these tissue types, there is limited endogenous regenerative capacity (though adjacent tissues such as epidermis, or vasculature may recover to near identical functionality). Therefore there is great interest in inventions and methods to improve the regenerative capacity of these tissues, such that there is recovery or restoration of functional ability for an affected patient.

Bone morphogenetic proteins (BMPs) belong to the TGF-superfamily and play critical roles in the development, growth, cell differentiation and cartilage and bone morphogenesis. The identification of the functional roles of BMPs in regulating and promoting bone regeneration process following a bone fracture or amputation is of great interest to human clinical application. It have been demonstrated that several members of BMPs, like BMP2, BMP4 and BMP7, have multiple crucial roles in osteogenic differentiation and induces bone formation in animal models. Several forms of recombinant BMPs, especially rhBMP2 and rhBMP7, have been used as an adjunctive treatment in clinical trials to increase the efficacy bone fracture healing.

BMP-9 also known as growth differentiation factor 2 (GDF-2), is a BMP family member with variable expression and eclectic functionality. It is shown to be highly expressed in the developing mouse liver and stimulates hepatocyte proliferation. It is also expressed in the central nervous system and human intramembranous and endochondral bone. Further, studies in prostate and breast cancer cell have revealed that BMP9 induces prostate cancer cell apoptosis and inhibits proliferation in breast cancer cells. BMP9 has also been shown to have an inhibitory effect on both the migration and invasion of prostate and breast cancer cells after over expression. In addition, it has been shown that BMP9 acts as a potent factor enhancing hemopoietic progenitor cell generation.

BMP-9 also regulates aspects of angiogenesis. It binds with high affinity to ALK1 (activin receptor-like kinase-1) receptors and has inhibitory effects on proliferation and migration of endothelial cells. It has also been shown to inhibit vascular endothelial growth factor (VEGF)-stimulated angiogenesis and induce sprouting angiogenesis in vivo in the mouse sponge angiogenesis assay. In contrast, another recent report has shown that BMP9 promotes the proliferation of multiple types of endothelial cells via ALK-1 and enhance the angiogenesis in vivo in a matrigel plug assay.

BMP9 expression has been reported to be restricted to the developing mouse liver, central nervous system and human bone. However, the exact role of BMP9 in the skeletal development and bone regeneration remains unclear. A recent review (please see Luther, G., Wagner, E. R., Zhu, G., Kang, Q., Luo, Q., Lamplot, J., Bi, Y., Luo, X., Luo, J., Teven, C. et al. (2011). BMP-9 induced osteogenic differentiation of mesenchymal stem cells: molecular mechanism and therapeutic potential. Curr Gene Ther 11, 229-40) has shown that BMP9 is one of the most potent BMPs in inducing osteogenic differentiation in mesenchymal stem cells (MSCs) both in vitro and in vivo. The authors also suggested that BMP9 is a potent inducer of osteogenesis and may be more effective than current methods for clinical therapeutic applications in inducing bone regeneration.

In higher vertebrates, such as human and mice, skeletal endogenous bone regeneration capacity is highly restricted. The only bone capable of regeneration following injury is the terminal phalangeal bone (P3), which if amputated in the distal half will regenerate, but will not if amputated in the proximal half. This regeneration is marked by the formation of a blastema, a region of proliferating cells from where the new tissue develops.

Similar to the effects of amputation in the P3, if the subterminal phalangeal element (P2) is amputated it does display ossification, however the newly deposited bone is unorganized. While the regenerating P3 first displays regression and then subsequently displays proximal to distal non-chondrogenic, re-ossification, the amputated P2 displays ossification concomitant with chondrogenesis and degradation and it is seemingly non-directional. The net result is that the amputated P3 reforms a marrow cavity and functional equivalence and the P2 does not.

As potent inducers of osteogenesis, BMP2 and BMP7 have been found to induce regeneration in proximal non-regenerating amputation-level (P3) and second phalanx-amputated (P2) in mice. Recently acquired data that forms the basis for this invention examined the osteogenic potential of BMP-9 after application to a regenerating (and ossifying) P3 digit and found that BMP9 inhibited regeneration and new bone growth. BMP-9 application to cell lines isolated from the terminal and subterminal digits resulted in the formation of joint-like structures and articular cartilage in vivo. BMP-9 application to the amputed stump of a subterminal mouse digit was able to create an endochondral cap on the apical surface of the bone. Co-application of BMP2 and BMP9 to an amputated subterminal digit stump resulted in the formation of an apical bone and the formation of a joint positively expressing articular cartilage markers. These experiments suggest that BMP-9 application to extant ossification centers or cells from digit cells induces joint-like structures and articular cartilage.

There is a considerable economic interest in methods to regenerate or repair hyaline articular cartilage. This tissue is located at the end of bones at skeletal joints, and damage to this tissue, through mechanical injury, fibrotic invasion or osteoarthritic disease can lead to significant pain for those affected. Currently, $65 billion is spent each year on treatment for osteoarthritis in the US and over $1.8 billion for sports related joint injuries.

There can be many types of injury to articular cartilage. For example, the types of injury of that can occur to the joint and articular cartilage include; mechanical injury such as repeated loading and unloading, exogenous injuries such as irritants in the joint, (Burrs, delaminated cartilage, cartilage defects, and cartilage flaps) and age-related disease such as osteoarthritis which decreases chondrocytic cellular matrix regulation. Broadly, significant injury to articular cartilage results in the inability to regenerate. Studies suggest that articular cartilage cannot regenerate because there seems to be a slow feedback loop where the initial injury perpetuates eventual tissue degradation. Other studies have shown that even repeated low level injury can hamper the endogenous repair response and alter the molecular composition of the tissue, which, over time, may inhibit the functional capability of the tissue.

One general means for treatment of articular cartilage injury is to provide temporary relief of pain associated with the malady. While effective in the short term, these treatment options do not address the underlying cause. For example, treatments that temporarily alleviate the pain associated with articular cartilage damage, include (1) weight loss to relieve stress on the joints, (2) injections of hyaluranon or corticosteroids, or (3) over the counter medications or supplements such as aspirin, ibuprofen, chondroitin, glucosamine or COX-2 inhibitors. Mechanisms that can permanently repair articular cartilage therefore have considerable demand.

Accordingly, there is also considerable investment in surgical methods that attempt to repair the underlying tissue. While, many of these surgical methods are effective at providing relatively long term temporary relief, the considerable expense, variability of patient outcome and recurrence of symptoms leaves much room for innovation. Some of the surgical methods include, the induction of microfractures, autologous tissue and cellular implants, allogenic tissue transplants and xenografts, but none result in the permanent repair of the injured tissue.

One of the most widely used surgical methods to treat articular cartilage damage is microfracture surgery, which procedure is as follows: Impediments to movement or chondral defects will be removed from on or near the articular surface. These defects may include any physical object or cartilage delamination or flaps. Subsequently, the cartilage is removed down to the bone and microfractures are induced that allow passage way to the subchondral bone. Therein, blood will fill the articular surface which will contain cell progenitors, capable of activating a rapid wound response. This results in the formation of a clot and fibrocartilage production at the articular surface. The draw back to this methodology is that fibrocartilage (as stated above) is less durable than hyaline cartilage and over time the tissue again begins to degrade.

Besides microfracture surgery, autologous tissue can also be used in an attempt to get the endogenous tissue to remodel like healthy articular cartilage. This tissue can be taken from non load bearing regions of the body and transplanted into the affected joint. One method of transplantation is an osteochondral plug. In this procedure, the transplant is first shaped to recapitulate the articular surface, then the articular surface is removed such that transplant can be installed.

The advantage of autologous implants is that there is decreased risk for rejection. However, there are some drawbacks. First, autologous tissue is in short supply, and there is a dearth of acceptable tissue, that can be used for transplantation. Second, integration of cells or tissue into the articular surface is difficult and mechanical stimulation is necessary in order to get the cells to establish the necessary physical properties to handle the load bearing stress. However, these stresses will often cause implant failure as it does not allow the transplant to integrate into the new region. Third, these methods are considerably expensive, and require very specific technical expertise.

As an alternative to autologous transplants, allogenic transplants can be performed. There has been considerable success using donor tissue as some allogenic transplants exhibit remodeling properties. Allogenic tissue has been shown to be alive up to 15 years after transplantation, suggesting successful integration that mimics the original tissue. However, obvious factors such as short supply, considerable expense and expertise, and the antigenic response induced by collagens II, IX and XI, create a need for simple methods of articular cartilage generation.

Application of BMP is another option for creation of osteochondral tissues. There are currently many cartilage and bone-induction BMP-related applications. However, when considering clinical treatment options and methods to repair or regenerate tissue, it is important to understand that the same BMP protein application will have different results based on it's spatiotemporal context. Further, application of different BMP family members in the same spatiotemporal context, will exhibit different results. This is particularly important when considering the mechanical role that osteochondral tissue plays in a human being and the putative raison de etre of generating osteochondral tissue. The types of cartilage and bone in the human body are both defined by their mechanical properties and anatomical location. Further, their mechanical properties are largely a function of their collagen composition and proteoglycan content. Because BMP application to various tissues in vitro and in vivo, often results in highly variable production of collagen and proteoglycan content, the mechanical properties of the tissue are therefore dependent on the spatiotemporal context of application. Therefore, when considering BMP application for clinical application and the engineering of osteochondral tissue, it is important to identify the subtype of cartilage or bone, and the expected mechanical properties of said tissue.

Further, it is important to consider the generation of osteochondral tissue as different from the in vitro generation of osteal or chondral cells by pushing progenitors down the path to cellular differentiation. While the subtype of osteocyte/chondrocyte or progenitor is one factor that ultimately determines the functional or mechanical properties of the generated tissue, there are many other factors such as integration, environmental cues, growth factors, mechanical stress. This is why BMP application can be used for both differentiation, plating onto scaffolds, or implantation in vivo and also be used after cells have been seeded on scaffolds. Dependent on the temporal application of the BMP the resultant tissue will have different mechanical properties.

There are numerous patents detailing the use of bone morphogenetic proteins for regenerating tissue and thus it is reasonable considering that individually these proteins are capable of producing inducing tissue changes, that a combination of these proteins applied in tandem would also produce tissue changes. Similar to the current invention, some applications broadly disclose the application of two bone morphogenetic proteins for the purposes of tissue creation.

However, the specific details required to use this particular invention, e.g. enhance tissue creation through the complementary application of any of the proposed protein combinations, lacks the necessary details with which one could use their invention without undue experimentation. The inventors in EP/04708263 fail to disclose any specific spatiotemporal situations or combinations of the proposed proteins to actually create any tissues and broadly claim that any of these combinations may have the proposed effect. In the field of regenerative medicine a skilled person in the art, would recognize this application as overly broad, lacking convincing evidence of possession, and would not enable a skilled person in the art, to create bones, ligaments, tendons etc.

For example, one problem with the invention, which would suggest that the inventor does not have possession of the idea as required by USC 112 paragraph 1, is with the definition of "synergistic interaction", detailed in paragraph 0045, which says "The term synergistic interaction refers to an interaction in which the combined effect of two agents is greater then the algebraic sum of each of their individual cells". The assay supporting this assertion in the disclosure is the addition of one protein, and then a second subsequent protein in vitro to C2C12 cell and a subsequent non-linear increase in alkaline phosphatase expression. However, in pharmacology, normal dose response curves do not sum algebraically, but rather are sigmoidal and exponential in nature, suggesting that the "synergistic interaction" observed by the inventor is a normal consequence of a linear increase in a pharmacological application of the proteins. The proper control for the experiments as detailed in the disclosure should have been to add a comparable amount of the same concentration of the first protein, to determine whether doubling the protein concentration of the initial protein, results in an exponential increase in the expression of alkaline phosphatase and subsequently whether the second protein application is greater than this exponential increase. However, this is not performed by the inventor and therefore would cast doubt in the skilled person in the art, in the field of regenerative medicine that this is an enabled specification.

Additionally the inventors of EP/04708263 incorrectly assume (as would be recognized by a skilled person in the art,) that changes in vitro of a single protein, e.g. alkaline phosphatase expression (as a result of the application of combinations of exogenous protein to C2C12 cells), would in some manner be related to the ability tissue to be created when implanted in vivo. When considering tissue inductive activity in vivo, it is likely that it is also necessary to have an in vivo assay in order to assay the tissue creation abilities of the proposed combination of proteins. This is because, the creation of bone or osteoblasts is not the only cell type part that is required for tissue creation. Rather, tissues such as bone, ligament and tendon, not only have multiple cell types, but the organization and integration of other tissue-specific cell types such as vascular cells, mesenchymal cells, epidermis, and fibroblasts which are necessary for proper tissue functionality.

Further, from paragraph 0043 the applicant states, "The terms morphogenic activity, inducing activity, and tissue inductive activity all refer to the ability of an agent to stimulate a target cell to undergo one or more cell divisions (proliferation) that may optionally lead to cell differentiation." A skilled person in the art, would recognize that as per the inventors definition of the term "tissue-inductive activity" that the inventor is stating that the application of two proteins of the invention simply increases cellular proliferation. Therefore, the term "tissue-inductive" is a definition that is misleading in this invention because it implies tissue creation, but is defined by the inventor to only mean an increase in cell proliferation. Well known in the art of regenerative medicine there are possibly thousands of concurrent protein applications when applied in vitro to cells would increase cellular proliferation. These proteins are termed simply growth factors in the art.

Further, there is evidence from the specification that there actually is no change in tissue inductive activity, defined as increase in proliferation by the inventor. Paragraph 0242 states that "the number of AP-positive cells in cultures treated with the combination of CDMP and OP-1, appeared to be similar to that treated with OP-1 alone." Therefore, it is unclear where the presumption that coapplication of combinations of the proteins in the invention actually do increase "tissue inductive activity".

In addition a skilled person in the art, in regenerative medicine knows that there is no evidence that accelerated proliferation, one of the metrics that would actually increase the rate which a tissue would be formed, as tissue formation is more than simply the number of cells, as tissue induction e.g the formation of tissue, is a complex multicellular structure formed by coordinated proliferation and cell death. Also, a skilled person in the art, would recognize that in some instances enhancing the differentiation speed may inhibit functional tissue creation and induce unwanted structures such as ectopic bone, a major concern for current BMP-related products on the market.

The vagueness of the disclosure is also apparent when they suggest that numerous types of tissues that can be constructed from the multiple combinations of proteins. None of the preliminary data indicates that any other type of tissue but bone is able to be created, (which is well known in the art). In addition, none of the three markers, MyoD, alkaline phosphatase or scleraxis are indicative of chondrogenic differentiation for the induction or differentiation of C2C12 cells into chondrocytes. As cartilage, composed of chondrocytes, is a different cell type than the preliminary data that led to the invention, undue experimentation would be necessary to determine if the putative synergistic enhancement claimed by the inventor also applied to chondrocytes.

Further, the inventors ask the user of the invention to determine the effective combinations themselves for tissue induction. They correctly ascertain in paragraph 0129 that "It may not hold true for every first morphogenic/second morphogenic protein combination that co-administration is optimal for inducing morphogenic activity", but than fail to detail any reason for why that may be the case if indeed they are functional equivalents. If we presume that all of the combinations of all of the proteins (as detailed in paragraph 0010), are functional equivalents, and that any combination of the proteins would at least have some increase in "synergistic interaction", (defined as greater than the proliferative algebraic sum in paragraph 0045) than it would not be necessary for the inventors to detail testing and assay methods (in paragraphs 123-133) by which to determine which of the protein combinations may be the best.

In addition, in paragraph 0038, the applicant states that "morphogenic proteins may be capable of inducing progenitor cells to proliferate and or initiate differentiation pathways that lead to cartilage, bone, tendon, ligament or other types of tissue formation depending on the local environmental cues, and thus morphogenic proteins may behave differently in different surroundings." Therefore, the inventor suggests that the decision of which combination of proteins to use to create a desired tissue, is left to the user to empirically determine what would be effective and thus the inventor offers no predictive value of any of the combinations of proteins to induce tissue formation without undue experimentation.

Further, a person skilled in the art in regenerative medicine would recognize that just because the proposed proteins are part of larger gene family associated with a functional application, that this does not translate to functional equivalency for individual members (in terms of "synergistic enhancement") of these proteins or application of combinations of these proteins. For just one example, the inventors contend that combining BMP-3 and subsequently BMP-7, would have the same effect on "synergistically enhancing" tissue induction, as BMP-2 and BMP-7. In fact BMP-3, is well known to a skilled person in the art, as a BMP family member that inhibits bone formation and would not enhance, but detract from the tissue induction capability, as defined by the inventor. This is evidence that the inventor in the EP/04708263 is not as required by USC 112 paragraph 1 to be in possession of the invention.

Finally, the applicant posits in paragraph 0122, "a skilled practitioner will appreciate, the preferred combination of morphogenic proteins of this invention will depend in part on the tissue type to be generated and on the selected implantation or treatment site. These variables may be tested empirically" Thus, the inventor expects that the actual combination that is effective for producing the desired tissue, which may be variable, can be determined by the user of the invention. In paragraph, 0010, the applicant states that the invention includes but is not limited to 47 different proteins, which in any combination of said proteins may produce this effect. This is $47^2$ potential combinations or 2209 different possible combinations that the inventors posit as their invention. If one conservatively estimates only one week to definitively determine the efficacy of one of the inventors proposed protein combinations, it would take greater than 40 years to test whether each of the 47 proteins and their possible combinations are truly capable of creating tissue as suggested by the inventor. This lack of specificity along with lack of experimental evidence requires undue experimentation on the part of the user in order to create tissue as envisioned by the inventor.

Rather, we suggest that there is some precedent for already awarded patents that are sufficiently detailed both in protein specificity and spatiotemporal application parameters, for example U.S. Pat. No. 5,902,785, (herein incorporated by reference) shows complementary application of BMP's in order to create and maintain chondrogenic tissue, including articular cartilage. The claims, disclosure and experimental evidence of this invention are very specific that would allow one to practice the invention without undue experimentation. The invention herein is similar to said patent but uses a different combination of bone morphogenetic proteins in order to creates a de novo bone template from which cartilage can also be derived, that largely mimics joint creation. In an effort to show the differences between U.S. Pat. No. 5,902,785 and the invention herein and show how these inventions are distinct and complementary, both disclosures are examined below for their novel elements and teachings.

Both inventions involve the creation of a tissue by application of a bone morphogenetic protein and the subsequent application of another bone morphogenetic protein, the latter specifically including BMP-9. However, U.S. Pat. No. 5,902,785 teaches the initial application of BMP-13 to induce cartilage formation and BMP-9, 2, 4, 5, 6, 7 to stabilize this formation, whereas this invention uses the consecutive application of BMP-2 and BMP-9 each for alternative purposes. BMP-2 is used for the creation of creating a bone ossification center, and BMP-9 is subsequently applied for it's anti-osteogenic properties, not it's cartilage maintenance properties, in order to create a cavitation within said ossification center. This structure mimics a joint cavity and cells that line the cavity are immunoreactive for articular cartilage markers.

Part of the basis of the invention herein is from recently acquired data by the inventors, that shows a dual role of BMP-9, as both osteogenic and anti-osteogenic dependent on the spatiotemporal context. This is not taught by U.S. Pat. No. 5,902,785 and understanding the regions or delivery mechanisms in which BMP-9 may putatively react as osteogenic or anti-osteogenic in fact may further enhance the U.S. Pat. No. 5,902,785 invention by pointing to better methods for articular cartilage formation. In addition, this dual role of BMP-9 both highlights the unpredictability and variability of tissue that can be generated by application of BMP's and that the necessity for a proper spatiotemporal context for an enabled specification.

SUMMARY OF THE INVENTION

The invention is a method of applying a joint inducing protein, preferably BMP-9 (SEQ ID #01), or alternatively BMP-3 (SEQ ID NO: 02) to an ossification center in order to create a joint, articular cartilage, or an endochondral cap. The ossification center may be one that occurs naturally such as in the case of amputation, wound healing or fracture, or, it may be artificially induced by the application of an ossification center inducing protein, which may include other BMP family proteins such as BMP2 (SEQ ID NO: 03), BMP4 (SEQ ID NO: 04) or BMP7 (SEQ ID NO: 05). Further, this invention is a method of producing joints, or joint-like structures in vitro by application of BMP-9 to cells derived from tissue regions capable of producing ossification centers, such as limb-derived fibroblasts.

Experiments in embryonic mice that have formed the basis for this invention suggest that BMP-9 is involved in joint formation and can function as inhibitor of bone formation. In situ hybridization shows that BMP-9 is expressed in the joint region during development at E 16.5. Embryonic and early postnatal joints also express articular cartilage markers CD-44 and doublecortin. When agaraose-gel beads treated with BMP-9 are placed in the developing digits via ex utero surgery, it prevents bone formation distal to the implantation site.

Additional experiments in early postnatal or adult mice show that if a bead containing BMP9 is implanted into a terminal mouse digit after a regenerating level amputation, it prevents new bone growth and digit regeneration. Further, if BMP-9 is implanted in the wound epidermis after a non-regnerating second phalangeal element amputation it induces an endochondral cap at the amputation plane. This endochondral cap is considered by the inventors as having the phenotype of a half joint. Application of BMP-9, to mid-bone fractures results in the formation of chondrogenic structures that separate the bone, similar to the formation of joint, complete with cells exhibiting histological similarity to articular cartilage.

Additional experiments that have formed the basis for this invention show that application of BMP-2 to the apical plane of a P2 level amputated digit and then a subsequent application of BMP-9 induces distal bone and proximal cavitation. The cavitation between the newly formed apical bone and the original amputation plane has histological and immunohistochemical similarities to articular cartilage as examined with antibodies for collagen II and doublecortin.

Additional experiments that have formed the basis for this invention show that application of BMP-9 to cultured fibroblast cell lines from the murine digit, show the accumulation of and aggregation of microstructures that are phenotypically similar to small joint-like structures. These joint-like structures stain positive for doublecortin, an articular cartilage marker.

Overall, the experiments that have formed the basis for this invention data show that some family members of BMP, such as BMP-9, have bone-independent morphogenic activities, which may be used to repair or artificially create new tissue types in vivo, when applied to an extant ossification center. Based on the results of these experiments this invention contemplates multiple methods for application of a joint-, articular cartilage-, or endochondral cap inducing protein, preferably BMP-9, to an ossification center in order to regenerate tissues in vivo and in vitro that may be used to treat patients with osteochondral defects.

It is an aim of this invention to create a joint in vivo apical to the amputation plane after a limb amputation.

It is another aim of this invention to create an ectopic joint in vivo in order to harvest the articular cartilage from the joint for grafting as an allogenic, autologous, or xenograft-type transplantation.

It is yet another aim of this invention to create an ectopic joint in vivo in order to harvest the articular cartilage from the joint for dissociation and growth of articular chondrocytes in vitro.

It is yet another aim of this invention to create an ectopic joint in vivo in order to harvest the articular cartilage from the joint for dissociation and growth of articular chondrocytes in vitro and then seed said articular chondrocytes within a matrix or scaffold for allogenic, autologous, or xenograft-type transplantation.

It is yet another aim of this invention to create an ectopic joint in vivo in order to harvest the articular cartilage from the joint for dissociation and growth of articular chondrocytes in vitro and then seed said articular chondrocytes within a bioreactor for expansion and designing tissues for allogenic, autologous, or xenograft-type transplantation.

It is yet another aim of this invention to create an ectopic joint in vivo in order to harvest the articular cartilage from the joint for dissociation and growth of articular chondrocytes in vitro and then injection of said articular chondrocytes into an extant region of injured articular cartilage for allogenic, autologous, or xenograft-type implantation.

It is yet another aim of this invention to create an endochondral cap on an amputation stump in vivo.

It is yet another aim of this invention to create an endochondral cap on an amputation stump in vivo, and harvest the chondrocytes for expansion in vitro.

It is yet another aim of this invention to create an endochondral cap on an amputation stump in vivo, and apply a second protein in order to elongate the bone from the amputation stump.

It is yet another aim of this invention to create an apical bone template for a limb segment in vivo.

It is yet another aim of this invention to create an apical bone segment for generation of a marrow cavity with potential stem cell niche in vivo.

It is yet another aim of this invention to create joint-like segmentation within a bone fracture in vivo.

It is yet another aim of this invention to create a limb or digit in vivo through piecemeal assembly and construction of joints and the skeletal structures in between.

It is yet another aim of this invention to create joint-like structures in vitro by application of joint inducing protein, preferably BMP-9, to competent cell types, preferably fibroblasts derived from tissue ossifying regions, for allogenic, autologous, or xenograft-type implantation.

It is yet another aim of this invention to create joint-like structures in vitro by application of joint inducing protein, preferably BMP-9, to competent cell types, preferably fibroblasts derived from tissue ossifying regions, and select for articular cartilage marker expressing cells for expansion in vitro.

It is yet another aim of this invention to create joint-like structures in vitro by application of joint inducing protein, preferably BMP-9, to competent cell types, preferably fibroblasts derived from tissue ossifying regions, and select for articular cartilage marker expressing cells for expansion in vitro and subsequent seeding of said cells within a matrix or scaffold for allogenic, autologous, or xenograft-type implantation.

It is yet another aim of this invention to create joint-like structures in vitro by application of joint inducing protein, preferably BMP-9, to competent cell types, preferably fibroblasts derived from tissue ossifying regions, and select for articular cartilage marker expressing cells for expansion in vitro and subsequent seeding of said cells within a bioreactor for expansion and designing tissues for allogenic, autologous, or xenograft-type transplantation.

DESCRIPTION OF THE DRAWINGS

FIG. 23. A series of diagrammed steps showing possible variations of the step wherein a person identifies a joint molecule induction substrate for application of the joint induction molecules to said joint molecule induction substrate FIG. 24. A series of diagrammed steps showing possible variations of the step wherein a person identifies a joint molecule induction substrate for application of the joint induction molecules to said joint molecule induction substrate FIG. 25. A series of diagrammed steps showing possible variations of the step wherein a person chooses a joint molecule delivery technique FIG. 26. A series of diagrammed steps showing possible variations of the step wherein a person identifes an ossification center within the joint molecule induction substrate FIG. 27. A series of diagrammed steps showing possible variations of the step wherein a person creates an ossification center within the joint molecule induction substrate FIG. 28. A series of diagrammed steps showing possible variations of the step wherein a person applies the joint induction molecules with the joint molecule delivery technique to the joint molecule induction substrate FIG. 29. A series of diagrammed steps showing possible variations of the step wherein joint related tissue is created FIG. 30. A series of diagrammed steps showing possible variations of the step wherein joint related tissue is used to benefit a patient FIG. 31. A series of diagrammed steps showing possible variations of the step wherein joint related tissue is used to benefit a patient

DETAILED DESCRIPTION OF THE INVENTION

The present invention comprises the application of an effective amount of a joint inducing protein, preferably BMP-9 (SEQ 01), or alternatively BMP-3 (SEQ 02), or alternatively joint induction molecules that are applied to a joint induction molecule substrate in order to create a joint-related tissue which some examples may include a joint, articular cartilage, or an endochondral cap to an ossification center. In some embodiments, this ossification center may be induced by injury, such as after an amputation, wounding or fracture. And in other embodiments an effective amount of ossification center inducing protein, such as BMP-2 (SEQ 03), BMP-4 (SEQ 04) or BMP-7 (SEQ 05), may be used to create an ossification center. In another embodiment, an effective amount of BMP-9 application to cell lines derived from ossification center supportive environments may be used to create induced-joint-like structures and articular cartilage.

Example 1

In order to examine the embryonic expression pattern of BMP-9 in the developing digit to determine if BMP-9 is linked to joint formation or development, experiments were conducted in mice tissue sections. For histological section analysis, samples were embedded in paraffin, sectioned at 8-10 um and stained with Mallory staining. For in situ hybridization, samples were fixed in 4% paraformaldehyde (PFA) in PBS at 4° C. overnight, and then were paraffin embedded and sectioned at 8-10 um. The antisense probe (Roche): BMP9 (707 bp) was generated by using the Digoxigenin-UTP transcription labeling according to the manufacturer's introduction. At least two identical samples of BMP9 or BSA as control treated were used for in situ hybridization.

Figure 1:
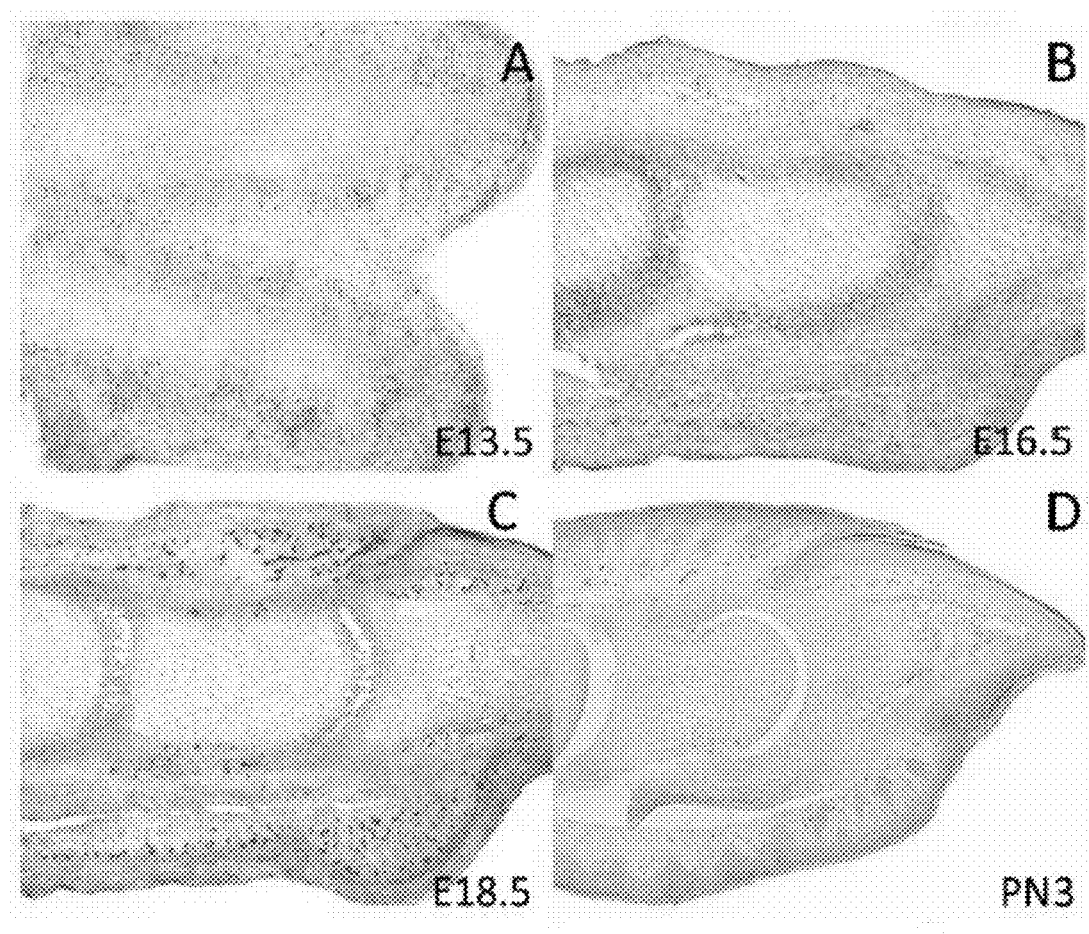
FIG. 1. A series of color photographs of developing limb mouse tissue examined with in situ hybridization. The series of photos shows the time-dependent initiation and loss of BMP-9 expression in the joints. Histologically, the tissue starts from the mesenchymal condensation in A at embryonic day 13.5, joint development at embryonic day B 16.5, and embryonic day C 18.5, and finally loss of expression as 3 days post natal D.

Results: At E10.5, when the mouse limb bud elongates, BMP9 expression was not detectable in the whole limb bud. At E13.5, when the mouse digit development initiated, BMP9 expression was found in the mesenchyme surrounding the condensation cartilaginous of digit (FIG. 1A). At a later stage, when differentiated mesenchymal interzones have appeared at each prospective joint site in digit, BMP9 expression was detected in a restricted pattern in both the perichondrium and interzone region of the digit at E16.5 (FIG. 1B). Subsequently, BMP9 expression began to decrease at E17.5, and the expression was relatively weak and was specifically restricted to the joint region at E18.5 (FIG. 1C). The BMP9 expression was not detected in the postnatal digit at PN3 (FIG. 1D). The unique expression pattern of BMP9 in the developing digit suggests that BMP9 plays a role in the digit skeleton.

Example 2

In order to determine if joints expressed markers for articular cartilage, we first examined for two joint-specific immunohistocehmical markers, CD44 and doublecortin (doublecortin). In order to perform immunochemistry 3-4 µM paraffin or frozen sections were gathered from treated mice and heat antigen retireival was used. The following primary/secondary antibodies combinations were used: (1) Primary Antibody-Goat Polyconal to Human Doublecortin Santa Cruz SC-8066: Secondary Antibody—Fluor Source Anti-Target Invitrogen A11036 G@ Rabbit-586 (2) Primary Antibody—Rat Anti-Human/Mouse CD44 Purified: Secondary Antibody—Biotin Anti-Target Dako, Streptavidin-HRP. Nuclei were labeled with 4',6-diamidino-2-phenylindole (DAPI) (Invitrogen; D3571). We examined at three time points of CD-1 mice; embryonic Day 15, postnatal Day 10 joints, and postnatal day 42.

Figure 2:
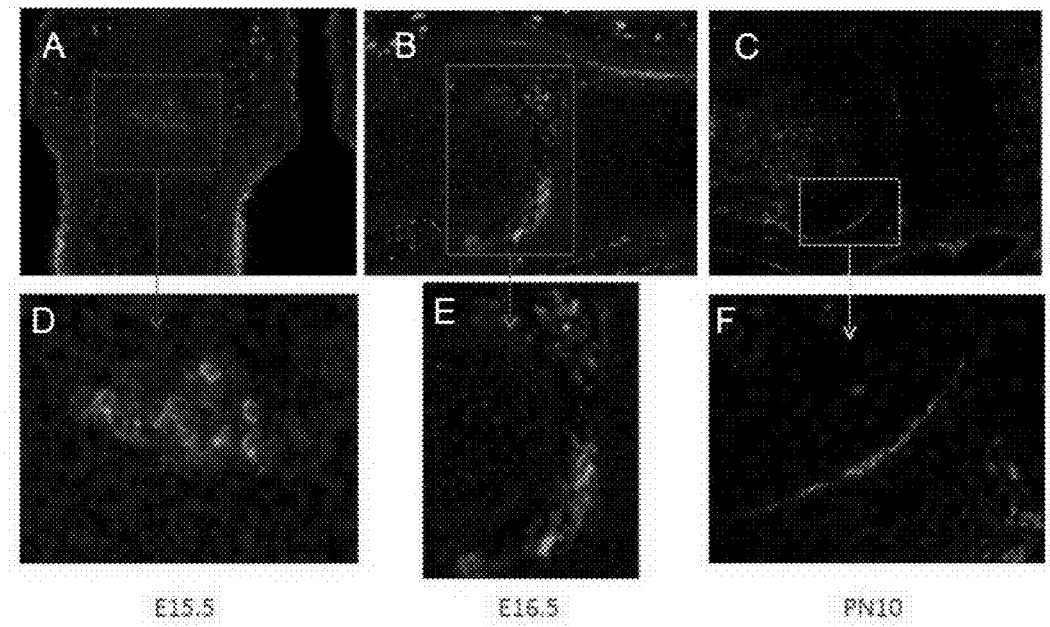
FIG. 2. A series of color photographs of developing limb mouse tissue examined with immunohistochemistry. The series of photos shows the appearance of CD44, a hyularanon receptor, used as a marker for joints. A shows the appearance of CD44 in the mesenchymal condensation at embryonic day 15.5, (the box marks the inset, for magnified image D indicated by the arrow). B shows the appearance of CD44 in the developing joint at embryonic day 16.5, (the box marks the inset, for magnified image E indicated by the arrow). C shows CD44 in the post natal joint, (the box marks the inset, for magnified image F, indicated by the arrow).
Figure 3:
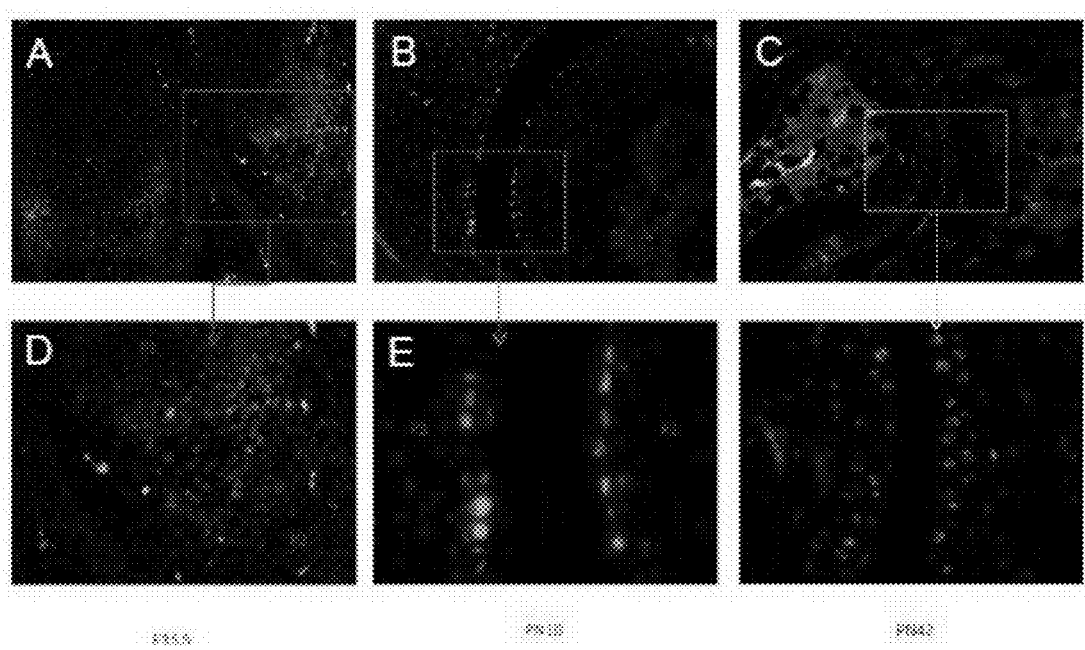
FIG. 3. A series of color photographs of developing limb mouse tissue examined with immunohistochemistry. The series of photos shows the appearance of doublecortin, an articular cartilage specific-marker for joints. A shows the appearance of doublecortin in the mesenchymal condensation at embryonic day 15.5, (the box marks the inset, for magnified image D indicated by the arrow). B shows the appearance of doublecortin in the 10 day postnatal developing joint, (the box marks the inset, for magnified image E indicated by the arrow). C shows doublecortin 42 days post natal in the juvenile mouse, (the box marks the inset, for magnified image F, indicated by the arrow).
Figure 4:
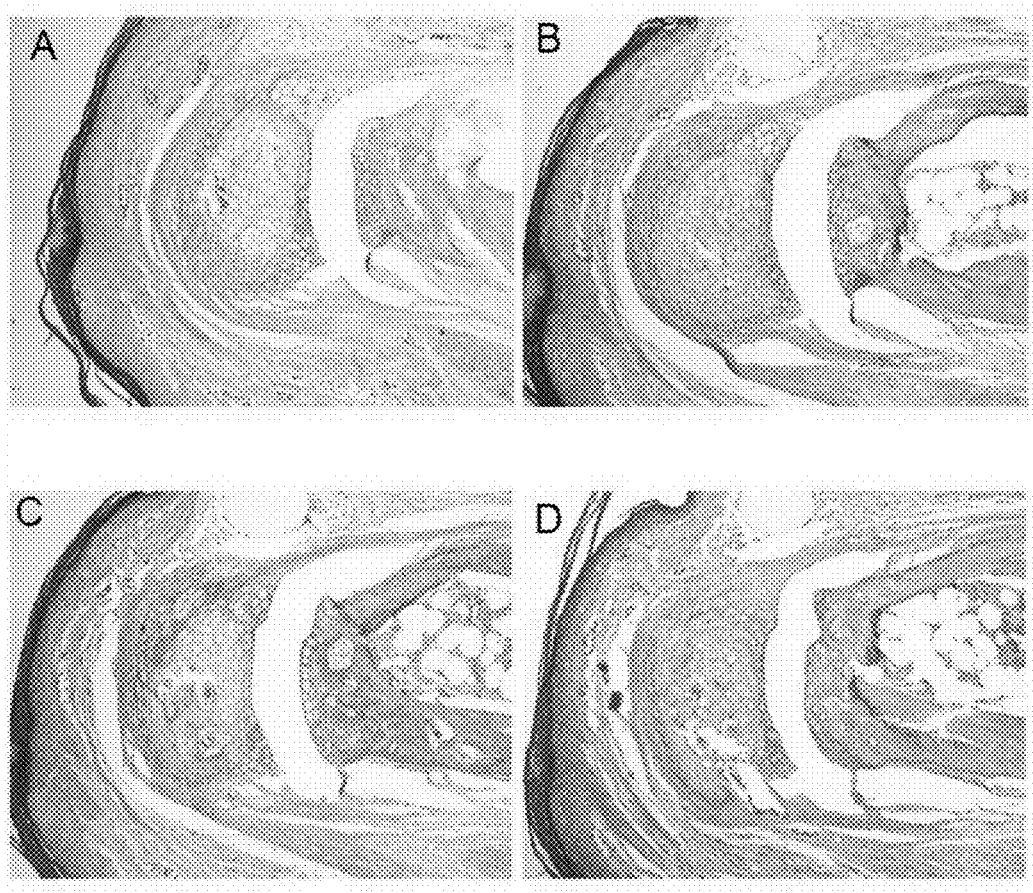
FIG. 4. A series of color photographs of limb mouse tissue examined with mallory staining. The series of photos are adjacent sections (A-D) through an amputated digit that was treated first with an ossifying-center protein (BMP-2), and second with a joint-inducing protein (BMP-9). The images show the development of a second apical ossification distal to the original amputation plane with a cavitation resembling a joint or joint-like structure. Additionally, there is a cellular ultrastructure adjacent to the developing joint resembling articular cartilage.

Results: We found that the at embryonic day 15.5 CD44 was expressed in the mesenchymal condensations of developing limbs (FIG. 2A, inset FIG. 2D). At embryonic day 16.5 (FIG. 2B, inset FIG. 2D) this expression was more visible in the joint region and by ten days post natal (FIG. 2C, inset FIG. 2F) expression was restricted to a single layer. Further we found a similar expression pattern for the expression of doublecortin, an articular cartilage specific marker. We found that the at embryonic day 15.5 doublecortin was expressed in the mesenchymal condensations of developing limbs (FIG. 2A, inset FIG. 2D). At post natal day 10 (FIG. 2B, inset FIG. 2D) and 42 (FIG. 2C, inset FIG. 2F) this expression was seen in individual cells in the articular cartilage region.

Example 3

In order to examine if joints can be induced after amputation, we applied BMP-2 with agarose-gel blue beads and/or gel and subsequently BMP-9 was applied with agarose-gel blue beads. These samples were then examined with Mallory staining.

Results: BMP-2 was applied with gel or agarose-gel beads in early post natal mice and subsequently BMP-9 was applied. Serial sections examined with mallory staining (FIG. 4A-D) showed the development of apical joint-like structures with a cavitation in between the amputated stump and the new apical bone. On either side of this cavitation the cellular ultrastructure was reminiscent of articular cartilage.

Figure 5:
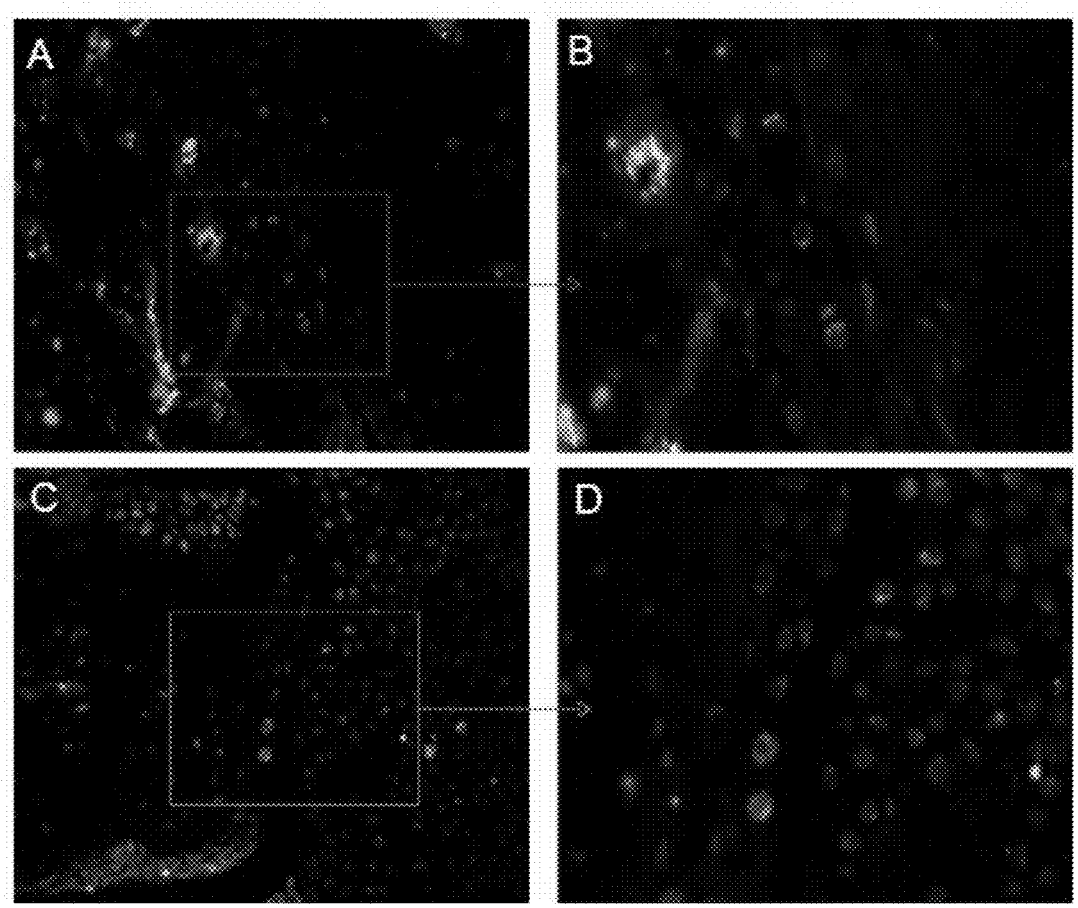
FIG. 5. A series of color photographs of limb mouse tissue examined with immunohistochemistry. An amputated digit that was treated first with an ossifying-center protein (BMP-2), and second with a joint-inducing protein (BMP-9). The images show the expression of articular cartilage marker doublecortin in tissue sections within the cavitation that develops from the treatment. A and C show the appearance of doublecortin in the cavitation of the newly created joint (for each the box marks the inset, for magnified images B and D indicated by the arrow).

In order to determine if induced joints from amputated stumps treated with BMP-2→BMP-9 expressed articular cartilage, doublecortin was used to examine expression in the cavitation region. Example sections (FIG. 5A, FIG. 5C with insets FIG. 5B, FIG. 5D) suggest that doublecortin was upregulated in the cell layers adjacent to one another, on either side of the apical cavitation.

The term joint is meant to mean an in vivo or in vitro structure that has initially none or 1 osteal or chondral tissues and after treatment has 2 closely opposite osteal or chondral tissues, divided by a cavitation. The term ossification center is one that means new bone is expected to be forming in a specific region. The term cartilage is meant to mean tissue consisting of chondrocytes. Articular cartilage is meant to mean, a one or more layer of cells in a joint, induced joint or culture that abuts a cavitation and may expresses articular cartilage markers or have similar cellular morphological characteristics to articular cartilage. The term joint-inducing protein is a protein that is capable of inducing a joint at an extant ossification center in vivo, or capable of producing a joint in vitro when applied to cells derived from a region capable of being an ossification center. The term ossification center inducing protein is a protein that is capable of creating an environment where bone forms, prior to application of our protein. Endochondral cap is defined as a chondeogenic or osteogenic cellular mass on the apical end of an amputated stump. The human and vertebrate nucleic acid and amino acid sequences for BMP-9, BMP-3, BMP-2, BMP-4, and BMP-7 are published and well known in the art.

Compositions of the joint forming protein may further include at least one other anti-osteogenic agents, such as BMP-3, or non-BMP related proteins such as proteins from the fibroblast growth factor (FGF) family, epidermal growth factor family (EGF), pigmented epithelial-derived factor family (PEDF), or platelet-derived growth factor family (PDGF).

The proteins in this invention will typically be of mammalian origin e.g. human, mouse, (or any vertebrate origin, in accordance with a phylogenetic similarity in amino acid sequence, as established by the relevant literature in the art). They can be created with recombinant DNA technology. For a general discussion of cloning and recombinant DNA technology see Ausubel et al., supra; see also Watson et al, Recombinant DNA, 2d ed. 1992 (W. H. Freeman and Co., New York). The DNA and amino acid sequences of many BMPs have been reported, and methods for their recombinant production are published and otherwise known to those of skill in the art. For example, plasmids or virus vectors that contain full, partial, or synthetic cDNA sequences can be used to create significant quantities of proteins from within host cells such as prokaryotes including *E. coli* or eukaryotes including yeast, or mammalian cells, such as CHO, COS or BSC cells. These proteins can be purified, cleaved, folded, and dimerized to form the proteins for this invention.

This invention also provides for native forms of proteins to induce tissue formation. These proteins can be purified from tissue sources, using conventional physical and chemical separation techniques well known to those of skill in the art. When available, immunological reagents may be used alone or in conjunction with these techniques to purify the proteins. Further, proteins isolated from native tissue that are mutants and/or variants of the protein of interest, and exhibits the ability to modify or create tissue per this invention are considered as proteins as well.

Numerous applications detail The proteins provided herein also include those created by sequences similar to those of naturally-occurring BMP9, BMP2, BMP4 and BMP7 proteins, but into which modifications are naturally provided (e.g. allelic variations in the nucleotide sequence which may result in amino acid changes in the polypeptide) or deliberately engineered. well known or example, synthetic polypeptides may wholly or partially duplicate continuous sequences of the amino acid residues of BMP9, BMP2, BMP4 or BMP 7. In another embodiment, useful proteins include biologically active biosynthetic constructs, including novel biosynthetic morphogenic proteins and chimeric proteins designed using sequences from two or more known morphogens. These sequences, by virtue of sharing primary, secondary, or tertiary structural and conformational characteristics may possess cartilaginous or other tissue growth or maintenance factor biological properties in common therewith. Thus, they may be employed as biologically active substitutes for naturally-occurring joint or bone tissue inducing polypeptides in therapeutic compositions and processes.

As described in US patent application 20070122396 Lee and Yeh (hereby incorporated by reference), there are multiple protein quaternary formations and bond-types that can be considered functional equivalents and are contemplated as embodiments herein:

"As noted above, proteins useful in the present invention generally are dimeric proteins comprising a folded pair of the above polypeptides. In some embodiments, the pair of polypeptides are not disulfide bonded. In some embodiments the pair of polypeptides are disulfide bonded. Such disulfide bonded morphogenic proteins are inactive when reduced, but are active as oxidized homodimers and when oxidized in combination with others of this invention to produce heterodimers. Thus, members of a folded pair of morphogenic polypeptides in a morphogenically active protein can be selected independently from any of the specific polypeptides mentioned above."

As described in US patent application 6287816 Rosen and Wozney (hereby incorporated by reference), there are well known modifications of glycoslyation sites that can be considered functional equivalents and are contemplated as embodiments herein:

"These modifications may involve O-linked or N-linked glycosylation sites. For instance, the absence of glycosylation or only partial glycosylation results from amino acid substitution or deletion at asparagine-linked glycosylation recognition sites. The asparagine-linked glycosylation recognition sites comprise tripeptide sequences which are specifically recognized by appropriate cellular glycosylation enzymes. These tripeptide sequences may be asparagine-X-threonine, asparagine-X-serine or asparagine-X-cysteine, where X is usually any amino acid except proline. A variety of amino acid substitutions or deletions at one or both of the first or third amino acid positions of a glycosylation recognition site (and/or amino acid deletion at the second position) results in non-glycosylation at the modified tripeptide sequence. Additionally, bacterial expression of protein will also result in production of a non-glycosylated protein, even if the glycosylation sites are left unmodified."

Another aspect of the invention provides pharmaceutical compositions containing a therapeutically effective amount joint-, articular cartilage- or endochondral cap-inducing protein, such as BMP-9, in a pharmaceutically acceptable vehicle or carrier. These compositions may be used to induce the tissues when applied to an ossification center. Example carriers include but are not limited to matrices such as biodegradable-synthetic or a synthetic-inorganic matrix (e. g., hydroxyapatite (HAP), collagen, carboxymethyl-cellulose, tricalcium phosphate or polylactic acid, polyglycolic acid, polybutyric acid and various copolymers thereof). Scaffolds and/or matrices such as collagen scaffolds or matrices, polygliacolic acid scaffolds, or tissue isolated extracellular matrix. The mase carrier, or as a collagenous coating for orthopedic or general prosthetic implants. Other well known methods of protein delivery in matrices or scaffolds are also contemplated as in U.S. Pat. No. 6,048,964 (hereby incorporated by reference) and are contemplated as embodiments herein:

"The matrix may comprise a shape-retaining solid made of loosely-adhered particulate material, e. g., collagen. It may also comprise a molded, porous solid, or simply an aggregation of close-packed particles held in place by surrounding tissue. Masticated muscle or other tissue may also be used. Large allogenic bone implants can act as a carrier for the matrix if their marrow cavities are cleaned and packed with particles comprising dispersed morphogenic protein combinations. The matrix may also take the form of a paste or a hydrogel. When the carrier material comprises a hydrogel matrix, it refers to a three dimensional network of cross-linked hydrophilic polymers in the form of a gel substantially composed of water, preferably but not limited to gels being greater than 90% water. Hydrogel matrices can carry a net positive or net negative charge, or may be neutral. A typical net negative charged matrix is alginate. Hydrogels carrying a net positive charge may be typified by extracellular matrix components such as collagen and laminin. Examples of commercially available extracellular matrix components include Matrigel and Vitrogen. An example of a net neutral hydrogel is highly crosslinked polyethylene oxide, or polyvinylalcohol. Various growth factors, cytokines, hormones, trophic agents and therapeutic compositions including antibiotics and chemotherapeutic agents, enzymes, enzyme inhibitors and other bioactive agents also may be adsorbed onto or dispersed within the carrier material comprising combinations of the morphogenic proteins, and will also be released over time at the implantation site as the matrix material is slowly absorbed."

The substrate by which the proteins of this invention act are typically cells from within it about an ossification center in vivo or fibroblast progenitors in vitro. These cells may be induced to proliferate and/or differentiate by application of proteins of this invention. Cells pertinent to this invention may include mammalian chondroblasts, osteoblasts, all earlier developmental precursors thereof, and all cells that develop therefrom (e. g., chondroblasts, pre-chondroblasts and chondrocytes). It is also possible that non-mammalian responsive cells may be stimulated by same- or cross-species proteins due to the phylogenetic similarities across species of this invention's protein family.

This invention also contemplates that the BMP-9 may not be the only BMP protein that is able to create joints, articular cartilage or an endochondral cap within an ossification center. The variability with which a protein other than BMP-9 may or may not be able to create new tissues is likely dependent on the spatiotemporal context of application and the region within which is it applied. One means by which a practitioner of the invention may be able to determine if another BMP protein is comparable to BMP-9 in it's ability to create joint-like structures and articular cartilage is to implant an agarose-gel bead carrying the putative protein into a regenerating terminal mouse digit. If application of the BMP protein to the digit prevents ossification, rather than enhance ossification (as with BMP2, 4, 7) than it would fall under the scope of this invention, as a likely candidate for one that may create joint-like structures and articular cartilage in an ossification center. For example, one possible BMP protein that may fall within the scope of this invention is BMP3, which unlike other BMP's is primarily known by it's anti-osteogenic properties.

Example 4

In order to examine the osteogenic potential that BMP-9 has on the regenerating digit, beads containing rhBMP-9 (0.5 mg/ml) were implanted at PN7 (4 days after digit amputation) into 2 regions: 1) the blastema region following a regenerating level amputation and 2) apical to the stump following a non-regenerating level P3 amputation. We analyzed the response of treatment samples by using whole-mount skeletal staining by 14 DPI (14 days post-implantation). Wild type CD1 mice line were purchased from Charles River Lab (Wilmington, Mass., USA). For the neonates, distal amputations of terminal phalanx (P3) were carried out at postnatal day 3 (PN3). agarose-Gel Blue Gel beads (150-200 um in diameter, Bio-Rad, Hercules, Calif., USA) were soaked with recombinant human protein BMP9 (R&D Systems, Minneapolis, Minn., USA) at 10 ng/ul; 50 ng/ul; 200 ng/ul; 500 ng/ul) and control beads were soaked in PBS containing 0.1% BSA. 4 days after digit amputation.

Figure 6:
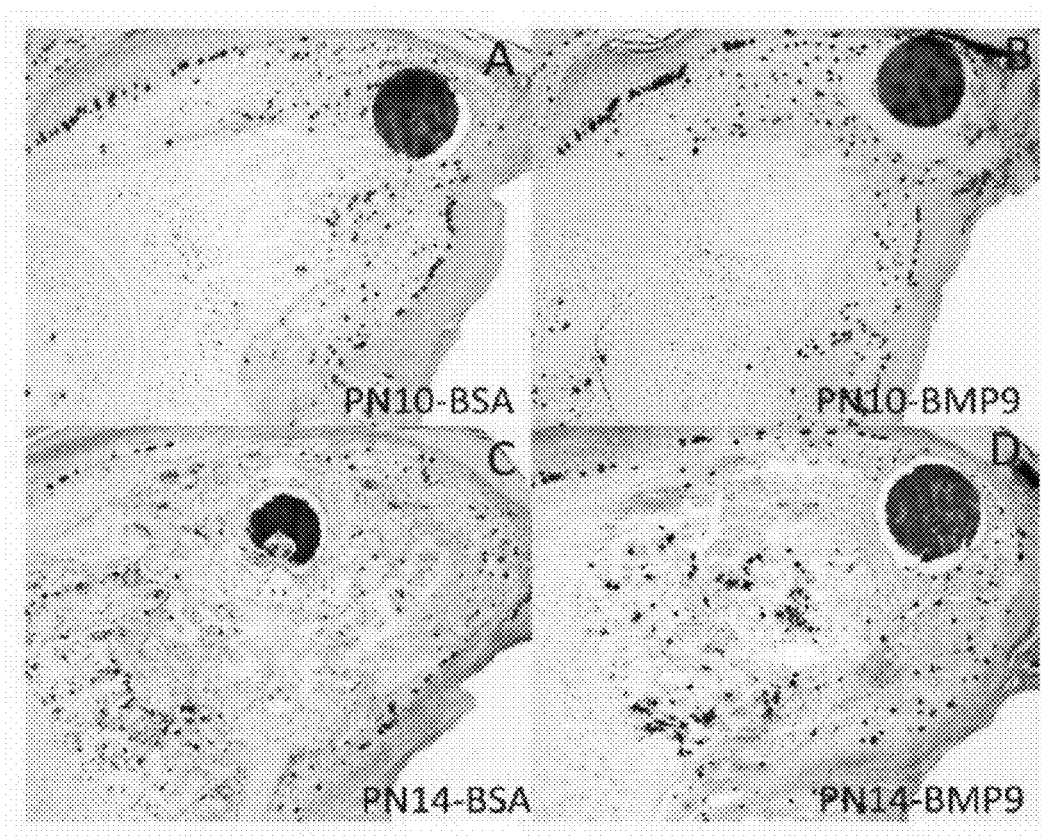
FIG. 6. A series of color photographs of limb mouse tissue examined with an apotosis assay. A post natal day 3 terminal phalanx was amputated and subsequently was treated with bovine serum albumin as a control or BMP-9 as a joint induction protein. Application of BMP-9 inhibited regeneration of the digit. In order to determine if the inhibition or regeneration was mediated by an increase in apoptosis, an assay was performed which indicated no difference in apoptosis. A and C show BSA treated sections at postnatal days 10 and 14 respectively, B and D show BMP-9 treated sections at postnatal days 10 and 14 respectively.

Results: For proximal amputation P3 digit, BMP9 (FIG. 6B) treatment failed to display any induced regenerative response similar to the BSA control (FIG. 6A) In the group of distal amputation P3 digit, BMP9 inhibited regeneration (FIG. 6D, FIG. 6C as BSA control). Next, we reduced the concentration of BMP9 protein to 200 ng/ul or 50 ng/ul and then did bead implantation in the distal amputated P3 digit. Concentrations as low 50 ng/ul were able to inhibit regeneration (FIG. 6E). BMP-9-implanted regenerating-level amputated P3 digits collected at 28 DPI, 35 DPI and 42 DPI also did not display delayed regeneration, suggesting that it's effects were long-lasting (FIG. 6F).

Example 5

In order to examine if cells in the blastema region are affected by BMP-9 application, cell proliferation and apoptosis assays were carried out. Digit samples were fixed with Z-Fix (Anatech LTD) at room temperature overnight and then treated with Decalcifier II (Surgipath) for 2 hours. Paraffin-embedded samples were sectioned at 4-5 µm. Cell proliferation studies was carried out by using the BrdU labeling and detection Kit II (Roche) and Click-iT EdU Imaging Kit (Invitrogen) following the manufacturer's suggested protocol for immunostaining. To detect the cell apoptosis, the Cell Death Detection Kit (Roche Applied Sciences, IN), (Roche) was used and performed in paraffin sections as previously described.

Figure 7:
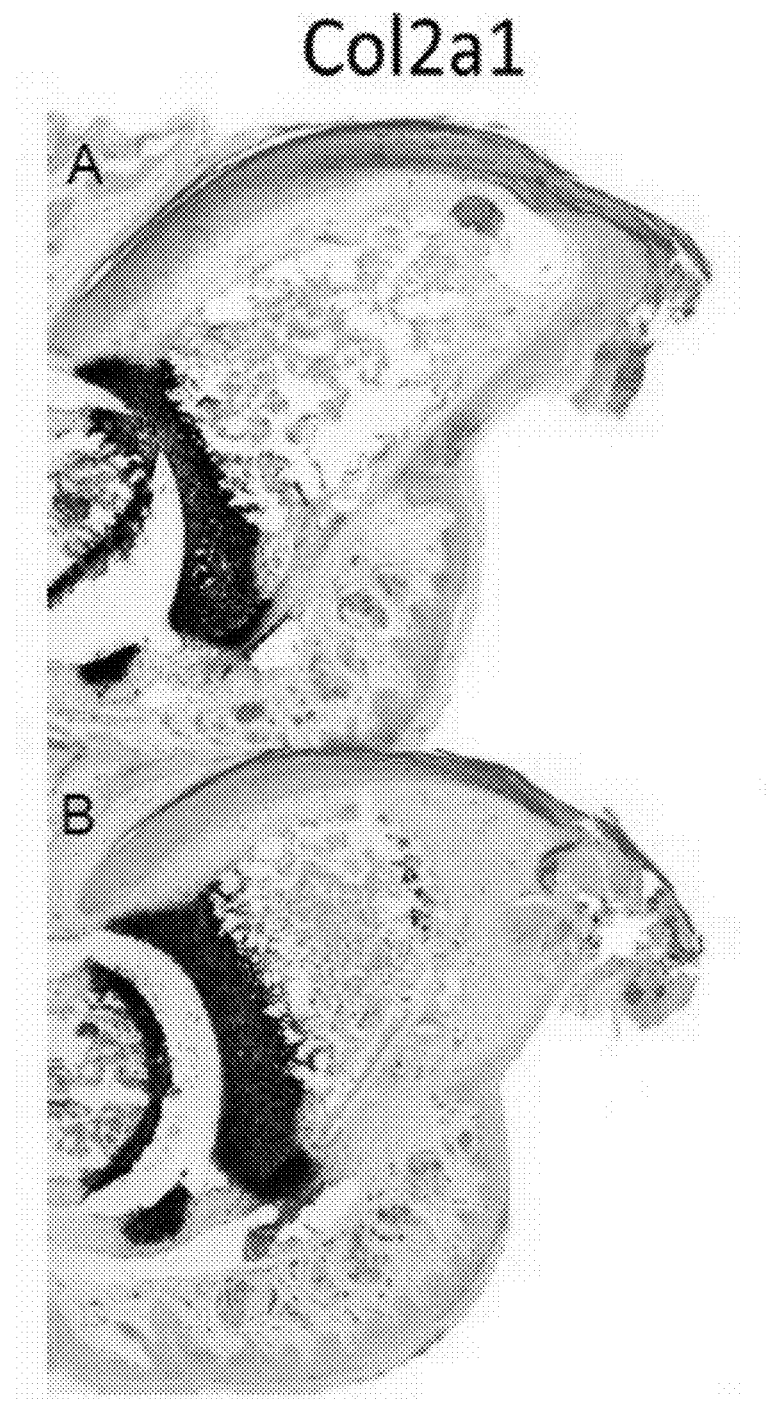
FIG. 7. A series of color photographs of limb mouse tissue examined with an in situ hybridization. A post natal day 3 terminal phalanx was amputated and was subsequently was treated with bovine serum albumin as a control or BMP-9 as a joint induction protein. Application of BMP-9 inhibited regeneration of the digit. In situ hybridization for Col2a1 was examined for generation of cartilage as a means of inhibiting regeneration. A shows in BSA treated digits, Col2a1 expression limited to the proximal portion of the terminal phalanx. B shows in BMP-9 treated digits, the Col2a1 expression at the apical tip.

Results: Cell apoptosis was detected in the distal region of distal amputated P3 digit at 10 (FIG. 7A) and 14 days postnatal (FIG. 7B), treated with BMP-9. When compared to BSA control at 10 (FIG. 7C) and 14 days postnatal (FIG. 7D) was unaltered. In addition, a population of BrdU positive cells accumulated throughout the distal connective tissue and bone stump at 3 DPI and 7 DPI, and was not significantly different when compared between control and BMP-9. Further, proliferation data acquired with Click-iT EdU were similar to that as with Brdu incorporation. Our data suggested that BMP9 treatment does not induce cell death or affect cell proliferation in the distal region of amputated digit.

Example 6

Previous studies have shown that regeneration of the distal amputated P3 is accomplished by direct ossification. In order to determine if the mechanism of regeneration inhibition after BMP-9 application was the prevention of osteogenic differentiation, we examined for changes in chondrogenic (Col2a1, Ihh, Col10a1) and osteogenic cell marker (osteocalcin, Dlx5, Runx2) expression. Runx2 and Dlx5 are the marker genes of osteoblast differentiation and play crucial role in osteogenic differentiation. Also, Osteocalcin is an osteoblastic marker gene present during the process of bone regeneration. In addition, we examined for changes in noggin expression, a potent BMP-inhibitor.

Results: After BSA or BMP-9 bead implantation, we examined at 7 DPI because at this stage direct ossification in distal amputated P3 (or the BMP2 or BMP7 induced endochondral ossification in proximal amputated P3) can be detected. For histological section analysis, samples were embedded in paraffin, sectioned at 8-10 um and stained with Mallory staining. For in situ hybridization, samples were fixed in 4% paraformaldehyde (PFA) in PBS at 4° C. overnight, and then were paraffin embedded and sectioned at 8-10 um. The following antisense probes were generated by using the Digoxigenin-UTP transcription labeling according to the manufacturer's introduction (Roche): DLx5 (900 bp), Runx2 (550 bp), Noggin (950 bp), ColII (500-bp), ColX (650 bp), Osteocalcin (300 bp) At least two identical samples of BMP9 or BSA as control treated were used for in situ hybridization.

Figure 8:
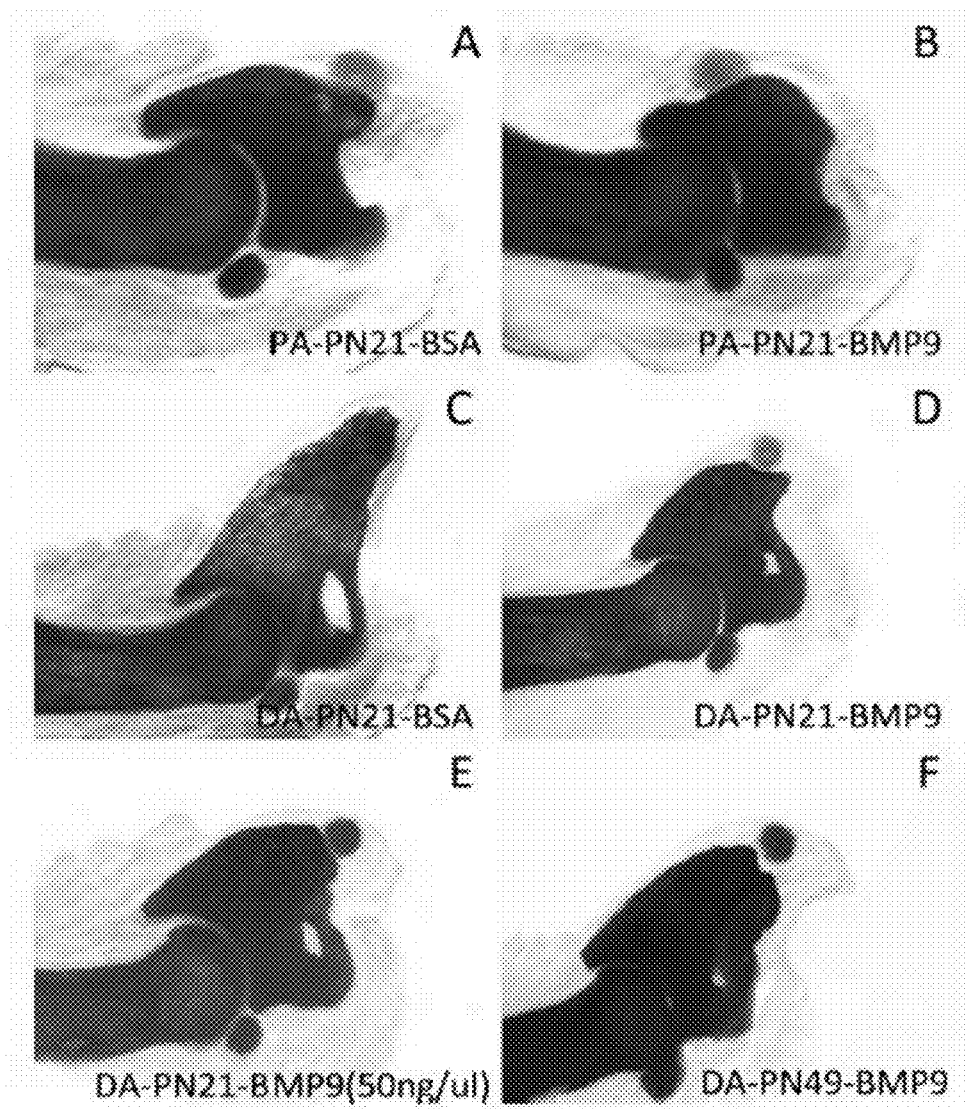
FIG. 8. A series of color photographs of whole limb mouse tissue showing whole-mount effects of BMP-9 application to a regenerating digit. After application of BSA and BMP-9 (A and B respectively) to a proximal non-regenerating digit, neither digit exhibited significant distal ossification. C shows a BSA treated-regenerating digit in which distal ossification was present, D-F shows BMP-9 application inhibiting distal ossification at at various time points and concentrations of bead delivery.
Figure 9:
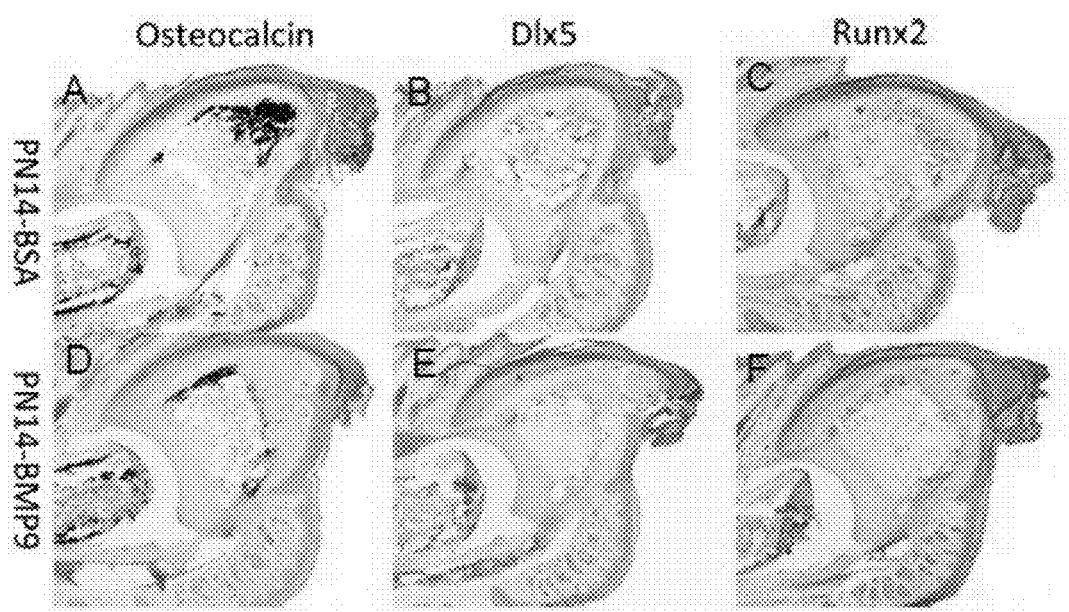
FIG. 9. A series of color photographs of limb mouse tissue examined with an in situ hybridization. A post natal day 3 terminal phalanx was amputated and was subsequently was treated with bovine serum albumin as a control or BMP-9 as a joint induction protein. Application of BMP-9 inhibited regeneration of the digit. In situ hybridization for Osteocalcin, Dlx5 and Runx2, was examined for expression following BSA treatment (A-C). In situ hybridization for Osteocalcin, Dlx5 and Runx2, was also examined for expression following BMP-9 treatment (D-F).
Figure 10:
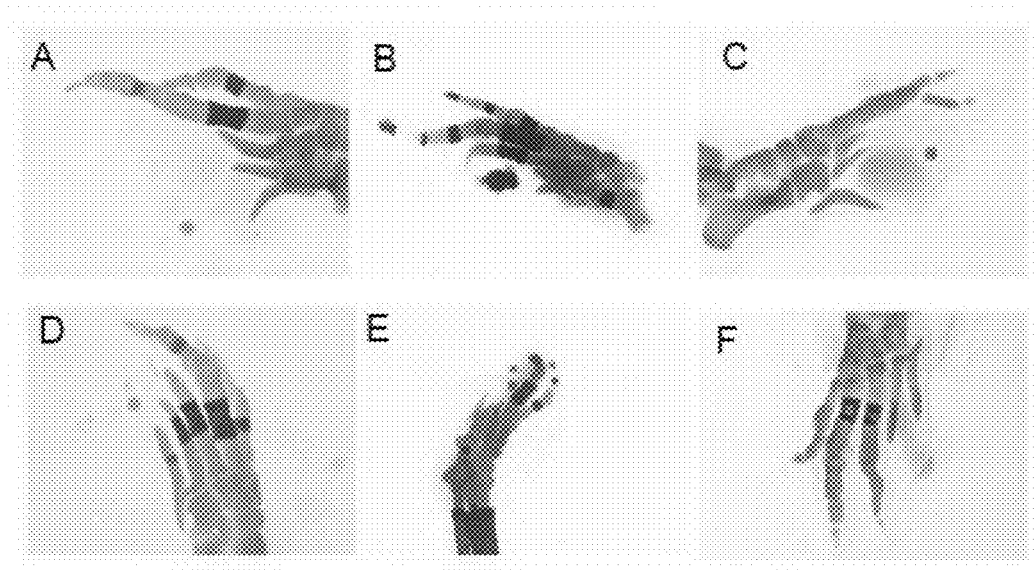
FIG. 10. A series of color photographs of whole limb mouse tissue showing whole-mount effects of BMP-9 application to a developing nouse digit. A-F are individual examples of BMP-9 application inhibiting digit development.

In BSA-treated control, we found no change in expression of any endochondral marker genes, and the expression domains of Col2a1 (FIG. 8A), Ihh and Col10a1 were localized to the proximal base of the distal amputated P3 digit. In a BMP9 treated distally-amputated digit, the ectopic expression domains of Col2a1, a chondrocyte specific maker gene, was found at the top region of the amputated stump (FIG. 8B). However, the expression of Ihh and Col10a1, the prehypertrophic and hypertrophic chondroctye marker gene, were not altered compared to the BSA control and only localized to the proximal base of amputated P3 digit. This result suggested that BMP9 could induce some blastema cell differentiation towards chondrocytes and that further differentiation seemed to be inhibited. It also indicates that BMP9 application to the regenerating P3 digit does not play the same function as BMP7 or BMP2 which would induce endochondral ossification We further analyzed the expression pattern of osteogenic marker genes. Compared with BSA-treated control, the expression of Dlx5 (FIG. 9B BSA, and FIG. 9E BMP-9) and Runx2 (FIG. 9C BSA, and FIG. 9C BMP-9) are also strongly down-regulated in both the bone marrow and distal blastema regions in distal amputated P3 digit after BMP9 treatment. Strong expression of osteocalcin was found in the regenerated digit tip region in BSA-treated control (FIG. 9A), but osteocalcin expression was lower and only expressed in the ossification cap across the amputated stump after BMP9 socked beads treated distal amputated P3 digit (FIG. 9C). The strong down-regulation of all these three genes suggest that BMP9 treatment inhibits regeneration of distal amputated P3 digit, by preventing osteogenic differentiation. We further found that BMP9 could induce Noggin ectopic expression in the top region of distal amputated P3 bone stump from 3 DPI until 7 DPI, suggesting that expression of Noggin induced by BMP9 may play a critical role in suppressing osteogenic differentiation.

Example 7

In order to examine the effect that BMP-9 has on embryonic digit development, beads containing rhBMP-9 (1, 0.1 and 0.025 mg/ml) were implanted at E 13.5 by exo utero surgery. The procedure for ex utero surgery can be found in Methods in Enzymology Volume 476, 2010, Pages 205-226 by Ngo-Muller and Muneoka.

Figure 11:
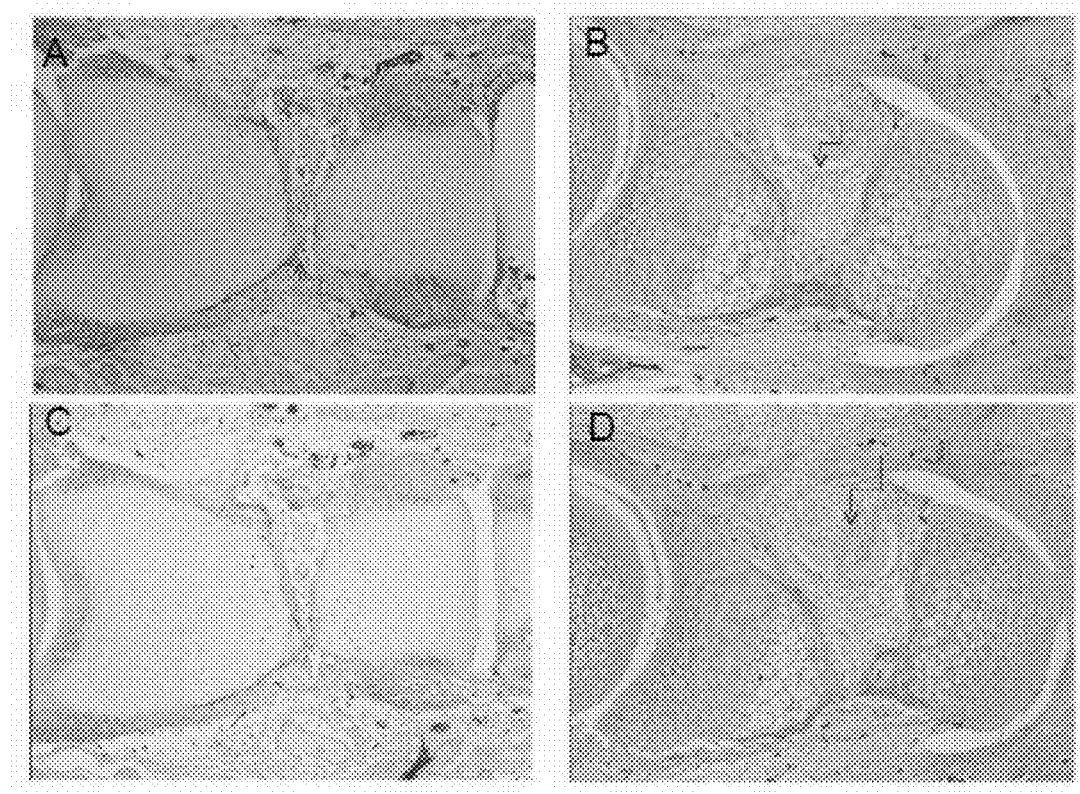
FIG. 11. A series of color photographs of whole limb mouse tissue showing mallory staining. A, C show fractured early post natal digits. B, D show fractured digits after treatment with BMP-9 at the fracture plane. BMP-9 application resulted in an increased cavitation and development of chondrogenic tissue within the fracture zone.

Results: In regions that were BMP-9 was implanted, there was a failure of digit development (examples FIG. 10A-F). At 8 days post natal, implantation of BMP-9 beads in a fractured P2 digit, prevents osteogenic differentiation and enhances the the chondrogenic phenotype (examples FIG. 11A, C before BMP-9 application, FIG. 11B, D after BMP-9 application). This enhancement is concomitant with an invasion of fibroblasts into the fractured region.

Example 8

In order to examine if an endochondral cap be induced after amputation, we applied BMP-9 with agarose-gel blue beads and/or gel and subsequently BMP-9 was applied with agarose-gel blue beads. These samples were then examined with Mallory staining.

Figure 12:
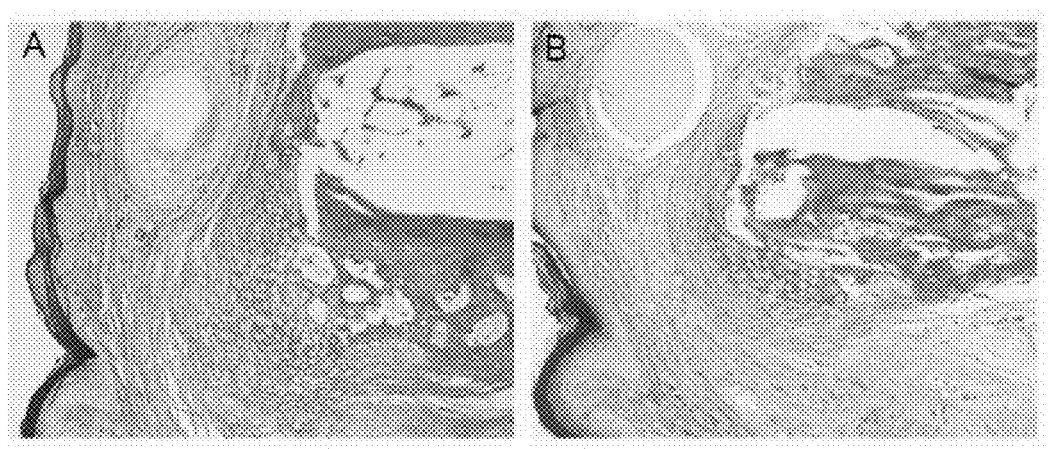
FIG. 12. A series of color photographs of whole limb mouse tissue showing mallory staining. Two examples of sections (A, B) showing that after limb amputation, BMP-9 applied distal to the amputation plane results in the formation of an endochondral cap over the amputation stump.

Results: Two examples of sections (FIG. 12A, B) showing that after limb amputation, BMP-9 applied distal to the amputation plane results in the formation of an endochondral cap over the amputation stump.

In one embodiment of the invention, joint inducing protein, is prepared preferably BMP-9, is delivered by administration into a tissue after treatment preparation of a target patient or animal. Herein, initial injection of joint inducing protein into the joint, inundates the target tissue, and acts over time to restore some of the functional properties of the joint, by inducing a proliferative, chemotactic and/or differentiation-like (such as a trans- or de-differentiation) response of cells in the region and results in restoration of damaged tissue Another embodiment of the invention, takes advantage of the joint inducing protein, preferably BMP-9, modulation of an endogenous bone response in order to create articular cartilage for an allograft or an autograft in to a damaged joint. Here, after a limb or bone injury, such as an amputation, there is often an endogenous generation of peripheral bone and/or cartilage near the amputation plane. Joint inducing protein can be applied to the region, via syringe which through modulation of the recruitment, differentiation, or proliferation of the local tissue creates a After an effective and nominal waiting period, layer of de novo articular cartilage either on the lateral or medial surface of the apical bone growth. Subsequently, the articular cartilage formed by the application of joint inducing protein protein can be extracted from the tissue with dissection or surgery tools and isolated from the new bone. This de novo articular cartilage can then be implanted into damaged joints and used for treatment of damaged tissue.

In another embodiment of the invention, focal application of joint inducing protein, preferably BMP-9, may be used to regenerate tissue is at the apical end of an amputated bone (an endogenous ossification center) when an extremity is lost. Here, after the epidermis has migrated such that the wound is closed and there is both epidermis and mesenchyme distal to the amputation plane, joint inducing protein can be administered to the tissue surrounding the amputation plane. This may recruit cells, either from the circulatory system or exposed marrow, or induce proliferation of local progenitors (or terminally differentiated cells) or redirect differentiation from local progenitors, induce trans-differentiation from local cells, or induce de-differentiation in differentiated cells. Subsequently, this application creates a half joint cap over the amputation plane, which may serve several functional purposes. (1) After a nominal effective time the amputation plane be converted to a half joint or joint like structure, which may allow the subsequent addition of a distal bone (or growing bone) in order to create a functional equivalent of an extra limb or digit. (2) The cap can also be used to modify the extant bone to form a stable mechanical androgenic or osteopathic structure over the exposed marrow upon which a prosthetic limb may be placed. This treatment would be in lieu of a more proximal re-amputation which is sometime necessary after traumatic limb damage in order to fit a patient with a prosthetic attachment.

In another embodiment of the invention, focal application of joint inducing protein, preferably BMP-9, can be used, is for the regeneration of ligaments. Here, injection of the joint inducing protein into the affected region, will, after time, repair a torn ligament, or extend the length of the tendon or ligament such that it can attach to the region of the bone where it was previously attached (or be surgically repaired).

In another embodiment of the invention, focal application of joint inducing protein, preferably BMP-9, can be used, is for the regeneration of damaged tendons. Here, injection of the joint inducing protein into the affected region can repair a damaged tendon, will, after time, extend the length of the tendon or such that it can attach to the region of the bone where it was previously attached (or be surgically repaired).

In another embodiment of the invention, focal application of joint inducing protein, preferably BMP-9, can be used is for protein-mediated amputation of a limb, for patients in need of an amputation. Here, in order to perform a "cleaner amputation", the bone can be fractured. Joint inducing protein can be injected into a perpendicular crack of a limb bone, which will act to modify the fissure such that each end of the now separated bones will form a cartilaginous region, similar to a joint when immobilized. The apical skeletal structures can them be removed, creating a smooth plane for prosthetics.

In another embodiment of the invention, besides the solo application of joint inducing protein to tissue regions, co-administration of joint inducing protein and another osteogenic protein, such as an (ossification center inducing protein) can be used to regenerate competent tissues, in vivo Temporally, it is contemplated that the application of ossification center inducing protein and joint inducing protein, such as BMP-9, (1) can be simultaneous, (2) ossification center inducing protein can be applied and subsequently joint inducing protein then applied, or (3) joint inducing protein can be applied and then ossification center inducing protein. For all of these embodiments, after an effective duration of treatment a joint or joint-like structure is created.

In the case of simultaneous application while the exact mechanism of interaction of the ossification center inducing protein and joint inducing protein co-application is not understood, the response is unlike application of either protein individually. For example, there is not an ectopic, or robust bone forming response as in ossification center inducing protein application, neither is there a joint formed as in solo joint inducing protein application. Rather, simultaneous application of these proteins has the effect of a modified or graded response which depending on the tissue region, may modify or regenerate tissue to the desired effect. Variation of the concentrations of joint inducing protein and ossification center inducing protein during co-application may also regulate the result and may be tuned for the desired response.

When ossification center inducing protein is first applied and then subsequently joint inducing protein is applied, there is an induction of a bone-response which is subsequently tapered with focally applied joint inducing protein. The induced ossification center inducing protein-response, creates a template upon which the antagonistic/recruitment or differentiation properties of joint inducing protein can specifically modify an already existing bone structure. This response can be clinically useful for a number of reasons as detailed below.

When joint inducing protein is first applied and then subsequently ossification center inducing protein is applied, there is a pre-induction of competent cells at the application site, to form cartilaginous tissue. Depending on the application site, the pre-induction of a receptive joint cap and subsequent application of ossification center inducing protein, induces may serve to transdifferentiate the cells to bone, or induce proliferation of cells in the cartilagenous zone to grow in the desired spatial direction.

Besides in vivo applications there are numerous applications for competent cells in vitro. Here, in another embodiment of the invention, application of joint inducing protein or co-application of ossification center inducing protein and joint inducing protein in vivo, modification of competent cells can be used to make tissue structures (for example in a bioreactor), modify the differentiation capabilities of in vitro cells for later injection, or modify implantable cell-seeded scaffolds for enhanced integration and functionality.

For example, specific types of receptive cells can be treated with joint inducing protein in culture. These types of cells may include; fibroblasts isolated from the the regenerating terminal phalanx or second phalanx donor, osteocytes, chondrocytes or their and/or their precursors Example 8

In order to determine if fibroblasts cell lines isolated from regnerating (P3 cells) and non-regnerating (P2 cells) digit regions are differentially effected by BMP-9 application, we applied BMP-9 to P3 and P2 cell cultures. To establish P2 and P3 connective tissue fibroblast lines, cells were isolated from adult female mice 7-8 weeks old. All digits from both hindlimb and forelimbs were collected in dissection media (DMEM high glucose, 2 mM glutamine, 0.5 mg/ml gentamycin, 2% FBS; Gibco) and manually dissected. Skeletal elements were isolated away from skin, fat pad and nail, and P2 and P3 phalangeal elements were isolated by separating the joints with a sharp needle. P2 and P3 phalangeal elements were sorted and treated separately. Histological analyses of P2 and P3 elements showed connective tissue associated with the skeletal elements. P2 or P3 elements were transferred into dissection medium supplemented with 1 Wunsch unit/ml liberase blendzyme I (Roche applied science, catalogue#11988409001) and incubated overnight at 37° C. in a tissue culture incubator (5% $CO_2$). Skeletal elements were removed, cells were pelleted, re-suspended in mesenchymal stem cell medium and plated on fibronectin coated dishes. During expansion the media was changed every 3-4 days. Histological analyses of the skeletal elements demonstrated the successful removal of all adherent connective tissue. In order to perform alcian blue staining, 1.

Deparaffinize and hydrate slide to water. 2. Rinse in 3% acetic acid, 3 min. 3. Stain in Alcian blue, 30 min. 4. Wash in running water, 10 min. 5. Counter staining. 6. Dehydrate, clear, and mount.

Figure 13:
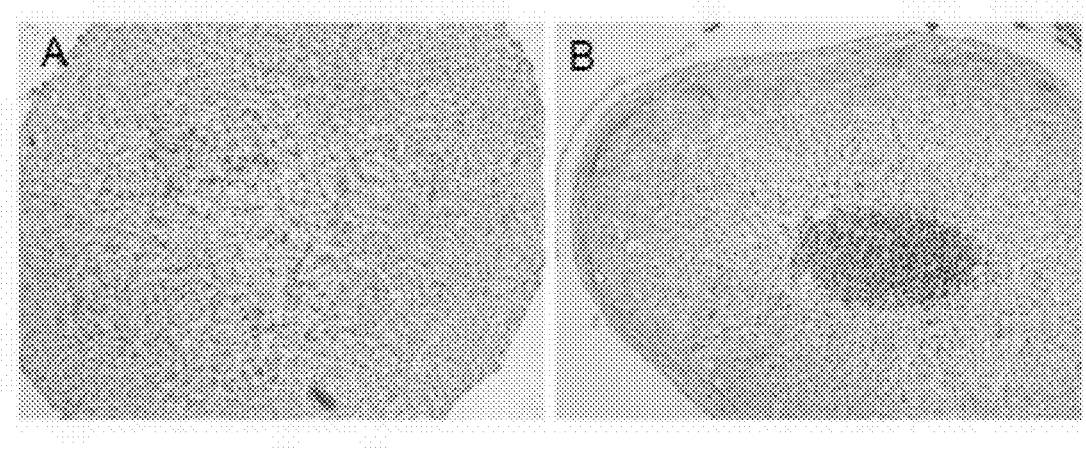
FIG. 13. A series of color photographs of cultured cells stained for alcian blue a chondrogenic marker. A shows mesenchymal stem cells after treatment with BMP-9 and lack of alcian blue staining. B shows cultured fibroblasts derived from the phalanx of the mouse and the accumualtion of alcian blue indicating chondrogenic differentitation.
Figure 14:
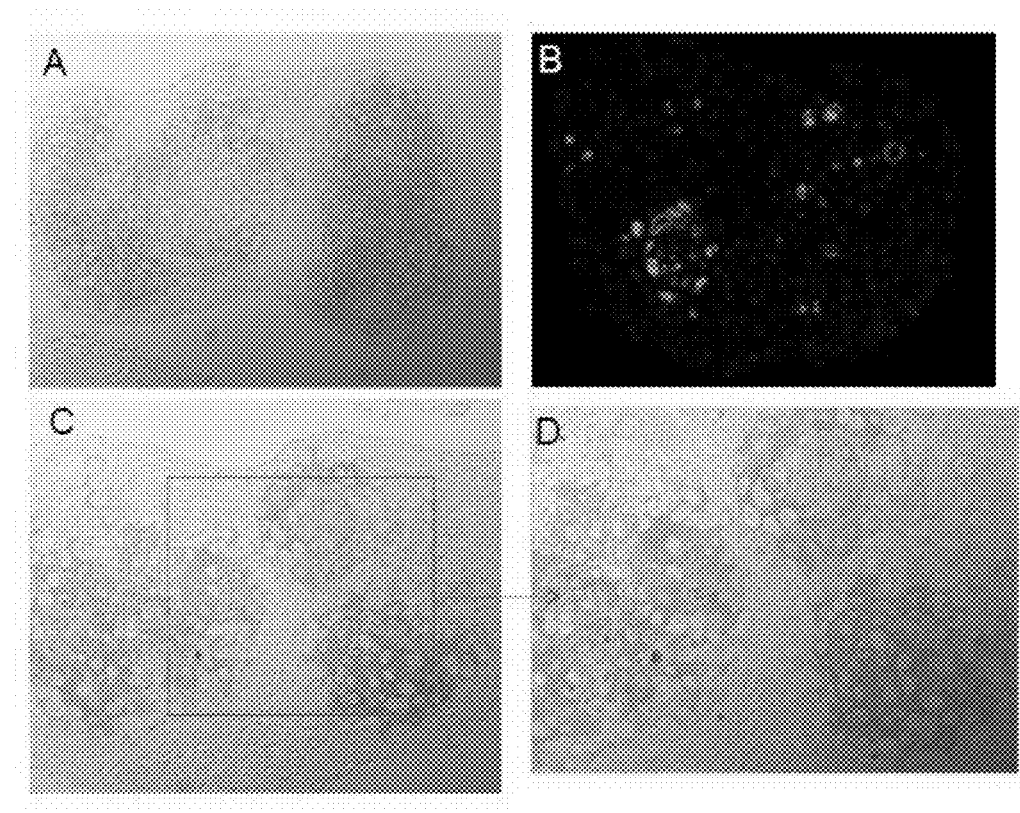
FIG. 14. A series of color photographs examining the organization of cultured cells after BMP-9 staining. A shows a bipolar accumulation of cellular mass with a cavitation in between, suggestive of in vitro joint formation. B shows immunocytochemical expression of doublecortin within these masses, suggestive of articular cartilage formation. C shows another example of the resultant cavitation from BMP-9 treatment (the box marks the inset, for magnified images D indicated by the arrow).
Figure 15:
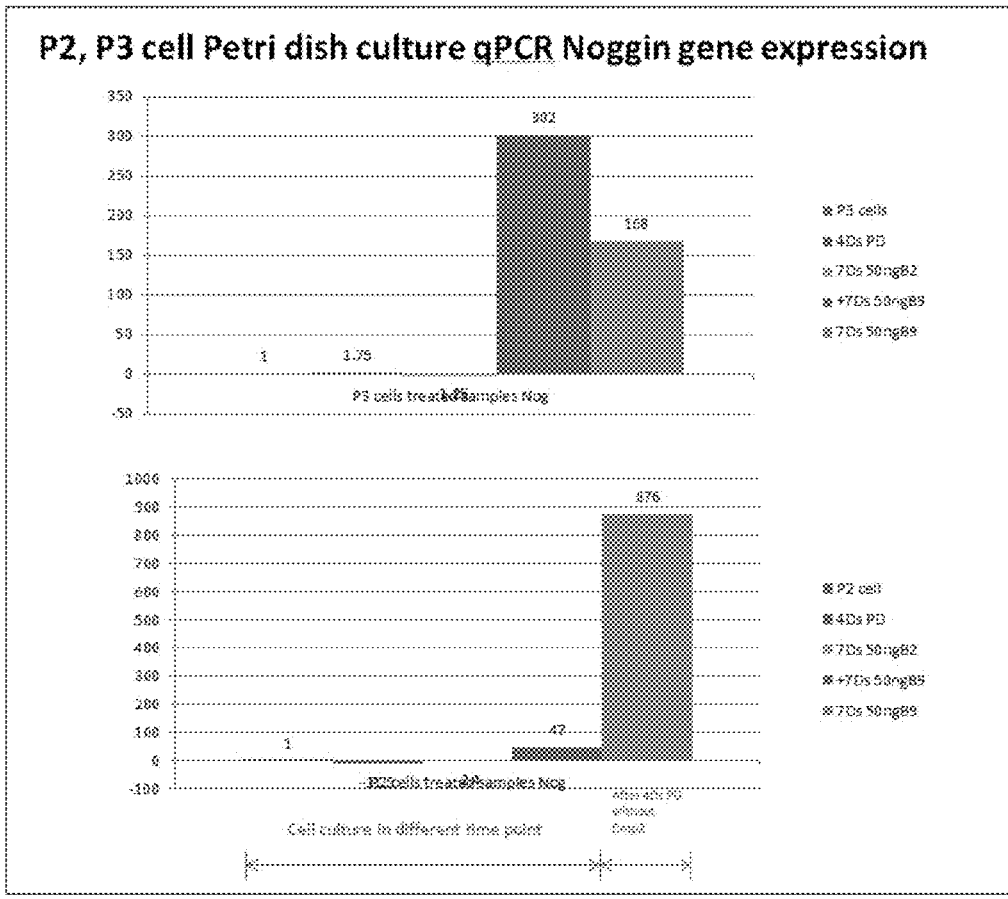
FIG. 15. A series of color photographs that shows Noggin qPCR expression in P2 and P3 Cells after 7 days treatment of BMP-9
Figure 16:
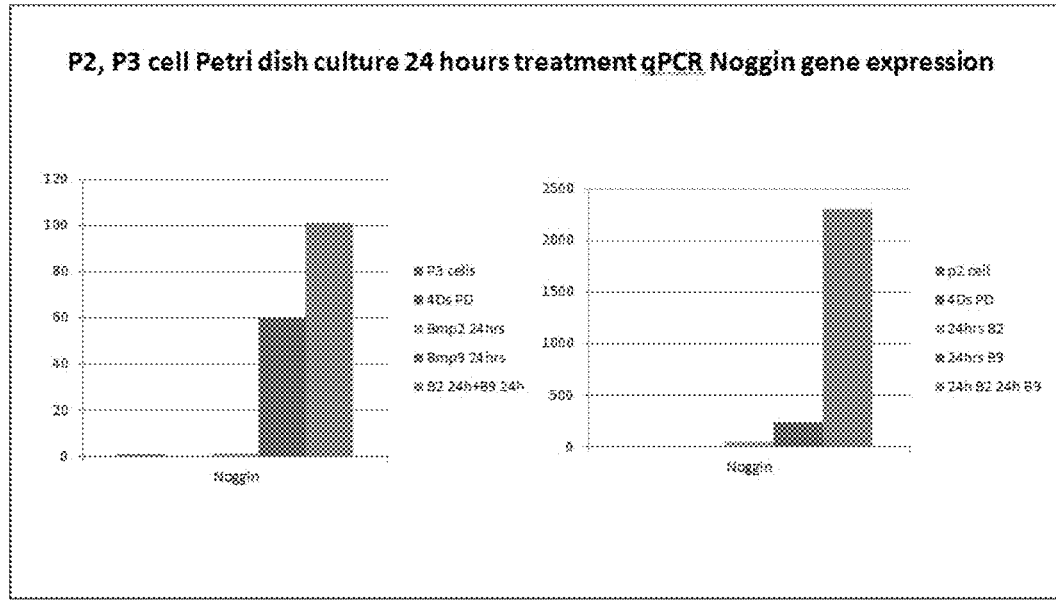
FIG. 16. A series of color photographs that shows Noggin qPCR expression in P2 and P3 Cells after 24 hours treatment of BMP-9
Figure 17:
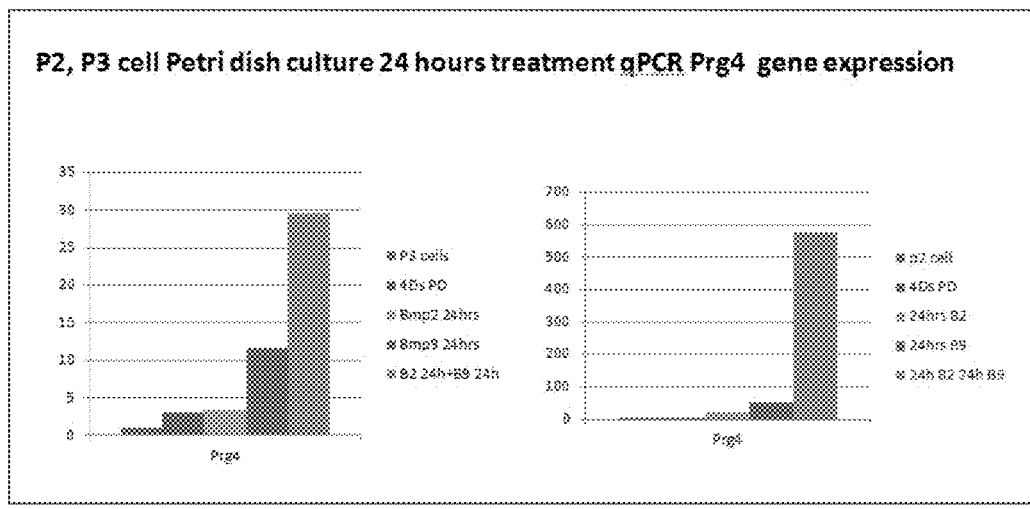
FIG. 17. A series of color photographs that shows Prg4 qPCR expression in P2 and P3 Cells after 24 hours treatment of BMP-9
Figure 18:
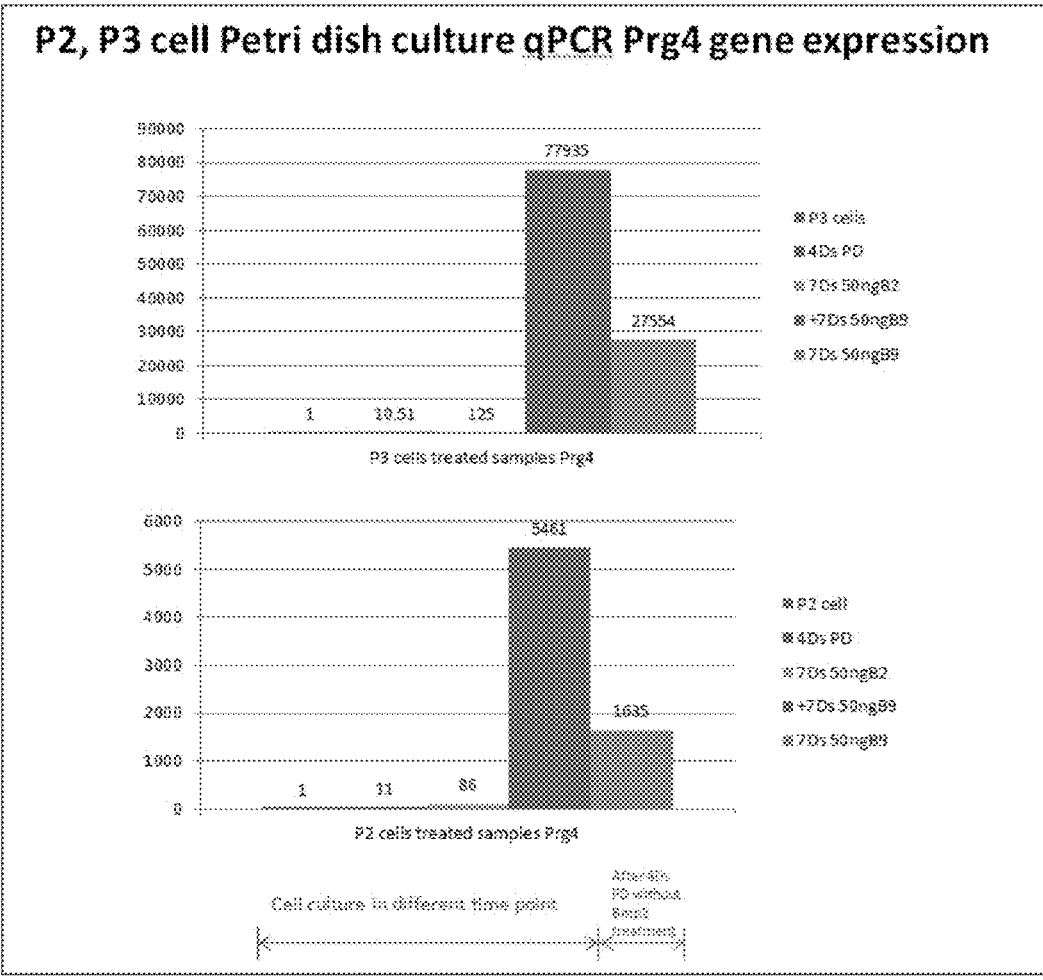
FIG. 18. A series of color photographs that shows Prg4 qPCR expression in P2 and P3 Cells after 7 days treatment of BMP-9
Figure 19:
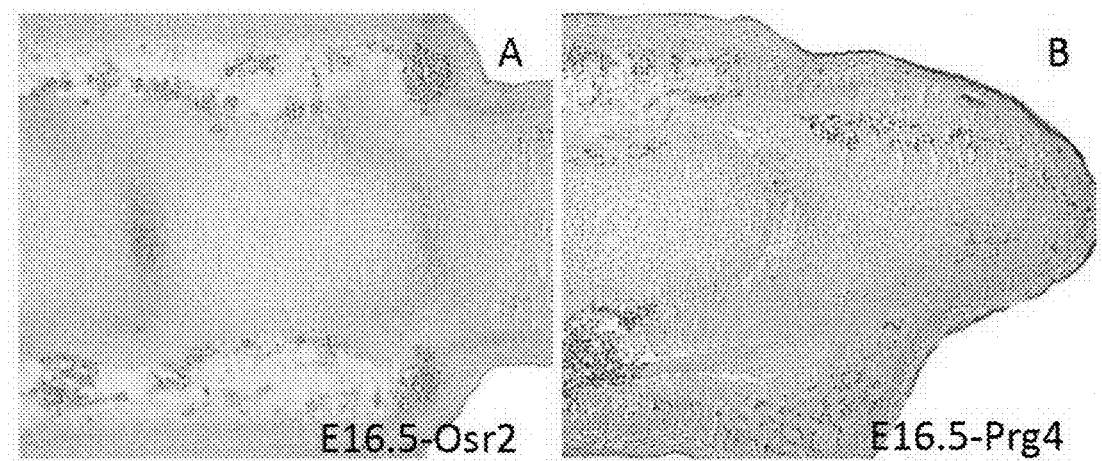
FIG. 19. A series of color photographs showing that A Osr2 and B Prg4 are expressed in the interzone region of the digit joint at E16.5
Figure 20:
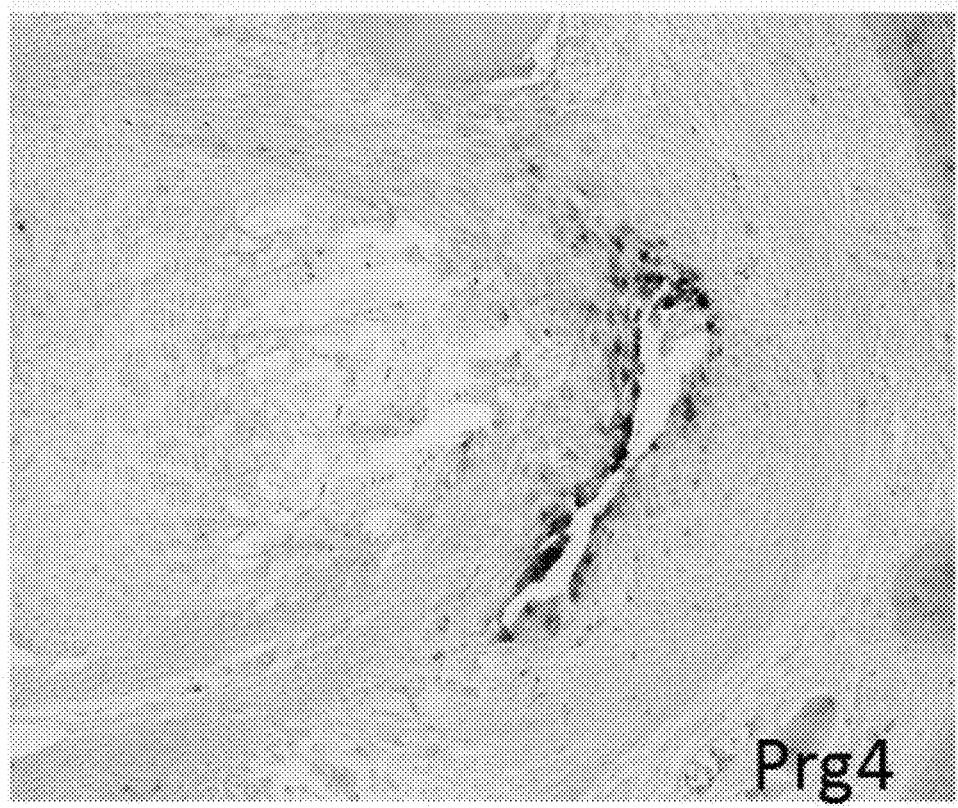
FIG. 20. A color photograph that shows the expression of joint-specific marker gene, Prg4, being induced within the cells lining the forming cavity structure (arrows) 3 days after BMP9 treatment.
Figure 21:
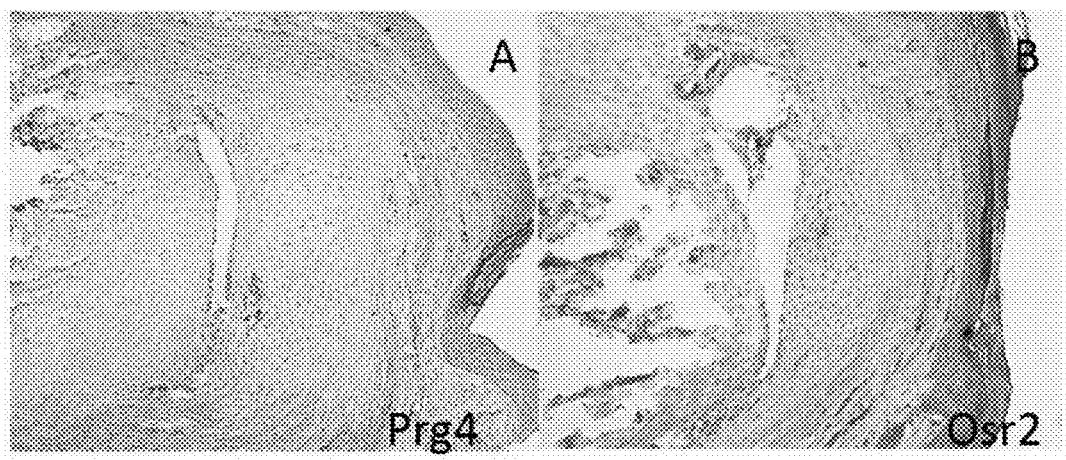
FIG. 21. A series of color photographs that shows that after consecutive treatments of BMP2 and BMP9, the expression of joint-specific marker gene, Prg4 (A) and Osr2(B) were also induced within the cells lining the forming cavity structure after 4 days BMP9 treatment (PN14).
Figure 22:
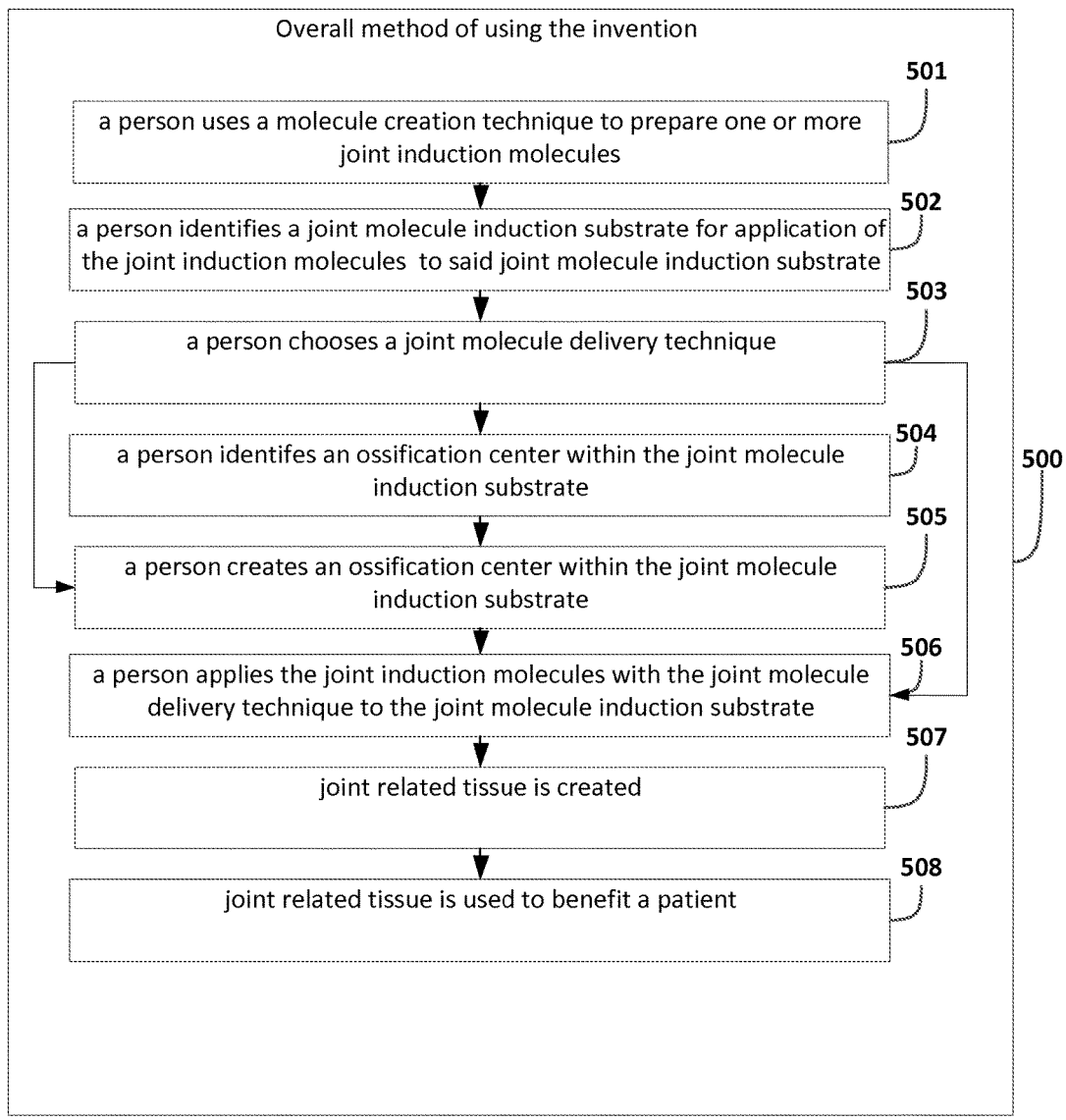
FIG. 22. A series of diagrammed steps showing the overall use of the invention
Figure 24:
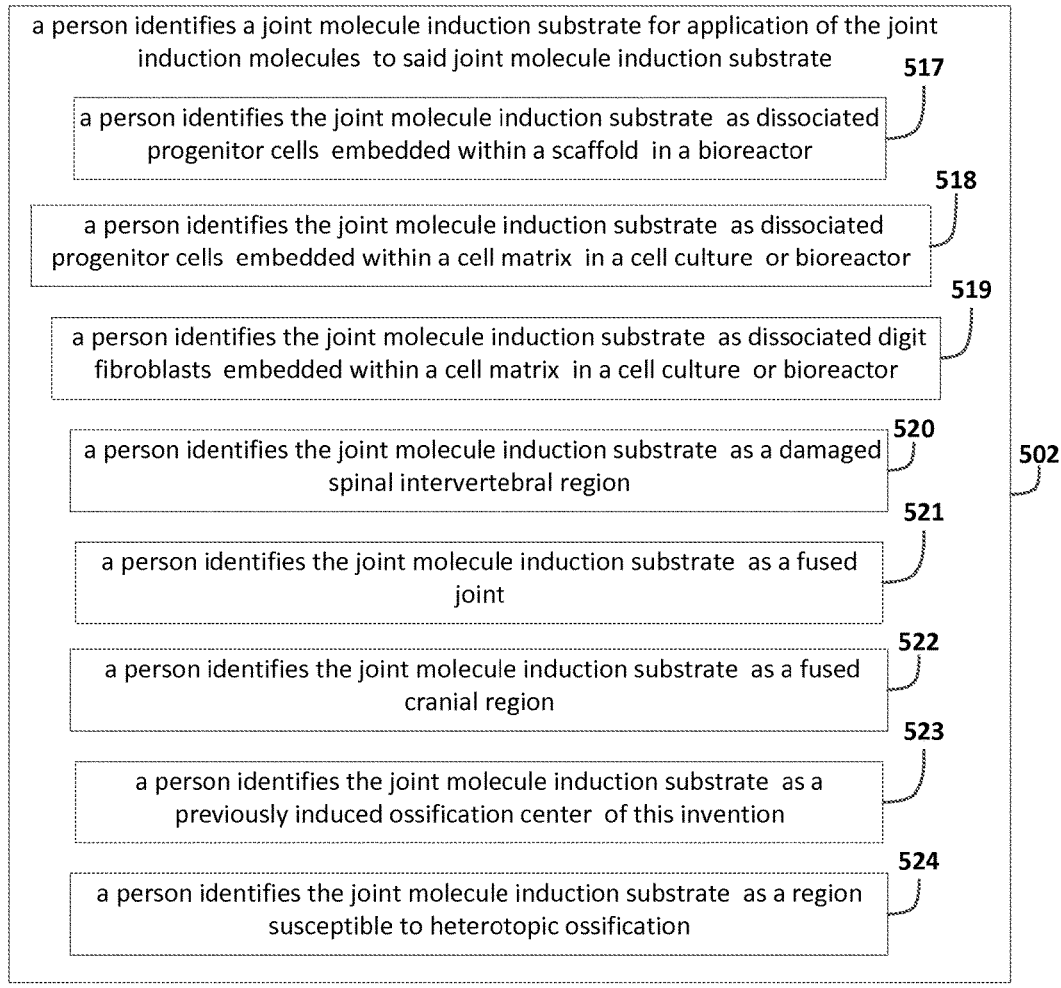
Figure 25:
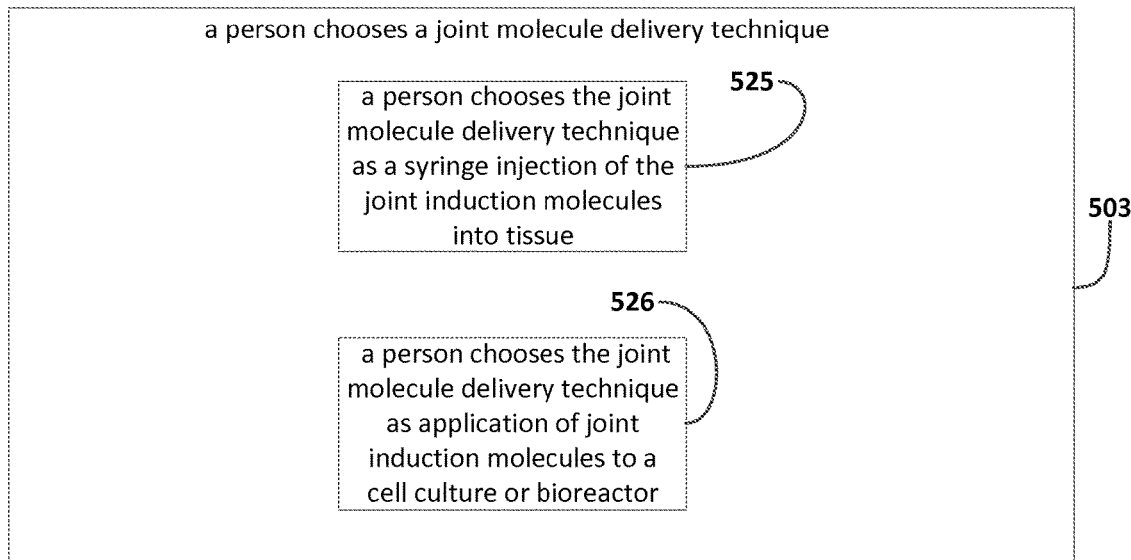
Figure 26:
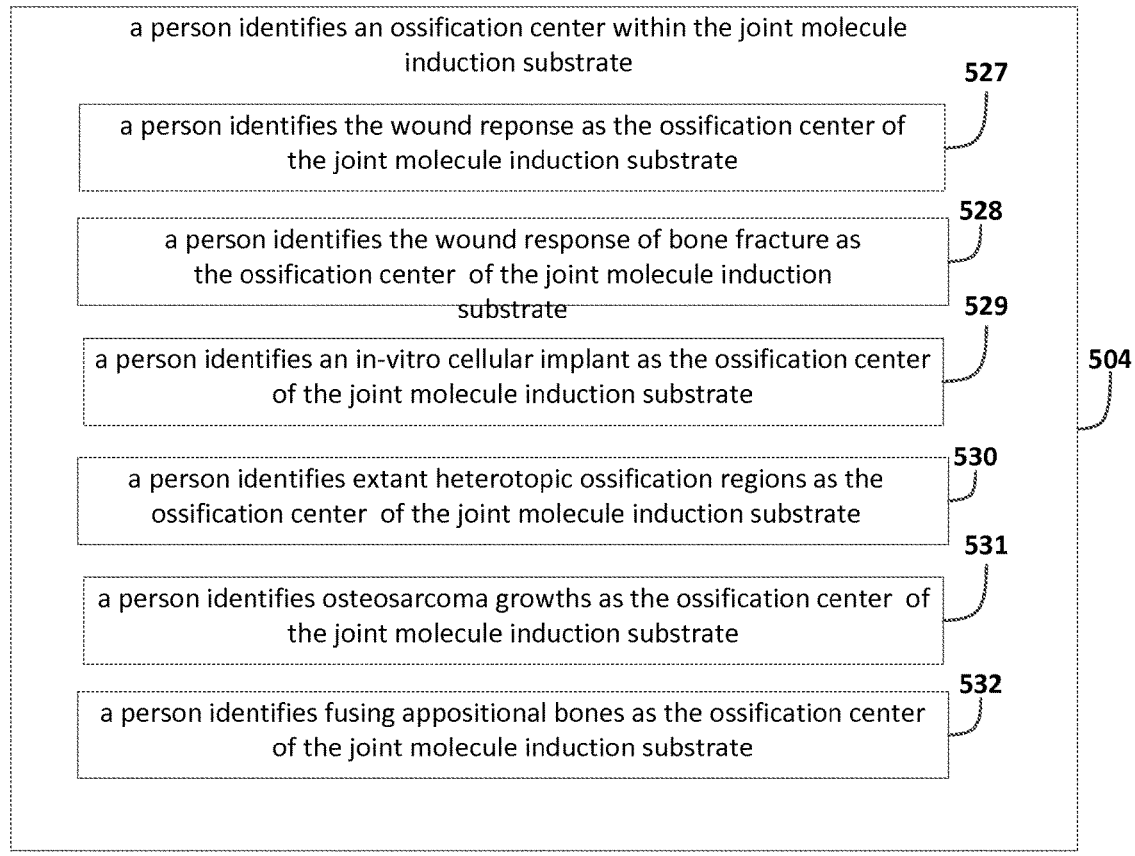
Figure 27:
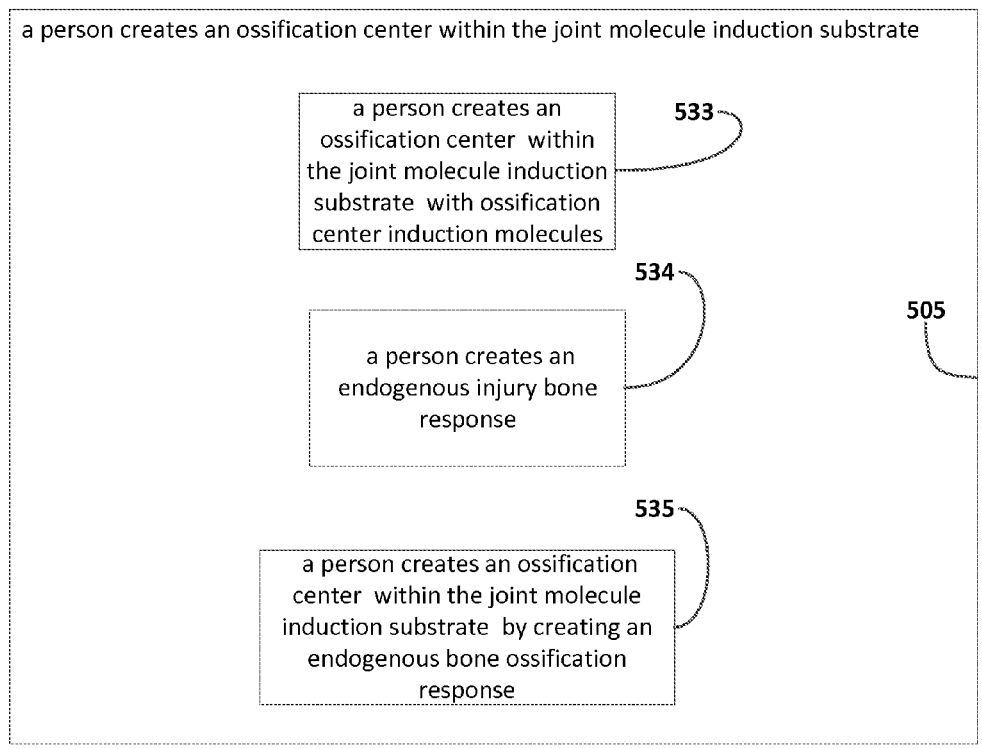
Figure 28:
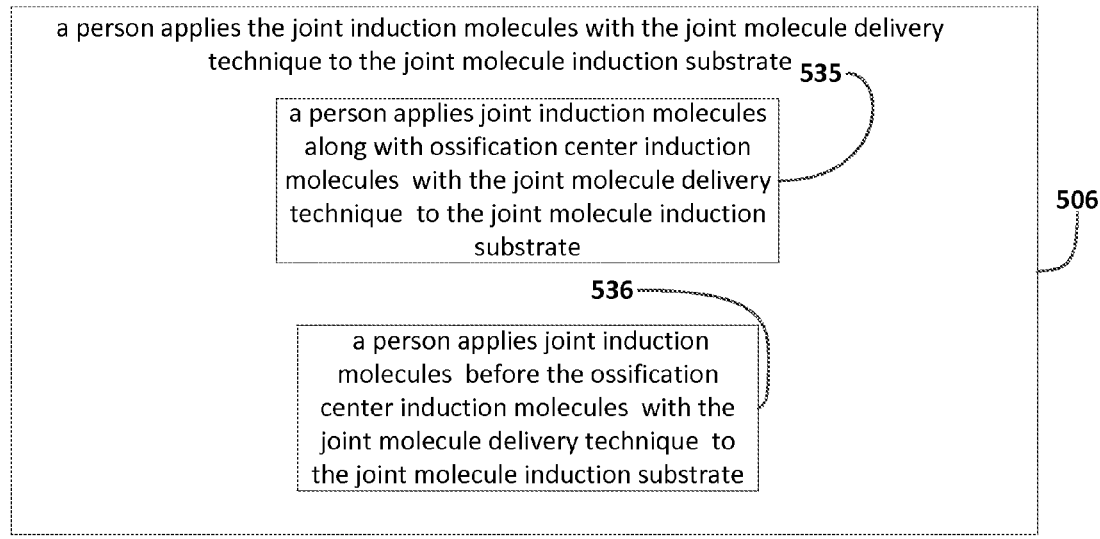
Figure 29:
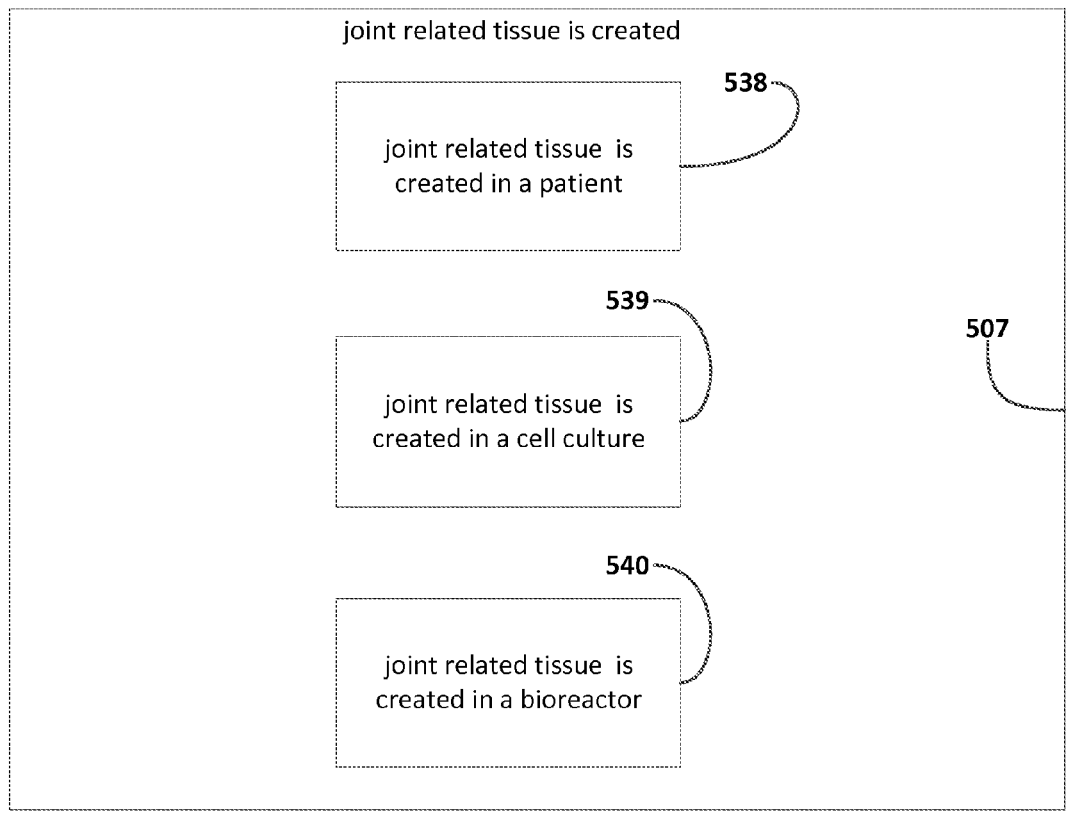
Figure 30:
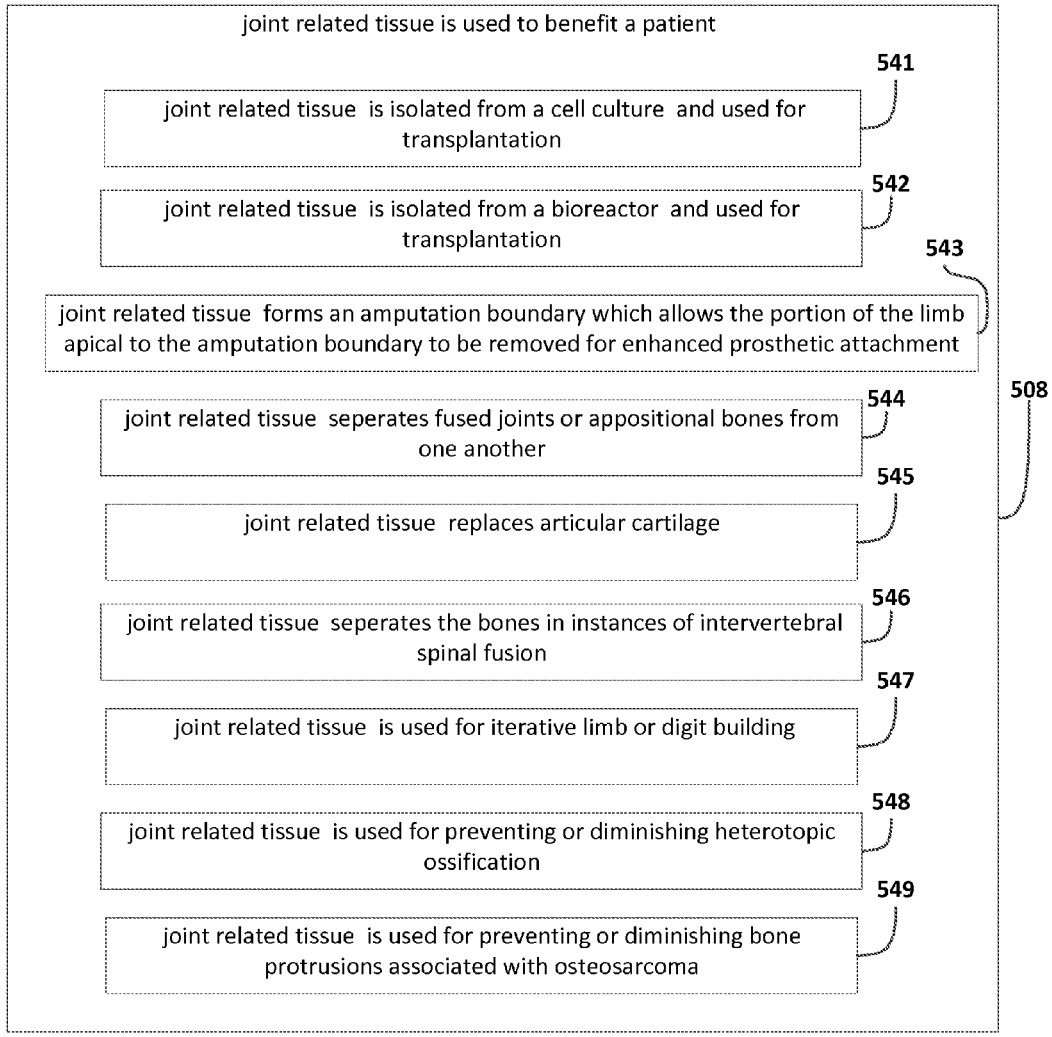
Figure 31:
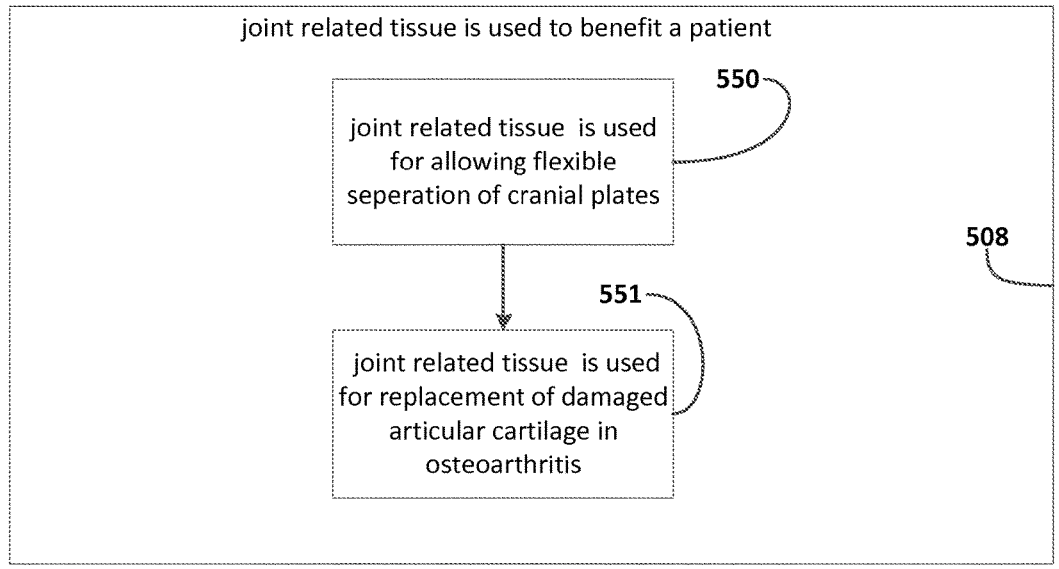

Results: In P2 and P3 cells there was a dose dependent accumulation of cell aggregations that stained positive for chonrocyte marker alcine blue, suggesting that P3 cells were differentiating into chondorytes, and aggregating into culture masses (FIG. 13B). P2 and P3 cells were not treated with BMP-9 did not exhibit aggregation or alcian blue reactivity. Further, mesenchymal stem cells treated with BMP-9 did not display alcian blue staining (FIG. 13A). Examining sections of P3 culture masses show similar separation of chondrocytes into alcian positive-masses separated by joint-like shapes (FIG. 14A, C with FIG. 14D as the inset of FIG. 14C), which controls did not display. Further there was expression of of doublecortin an articular cartilage marker (FIG. 14B). When these P3 cell micromasses are placed into the P2 region after amputation, they are capable of forming joint like structures.

Overall this data suggested that P2 and P3 cell lines are capable of being stimulated by BMP-9 to form joint like structures in vitro and in vivo with upregulation of articular cartilage expression and that other progenitor cell types are not. Other cell types known to differentiate or transdifferentiate into cartilage and/or bone may also be considered receptive to joint inducing protein treatment. Additionally, similar to the above concatenative application of joint inducing protein and ossification center inducing protein, (1) either the first application temporal application of joint inducing protein followed by the subsequent application of ossifying center induction protein, can be applied to in vitro cells or (2) a first temporal application of ossification center inducing protein followed by joint inducing protein.

In another embodiment of the invention, application of joint inducing protein can be used for treatment of damaged tissue is by applying joint inducing protein with/or without ossification center inducing protein to cultured adherent cells. These cells are capable of osteogenesis or chondrogenesis form application of joint-inducing protein or ossification inducing protein, such as fibroblasts isolated from (or near) a regeneration capable region. After isolation and culturing of these cells, application of joint-inducing protein and/or ossification-center inducing protein (to the above mentioned types of receptive cells) induces changes the adherent cells, such that the joint inducing protein-treated cells now possess different phenotypic properties and differentiation capabilities. This allows the cells to integrate into the damaged tissue regions with greater compatibility. After treatment, these cells may be dissociated. Injection of these dissociated cultured cells into nominal tissue may be used to may speed healing. Alternatively, these treated (dissociated cells) may be seeded onto an implantable scaffold or matrix. Some example types of scaffolds and/or matrices may include, collagen scaffolds or matrices, polygliacolic acid scaffolds, matrigel, hydrogel, or tissue isolated extracellular matrix. After an effective waiting period, these scaffolds or matrices, seeded with joint inducing protein treated cells dissociated cells, can then be administered to the damaged tissue to repair or regenerate the tissue.

In another embodiment of the invention, rather than having cells be initially plated, they can be first seeded onto a scaffold or within a matrix, and then treated with joint inducing protein with or without ossification center inducing protein. For, example, adherent cells, can be dissociated, and these non-treated dissociated cells can be seeded onto a scaffold and then treated with joint inducing protein with/or without ossification center inducing protein. After an effective waiting time for differentiation, proliferation and/or development, the scaffold can them be administered into the tissue to facilitate functional restoration of the tissue.

In another embodiment of the invention, treatment of joint inducing protein to some cell lines such as (but not limited to) fibroblasts isolated from the mouse digit, may induce not only the differentiation of receptive cells, but the aggregation and formation of microstructures that resemble in vivo tissues. For example, after isolation and culturing, cells can be treated with joint inducing protein with/or without ossification center inducing protein, over time will induce the formation of a microstructure in the well. These in vitro microstructures may be than be used as a source for administration or implantation into the damaged tissue region. These microstructures, may be (1) implanted in part, as a portion of the microstructure implanted in total, as the whole microstructure grown in vitro (3) dissociated into a group of microstructure-derived cells and injected, or (4) decellularilized into a microstructure-derived acellular matrix and implanted as a matrix into the damaged tissue region.

Example 9

In order to determine the down stream genes and proteins that were regulated by BMP-9, 1) tissue was collected in juvenile mice after BMP-9 administration to the amputated limb then 2) microarray was performed and compared to BSA controls for evaluation of changes in gene expression.

Results. The following genes associated with cartilage signaling were significantly upregulated suggesting that they may have been affected or preceipitated the tissue through a morphogenic mechanism. *Mus musculus* chordin-like 2 (Chrdl2), mRNA [NM_133709]; 1.91 fold increase., *Mus musculus* fibroblast growth factor receptor-like 1 (Fgfrl1) 1.97 fold increase, *Mus musculus* syndecan 3 (Sdc3), mRNA [NM_011520] 1.95 fold increase, *Mus musculus* SPARC related modular calcium binding 1 (Smoc1) 2.39 fold increase, *Mus musculus* thrombospondin 1 (Thbs1), mRNA [NM_011580] 1.53 fold increase, *Mus musculus* Wnt inhibitory factor 1 (Wif1), mRNA [NM_011915] 2.04 fold increase, *Mus musculus* snail homolog 1 (*Drosophila*) (Snai1) 2.01 fold increase, mRNA [NM_011427] 2.01 fold increase, *Mus musculus* frizzled-related protein (Frzb), mRNA [NM_011356] 2.59 fold increase, *Mus musculus* dickkopf homolog 4 (*Xenopus laevis*) (Dkk4), mRNA [NM_145592] 2.33 fold increase. It is thought that these proteins may mimic the activity of joint tissue creation, similar to BMP-9. The mouse protein and gene sequences of these genes are included this application and it is thought that human or other mammalian genes that have phylogenetically similar sequences may similarly be applicable for purposes of this invention.

Results. The following structural genes associated with cartilage in the joint region were also significantly upregulated: *Mus musculus* aggrecan (Acan), mRNA [NM_007424] (2.41) fold increase,
*Mus musculus* CD40 antigen (Cd40) (3.27) fold increase, *Mus musculus* fibromodulin (Fmod), mRNA [NM_021355] (2.36) fold increase, *Mus musculus* osteomodulin (Omd), mRNA [NM_012050] (3.19) fold increase, *Mus musculus* proteoglycan 4 (articular superficial zone protein) (2.58) fold increase, *Mus musculus* sushi-repeat-containing protein, X-linked 2 (Srpx2) (1.55) fold increase, *Mus musculus* upper zone of growth plate and cartilage matrix associated (Ucma) (35.64) fold increase, *Mus musculus* cartilage acidic protein 1 (Crtac1), mRNA [NM_145123] (2.62) fold increase, *Mus musculus* cartilage oligomeric matrix protein (Comp), mRNA [NM_016685] (2.46) fold increase, *Mus musculus* chondroadherin (Chad), mRNA [NM_007689] (2.16) fold increase, *Mus musculus* matrilin 3 (Matn3), mRNA [NM_010770] (5.48) fold increase, *Mus musculus* collagen, type IX, alpha 1 (Col9a1), mRNA [NM_007740] (3.64) fold increase, *Mus musculus* collagen, type IX, alpha 2 (Col9a2), mRNA [NM_007741] (3.93) fold increase, *Mus musculus* collagen, type XI, alpha 2 (Col11a2), mRNA [NM_009926] (2.67) fold increase, *Mus musculus* collagen, type IX, alpha 3 (Col9a3), mRNA [NM_009936] (4.38) fold increase, *Mus musculus* scrapie responsive gene 1 (Serg1), mRNA [NM_009136] (2.37) fold increase, *Mus musculus* hyaluronan and proteoglycan link protein 1 (Hapln1), mRNA [NM_013500] (2.64) fold increase. It is thought that joint induction molecules that upregulate these genes may be effective for using the invention. The mouse protein and gene sequences of these genes are included this application and it is thought that human or other mammalian genes that have phylogenetically similar sequences may similarly be applicable for purposes of this invention.

In general, this invention has several steps for using it which are as follows: First, a person uses a molecule creation technique 1 to prepares one or more joint induction molecules 3 (herein termed the Method (1)-Step(1) 501). Then, a person identifies a joint molecule induction substrate 10 for application of the joint induction molecules 3 to said joint molecule induction substrate 10, (herein termed the Method (1)-Step(2) 502). Then, a person chooses a joint molecule delivery technique 2, (herein termed the Method (1)-Step(3) 503). Then, a person identifes an ossification center 15 within the joint molecule induction substrate 10, (herein termed the Method (1)-Step(4) 504). Then, a person creates an ossification center 15 within the joint molecule induction substrate 10, (herein termed the Method (1)-Step (5) 505). Then, a person applies the joint induction molecules 3 with the joint molecule delivery technique 2 to the joint molecule induction substrate 10, (herein termed the Method (1)-Step(6) 506). Next, joint related tissue 7 is created, (herein termed the Method (1)-Step(7) 507). Finally, joint related tissue 7 is used to benefit a patient, (herein termed the Method (1)-Step(8) 508). The aforementioned method is herein termed Method (1) 500.

In some versions of the invention, functionally, Step 502 could be any of the following: the step of 1) a person identifies the joint molecule induction substrate 10 as the apical end of an amputated limb herein termed the method (1)-step(9) 509, the step of 2) a person identifies the joint molecule induction substrate 10 as damaged articular cartilage herein termed the method (1)-step(10) 510, the step of 3) a person identifies the joint molecule induction substrate 10 as ligament tissue herein termed the method (1)-step(11) 511, the step of 4) a person identifies the joint molecule induction substrate 10 as tendon tissue herein termed the method (1)-step(12) 512, the step of 5) a person identifies the joint molecule induction substrate 10 as a limb to be amputated herein termed the method (1)-step(13) 513, the step of 6) a person identifies the joint molecule induction substrate 10 as dissociated progenitor cells 13 in a cell culture 8 herein termed the method (1)-step(14) 514, the step of 7) a person identifies the joint molecule induction substrate 10 as dissociated digit fibroblasts 14 in a cell culture 8 herein termed the method (1)-step(15) 515, the step of 8) a person identifies the joint molecule induction substrate 10 as dissociated digit fibroblasts 14 seeded on a scaffold 9 in a bioreactor 11 herein termed the method (1)-step(16) 516, the step of 9) a person identifies the joint molecule induction substrate 10 as dissociated progenitor cells 13 embedded within a scaffold 9 in a bioreactor 11 herein termed the method (1)-step(17) 517, the step of 10) a person identifies the joint molecule induction substrate 10 as dissociated progenitor cells 13 embedded within a cell matrix 12 in a cell culture 8 or bioreactor 11 herein termed the method (1)-step(18) 518, the step of 11) a person identifies the joint molecule induction substrate 10 as dissociated digit fibroblasts 14 embedded within a cell matrix 12 in a cell culture 8 or bioreactor 11 herein termed the method (1)-step(19) 519, the step of 12) a person identifies the joint molecule induction substrate 10 as a damaged spinal intervertebral region herein termed the method (1)-step(20) 520, the step of 13) a person identifies the joint molecule induction substrate 10 as a fused joint herein termed the method (1)-step(21) 521, the step of 14) a person identifies the joint molecule induction substrate 10 as a fused cranial region herein termed the method (1)-step(22) 522, the step of 15) a person identifies the joint molecule induction substrate 10 as a previously induced ossification center 15 of this invention (for iterative segmentation and limb or digit building) herein termed the method (1)-step(23) 523, or finally the step of 16) a person identifies the joint molecule induction substrate 10 as a region susceptible to heterotopic ossification herein termed the method (1)-step(24) 524.

In some embodiments, it is reasonable to contemplate that Step 503 may be 1) a person chooses the joint molecule delivery technique 2 as a syringe injection of the joint induction molecules 3 into tissue, herein termed as method (1)-step(25) 525 or perhaps 2) a person chooses the joint molecule delivery technique 2 as application of joint induction molecules 3 to a cell culture 8 or bioreactor 11, herein termed as method (1)-step(26) 526. See definitions below for additional joint molecule delivery techniques 2.

In some iterations of the invention, one may reason that if Step 504 is not required than the person may skip directly to Step 505 or Step 506. Instead of Step 504 some embodiments may use any of the following steps: the step of 1) a person identifies the wound reponse of an as the ossification center 15 of the joint molecule induction substrate 10 herein termed the method (1)-step(27) 527, the step of 2) a person identifies the wound reponse of bone fracture as the ossification center 15 of the joint molecule induction substrate 10 herein termed the method (1)-step(28) 528, the step of 3) a person identifies an in-vitro cellular implant the ossification center 15 of the joint molecule induction substrate 10 herein termed the method (1)-step(29) 529, the step of 4) a person identifies extant heterotopic ossification regions as the ossification center 15 of the joint molecule induction substrate 10 herein termed the method (1)-step(30) 530, the step of 5) a person identifies osteosarcoma growths as the ossification center 15 of the joint molecule induction substrate 10 herein termed the method (1)-step(31) 531, or finally the step of 6) a person identifies fusing appositional bones as the ossification center 15 of the joint molecule induction substrate 10 herein termed the method (1)-step(32) 532.

If Step 505 is not included, it is reasonable to contemplate that the person may skip directly to Step 506. In some versions of the invention, functionally, Step 505 could be replaced by any of the following: the step of 1) a person creates an ossification center 15 within the joint molecule induction substrate 10 with ossification center induction molecules 16 herein termed the method (1)-step(33) 533, the step of 2) a person creates an endogenous injury bone response herein termed the method (1)-step(34) 534, or finally the step of 3) a person creates an ossification center 15 within the joint molecule induction substrate 10 by creating an endogenous bone ossification response (such as in wounding) herein termed the method (1)-step(35) 535.

In some embodiments, it is reasonable to contemplate that Step 506 may be replaced by 1) a person applies joint induction molecules 3 along with ossification center induction molecules 16 with the joint molecule delivery technique 2 to the joint molecule induction substrate 10, herein termed as method (1)-step(36) 536 or perhaps a person applies joint induction molecules 3 before the ossification center induction molecules 16 with the joint molecule delivery technique 2 to the joint molecule induction substrate 10, herein termed as method (1)-step(37) 537.

Instead of Step 507 some embodiments may use any of the following steps: the step of 1) joint related tissue 7 is created in a patient herein termed the method (1)-step(9) 509, or the step of 2) joint related tissue 7 is created in a cell culture 8 herein termed the method (1)-step(38) 538, the step of 3) joint related tissue 7 is created in a bioreactor 11 herein termed the method (1)-step(39) 539, or finally the step of 4) joint related tissue 7 is created in an animal herein termed the method (1)-step(40) 540.

In some versions of the invention, functionally, Step 508 could be replaced by any of the following: the step of 1) joint related tissue 7 is isolated from a cell culture 8 and used for transplantation herein termed the method (1)-step(41) 541, the step of 2) joint related tissue 7 is isolated from a bioreactor 11 and used for transplantation herein termed the method (1)-step(42) 542, the step of 3) joint related tissue 7 forms an amputation boundary which allows the portion of the limb apical to the amputation boundary to be removed for enhanced prosthetic attachment herein termed the method (1)-step(43) 543, the step of 4) joint related tissue 7 separates fused joints or appositional bones from one another herein termed the method (1)-step(44) 544, the step of 5) joint related tissue 7 replaces articular cartilage herein termed the method (1)-step(45) 545, the step of 6) joint related tissue 7 separates the bones in instances of intervertebral spinal fusion herein termed the method (1)-step(46) 546, the step of 7) joint related tissue 7 is used for iterative limb or digit building herein termed the method (1)-step(47) 547, the step of 8) joint related tissue 7 is used for preventing or diminishing heterotopic ossification herein termed the method (1)-step(48) 548, the step of 9) joint related tissue 7 is used for preventing or diminishing bone protrusions associated with osteosarcoma herein termed the method (1)-step(49) 549, the step of 10) joint related tissue 7 is used for allowing flexible separation of cranial plates herein termed the method (1)-step(50) 550 or finally the step of 11) joint related tissue 7 is used for replacement of damaged articular cartilage in osteoarthritis herein termed the method (1)-step(51) 551.

The invention comprises numerous terms that are necessary to define the scope of for purposes of interpretation. The definition of these terms below allows numerous embodiments of the invention that may arise, rather than just the preferred embodiment as described above. In some embodiments, not just the preferred, the term molecule creation technique 1 may include any combination of technical means to create joint induction molecules 3 or ossification center induction molecules 16. Some embodiments may use recombinant DNtechnology for protein production 17, isolation of native proteins capable of joint related tissue induction 18, biosynthetic protein construction 19, chimeric protein construction 20, or small molecule production 21 as the molecule creation technique 1. In some embodiments, not just the preferred, the term joint molecule delivery technique 2 may include approaches, formulations, technologies, and systems for transporting joint induction molecules 3 or ossification center induction molecules 16 so that they can achieve their therapeutic effect. Alternatively, in other embodiments of the invention, the joint molecule delivery technique 2 may be a topical technique 22, injection 23, a nanoneedle 24, biodegradable particles 25, artificial DNA nanostructures 26, polystyrene microparticles 27, agarose 28, collagen 29, or sol-gel 30

In some embodiments, not just the preferred, the term joint induction molecules 3 may include molecules that enhance joint related tissue 7 creation, which may be molecules derived from joint induction gene 4, joint induction disinhibition gene 6 or joint structural gene 5 or allelic or phylogenetic variants thereof (including human or mouse variants); or molecules that mimic that activity of molecules derived from joint induction gene 4, joint induction disinhibition gene 6 or joint structural gene 5. The term joint induction gene 4 is thought to encompass gene that enhances joint related tissue 7 creation which may be joint induction disinhibition gene 6 or result in joint structural gene 5. In some versions of the invention, functionally, the joint induction gene 4 could be either BMP-9—Bone Morphogenetic Protein 9 31, BMP-3—Bone Morphogenetic Protein 3 32, Fgfr1—fibroblast growth factor receptor-like 1 33, Chrdl2—chordin-like 2 34, Sdc3—syndecan 3 35, Smoc1—SPARC related modular calcium binding 1 36, Thbs1—thrombospondin 1 37, Snai1—snail homolog 1 38, Dkk4—dickkopf homolog 4 39, Frzb—frizzled-related protein 40, or Wif1-Wnt inhibitory factor 1 41.

The term joint structural gene 5 is broadly thought to include gene that is an indicator of application of the joint induction molecules 3. When using the invention, one can contemplate that in some embodiments either Acan—aggrecan 42, Cd40 43, Fmod—fibromodulin 44, Omd—osteomodulin 45, Prg4—proteoglycan 4 (articular superficial zone protein) 46, Srpx2—sushi-repeat-containing protein, X-linked 2 47, Ucm—sushi-repeat-containing protein, X-linked 2 48, Crtac1—sushi-repeat-containing protein, X-linked 2 49, Comp—cartilage oligomeric matrix protein 50, Chad—chondroadherin 51, Matn3—matrilin3 52, Col9a1—collagen, type IX, alph1 53, Col9a2—collagen, type IX, alph2 54, Col11a2—collagen, type IX, alpha 55, Col9a3—collagen, type IX, alpha 56, Scrg1—scrapie responsive gene 1 57, or Hapin1-hyaluronan and proteoglycan link protein 1 58 may be the joint structural gene 5.

In some embodiments, not just the preferred, the term joint induction disinhibition gene 6 may include gene that enhances joint related tissue 7 creation by inhibition of repressors of joint induction gene 4. The term joint related tissue 7 is broadly thought to include tissue which may contain or more components that are genetically or mechanically similar to a joint. When using the invention, it is reasonable to contemplate that in some embodiments either the synovial cavity 59, synovial fluid 60, articular capsule 61, synovial membrane 62, articular cartilage 63, articular discs 64, articular fat pads 65, tendons 66, ligaments 67, bursae 68, perichondrium 69, chondrocytes 70, fibrocartilage 71, type 1 collagen 72, type 2 collagen 73, intervertebral disc 74, annulus fibrosis 75, nucleus pulposus 76, peritoneal ligament 77, or hyaline cartilage 78 may be the joint related tissue 7. In some embodiments, not just the preferred, the term cell culture 8 may include any process by which cells are grown under controlled conditions, generally outside of their natural environment. In some versions of the invention, functionally, the cell culture 8 could be either a 2d cell culture 79, 3d cell culture 80, or 3d cell culture by magentic levitation 81

The term scaffold 9 is thought to encompass artificial structure capable of supporting three dimensional tissue formation. In some embodiments, one may reason that the scaffold 9 may be also be extracellular matrix 82, scaffolds made of collagen 83, scaffolds made of fibrin 84, scaffolds made of chitosan 85, scaffolds made of glycosaminoglycans 86, or scaffolds made of hyaluronic acid 87 In some embodiments, not just the preferred, the term joint molecule induction substrate 10 may include tissue wherein the joint induction molecules 3 are applied to. In some embodiments, it is reasonable to contemplate that the joint molecule induction substrate 10 may be also be apical end of recently amputated limb 88, apical end of previously amputated than healed limb 89, damaged articular cartilage in vivo or in vitro 90, ligament tissue in vivo or in vitro 91, tendon tissue in vivo or in vitro 92, limb to be amputated 93, dissociated progenitor cells 94, dissociated digit fibroblasts 95, damaged spinal intervertebral region 96, fused joint 97, fused cranial region 98, previously induced ossification center of this invention (for iterative segmentation and limb or digit building) 99, or heterotopic ossification 100 The term bioreactor 11 is broadly thought to include manufactured or engineered device or system that supports biologically active environment.

The term cell matrix 12 is thought to encompass components of the extracellular part of tissue that provide structural support to cells. In some embodiments, it is reasonable to contemplate that the cell matrix 12 may be also be Proteoglycans 101, Heparan sulfate 102, Chondroitin sulfate 103, Keratan sulfate 104, Non-proteoglycan polysaccharides 105, Hyaluronic acid 106, Collagen 107, Elastin 108, Fibronectin 109, or Laminin 110 The term dissociated progenitor cells 13 is broadly thought to include undifferentiated or non-terminally differentiated biological cells, that can differentiate into specialized cells and can divide (through mitosis) to produce stem cells. Some embodiments may use totipotent stem cells 111, pluripotent stem cells 112, multipotent stem cells 113, induced pluripotent stem cells 114, fibroblast induced pluripotent stem cells 115, human urine isolated induced pluripotent stem cells 116, pericytes 117, embryonic stem cells 118, adult stem cells 119, Hematopoietic stem cells 120, Mammary stem cells 121, Intestinal stem cells 122, Mesenchymal stem cells 123, Endothelial stem cells 124, Neural stem cells 125, Olfactory adult stem cells 126, or neural crest stem cells 127 instead of the dissociated progenitor cells 13. The term dissociated digit fibroblasts 14 is thought to encompass fibroblasts derived from mouse or human digits.

The term ossification center induction molecules 16 is thought to encompass molecules that enhance creation of bone or allelic or phylogenetic variants thereof; or molecules that mimic that activity of molecules that enhance creation of bone. Alternatively, in other embodiments of the invention the ossification center induction molecules 16 may be BMP-2 130, BMP-4 131, or BMP-7 132.

The invention claimed is:

1. A method for bone and cartilage tissue formation comprising the steps: administering a first vehicle comprising BMP-2 and/or BMP-7 to an apical end of an amputated limb bone, a fractured limb bone, or a limb bone having traumatic damage, waiting for an effective period of time for bone formation, administering a second vehicle comprising BMP-9 to the site of the bone formation, and waiting for an effective period of time for cartilage tissue formation.

2. The method of claim 1 wherein said first vehicle comprises one or more of the following: a biodegradable-synthetic or a synthetic-inorganic matrix, collagen scaffolds, matrices, polyglycolic acid scaffolds, tissue isolated extracellular matrix, a nanoneedle, biodegradable particles, artificial DNA nanostructures, polystyrene microparticles, agarose, collagen, or sol-gel.

3. The method of claim 1 wherein said second vehicle comprises one or more of the following: a biodegradable-synthetic or a synthetic-inorganic matrix, collagen scaffolds, matrices, polyglycolic acid scaffolds, tissue isolated extracellular matrix, a nanoneedle, biodegradable particles, artificial DNA nanostructures, polystyrene microparticles, agarose, collagen, or sol-gel.

4. The method of claim 1, wherein both of said first vehicle and said second vehicle comprises one or more of the following: a biodegradable-synthetic or a synthetic-inorganic matrix, collagen scaffolds, matrices, polyglycolic acid scaffolds, tissue isolated extracellular matrix, a nanoneedle, biodegradable particles, artificial DNA nanostructures, polystyrene microparticles, agarose, collagen, or sol-gel.

5. The method of claim 1, wherein said cartilage tissue expresses the articular cartilage marker collagen II and/or doublecortin.

6. The method of claim 1, wherein said cartilage tissue is in the form of an endochondral cap.

7. The method of claim 1, wherein said cartilage tissue is in the form of a cavitation structure.

* * * * *

UNITED STATES PATENT AND TRADEMARK OFFICE
CERTIFICATE OF CORRECTION

| | |
|---|---|
| PATENT NO. | : 9,833,481 B2 |
| APPLICATION NO. | : 14/016071 |
| DATED | : December 5, 2017 |
| INVENTOR(S) | : Ken Muneoka, Minqan Yan and Ling Yan |

It is certified that error appears in the above-identified patent and that said Letters Patent is hereby corrected as shown below:

In the Specification

Column 1, Line 38 - Change "morphogenic" to "morphogenetic"
Column 3, Line 45 - Change "of hyaluranon" to "of hyaluronan"
Column 4, Line 45 - Change "it's" to "its"
Column 7, Line 1 - Change "but than" to "but then"
Column 8, Line 24 - The word "creating" should be deleted
Column 8, Line 67 - Change "agaraose-gel" to "agarose-gel"
Column 10, Lines 63-64 - Change "hyulara-non" to "hyaluronan"
Column 11, Line 38 - Change "apotosis" to "apoptosis"
Column 11, Line 42 - Change "inhibition or" to "inhibition of"
Column 12, Line 13 - Change "nouse" to "mouse"
Column 12, Line 31 - Change "accumualtion" to "accumulation"
Column 12, Line 44 - Insert a --.-- after "of BMP-9"
Column 12, Line 47 - Insert a --.-- after "of BMP-9"
Column 12, Line 50 - Insert a --.-- after "of BMP-9"
Column 12, Line 53 - Insert a --.-- after "of BMP-9"
Column 12, Line 56 - Insert a --.-- after "E16.5"
Column 12, Line 67 - Insert a --.-- after "invention"
Column 13, Line 5 - Insert a --.-- after "strate"
Column 13, Line 10 - Insert a --.-- after "strate"
Column 13, Line 13 - Insert a --.-- after "delivery technique"
Column 13, Line 15 - Change "identifes" to "identifies"
Column 13, Line 16 - Insert a --.-- after "molecule induction substrate"
Column 13, Line 20 - Insert a --.-- after "molecule induction substrate"
Column 13, Line 24 - Insert a --.-- after "molecule induction substrate"
Column 13, Line 29 - Insert a --.-- after "benefit a patient"
Column 13, Line 32 - Insert a --.-- after "benefit a patient"
Column 14, Line 24 - Delete the word "for"
Column 14, Line 25 - Change "immunohistocehmical" to "immunohistochemical"

Signed and Sealed this
Tenth Day of July, 2018

Andrei Iancu
*Director of the United States Patent and Trademark Office*

CERTIFICATE OF CORRECTION (continued)
U.S. Pat. No. 9,833,481 B2

Column 14, Line 28 - Change "retireival" to "retrieval"
Column 16, Line 4 - Replace the "." after "engineered" with a ","
Column 17, Line 7 - Change "mase" to "mass"
Column 17, Line 64 - Change "it's" to "its"
Column 20, Line 52 - Change "creates a After an effective" to "creates, after an effective..."
Column 22, Line 24 - Change "cartilagenous" to "cartilaginous"
Column 22, Line 39 - Delete the phrase "or their" and insert --.-- after "precursors"
Column 23, Line 7 - Change "alcine" to "Alcian"
Column 23, Line 8 - Change "chondorytes" to "chondrocytes"
Column 23, Line 17 - Delete the second instance of the word "of"
Column 23, Line 52 - Delete the word "may"
Column 24, Line 15 - Delete the phrase "than be"
Column 24, Line 33 - Change "preceipitated" to "precipitated"
Column 24, Line 35 - Delete the "." after "increase"
Column 25, Line 32 - Change "identifes" to "identifies"
Column 26, Line 40 - Change "reponse" to "response"
Column 26, Line 43 - Change "reponse" to "response"
Column 27, Line 62 - Change "DNtechnology" to "DNA technology"
Column 28, Line 9 - Insert --.-- after "...or sol-gel 30"
Column 29, Line 10 - Insert --.-- after "acid 87"
Column 179, <213> ORGANISM: - Change "Huiman" to "Human"

SEQUENCE LISTING

```
<160> NUMBER OF SEQ ID NOS: 61

<210> SEQ ID NO 1
<211> LENGTH: 429
<212> TYPE: PRT
<213> ORGANISM: Homo Sapiens

<400> SEQUENCE: 1

Met Cys Pro Gly Ala Leu Trp Val Ala Leu Pro Leu Leu Ser Leu Leu
1               5                   10                  15

Ala Gly Ser Leu Gln Gly Lys Pro Leu Gln Ser Trp Gly Arg Gly Ser
                20                  25                  30

Ala Gly Gly Asn Ala His Ser Pro Leu Gly Val Pro Gly Gly Gly Leu
            35                  40                  45

Pro Glu His Thr Phe Asn Leu Lys Met Phe Leu Glu Asn Val Lys Val
        50                  55                  60

Asp Phe Leu Arg Ser Leu Asn Leu Ser Gly Val Pro Ser Gln Asp Lys
65                  70                  75                  80

Thr Arg Val Glu Pro Pro Gln Tyr Met Ile Asp Leu Tyr Asn Arg Tyr
                85                  90                  95

Thr Ser Asp Lys Ser Thr Thr Pro Ala Ser Asn Ile Val Arg Ser Phe
                100                 105                 110

Ser Met Glu Asp Ala Ile Ser Ile Thr Ala Thr Glu Asp Phe Pro Phe
            115                 120                 125

Gln Lys His Ile Leu Leu Phe Asn Ile Ser Ile Pro Arg His Glu Gln
        130                 135                 140

Ile Thr Arg Ala Glu Leu Arg Leu Tyr Val Ser Cys Gln Asn His Val
145                 150                 155                 160

Asp Pro Ser His Asp Leu Lys Gly Ser Val Val Ile Tyr Asp Val Leu
                165                 170                 175
```

Asp Gly Thr Asp Ala Trp Asp Ser Ala Thr Glu Thr Lys Thr Phe Leu
            180                 185                 190

Val Ser Gln Asp Ile Gln Asp Glu Gly Trp Glu Thr Leu Glu Val Ser
        195                 200                 205

Ser Ala Val Lys Arg Trp Val Arg Ser Asp Ser Thr Lys Ser Lys Asn
210                 215                 220

Lys Leu Glu Val Thr Val Glu Ser His Arg Lys Gly Cys Asp Thr Leu
225                 230                 235                 240

Asp Ile Ser Val Pro Pro Gly Ser Arg Asn Leu Pro Phe Phe Val Val
                245                 250                 255

Phe Ser Asn Asp His Ser Ser Gly Thr Lys Glu Thr Arg Leu Glu Leu
            260                 265                 270

Arg Glu Met Ile Ser His Glu Gln Glu Ser Val Leu Lys Lys Leu Ser
        275                 280                 285

Lys Asp Gly Ser Thr Glu Ala Gly Glu Ser Ser His Glu Glu Asp Thr
290                 295                 300

Asp Gly His Val Ala Ala Gly Ser Thr Leu Ala Arg Arg Lys Arg Ser
305                 310                 315                 320

Ala Gly Ala Gly Ser His Cys Gln Lys Thr Ser Leu Arg Val Asn Phe
                325                 330                 335

Glu Asp Ile Gly Trp Asp Ser Trp Ile Ile Ala Pro Lys Glu Tyr Glu
            340                 345                 350

Ala Tyr Glu Cys Lys Gly Gly Cys Phe Phe Pro Leu Ala Asp Asp Val
        355                 360                 365

Thr Pro Thr Lys His Ala Ile Val Gln Thr Leu Val His Leu Lys Phe
370                 375                 380

Pro Thr Lys Val Gly Lys Ala Cys Cys Val Pro Thr Lys Leu Ser Pro
385                 390                 395                 400

Ile Ser Val Leu Tyr Lys Asp Asp Met Gly Val Pro Thr Leu Lys Tyr
                405                 410                 415

His Tyr Glu Gly Met Ser Val Ala Glu Cys Gly Cys Arg
            420                 425

<210> SEQ ID NO 2
<211> LENGTH: 472
<212> TYPE: PRT
<213> ORGANISM: Homo Sapiens

<400> SEQUENCE: 2

Met Ala Gly Ala Ser Arg Leu Leu Phe Leu Trp Leu Gly Cys Phe Cys
1               5                   10                  15

Val Ser Leu Ala Gln Gly Glu Arg Pro Lys Pro Pro Phe Pro Glu Leu
            20                  25                  30

Arg Lys Ala Val Pro Gly Asp Arg Thr Ala Gly Gly Gly Pro Asp Ser
        35                  40                  45

Glu Leu Gln Pro Gln Asp Lys Val Ser Glu His Met Leu Arg Leu Tyr
    50                  55                  60

Asp Arg Tyr Ser Thr Val Gln Ala Ala Arg Thr Pro Gly Ser Leu Glu
65                  70                  75                  80

Gly Gly Ser Gln Pro Trp Arg Pro Arg Leu Leu Arg Glu Gly Asn Thr
                85                  90                  95

Val Arg Ser Phe Arg Ala Ala Ala Ala Glu Thr Leu Glu Arg Lys Gly
            100                 105                 110

Leu Tyr Ile Phe Asn Leu Thr Ser Leu Thr Lys Ser Glu Asn Ile Leu

```
                      115                 120                 125
Ser Ala Thr Leu Tyr Phe Cys Ile Gly Glu Leu Gly Asn Ile Ser Leu
130                 135                 140

Ser Cys Pro Val Ser Gly Gly Cys Ser His His Ala Gln Arg Lys His
145                 150                 155                 160

Ile Gln Ile Asp Leu Ser Ala Trp Thr Leu Lys Phe Ser Arg Asn Gln
                165                 170                 175

Ser Gln Leu Leu Gly His Leu Ser Val Asp Met Ala Lys Ser His Arg
            180                 185                 190

Asp Ile Met Ser Trp Leu Ser Lys Asp Ile Thr Gln Leu Leu Arg Lys
        195                 200                 205

Ala Lys Glu Asn Glu Glu Phe Leu Ile Gly Phe Asn Ile Thr Ser Lys
210                 215                 220

Gly Arg Gln Leu Pro Lys Arg Leu Pro Phe Pro Glu Pro Tyr Ile
225                 230                 235                 240

Leu Val Tyr Ala Asn Asp Ala Ala Ile Ser Glu Pro Glu Ser Val Val
                245                 250                 255

Ser Ser Leu Gln Gly His Arg Asn Phe Pro Thr Gly Thr Val Pro Lys
            260                 265                 270

Trp Asp Ser His Ile Arg Ala Ala Leu Ser Ile Glu Arg Lys Lys
        275                 280                 285

Arg Ser Thr Gly Val Leu Leu Pro Leu Gln Asn Asn Glu Leu Pro Gly
290                 295                 300

Ala Glu Tyr Gln Tyr Lys Lys Asp Glu Val Trp Glu Glu Arg Lys Pro
305                 310                 315                 320

Tyr Lys Thr Leu Gln Ala Gln Ala Pro Glu Lys Ser Lys Asn Lys Lys
                325                 330                 335

Lys Gln Arg Lys Gly Pro His Arg Lys Ser Gln Thr Leu Gln Phe Asp
            340                 345                 350

Glu Gln Thr Leu Lys Lys Ala Arg Arg Lys Gln Trp Ile Glu Pro Arg
        355                 360                 365

Asn Cys Ala Arg Arg Tyr Leu Lys Val Asp Phe Ala Asp Ile Gly Trp
370                 375                 380

Ser Glu Trp Ile Ile Ser Pro Lys Ser Phe Asp Ala Tyr Tyr Cys Ser
385                 390                 395                 400

Gly Ala Cys Gln Phe Pro Met Pro Lys Ser Leu Lys Pro Ser Asn His
                405                 410                 415

Ala Thr Ile Gln Ser Ile Val Arg Ala Val Gly Val Val Pro Gly Ile
            420                 425                 430

Pro Glu Pro Cys Cys Val Pro Glu Lys Met Ser Ser Leu Ser Ile Leu
        435                 440                 445

Phe Phe Asp Glu Asn Lys Asn Val Val Leu Lys Val Tyr Pro Asn Met
450                 455                 460

Thr Val Glu Ser Cys Ala Cys Arg
465                 470

<210> SEQ ID NO 3
<211> LENGTH: 396
<212> TYPE: PRT
<213> ORGANISM: Homo Sapiens

<400> SEQUENCE: 3

Met Val Ala Gly Thr Arg Cys Leu Leu Ala Leu Leu Leu Pro Gln Val
1               5                   10                  15
```

Leu Leu Gly Gly Ala Ala Gly Leu Val Pro Glu Leu Gly Arg Lys
          20                  25                  30

Phe Ala Ala Ser Ser Gly Arg Pro Ser Ser Gln Pro Ser Asp Glu
         35                  40                  45

Val Leu Ser Glu Phe Glu Leu Arg Leu Leu Ser Met Phe Gly Leu Lys
 50                  55                  60

Gln Arg Pro Thr Pro Ser Arg Asp Ala Val Val Pro Pro Tyr Met Leu
 65                  70                  75                  80

Asp Leu Tyr Arg Arg His Ser Gly Gln Pro Gly Ser Pro Ala Pro Asp
             85                  90                  95

His Arg Leu Glu Arg Ala Ala Ser Arg Ala Asn Thr Val Arg Ser Phe
            100                 105                 110

His His Glu Glu Ser Leu Glu Glu Leu Pro Glu Thr Ser Gly Lys Thr
            115                 120                 125

Thr Arg Arg Phe Phe Phe Asn Leu Ser Ser Ile Pro Thr Glu Glu Phe
130                 135                 140

Ile Thr Ser Ala Glu Leu Gln Val Phe Arg Glu Gln Met Gln Asp Ala
145                 150                 155                 160

Leu Gly Asn Asn Ser Ser Phe His His Arg Ile Asn Ile Tyr Glu Ile
                165                 170                 175

Ile Lys Pro Ala Thr Ala Asn Ser Lys Phe Pro Val Thr Arg Leu Leu
            180                 185                 190

Asp Thr Arg Leu Val Asn Gln Asn Ala Ser Arg Trp Glu Ser Phe Asp
            195                 200                 205

Val Thr Pro Ala Val Met Arg Trp Thr Ala Gln Gly His Ala Asn His
210                 215                 220

Gly Phe Val Val Glu Val Ala His Leu Glu Glu Lys Gln Gly Val Ser
225                 230                 235                 240

Lys Arg His Val Arg Ile Ser Arg Ser Leu His Gln Asp Glu His Ser
                245                 250                 255

Trp Ser Gln Ile Arg Pro Leu Leu Val Thr Phe Gly His Asp Gly Lys
            260                 265                 270

Gly His Pro Leu His Lys Arg Glu Lys Arg Gln Ala Lys His Lys Gln
            275                 280                 285

Arg Lys Arg Leu Lys Ser Ser Cys Lys Arg His Pro Leu Tyr Val Asp
290                 295                 300

Phe Ser Asp Val Gly Trp Asn Asp Trp Ile Val Ala Pro Pro Gly Tyr
305                 310                 315                 320

His Ala Phe Tyr Cys His Gly Glu Cys Pro Phe Pro Leu Ala Asp His
                325                 330                 335

Leu Asn Ser Thr Asn His Ala Ile Val Gln Thr Leu Val Asn Ser Val
            340                 345                 350

Asn Ser Lys Ile Pro Lys Ala Cys Cys Val Pro Thr Glu Leu Ser Ala
            355                 360                 365

Ile Ser Met Leu Tyr Leu Asp Glu Asn Glu Lys Val Val Leu Lys Asn
370                 375                 380

Tyr Gln Asp Met Val Val Glu Gly Cys Gly Cys Arg
385                 390                 395

<210> SEQ ID NO 4
<211> LENGTH: 408
<212> TYPE: PRT
<213> ORGANISM: Homo Sapiens

<400> SEQUENCE: 4

-continued

```
Met Ile Pro Gly Asn Arg Met Leu Met Val Leu Leu Cys Gln Val
1               5                   10                  15

Leu Leu Gly Gly Ala Ser His Ala Ser Leu Ile Pro Glu Thr Gly Lys
                20                  25                  30

Lys Lys Val Ala Glu Ile Gln Gly His Ala Gly Gly Arg Arg Ser Gly
            35                  40                  45

Gln Ser His Glu Leu Leu Arg Asp Phe Glu Ala Thr Leu Leu Gln Met
    50                  55                  60

Phe Gly Leu Arg Arg Arg Pro Gln Pro Ser Lys Ser Ala Val Ile Pro
65                  70                  75                  80

Asp Tyr Met Arg Asp Leu Tyr Arg Leu Gln Ser Gly Glu Glu Glu Glu
                85                  90                  95

Glu Gln Ile His Ser Thr Gly Leu Glu Tyr Pro Glu Arg Pro Ala Ser
                100                 105                 110

Arg Ala Asn Thr Val Arg Ser Phe His His Glu Glu His Leu Glu Asn
                115                 120                 125

Ile Pro Gly Thr Ser Glu Asn Ser Ala Phe Arg Phe Leu Phe Asn Leu
                130                 135                 140

Ser Ser Ile Pro Glu Asn Glu Val Ile Ser Ser Ala Glu Leu Arg Leu
145                 150                 155                 160

Phe Arg Glu Gln Val Asp Gln Gly Pro Asp Trp Glu Arg Gly Phe His
                165                 170                 175

Arg Ile Asn Ile Tyr Glu Val Met Lys Pro Pro Ala Glu Val Val Pro
                180                 185                 190

Gly His Leu Ile Thr Arg Leu Leu Asp Thr Arg Leu Val His His Asn
                195                 200                 205

Val Thr Arg Trp Glu Thr Phe Asp Val Ser Pro Ala Val Leu Arg Trp
210                 215                 220

Thr Arg Glu Lys Gln Pro Asn Tyr Gly Leu Ala Ile Glu Val Thr His
225                 230                 235                 240

Leu His Gln Thr Arg Thr His Gln Gly Gln His Val Arg Ile Ser Arg
                245                 250                 255

Ser Leu Pro Gln Gly Ser Gly Asn Trp Ala Gln Leu Arg Pro Leu Leu
                260                 265                 270

Val Thr Phe Gly His Asp Gly Arg Gly His Ala Leu Thr Arg Arg Arg
                275                 280                 285

Arg Ala Lys Arg Ser Pro Lys His His Ser Gln Arg Ala Arg Lys Lys
                290                 295                 300

Asn Lys Asn Cys Arg Arg His Ser Leu Tyr Val Asp Phe Ser Asp Val
305                 310                 315                 320

Gly Trp Asn Asp Trp Ile Val Ala Pro Pro Gly Tyr Gln Ala Phe Tyr
                325                 330                 335

Cys His Gly Asp Cys Pro Phe Pro Leu Ala Asp His Leu Asn Ser Thr
                340                 345                 350

Asn His Ala Ile Val Gln Thr Leu Val Asn Ser Val Asn Ser Ser Ile
                355                 360                 365

Pro Lys Ala Cys Cys Val Pro Thr Glu Leu Ser Ala Ile Ser Met Leu
370                 375                 380

Tyr Leu Asp Glu Tyr Asp Lys Val Val Leu Lys Asn Tyr Gln Glu Met
385                 390                 395                 400

Val Val Glu Gly Cys Gly Cys Arg
                405
```

<210> SEQ ID NO 5
<211> LENGTH: 431
<212> TYPE: PRT
<213> ORGANISM: Homo Sapiens

<400> SEQUENCE: 5

```
Met His Val Arg Ser Leu Arg Ala Ala Pro His Ser Phe Val Ala
1               5                   10                  15

Leu Trp Ala Pro Leu Phe Leu Leu Arg Ser Ala Leu Ala Asp Phe Ser
            20                  25                  30

Leu Asp Asn Glu Val His Ser Ser Phe Ile His Arg Arg Leu Arg Ser
        35                  40                  45

Gln Glu Arg Arg Glu Met Gln Arg Glu Ile Leu Ser Ile Leu Gly Leu
    50                  55                  60

Pro His Arg Pro Arg Pro His Leu Gln Gly Lys His Asn Ser Ala Pro
65                  70                  75                  80

Met Phe Met Leu Asp Leu Tyr Asn Ala Met Ala Val Glu Glu Gly Gly
                85                  90                  95

Gly Pro Gly Gly Gln Gly Phe Ser Tyr Pro Tyr Lys Ala Val Phe Ser
            100                 105                 110

Thr Gln Gly Pro Pro Leu Ala Ser Leu Gln Asp Ser His Phe Leu Thr
        115                 120                 125

Asp Ala Asp Met Val Met Ser Phe Val Asn Leu Val Glu His Asp Lys
    130                 135                 140

Glu Phe Phe His Pro Arg Tyr His His Arg Glu Phe Arg Phe Asp Leu
145                 150                 155                 160

Ser Lys Ile Pro Glu Gly Glu Ala Val Thr Ala Ala Glu Phe Arg Ile
                165                 170                 175

Tyr Lys Asp Tyr Ile Arg Glu Arg Phe Asp Asn Glu Thr Phe Arg Ile
            180                 185                 190

Ser Val Tyr Gln Val Leu Gln Glu His Leu Gly Arg Glu Ser Asp Leu
        195                 200                 205

Phe Leu Leu Asp Ser Arg Thr Leu Trp Ala Ser Glu Glu Gly Trp Leu
    210                 215                 220

Val Phe Asp Ile Thr Ala Thr Ser Asn His Trp Val Val Asn Pro Arg
225                 230                 235                 240

His Asn Leu Gly Leu Gln Leu Ser Val Glu Thr Leu Asp Gly Gln Ser
                245                 250                 255

Ile Asn Pro Lys Leu Ala Gly Leu Ile Gly Arg His Gly Pro Gln Asn
            260                 265                 270

Lys Gln Pro Phe Met Val Ala Phe Phe Lys Ala Thr Glu Val His Phe
        275                 280                 285

Arg Ser Ile Arg Ser Thr Gly Ser Lys Gln Arg Ser Gln Asn Arg Ser
    290                 295                 300

Lys Thr Pro Lys Asn Gln Glu Ala Leu Arg Met Ala Asn Val Ala Glu
305                 310                 315                 320

Asn Ser Ser Ser Asp Gln Arg Gln Ala Cys Lys Lys His Glu Leu Tyr
                325                 330                 335

Val Ser Phe Arg Asp Leu Gly Trp Gln Asp Trp Ile Ile Ala Pro Glu
            340                 345                 350

Gly Tyr Ala Ala Tyr Tyr Cys Glu Gly Glu Cys Ala Phe Pro Leu Asn
        355                 360                 365

Ser Tyr Met Asn Ala Thr Asn His Ala Ile Val Gln Thr Leu Val His
    370                 375                 380
```

```
Phe Ile Asn Pro Glu Thr Val Pro Lys Pro Cys Cys Ala Pro Thr Gln
385                 390                 395                 400

Leu Asn Ala Ile Ser Val Leu Tyr Phe Asp Asp Ser Ser Asn Val Ile
            405                 410                 415

Leu Lys Lys Tyr Arg Asn Met Val Val Arg Ala Cys Gly Cys His
        420                 425                 430

<210> SEQ ID NO 6
<211> LENGTH: 4962
<212> TYPE: DNA
<213> ORGANISM: Human

<400> SEQUENCE: 6
tgggaggctc caagagctgc agtgacttgt tccaggtgac atttgcaggg aatcggtgag     60
ggagttgaga tcccagcctg tgtctagttt gactcatcac cgcactaaat tgcacgggag    120
ccatattcac tcgtgatctc taatgctcag cagtgcatcc caccaacaga gcagggaggc    180
ttgctggcag gttccgattc tgcaaggagc aggcctcttc tgagccctga tgtggtcccc    240
acactctccc catctcccca gcccccacgg ttcactgtga tcttgtgctg tcctttctat    300
atttggagga ctacttggtc ttgtttcctg gattcttcac tcctgtggcc caggagatgg    360
agcatatgtc accctgcctg gagattcttc tgaagagccc tggcaaggaa atgagaaagt    420
atcctaatta gggggcaata acccctgga gaagcacaga ttcttacag taggccgtgt    480 ccttcccgca tgccctgtgt gtttgtcaga tgtttataga gccttcatta acggaaggct    540
ccctcagata agacgtcgga gcgcggcatc gaggaccaga taagcacaag tggaggacaa    600
tccagcccgg cagcgggtga gagtgggtgc tggccaggac ggttccttca gagcaaacag    660
cagggagatg ccggcccgct ccttcccagc tcctccccgt gcccgctaac acagcacggc    720
cgcctgcagt ctcctctctg ggtgattgcg cgggcctaag atgtgtcctg ggcactgtg    780 ggtggccctg ccctgctgt ccctgctggc tggctcccta caggggaagc cactgcagag    840
ctggggacga gggtctgctg ggggaaacgc ccacagccca ctggggtgc ctggaggtgg    900 gctgcctgag cacaccttca acctgaagat gtttctggag aacgtgaagg tggatttcct    960
gcgcagcctt aacctgagtg gggtcccttc gcaggacaaa accagggtgg agccgccgca   1020
gtacatgatt gacctgtaca caggtacac gtccgataag tcgactacgc cagcgtccaa   1080
cattgtgcgg agcttcagca tggaaggtag ggtctccgct tgcaccatgc gcgctgggggt   1140 gggactcaca ggtccacagc tgctttcccc agggtggagg ccactggcca taggaggctc   1200
ttcaagcttc catttaaatt agttacaatg aaataaaatt aaaacttatt tctttagcct   1260
caccagcttc ctttcaaatg cgtggctaat ggcttcccta tcaggcagtg cagactgaag   1320
aacatttcca tggttactga gagttctact cagcacttct gttgtgaagg attcaccttc   1380
cccaagctgt gtgccacatt tcacacagca ggtgcacagg gatgccagct ctcttttttc   1440
caccccttct ctttactctc ctcttctttg catcactccc ctctgattca cttctcttcc   1500
tttccccctt cccttcctgt cccttcctca cttcagaaca gaacaggcaa cctatttcac   1560
ctccaactaa ctgggatatt tttaaatttt caaagcacat ctattccttt cttatgaaac   1620
ggttttaaaa atcagataaa attcttggac agagaagtgt tggcagagaa cctaattgtt   1680
tttaaataga aatatatctg atttagaagg actagaagat aacaaacacg gacctaggac   1740
ctatgtccta actcagacaa gctcacatga tgcaggggaa ataagtttct gaagagcaaa   1800
actgttcagt caaagcttgc agccaccaag ggtacccacc catgtcacct aggaagtgtt   1860
```

```
aagcctgcac acctaggaag tgttaaacct gtctgcctgc agagctggct tttcctgctg    1920
ctgctgtctc cctctgaatg tccaggagca cagagcctct cccttcctgg gtctgagact    1980
tgcaaatggc taagggcct ggctccatac cacgcccagg ccagacctaa ctggtctgca    2040
gaggcaggac tggcacttca aaacctgcca gctaggtttc cctatagcac agggtctcca    2100
cacatgtggg tatatagcaa gtgctgaaaa aatgcaacct cttttccctg tctgtgaacc    2160
agccattgta tagcaggagc gtgctaatga caaagtgtca gcccaggata aatgggatat    2220
cgagataact atgtggctaa aagccaagcc ccattttgc ttgacatgac aaagcaattg     2280
aagctaatag attttgttcc tgaaacacta aaaccaatta tccacttttg ctttgtttgg    2340
aaattacaat ttcaaacgat ttatacactg tttagaggct gagattttg atattgtctt     2400 aatattgggg tttcactgtc cccacccagg atctctcctt taaattcata cactcaggat    2460
cttcactcag gatctgacag tgagtttttc tgttttcttt atgtactcaa tagctgtgtg    2520
ctagtaagtc ccagaatact taactagctg tatgcatttt ggcaattaac tgccttgaat    2580
cccagtctcc acatctgcaa atgtggaata ataattagat cctcccaggg taagtgagag    2640
gattaaggtg aaatgtattc tgcaaagctc ccagtgtaat gcctggcaca tagtagatgc    2700
tcgataaaca gtaggaactc tcaatcccaa ttggaggcat ctcctttgga agatcttaag    2760
tgtacctttc aaaatactct tatactttaa gggcttgggt gaaaccaaat agagataata    2820
cagaccaaaa ttgttatccc agatgctctt ctgtctaaac cctgagactc agcttcagtg    2880
tcatggaaac agaccctcca gcagatgccc accacgtgtg tttgcatttc agatgccatc    2940
tccataactg ccacagagga cttccccttc cagaagcaca tcttgctctt caacatctcc    3000
attcctaggc atgagcagat caccagagct gagctccgac tctatgtctc ctgtcaaaat    3060
cacgtggacc cctctcatga cctgaaagga agcgtggtca tttatgatgt tctggatgga    3120
acagatgcct gggatagtgc tacagagacc aagaccttcc tggtgtccca ggacattcag    3180
gatgagggct gggagacctt ggaagtgtcc agcgccgtga agcgctgggt ccggtccgac    3240
tccaccaaga gcaaaaataa gctggaagtg actgtggaga gccacaggaa gggctgcgac    3300
acgctggaca tcagtgtccc cccaggttcc agaaacctgc ccttctttgt tgtcttctcc    3360
aatgaccaca gcagtgggac caaggagacc aggctggagc tgagggagat gatcagccat    3420
gaacaagaga gcgtgctcaa gaagctgtcc aaggacggct ccacagaggc aggtgagagc    3480
agtcacgagg aggacacgga tggccacgtg gctgcggggt cgactttagc caggcggaaa    3540
aggagcgccg gggctggcag ccactgtcaa aagacctccc tgcgggtaaa cttcgaggac    3600
atcggctggg acagctggat cattgcaccc aaggagtatg aagcctacga gtgtaagggc    3660
ggctgcttct tccccttggc tgacgatgtg acgccgacga acacgctat cgtgcagacc      3720 ctggtgcatc tcaagttccc cacaaaggtg ggcaaggcct gctgtgtgcc caccaaactg    3780
agccccatct ccgtcctcta caaggatgac atggggtgc ccaccctcaa gtaccattac    3840
gagggcatga gcgtggcaga gtgtgggtgc aggtagtatc tgcctgcggg gctggggagg    3900
caggccaaag gggctccaca tgagaggtcc tgcatgcccc tggcacaac aaggactgat     3960 tcaatctgca tgccagcctg gaggaggaaa gggagcctgc tctccctccc cacacccac     4020 ccaaagcata caccgctgag ctcaactgcc agggaaggct aaggaaatgg ggatttgagc    4080
acaacaggaa agcctgggag ggttgttggg atgcaaggag gtgatgaaaa ggagacaggg    4140
ggaaaaataa tccatagtca gcagaaaaca acagcagtga gccagaggag cacaggcggg    4200
```

| | |
|---|---|
| caggtcactg cagagactga tggaagttag agaggtggag gaggccagct cgctccaaaa | 4260 |
| cccttgggga gtagagggaa ggagcaggcc gcgtgtcaca cccatcattg tatgttattt | 4320 |
| cccacaaccc agttggaggg gcatggcttc caatttagag acataaaaca caggcagatc | 4380 |
| aagtagcatt gatcaatggc atgattccaa ctcagatttg tgggacacca aagcccagga | 4440 |
| tcttcccaag tgccctgctg cagtttagca ggtcctctcc agctaaagag cagtgagaca | 4500 |
| ttgggagccc aggagtgttg aggccaggcc aggctgaggc ccatcagtca caggtgtgac | 4560 |
| tgggctgctt gtcacacaca gggcgtggtc tggccactgt tgccagtgct cactcagcgg | 4620 |
| ccacatgctt tttaatatga cccctgaggc actgaaaaat aaccccaggc caactgcagg | 4680 |
| atagagagag aggtcaggac agcagccctg tgggctgcat gatacactgt ggctggagtt | 4740 |
| attgtgaccc cctggtgcag tgctcccacg gccagtggtg cacacagggc cattcactgt | 4800 |
| ccatagactg aaaccatgtg accatttgag agggccgggc acactttccc ctgagggatg | 4860 |
| gggcagcctg tggccagcac ctctgcagtt actctgcata gccagctcac cagcatgcca | 4920 |
| tgcccagggt gcccccccagt gacaacctca tgggagacgg gc | 4962 |

```
<210> SEQ ID NO 7
<211> LENGTH: 10226
<212> TYPE: DNA
<213> ORGANISM: Human

<400> SEQUENCE: 7
```

| | |
|---|---|
| aacatgaaaa ttcacaggta agtttgagat acagaaaata actaaactga ttcttctcac | 60 |
| gaactctgat cactaggctg tggttgattt agctctctaa ccaacaagta atttgttctt | 120 |
| tggcatgagt aaggggggaa aaggaggagt gggtaaaagc agctgataac agatggcttg | 180 |
| cgcccatcta aatgtggggg agagaaataa agctgtccca agagaactaa agctgagttc | 240 |
| tctcgtcata tatctgaaga ttcatatcag gggtctaaac atggtatgtc gggtagctta | 300 |
| attggaaact cctggactgt gagtgtcaca gactcatgga tgggccaatc agtggccact | 360 |
| ttagtgtctg ggctgcagca aaatgagaca atagctgtca ttcaaaaacc tttggaatta | 420 |
| aaaaaacccc gaaatgacat tggtgctttaa agtaaaaata aagtcctgcc tttaagtcca | 480 |
| gcatatcact gttgtttctg agtttaaata ttaagaacca catttcgtta atgattaaaa | 540 |
| caacagtgat tgatttaggg gctcagtgag catttaatct gtcctgactt caggtaccat | 600 |
| gctaaaggag cacaatgcct gatgctgcag gagaaacatt aggtaactat ttaatggagt | 660 |
| tttaattttc tgttattatt tttaataatt aattgtgatt ttgactattt ggaagctaca | 720 |
| ggtatatttt gtcctccttt tggggtggtg ttattgccct gccctgtttt aatcagtggt | 780 |
| tcttagagaa agtgaactca ggagtgactt aaaatgaagg aagacggact ttggctaaaa | 840 |
| ttacaattaa ataatcaaat cattttcaaa tataaaggga gcatgcagat gatctggccc | 900 |
| aatcctttca ttctgcagat gagaaaactg agactcatag gaatgaaaag acttgcccaa | 960 |
| agccatacag cttgtttctg ttgtttggtg cattaggcca aaagacctag gcctaataga | 1020 |
| tggaaaagat ggcaggatgt cttggccttg ctctgacagt tgcttctctg atctcagata | 1080 |
| tttcccaccc tttgtaatct gtgttccaca caggaagtag ttcttgtttt ttaaatatcg | 1140 |
| aaggtgtata aacgtaaagt ttttatagat gagccaccca gggccaatat ctgtttaagt | 1200 |
| aaagacctaa atgctttgca gagacagtaa agtgtcatgt ctgtcccagg gaaagaaatc | 1260 |
| caggacagga aatgctcagt cttccagcac tcctctggct acctggagct caggctatga | 1320 |
| gcctcaaccc ctccctgaag cattagctct ggagcagagg ctgtgattta cttcagagat | 1380 |

```
ctgggcaagt ccctttaacc tggtagtcct gcctttcctt gtttgtaaaa cagagagatg   1440
aggctgatag ctccctcaca gctccatcag aggcagtgtg tgaaattagt tcctgtttgg   1500
gaaggtttaa aagccaccac attccacctc cctgctaata tgattactaa aatgttttta   1560
tatgaaaggg ccaattcctc atctcccctc ttccttaaaa aacagaccaa ggggcatctt   1620
ttcttgtctc cctgtggcct aaaaggttac tgcttctgtg gttatctcct tggaaagaca   1680
gagtgtcagg actcttaggt acaccaaaaa tgaacaaaaa aatcaacaac aaccataaca   1740
ccaacaaaaa taactgctgt gtcggttctt aagacggctt ctgagctaga aacagatttt   1800
tctaactgta aaaaacgtgg ccccagcctg tctgcaggcc acctctgtct ttaggccttg   1860
gggggaggag ggaagtgagc tcatttactg gggtctacct caggdtcatc accaaggtgt   1920
tctacaaaac gcacttttaag aatgttttgg aaggaaattc accttttaac agcccaagag   1980
gtatctctct ctggcacaca gttctgcaca cagcctgttt ctcaacgttt ggaaatcttt   2040
taacagttta tggaaggcca ccttttaaac cgatccaaca gctcctttct ccataacctg   2100
attttagagg tgtttcatta tctctaatta ctcagggtaa atggtgatta ctcagtgttt   2160
taatcatcag tttgggcagc agttacacta aactcaggga agcccagact cccatgggta   2220
tttttggaag gtacggcgac tagtcggtgc atgctttcta gtacctccgc acgtggtccc   2280
caggtgagcc ccagccgctt cccagagctg gaggcagcgg cgtcccagct ccgacgcag   2340 ctgcggactc gggcgctgcc tgggcttccg ggacccgggc ctgctaggcg aggtcgggcg   2400
gctggagggg aggatgtggg cggggctccc atccccagaa agggaggcga gcagggagg   2460 agggaaggag ggaggggccg ccggggaaga ggaggaggaa ggaaagaaag aaagcgaggg   2520
agggaaagag gaggaaggaa gatgcgagaa ggcagaggag gagggaggga gggaaggagc   2580
gcggagcccg gcccggaagc taggtgagtg tggcatccga gctgagggac gcgagcctga   2640
gacgccgctg ctgctccggc tgagtatcta gcttgtctcc ccgatgggat tcccgtccaa   2700
gctatctcga gcctgcagcg ccacagtccc cggccctcgc ccaggttcac tgcaaccgtt   2760
cagaggtccc caggagctgc tgctggcgag cccgctactg cagggaccta tggtgagcaa   2820
ggctacctgg tgaggggaga caggcagagg gggtctagga gcctccttgg ggggaagaag   2880
ctggtcacag gctgtgaccg aggcaaaagg tggcctaatt attttccaat agtggtgctg   2940
gaggtgggga tgctggcgct gaaagacctt taaatatcgg ctactgcccc tgcccaggcc   3000
ttctctgtcc agcagtccct gggagattct caccttgggg aagtgcgggg caggagagca   3060
gaaacaagag aagcccttgg tagggggtc gttgggaaaa actgtggggt cttggctga   3120 acgcgttgcc cacgggctgg aggttgcgat ccccggacgg aaagcgcggg aggaggaagg   3180
agagaaccga ctctgaggtc cagagagagt gaggggcag agcgacgcg agatgggag   3240 agaacccta gctggagcag gttctgcggt agagagcgca gtcctgctgg cctctggaga   3300
gtgcgcgccg ctccggaggc tgcgtcgagg ggagtgtcac ccaatctggc ccccagctgg   3360
cggggcgccc tgagagcttg cgaactgcag ttgcaggacg cgccttctcc acgagctatt   3420
ttcgtcgact tgcggaaccc aaggaacctc gcctctatca tttcacggtg tagggtccct   3480
agagacgaca gccaagatcc cagggctcc caggacgctt gttcctgcgg tgtcgtgtcc   3540 tatgggagt tcctggcggg acgaaaggcg gacgcgcggc tcttcctggc cctccaggcc   3600
cggaaccgac gggaaaggtt cccgtgattc ccgagtccct gcaggcttct tccagcggga   3660
gttggtccgg gggccttaga ggcctccaag cactgctttg gaggatggtt tccaaggatc   3720
```

```
gcggtttgtg agttgaaggc tttgtgagag gttaaacccc caaaagatac atacttggta    3780
aactgaggct acctgtaaac acatttcggc attaggagaa gattcgagta gggaagtgaa    3840
ggacaaccac cccgagttac attcctttcc cccaataaaa agctctgggg atgaaagttc    3900
ttttggcttt tatcttttcg atttaaaaat ttgagaagaa aaatgtgact agagatgaat    3960
cctggtgaat ccgaaattga aacacaactc cccttcccc ttcctatcct ctcggtttta    4020
gaaccgcgct ctcccgcccc aggagattcc ttggggccga gggttttccg gggaacccgg    4080
gcgcccgccc cttctactgt cccttgccc cgcgggcaca gcttgcctcc gtctgctttc     4140
tctacttctg gacctctcct cgccgggctt tttaaagggc ttctgcgtct caaaacaaaa    4200
caaaaaaacc ctttgctctt cccaacccct tcgcagcccg cccagcggt ggcgcgggac     4260
cagcaaaggc gaaagccgcg cggctcttgc cgggcgcgga cggtcgcgca ggggcgcccg    4320
cggcctccgc acccggacct gaggtgttgg tcgactccgg gcatccacgg tcgggaggga   4380
gggctgagct gttcgatcct ttacttttct tcctcaaagt ctacctgcca atgcccctaa    4440
gaagaaaacc aagtatgtgc gtggagagtg gggcggcagg caacccgagt tcttgagctc    4500
cggagcgacc caaagcagca actgggaaca gcctcaggaa agggaggtcg ggtggagtgg    4560
gctttggggc aggagtcatg gggcccgggc cccggggacg acctggcgct cccggccctg    4620
ctgaacgctg agttgcgcct agtcgggttt tcgaagaggc ccttgcgcag agcgacccac    4680
gcgcgcggca gcatcttcga ttagtcagga catcccagta actgcttgaa ctgtaggtag    4740
gtaaaattct tgaaggagta tttgctgcgt gcgactctgc tgctggtgca acggaggaag    4800
gggtggggg aaggaagtgg cggggggaagg agtgtggtgg tggtttaaaa aataagggaa     4860
gccgaggcga gagagacgca gacgcagagg tcgagcgcag gccgaaagct gttcaccgtt    4920
ttctcgactc cggggaacat ggtgggattt cctttctgcg ccgggtcggg agttgtaaaa    4980
cctcggccac attaagatct gaaaactgtg atgcgtcctt tctgcagcga cgcctctttc    5040
tgaatctgcc cggagcttcg agccccgcg tctgtccctc agcctggcat ggcttcttcg     5100
ggggtctgct ttgcatgggg agaggggcca cgcagcggcg gactaggttt ggggattctc    5160
ggtaatggac ccggagcaat gactaacagc cgctccctct cactttccca cagcgatcac    5220
cctctaacac cctccctccc attcccggcc ccgcgcgtga caaggtcggc tgctttcagc    5280
cgggagctag atcggtggcc cggctcttcg gagccttagc aggcgttcgc caaggggtga    5340
ctggctgtca ttgggagcaa tatttggcct tgaggagacc ctggggagga agtggcgggg    5400
agctcgtgtt tgcttgtgtg tgtgtggggg ggtgtgtgtg tacacgcgcg tgggcagggt    5460
ccctctgcgc tttcctttt aagtgcctct cggtggtgag gctttgggcg ggtgagactt     5520
tcccgacctc gctcccggcc ccacttaagc cgggttcgag ctgggagacg cagtcccttc    5580
agtgcgcccc aaatcctctg gcttcaggtg gcccggcgcg ggcccagc acgacgcacc    5640
gcgccgagaa ccgggttctc cgtgcgctgc gccagtagcc ctgggagcgc gcggccgcg    5700
gggcaccggc cgagggctct gccgagcgcc gcgggagct cctcccggac cgctgaggct   5760
cgggcggcgg gcgcggaggt tggcctcgcc tggaggggcg ggcccgcgag gggcggggg    5820
ctgtggagga gggagggcg cgcaagccct ttcgccgcct gccgcgggag gggcctcggc    5880
gctcacgtga ctccgagggg ctggaagaaa aacagagcct gtctgcggtg gagtctcatt    5940
atattcaaat attcctttta ggagccattc cgtagtgcca tcccgagcaa cgcactgctg    6000
cagcttccct gagcctttcc agcaagtttg ttcaagattg gctgtcaaga atcatggact    6060
gttattatat gccttgtttt ctgtcagtga gtagacacct cttccttccc cctccccgga    6120
```

```
attcactctg ccctcaccac ccctgctcgc cggctgtccc ttccgtcgga cctcctttac    6180
aatatccaca ctctgctccc tggcagcact gtcgctccct tcttggcccg gcagccgggg    6240
cgctggaagc gtacgggttc cttttaaagt gctgctagcg cgcactcgcc ctctcagcgt    6300
tgcaagaaag gggagcgcga gggagctaaa gagatgaaag cccggggttg taccttgagg    6360
gctaaccact cccttcccct atccaacttg tctgggagag ccccagtgt ctccgtggcg     6420
cgttcccact ctcttgtcaa aactcacaga ggtctctccg gaatcgtctc tcaccccttc    6480
cctggggatg agcgggcacg atcaggcact tttggctgaa tatttcaaac tcatcggcca    6540
caataaaata agccctcaag ccacccggtt agctcccaga ccaccttctc ggcttctgga    6600
ccctgtcgcc ctctgtcttc gcccagcccc tgcctctcac tttccctccc tctggctctg    6660
aaccaactgg aagttgtgaa agttgggctc tgagggtgga ggaaaaggga gagaagctga    6720
aggtctaaag tggagagcaa tgccatttta attctccctc ccccacccct tttcaccccc    6780
tcaatgttaa ctgtttatcc ttcaagaagc cacgctgaga tcatggccca gatagcagtt    6840
aggacaaaaa aagattaaca ggatggaggc tatctgattt ggggttattt gactgtaaac    6900
aagttagacc aagtaattac agggcaattc ttactttcag gccgtgcatg gctgcagctg    6960
gtgggtgggc gggtggtgtg agggagaaga cacaaacttg atctttctga cctgctttcc    7020
atcttgcccc tccatttcta gccctaaatg catatgcaga cacatctcta tttctcccta    7080
tttattggtg tttatttatt ctttaacctt ccactcccct cccctcccc agagacacca     7140
tgattcctgg taaccgaatg ctgatggtcg ttttattatg ccaagtcctg ctaggaggcg    7200
cgagccatgc tagtttgata cctgagacgg ggaagaaaaa agtcgccgag attcagggcc    7260
acgcgggagg acgccgctca gggcagagcc atgagctcct gcgggacttc gaggcgacac    7320
ttctgcagat gtttgggctg cgccgccgcc cgcagcctag caagagtgcc gtcattccgg    7380
actacatgcg ggatctttac cggcttcagt ctggggagga ggaggaagag cagatccaca    7440
gcactggtct tgagtatcct gagcgcccgg ccagccgggc caacaccgtg aggagcttcc    7500
accacgaagg tcagtctctt cccccagtct gcgtggggga gggctggtgg gactggctag    7560
aggggcagtg aaagccctgg ggaagaagag ttcgggttac atcaaagccc cagtccagga    7620
ggctgaggaa cagagctgct tacctccaag aatttgcaga gctgccgccg aacttatttt    7680
ttggagacag agggggaggt gttcagggga aggggaatga cagcactcag acgtgggcta    7740
gccccagcgg tgtgttttg ctatatcaaa gccttttctg ctaggttttc tgcccgtttt     7800
tttcaaagca cctactgaat ttaatattac agctgtgtgt ttgtcgggtt tattcaatag    7860
gggccttgta atccgatctg aatgtttcct agcggatgtt tcttttccaa agtaaatctg    7920
agttattaat ccaccagcat cattactgtg ttggaattta ttttcccctc tgtaacatga    7980
tcaacaaggc atgctctgtg tttccaagat cgctggggaa atgtttagta acatactcaa    8040
tagtggaaga gggagagggt ggttgtctgc atgtttcctc ctgcctgtgc tctgttggcc    8100
cctcttttc tttacaacca cttgtaaaga aaactgtgga cacaaagcca aggtgggggg     8160
tttaaaagag gagtctgatt gtggtgccat agaggagttg acacatagaa attattagac    8220
atatcaagga ggctggatat agtttctgtc tttggtgctt gagaaatgct agctacattt    8280
tgctggtttg ttagctgccc cacttatctg ctccttcaaa ttaaggggta tgcttatttt    8340
cccccagtag gttccccctg cataagcaga attcaccatt cattgcccaa ccctgagcta    8400
tctcttgact cttccatctt tgaaaaaagt tcatatgctt tttcttttcc ccttccttcc    8460
```

| | | | | |
|---|---|---|---|---|
| taactgtgcc | tagaacatct | ggagaacatc | ccagggacca | gtgaaaactc tgcttttcgt | 8520 |
| ttcctcttta | acctcagcag | catccctgag | aacgaggtga | tctcctctgc agagcttcgg | 8580 |
| ctcttccggg | agcaggtgga | ccagggccct | gattgggaaa | ggggcttcca ccgtataaac | 8640 |
| atttatgagg | ttatgaagcc | cccagcagaa | gtggtgcctg | gcacctcat cacacgacta | 8700 |
| ctggacacga | gactggtcca | ccacaatgtg | acacggtggg | aaacttttga tgtgagccct | 8760 |
| gcggtccttc | gctggacccg | ggagaagcag | ccaaactatg | gctagccat tgaggtgact | 8820 |
| cacctccatc | agactcggac | ccaccagggc | cagcatgtca | ggattagccg atcgttacct | 8880 |
| caagggagtg | ggaattgggc | ccagctccgg | cccctcctgg | tcacctttgg ccatgatggc | 8940 |
| cggggccatg | ccttgacccg | acgccggagg | gccaagcgta | gccctaagca tcactcacag | 9000 |
| cgggccagga | agaagaataa | gaactgccgg | cgccactcgc | tctatgtgga cttcagcgat | 9060 |
| gtgggctgga | atgactggat | tgtggcccca | ccaggctacc | aggccttcta ctgccatggg | 9120 |
| gactgcccct | ttccactggc | tgaccactc | aactcaacca | accatgccat tgtgcagacc | 9180 |
| ctggtcaatt | ctgtcaattc | cagtatcccc | aaagcctgtt | gtgtgccac tgaactgagt | 9240 |
| gccatctcca | tgctgtacct | ggatgagtat | gataaggtgg | tactgaaaaa ttatcaggag | 9300 |
| atggtagtag | agggatgtgg | gtgccgctga | gatcaggcag | tccttgagga tagacagata | 9360 |
| tacacaccac | acacacacac | cacatacacc | acacacacac | gttcccatcc actcacccac | 9420 |
| acactacaca | gactgcttcc | ttatagctgg | acttttattt | aaaaaaaaaa aaaaaaaagg | 9480 |
| aaaaaatccc | taaacattca | ccttgacctt | atttatgact | ttacgtgcaa atgttttgac | 9540 |
| catattgatc | atatattttg | acaaaatata | tttataacta | cgtattaaaa gaaaaaaata | 9600 |
| aaatgagtca | ttattttaaa | ggtaaatcat | gatttttttt | ttctccttaa tcctttctct | 9660 |
| tttccttcgg | gctcatctct | tttgaatgag | gcttttttct | gttcaggtga gttggaggct | 9720 |
| ggatggaagt | caaaggtgg | tacctggagg | tggttaagtt | gtagggacag gaagtaaact | 9780 |
| gttggcagag | agagatggta | attgccagca | tgaattgttt | tctatttcta tttaatgtta | 9840 |
| acaaggatgc | agtatcctct | cccatctgga | tgacacatgc | cttggagaaa cactgggatg | 9900 |
| aaaggagtgt | aggtcagatt | aaagacttca | tttcaggccc | cttgtacatc ttctgtttca | 9960 |
| ctcacctgtt | gaggtgtatc | acagctgagc | gtgatgaggt | ctcaacccta gaaaaatgat | 10020 |
| acccacctct | gctttcatga | tacctcaggg | tatctccagt | tattacaggt accaatgtga | 10080 |
| tatttccaaa | tcaaaactaa | tttgtacact | aacatcataa | tgtgtgtgtg aaggcatgtt | 10140 |
| tttaaactta | ttttttttt | ctccaggtag | gactctttg | ttttttcttt tgtctttttt | 10200 |
| tttttttgaa | acaagttctc | tctttg | | | 10226 |

<210> SEQ ID NO 8
<211> LENGTH: 13800
<212> TYPE: DNA
<213> ORGANISM: Human

<400> SEQUENCE: 8

| | | | | | |
|---|---|---|---|---|---|
| atttacatgc | gtatggatat | gaaaataaat | gcatacacat | ttatgtaaaa aaatttgtac | 60 |
| acatgcattt | acatatgtaa | atacatacat | ctctatgtat | taatgtttaa aaacactcaa | 120 |
| tttccagcct | gctgtttct | tttaatttc | ctcctattcc | ggggaaacag aagcgtggat | 180 |
| cccacgtcta | tgctatgcca | aaatacgctg | taattgaggt | gttttgtttt gttttgtttt | 240 |
| ttgaaatcgt | atattaccga | aaaacttcaa | actgaaagtt | gaataacggg cccagcgggg | 300 |
| aaataagagg | ccagaccctg | accctgcatt | tgtcctggat | ttcgcctcca gagtccccgc | 360 |

```
gagggtccgg cgcgccagct gatctctcct ttgagagcag ggagtggagg cgcgagcgcc    420
cccttggcg gccgcgcgcc cccgccctcc gccccacccc gccgcggctg cccgggcgcg    480
ccgtccacac ccctgcgcgc agctcccgcc cgctcgggga tccccggcga gccgcgccgc   540
gaagggggag gtgttcggcc gcggccggga gggagccggc aggcggcgtc ccctttaaaa    600
gccgcgagcg ccgcgccacg gcgccgccgc cgccgtcgcc gccgccggag tcctcgcccc    660
gccgcgctgc gcccggctcg cgctgcgcta gtcgctccgc ttcccacacc ccgccgggga    720
ctggcagccg ccgccgcaca tctgccgcca cagcctccgc cggctacccg aacgttctcg    780
gggccagcgc cgagtggatc accggggacc gcgaggcacc cgcgcgccgc agaccccgcg    840
cgggctggag cacccggcag agcgcgccac agcgccgtgg cctctgctgc ccgggctgcg    900
ccagagccgc ggacgggcgc gcagagcgcc ggggactccg gagccgatcc ctagcgccgc    960
gatgcggagc acctactgca ggagatcggg ggcctgggac gcgctggccg aggtgtgatc    1020
ggaccccagc tagccacaa agggcacttg gccccagggc taggagagcg aggggagagc    1080
acagccaccc gcctcggcgg cccgggactc ggctcgactc gccggagaat gcgcccgagg   1140
acgacggggc gccagagccg cggtgctttc aactggcgag cgcgaatggg ggtgcactgg    1200
agtaaggcag agtgatgcgg gggggcaact cgcctggcac cgagatcgcc gccgtgccct    1260
tccctggacc cggcgtcgcc caggatggct gccccgagcc atgggccgcg gcggagctag   1320
cgcggagcgc ccgacccctcg accccgagt cccggagccg gccccgcgcg gggccacgcg    1380
tccctcgggc gctggttcct aaggaggacg acagcaccag cttctccttt ctcccttccc    1440
ttccctgccc cgcactcctc cccctgctcg ctgttgttgt gtgtcagcac ttggctgggg   1500
acttcttgaa cttgcaggga gaataacttg cgcaccccac tttgcgccgg tgcctttgcc    1560
ccagcggagc ctgcttcgcc atctccgagc cccaccgccc ctccactcct cggccttgcc    1620
cgacactgag acgctgttcc cagcgtgaaa agagagactg cgcggccggc acccgggaga    1680
aggaggaggc aaagaaaagg aacggacatt cggtccttgc gccaggtcct ttgaccagag    1740
ttttccatg tggacgctct ttcaatggac gtgtccccgc gtgcttctta gacggactgc    1800
ggtctcctaa aggtagagga cgcgggccag ggcccggggt gggtggtggg tgggagggggg    1860
atttgggcag ccactgcggt agagcccttc cttacgtcca ggccagaagt aaacagaccc     1920
ctctccagtc cacgtgcaac ggagccctgc aggggctccc acttccagct gccccggggcg    1980
accgtaagcc tcaccctccc ggcccgcact cttccacccc tctttcttcc cctctccctg    2040
gaatactttt ggagctgtta acacttagat gaggtgtttt atttatttat ttatttattt     2100
ttaattttt taaaaacttt tttgggtcaa agaaatccct ttgagagggt agccctggg     2160
tttcacccgt tagctgagaa cctgtccgct ctgccatggt gatctccatt cttcaagtgt    2220
ttccgggaga cttggtttct ttgctcagag ccgtgtccca tttaggaaag tactaggagt    2280
ttggggttct ccctacttgt ttccagaaat gcgaggggtc agtactgaag gatcacttgg    2340
tactgtgttt ttaacagctg acacgtgcat taatagatat tcaccattta cgtaatcccg    2400
ggaagataca tgtgtatctt gactgcactg tggggatgcg ggatggagct gcctttcgag    2460
acaccctga gggtaggggc ctgggacaca agtcataagt ggcttcagaa gttgtggcct    2520
tgagcttaca gggtctggaa gctataaggg tgtgtgtgtg tgtgtgtgtg tgtgtgtgtg    2580
tgtgtcagga agttctatac agtgcctcta aggaagtcac atgcaccatt tatgtgtgtt    2640
tatatgccag acagcgctca gcactccgca tttgggtttg tataggggac gcagggtgtc    2700
```

```
agatcaagcg gtggttttcc caggttcccg gcattggctg tcagcgctgt gtcacacaca    2760
aaaaagtgac agtcattggc gctggtttgg ttggggggga gggcaaatcc caaatctgat    2820
gtcagacgag ctaagcgttg gatgggagcg ataaatcatc tggttcagga acttgggacc    2880
cttcattatc ccaaacgttt gagcttcggt cggtcttacc tagactcgtg agtgtgccaa    2940
gccaggaggg catcctggag gaggcacgcc agccaaatgg gagaccgggc cgcggggggcg   3000 cgaggggggga ggactgggcg gggaactcgg gtgactcacg tcggtcctgt ccgcaggtcg   3060
accatggtgg ccgggacccg ctgtcttcta gcgttgctgc ttccccaggt cctcctgggc    3120
ggcgcggctg gcctcgttcc ggagctgggc cgcaggaagt tcgcggcggc gtcgtcgggc    3180
cgcccctcat cccagccctc tgacgaggtc ctgagcgagt tcgagttgcg gctgctcagc    3240
atgttcggcc tgaaacagag acccaccccc agcagggacg ccgtggtgcc cccctacatg    3300
ctagacctgt atcgcaggca ctcaggtcag ccgggctcac ccgccccaga ccaccggttg    3360
gagagggcag ccagccgagc caacactgtg cgcagcttcc accatgaagg tgaggcatgg    3420
agcagggcgt ggggggcgggg agtcaccctg caaagccctc caccgtgggc agactgcagc    3480
cgtccctgta gaggcagctt ggccggggca ccagcggacg tttccactct tgcttctgta    3540
ctatcgtttc tgaatctgat tttaactcac tgcttgtgtg gtgggggagc cagggattcc    3600
cctttagtaa ctccgcaccc tcttcctggc ttgcagccag aagagctact cctcctggaa    3660
gaattggaga gaaatcaagt gatggggaag atgagggcaa aaggcatgcc tctagtcagc    3720
taaacgtgca agaattccac agagggaaaa ggagaaaaag ggaggcagat tgagatttct    3780
ttaagtctgt ttggaagctt ttgctctata aatctgccgc ttaagccagg ttttagggt     3840 agacagagcc aagggcagag ttttcagaga tagtattgaa aaatcaaagc ccagggcccc    3900
aaagtctttc taatttatag ttgatctggg cctggtttgg aagattttga atcccaatct    3960
aatccccgtg ggagatcaat actacaatca atcttattgt ttccacaatg actttcttgt    4020
cctgtgctta aatctgagat aggctctgag tagagacaag gcaagccttc agataaaagc    4080
gtttgtagca gctgcctgtt tttttttcat gtgcaccgaa atgtggattt tttttttcttt   4140 tatgatacta catgtggttt ttctaaggtg ggatatttct gcttgtttca tcagaagggc    4200
atttagtgga ctggaaatgt cttacagcag ctattgaggt ctgctgtacc taagttctta    4260
gagcaattag tcaaaaatat gttccacttc aattctttt ctacactttt aaatgcttct     4320
ttggcttaat acatttaaaa tagagcatgg gtttcttcaa ttcctagaaa agagtacaaa    4380
agtgtatatc acagagcaac cacttggcag atatttgggg agttgggagt gaagttctct    4440
ttcttgcctt tccctgctta ggtggtaaat ttcaagtggg aaatttacac tgataataga    4500
ctaatgggaa atggcacttc cagatgtttt ctcccagtgt gaagggtgac ttatacttgt    4560
gagagtattt gttggtaatg ggaataagtc ccaaaggcaa gccacatagc agaagatacg    4620
ttctcattga ggcagctaca cattacgacg gggacactga attgatcatc agttcattta    4680
caagcacatt tctaagtgag gtgctctctg ctagcagaaa tcagatttga aaggcagtaa    4740
gatctcactc cactctttca gaattcatcc aatgaaagca gaaatcaccT gttgtcatat    4800
gtaaaatttg tgtgtatgtg tacattctgc catcttaacc ctgaaatgat tatagatcca    4860
gctaatcatt cccaggtaat gctgattaga atacttttt ttttgtatag gaatgtaata     4920
agaacaactg ttttagacac ctcttctgga aatttagcat ggaagctctc aactttattt    4980
ttaaggcctg gaagatgctg tgtctctgtt acaacttaaa aggaagatca tttaagttag    5040
ttaacaccta aaacattcca ttgtgtgagg attttatcag tgatgtctgc atattctcat    5100
```

```
cattcatcta gaagtggttt gatcagaact aaacaggcta cacgttattc aactgtgtta    5160
ttttaactta aaaagcatgc ttgagtttat aaaatcagaa tttatatctt tgtgagtgta    5220
aatgttacct gagaaacagt acagaagtga ccaacttgat taaaatcaac ttgtaataac    5280
ttcaggtctt aatgcagtta gataatggag aaaagctatg taattttgcc ccaaatttca    5340
actaatccat tcttgtctc attatgacta atatatcatc cttaatctgg atggatatag     5400 cactttttc aagactaatc attgttgtat acacccagga tttgcttttg ataaacatcc      5460
ttgtgccatg catgccacga aaaagttttt tggtaaacca tgtgatgaag gttgctggct    5520
caagaacaga atttagtttc tacagcatta atgagcattt atttgaaaaa agaccataaa    5580
gacccaatca taagaattac ctgttgggtt tcttttgtag gtgtgatcga atggtttggt     5640
ggaattactc gacgagatat catgatagca ttctttcaac caatatgagt ataatgcgac    5700
catatcatag gggatctgag acagaattat cagttgtatt tttcctattg aattttgtct     5760
agtcctttct ccagtggctt ttatttggga gaatatcagc tttgctaaaa tgttattgtt    5820
ttcaagatca ttaaaaagtg cttcagctac atagaccttt ggaaactgcc attgaacata   5880
gaaaagtcag ttctgcaagt ggaaagagtg ttttgtgtat tgctgtagtt ggaaacacat    5940
tgaaactggt tgacttcact ggccctccaa aaagtcttta tgctttttg tcagatggga     6000 gagagaaaga ccaggtgctt cttgttctcc tcactctgaa ggacacagtc ttctttctac     6060
atgaaataac tggattattt gcctctgtga ctgaagcttt caaatagaga ttaaccctct    6120
ttccacaaat ataattatta tgaaaatatc catataatag aaaagttcaa gaaataacta   6180
ttgccctgca ttagagactt tgtggcacaa attccccgt gcaaacaaca gatttggaca      6240
catagatcca ccaaaaccaa tacttacctg gtatggttcc ctagtggccc caggtatttc    6300
attgtcatta cagaggccac attaagtagg aaaattactc tatttggaaa tggttgttga    6360
gattgaggct ttggtgtcca gtgatacttc cttggcactg acatttttccg ttccacctgt    6420 ttttttagtgg ttcccctaaa tttctcttaa tcccctttgca gtgaactatt ttgcgttctt     6480
agacttgctc tttgtgtatt ttcactgaga caataagaga atatttcatc attccgaagg   6540
tgttggtgtt aagggtgggc agaggccaaa tcagggttgt tgatgacaac catgctctct    6600
attcctttat ttgccattcc cttgttgtat tttttttaaa atggaatgtt tttaaccttt      6660
tgtatttgat atttttttc tccttgatca gttgtctgtt attttattat ctggaaaatc       6720
ttatattata ctcagcctct ttcattttgt gttagggcag tgacttccag ccttactgat    6780
tgccagcata tccccaggtt ttgttgttgt tgttgttgtt ttactggaga ttttttagcc    6840
caaagtgtgt tttaaaatcc tcgaagcata acggtaactt acttttttga taaaacttac     6900
catactttat ttagaacaaa agggcagcca caaaatagca gtggctccct ataaaataga   6960
cacattccag tgggccccgt cacttttctg ctcatttctg tctgttctgt ccatcatacc    7020
taagtcatat atttctgttc atttagttgg gacagaactc acccaatgtt atcattgtac     7080
taaatataaa tgtgcccctta atggttttga cttttgctta agttttttgag tcctcatgta    7140 tgttaggtag tgccatctag tagccagaaa tttgggaact ggctgggcat gatggctaat   7200
acctgtaatc ccagcacttt gggaggctta ggtgggtgga tcacttgagg tcaggagttc    7260
cagaccagcc tggccaacat ggtgaaacca catctctact aaaatataaa aaaatagcca   7320
ggtatgatgg cccatgcctg taatccgagc taattgggag gctgagatgg gaggactgct   7380
tgaacctggg aggtggaggc tgctgtgagc caagattgtg ccactgcact ccagcctggg   7440
```

```
caacagagtg agaccctgtg tcacaaaaac aagaaacaaa acaaaacaaa agacaagaaa    7500
cctgagaagc gcagtagatt caattatata tatctacttt taatttgcta gctctgtgac    7560
cttaggaaag ttacataacc tctctgaact gcaactgttt catttacaaa atggagataa    7620
tgatagtttt tctctaattg gtttgttgtg agataattca tataaagctg atggtgccag    7680
attacactca aaaaaagcat tcagctgtca ttatcattat gacttctttt gttaatgtta    7740
tagcctttcc ttctctaggg aaaaggaggc cagagtggac ctaggctgac tgagagaatt    7800
cagctcagtc ttttgaatta ttttgaggta gaggaatgat tgatatagta tagattatta    7860
aattaggact tcacttttgg agaaaagttc agatatcatt gttgtcttat ttttcttcac    7920
tttcccacat ttttgcagcc atagctccat ccatttggtt aagaacttag aagctcacaa    7980
actcgggtca agacaggtc gaaatcctca aatcccttaa gaacttcagc ttattcagga    8040
agggatattt acagaaaact agcaattgta taagtctcca aaaaagcata cattacttga    8100
ggatccatat atttttggca tcctcagggt tgctgtgatg atttatagaa ggtttgttta    8160
tttaatttac tttatttcaa ataggtttta attttgtac ccttaagaaa agattcgtac    8220
tcttccctgg cagattaaag aaaatgagcg tatattccct aaccttggcc agttactttc    8280
ctgggtttga gggtttctgt gaacgtctaa cttacctctg tgacctgttt ctgcaaccag    8340
gggtgttgca atggatgctt ttgtcttgag gatgggacct ttcaagaaac agattcactg    8400
aggtgcagtg gaaggtcag agaaagatct tcgtatcgcc tattattatt tgctcgtcta    8460 tttttttctcc tttcttaagg ccactaactg attctccttt gctaaggctg cctacttcca    8520
ctgagacctt gaaccacatg aaattgttgt tgtctgtgtt tctggtcaaa tagtggcaat    8580
tttgtatgat tcaatcttgt catttaattt tttgggaggt tattattcta tttcatacct    8640
tttttatacc catcttcttt acttcattta cctgtccctc atacttgact tgtagccttgt    8700 cccttcactg tcatcgtctg gccatgtggg tgtgtacgtg tgtgcgagag agagaatgtg    8760
tgagaatgta tgtttcttta tgcattggga tttagggttt ttcttgcaat tgtgatttct    8820
ctgggcactt ttgttaatat agctagtcag cgagtgctct agataatttt ccttgcctcc    8880
ccctctttga agaaaagag ggtgttctta gatgtattct tatcagataa gccagtagct    8940
caggtgctgg tctggctttg gtgtcattgg ggtctgaggt tgctgacttt taccttctct    9000
gctgaaaaat taccttcagc agaaacgtct gaattgcaag gagaaggaga aaaaacagg    9060 ccaaacacag tccttggtac tccttgggag ccactgagaa gagtccaggt tcaaatggtc    9120
agaaggttat tttaatgatt gtgtctggcc taaagtacca ttagcttcca gtggagttta    9180
gaatgtggat ggatcctgaa aggtattccc cagaggtttg gattaatagg cacaagggaa    9240
ccctaaagga ctctattggc ctgatactcc ccatatccac gtagaagagc tttagaagaa    9300
ccttctgttc tgagaccctg gctgggccca cccagagctg gcccattcaa ctcttactcc    9360
tttgccacca ctaatggttc ttctactagt ttttatatta tttaacaaaa aggcacttta    9420
aaaatgcact cctggcaatc tatactggaa tatgaaaaac atgctgcaaa accttgacac    9480
tccaagtgtg gtcttacagt tcccagaatc ccctccttga ggagctgcta gaaatgctga    9540
atctcaagca tctccccaga cctactgaat cagagcctgc atctgaagct ttacggtgta    9600
caagctgttt tatgtgaagg ctgaagtttg aaaagcactg cattaaagcg ttagtttggt    9660
ataaactgcc ctgactgaac ttggtgtgtc cacttagctt gcatgatgac tgttgctttg    9720
atgatgaagg cttacacggg tagatccttt gagtgagtga tctgacatga ttctcctttg    9780
ctaaggcatc tagattcagt gcacaactta cagctgtttg tctttagggg aaatacaact    9840
```

```
gtaaaattaa taaaaacata gtctcttctt atgataacat ggaacgatgg caaaatagat    9900
tttgttagca cttgggtagg aattctgaat gaagcaggca aattctgttg gcagtgaaat    9960
gataggatgt ggtaaagtta gaataaaata aacttaaatg tctcaaactc tcatggtata   10020
tactaccagt ttaataataa tgttgtacct ttgatgattt gcagactaca agcattcaag   10080
gtgctgtgtt atatattact tgcttggaga ataatacttc ttaaaaattg aaattcagaa   10140
atttaaatc agacaaagct tttgtgcatg gcccacttaa atggctattt tgaaataatg    10200
atagtggata tagaaggatt attctgtaat aggatgagac tgttccttt gtcatggaga    10260
tcataatcat atttttgtaa attttatta ttttttggt tttgtgtcca tcctgcacac     10320
tattactggg taggtacatg gttttttaac atggtttatc tttcaaaact ataaaggcat   10380
tgcaaacaga agacaggtca tttatttttc ttccaaaagc atctaaaatg agattttgat   10440
atttgaggtc ataagaggt gagagaacag acaacagttg ggaaagctat ttctcttgaa    10500
attgtttggc cttaattact acagtgtcct agtaccaccc atacgtttcc aaagaagtag   10560
atccctgtaa atgcctttgt ctctggactt ttgagtaaaa tagtagggtg tgctttgcaa   10620
aatgtcatcg ttgatgttga gtttcagagt cttaattag gaagctgaaa tctgtatatc    10680
gagatttgta aatcatctaa attgcagagt aatgttttag aatactgctt aagggattgg   10740
cattaaagcc tttttaaaa aagaaatgca ataatttcct caaatcctca ctcattagac    10800
ctctactaac tatagtgctg actttttttt ttttttaccc taaagtctgg aattccaaag   10860
aaatgcttca ccatttcccc cattattata gccacctgga agcagtattc atgtattaga   10920
tcaaaacac aacaaagaat tatgaaaggt tgtttcctgg tatgcaatgc atgatgacat    10980
gaacttacag aacagagaga agggaggctc catgtttatt taaagaggaa atttttattt   11040
tctggttacc tactttaca tgggttacat caaatcccac gatgaggttt aaaaattctc    11100
atagataatc aaacgtcatt acttggctta ctgaaattca gacttttctt ttttcttccc   11160
tgttttctc tatcaaatta gaatctttgg aagaactacc agaaacgagt gggaaaacaa    11220
cccggagatt cttctttaat ttaagttcta tccccacgga ggagtttatc acctcagcag   11280
agcttcaggt tttccgagaa cagatgcaag atgcttagg aaacaatagc agtttccatc    11340
accgaattaa tatttatgaa atcataaaac ctgcaacagc caactcgaaa ttccccgtga   11400
ccagactttt ggacaccagg ttggtgaatc agaatgcaag caggtgggaa agttttgatg   11460
tcacccccgc tgtgatgcgg tggactgcac agggacacgc caaccatgga ttcgtggtgg   11520
aagtggccca cttggaggag aaacaaggtg tctccaagag acatgttagg ataagcaggt   11580
ctttgcacca agatgaacac agctggtcac agataaggcc attgctagta acttttggcc   11640
atgatggaaa agggcatcct ctccacaaaa gagaaaaacg tcaagccaaa cacaaacagc   11700
ggaaacgcct taagtccagc tgtaagagac acccttgta cgtggacttc agtgacgtgg    11760
ggtggaatga ctggattgtg gctcccccgg ggtatcacgc cttttactgc cacggagaat   11820
gccctttcc tctggctgat catctgaact ccactaatca tgccattgtt cagacgttgg    11880
tcaactctgt taactctaag attcctaagg catgctgtgt cccgacagaa ctcagtgcta   11940
tctcgatgct gtaccttgac gagaatgaaa aggttgtatt aaagaactat caggacatgg   12000
ttgtggaggg ttgtgggtgt cgctagtaca gcaaaattaa atacataaat atatatatat   12060
atatatattt tagaaaaaag aaaaaaacaa acaaacaaaa aaacccccacc ccagttgaca  12120
ctttaatatt tcccaatgaa gactttattt atggaatgga atggaaaaaa aaacagctat   12180
```

```
tttgaaaata tatttatatc tacgaaaaga agttgggaaa acaaatattt taatcagaga   12240
attattcctt aaagatttaa aatgtattta gttgtacatt ttatatgggt tcaaccccag   12300
cacatgaagt ataatggtca gatttatttt gtatttattt actattataa ccactttta    12360
ggaaaaaaat agctaatttg tatttatatg taatcaaaag aagtatcggg tttgtacata   12420
attttccaaa aattgtagtt gttttcagtt gtgtgtattt aagatgaaaa gtctacatgg   12480
aaggttactc tggcaaagtg cttagcacgt ttgcttttt gcagtgctac tgttgagttc    12540
acaagttcaa gtccagaaaa aaaaagtgga taatccactc tgctgacttt caagattatt   12600
atattattca attctcagga atgttgcaga gtgattgtcc aatccatgag aatttacatc   12660
cttattaggt ggaatatttg gataagaacc agacattgct gatctattat agaaactctc   12720
ctcctgcccc ttaatttaca gaaagaataa agcaggatcc atagaaataa ttaggaaaac   12780
gatgaacctg caggaaagtg aatgatggtt tgttgttctt ctttcctaaa ttagtgatcc   12840
cttcaagggg gctgatctgg ccaaagtatt caataaaacg taagatttct tcattattga   12900
tattgtggtc atatatattt aaaattgata tctcgtggcc ctcatcaagg gttggaaatt   12960
tatttgtgtt ttaccttac ctcatctgag agctctttat tctccaaaga acccagtttt    13020
ctaactttt gcccaacacg cagcaaaatt atgcacatcg tgttttctgc ccaccctctg    13080
ttctctgacc tatcagcttg cttttctttc caaggttgtg tgtttgaaca catttctcca   13140
aatgttaaac ctatttcaga taataaatat caaatctctg gcatttcatt ctataaagtc   13200
caacctgtaa gagaaaatgg tgcatttgta tagcgcttac aatgatgacc ttgtgtttgc   13260
attttttgttt ctgaagttat atattttaga ggggtgggg gaaaggtaat gaatggctgg   13320
aaaattgcag gcaagttatt tgataagtca tatttgcact aaaggtgtta ccagtgattt   13380
agtattttc aaatgaactt ctttgggggca gaaagattta agggaaaact aaagcctaca   13440
aaacaagcaa aacctggata acccgagata aagtttcaga gataatagcc catgcaacag   13500
aggcaacggt gccagaaaat tagaaaggga aagtgtcgga gatcagcttc tataagaaca   13560
tctgccagtt ggactgacgc ccaaacagaa tgaagtcaaa ttaggctgct cagattgaac   13620
acttaccaga gtgtcagggc ttctgtaccc tgggttagaa tcagaccaag gaagggttca   13680
gcagatgttc ataagagcag ggcacccaca actacccact attttactgg cagtatttta   13740
ggtcagtttc caggactttg catcccctct gatcctgcca tgcatgattg gtgaaaccta   13800
```

```
<210> SEQ ID NO 9
<211> LENGTH: 99082
<212> TYPE: DNA
<213> ORGANISM: Human

<400> SEQUENCE: 9
```

```
gaggggcgag gcgaggaaac aacctcagct tggcaggtct tggaggtctc tgggaggaga     60
aagcagcgtc tgatgggggc gggaggtggt gagtggggag aggtccaggc ggagggaatg    120
gcgagcgcag agacaggctg gcaacggctt caggaggcg cggaggggtc agcgtggctg     180
gcttaaaagg atacagggac tgaggggcaa gaccggctca agggtcaccg cttccaggaa    240
gccttctatt tccgcgccac ctccgcgctc ccccaacttt tcccaccgcg gtccgcagcc    300
cacccgtcct gctcgggccg ccttcctggt ccggaccgcg agtgccgaga gggcagggcc    360
ggctccgatt cctccagccg catccccgcg acgtcccgcc aggctctagg caccccgtgg    420
gcactcagta aacatttgtc gagcgctcta gaggggatga atgaacccac tgggcacagc    480
tggggggagg gcggggccga gggcaggtgg gaggccgccg gcgcgggagg ggcccctcga    540
```

```
agcccgtcct cctcctcctc ctcctccgcc caggccccag cgcgtaccac tctggcgctc    600
ccgaggcggc ctcttgtgcg atccagggcg cacaaggctg ggagagcgcc ccggggcccc    660
tgctatccgc gccggaggtt ggaagagggt gggttgccgc cgcccagggg cgagagcgcc    720
agaggagcgg gaagaaggag cgctcgcccg cccgcctgcc tcctcgctgc ctccccggcg    780
ttggctctct ggactcctag gcttgctggc tgctcctccc acccgcgccc gcctcctcac    840
tcgccttttc gttcgccggg gctgcttccc aagccctgcg gtgcgccggg gcgagtgcgg    900
ggcgaggggc ccggggccag caccgagcag ggggcggggg tccgggcaga gcgcggccgg    960
ccggggaggg gccatgtctg cgcgggcgc agcggggccc gtctgcagca agtgaccgag   1020
cggcgcggac ggccgcctgc cccctctgcc acctggggcg gtgcgggccc ggagcccgga   1080
gcccgggtag cgcgtagagc cggcgcgatg cacgtgcgct cactgcgagc tgcggcgccg   1140
cacagcttcg tggcgctctg ggcacccctg ttcctgctgc gctccgccct ggccgacttc   1200
agcctggaca cgaggtgca ctcgagcttc atccaccggc gcctccgcag ccaggagcgg   1260
cgggagatgc agcgcgagat cctctccatt ttgggcttgc cccaccgccc gcgcccgcac   1320
ctccagggca agcacaactc ggcacccatg ttcatgctgg acctgtacaa cgccatggcg   1380
gtggaggagg gcggcgggcc cggcggccag ggcttctcct acccctacaa ggccgtcttc   1440
agtacccagg gccccctct ggccagcctg caagatagcc atttcctcac cgacgccgac   1500
atggtcatga gcttcgtcaa cctcgtgag taagggcagg cgagggtacg cgtctccttt   1560
cgggggcact ttgagactgg gagggaggga gccgcttctt ctatgcagcc cgcccagctt   1620
tccgctcctg gctgaaatcg cagtgcctgc ccgagggtct cccacccaca gccctatgac   1680
tcccaagctg tgtgcgcccc caggtcgggc gcgctgggtt cggtgagcct gtaggggtta   1740
ctgggaagga gggatcctcc gaagtcccct ccatgttacg ccgccggccg catctctggg   1800
gctggaggca agggccgttc aaagcgcggg gctcggtcat gtgagctgtc ccgggccggc   1860
gcggctcgcg ctacctggat gtaaagggcc cttcccggcg aggctgcctt gccgcccttc   1920
ctgggcccct ctcagccctg cctggctctg catcgcggc cgtcgcaccc ccttaccctc   1980
cctgtcaagc cctacctgtc ccctcgtggt gcgcccgcct tagcgtaccg cgcgctccga   2040
gcgccttggg gcccctctcc gggccgccgg atgccccatt ctctcttggc tggagctggg   2100
gaagaaacgg tgccattgct aattttcttt gttttctttc tttgtttatt ttttctttt    2160
ttcttttttt ttcttttctt ttcttttttt ttttttttga cggagtttt cactcttgtc    2220
gcccagtctg gagtgcaatg gcgcgatctc tgctcaccgc aacctctgcc tcccgggttc   2280
aagcgattct cgtgcctcag cctcccgagt agctgggatt acaggcatgc gccaccatgc   2340
ctggctaatt ttgtattttt agtagagaca gggtttctcc atgttaggca ggctggtctc   2400
gaactcccga tctcaggtga tcctcccgcc tcagcctccc aaagtggtgc tgggattaca   2460
ggcgtgagcc actgtgccct gccgctagtc ttctatttta agtatttagt ggtaggtccc   2520
gggccggcag aatctatttt cagcatttac acgtgtggc gcgcaaacca caggtttttgg   2580
cgattgggtt gcgcgggatc tcagagctga cgccgcgggg cggctgggg gtcccggttt    2640
ccgactggag ccgcgacgac cccggcgacg cgagcctggg gctgcagcga gggccgggga   2700
gctcccctc catatgtgcg cgcacattct ccagacttgc tcaaactaac ccccccggcag   2760
cgccagcgcg ctgcgggact gatgatcaaa tatttggttt ccgagataac acaccccgat   2820
agcgctgttt cctgagccgc tttcattcta cttgtgtaac ttgctgcgaa aacccgaacc   2880
```

```
aagtcaagac agcaaactca cgcccacggg cgctgtgtca acatggaaat aatgatactg   2940
aagccccacg ctgggcacct ggggcgtgga ctggggcgc gggggaagcg cagatccgcc    3000
ttcatgcttc cccctcctga taaggtccct ggagttcccg ggaggccatt gtctgtactt   3060
aataataact aaatccaact agtgaaccaa gcttcagcga gcaaggggtg ggaggtttag   3120
atgccaaaat accttcaaaa aagtttaaat tatactaagc agccagttaa gaaggaagca   3180
gcaacatatg acctgattta gaaccatctc caagatgtat gaggtggaaa gaagcaaggt   3240
gcagatgagt gggctgcatg tgtgcttgta tatcatcgtg tcctcctgga ggaagacacc   3300
aggaactgga gagagatttt actgaggggg tagagaggcg ggggcatagc tggggcttac   3360
ggagtgggag gtggggtctg attttcgtc gtctgcactt ctgtatttgt gattttttta    3420
aaacaatgtg tatttattaa ctataccaaa aactaaagga aaattccaaa tacatacata   3480
taaataatga acgcagagct ctgtcgccct cctgaagcct ggggttagcc agggccttt    3540
ctctggtggg ggatttatag catcttccct tctgttgggt accccggact cccactgaat   3600
gtgcaggtcc cagtggctgc cttcagagcc tggctggaat cattaaaaag gtatttgtaa   3660
tctctggctt ctgcagaagg ccctgcaaac caagagcaaa aaagccccca gtgcttatgg   3720
gccggcagtg tgggctaggc cccggggctc cctgtcccca agagaaagac caggttgctc   3780
ggagggtgcc tctgggaact ttggtgcggg ctatttgctc ccccatggc ggcaggagca    3840
agctgggact tgtttgggaa ggccacagct gggtggtttt cctcctctgg ctgtacatac   3900
acctttcaat ccatttcttt catcttgaaa ggacaaagac cggcttgtct gagcctctta   3960
atcagtcagg ctggctttgg gctttgtggg accctgactt tctcaggtct agctttctgg   4020
gacatcactc caaattagat ggcagagtgg cttttaacag agcgcactga ccttgttttc   4080
tttctctctc tgtccctaaa ctcgaggtca ttagttaggt gaagacctgg gctgcagttt   4140
ggcgagacac ttcctgtaga tgcttctaat gttggccttt aatttctgct aagcagcagc   4200
acacaaataa atgccctgtc ccttctatcc tgttgtagct tggaatttct ccataggagg   4260
gacttggggg tggcagtagg gttggagagg gttgggggga ggtgtaggag acttgtctgg   4320
ccactgagtt tgctgagaaa gtactgctat agtgtttttc cttggattgc aaatcatgtt   4380
gatctgtagt attcgaagtt ttctaaaggc aagtttattc tcacaattta cataagagtg   4440
agaaaatatc acttgcacat atcaaactat tacttcttat tatggtggga gtttggcggg   4500
gggggcatgg gtgaggatct tggcagcctc tgctgcccct tcgccctgca ctgcagagct   4560
ctgctgtctt gcaggcaggc ggcctgcgtg cgcgggaggg gggacccttg cctgaattct   4620
gaaggctttt gcagacctgg tgcatttatt cttccttctg tctgccgcca aactggtttt   4680
tgttcctata agtcgttctt ggaattcaag ttttttgcca ggctgagcgg gatctaaact   4740
agaggggaaa ctagagggga atttacgaca aaaccaggtg gtgggaatga ggactaaagg   4800
ccgcaccta tgacaaagcc cagcctgtac cataaagccc caggcaatgt gaactgagct    4860
gcctgagtga gactcccatc ttcccagcct gggcccctta agttcaatgg caagatttgt   4920
aaactggttt ggattaacaa ccccgactcc tctttgtaga cttaattttg gaattcaaaa   4980
cagctaccct ctcttaaata atccccaggc aatggcgact ccgcacactg catctagcca   5040
tagcccgtta ccattctttc tctgggaaga tccagcagct ctgttaggaa tcttgtaaag   5100
tagccggctg gcactagggg agtggaagtc atcatgttta tctctggtcc aggtaatgaa   5160
ggcatgaaat ttgtgtaatc tttgaaggaa agaagagaa agttggaaac ctatcattat    5220
tggagtcagc ctataaaagt ggcttttgtt aatgtagctg aagagtaggg agaaggccgt   5280
```

```
gcagtttgat ttttgcttta tgccatctgg ctgtccttttt tgttgacaag tgtttggcat      5340
taagacctct cccactgccc gtcaagagca ggccctacca ctgtagagta ttagaaaaag      5400
attctgttac agtttaaaaa tttccttcag ggagtgcttc gcaaagggga gcgtggactg      5460
caggcatttg cagctgtaac ctggcttgtg ttaaaatttg aaggggctg ctccacattc       5520 cagcactcgg agcgccggcc ctcactggtg agcagccaaa ggttaatata gatgtcacac      5580 agctccccc ttctttcttt ctgcagagcg cctttgctat aggagtgcac caacagctgt       5640 gttttcgta acccttcaa atcacttct tttaaacctc attttcctgc ttatataaat         5700
caaagatttt cctccacttt tcccaagcat gtatgtgacc cagctttgaa ctttttttcat     5760 tttctatgta ttttccttct ggaatcaagg cagggtaagg ctgagccctg gatgccaact      5820
tgggtggctg ttttggttt tggttccagg gttgtcattc ggttgtggag cggtccccat       5880
ggaaggggta acagagatgg cccacttgca aatcagtttc agggcagcaa ggggatgat       5940 tgtctgaatg cacagacaga cgaaaccgct tttgagatgc agccctctca agctacggtt      6000
tggggcttta ccatggcgta gtaggctctc aagcctttgc cgagataaac acagctggtg     6060
cgcgatcccc tcaccaccgg aatgcctgcg atgtgagtga atatcacgtg tccgctgaac     6120
tcagagacaa ctggtgactt cattccaggg agagtcccat ctaagttgat tgatcactcc     6180
tatcacttta atatctctcc ctcatttggt aaggtcatat ttggcccatt gcaagaatca     6240
gcgtgcccta agtctccccc gtctccaccc ttccccatct gcccatccgt gtaacagcct     6300
gaatattttg aatggggagc cctttgcacc atgcttctgg ccacattaat tctttcacgc     6360
tcactcttca gtcttagcgg gggggctgtt ggcacactgg tttcttggca agccactgca     6420
aggcttcgcc ttaatgcact ctggcactgt caccggggtt agggcacagg cagggatgtg     6480
tgggacctgt catgttattg tcagaaggaa tgtgcggatt agcctttaca gcgtagtggt     6540
gggagagcac tgcagctgtg tacacttatt ataaaagatt taagtcccac tggtaaaatc     6600
aatatattga attgcacaac cctctgcttt taattagttt aaatcaaatg cgccggtgcc     6660
attttgcctt ctctcgcctt catggggtga ggaactacca atatttacat agaaactgtt     6720
aatttgtggt gaaaatgata acacatttag ctttacacac tcaaattgct ccaacttgat     6780
ggatcccaga tcaacgtgga gttgagctga ggagatgacg tcaccaggag cggggaggag     6840
acacccgtga tgtctgttgc ttggaccctg gattccagat gcaggtggac atgtgtgtag     6900
aggcagtgac tggggatgct ggtccttcaa gaagcgagct ggttctttct attgcaggtc     6960
aaaaacaatg agatttacct acatcatcta aaatcctttc tcggaagcat tcttacaaaa     7020
ttgcgaagtg ggcacttgct cttgggtcat tttgagcctg ttctcacagc atgcaagggt    7080
catgtactgg gcagctcaag gcacggtgct ttatttattc cagagcttca catgcttttc     7140
tttccaatcc ctgaaacagt ttatagagga agggcgtttg ttcactgcaa atgatcccat    7200
gtacgaccgc ggctattagt gagccgtttg gtattagctg tgtgttcaag ctgggattga    7260
attccgggtt ttgcagcaaa tggcatctga caaataataa ttgacaaaaa atgtgacttg    7320
gtatttctta atatggaaca gatagttcat ttaagcttcc ccggcaaaaa aaaaattgct    7380
caaactcaaa ctgaaatagc aatgccaggg aatactagga ctgctgctgt gtatttttt    7440 ccgctccaaa gtagagtgtt tatgatttgg ggggatatta gagtgcatga agtttgacac    7500
ttacttatgc gaaactcagg caagcatgtg caataccgcc ttttcaacat ttgtgtcgga    7560
aggcattgtg gggagccgcg caaagcctgt gctgatccgc gtggagtgga ttgaattaat    7620
```

```
gacaactccg agagcaccag cttttagggta attgctttat tgttttggag ccagggtgca     7680
tataatccgg ttcctgtgca aacatgttga acgtgtgtta atgcatttcc aaaccagagc     7740
ctctcacaca accctgcttt tcattaattg atgtcggtag catggtacag tatttcaaag     7800
ggctggccaa gtataaactg tgttccaat ttccttcctt tcctgtgttt ggaatgccaa      7860
tgttaatttg ttcccatgca ggagcggggg ctgccaaccg cggctttcta taaagggctt    7920
cacagtgaag gcttccagcc ctcgctgatg cttggggctg cctggccaag tctcctgaca    7980 cttttgcagct aattctgggt gatatatggg gtggggatt gggggcttca ctgccgtgta    8040
acggaagttc tcggtgacag cagtgggtgt gacttggcaa gggagattgg aacggcatcc    8100
acagtgattc tctttagaca cagcctaaac ctatgtgtct gtttccacta tgacagcaca    8160
ttagctgtgt gaccttgggc aagttactta acatctctgc atttgtgtcc tcattttata   8220
aaggctacaa gagaatctct tcctcaacag attctaaaga aatagaaatc atatcaccca    8280
tgcgcagagg ctgtcaccta gtaggtgtaa acaaatggt agctcttgtt tttattgtgt    8340
tggccagatg aagatttacg ttggtatatt agtccaaatt tcagttttta agtacttaat   8400
cttaaaatac tgagattaaa ctgcccatgt tatttaaat gtcaagaaaa tggtccccag     8460
agtgtgaata tgtgtgcgcc tccctctttc agagatcaat ggaatttgaa tgaatgcacc    8520
aaacttattt gaggatgaat agagtctaag gctgaatctt ttccccaatt ttagcatcta    8580
tggttattta atgattttac tacttgggaa actggaactc agtgagaggg tataccggaa    8640
ctctctgtag tgcctttgca actttgaatt aaaaattaat ttcaaaataa aatgtttcat    8700
ttaaaaaatt gcattattga agtatttctt cccaatcctt tctggaagat ggtcaaagta   8760
caaattgtct tttccttcaa gggagtgaca agcccaaagc attcattaac agaactgcac   8820
aacttcccca ctttttattg gagcaggtgc aaggctgccc aaggctcccg cagctggggt   8880
taggctgcaa caacaaagcc ctgtgtggat tcagcatgtt tagaagcctc tagagaccag    8940
aggacgaaag agaatggctt cagggccaga taccgagggg tggcgtttct cattcaagac     9000
tttccataaa ttcccttcag ctctttatac tgtttgaaaa atccgactca ccaagtatta    9060
ggtttccctg catctctgag gtcacgtgtt ctatcacatc tttatctccc tggagtagct    9120
ttcaagtttc aatcttttgt tgcctggctt aattaaaatt ggccacgaat aaaaacttgc    9180
accgttccca aaatcgagga cttgtgtgtt tctaagcatt gggtttaggc ctgccctgtc    9240
ttgtgcttcc agcctgtctt ctgctttcat gtagcttgga ctacatgaag aaaaagaaaa    9300
agctaagctc ttagcatgac agttggcata taatggtcca agtgctcatc cccctggcaa   9360
cttacacaca caaaggcagg caagtttttt ttttttttt ttttggtgg cttgtgttt       9420 ggccttcaat aaaggacact tttcctgttt tttttcagac agccttattc tcctgcccat    9480
gcacagcctt gcagaattct catggcatag aaggtgctca gatattggtt gtttcggtgc    9540
acatatggca tgaagacatt ctaagcagtc tcttctaaat gcttttgatc tccaattccc    9600
actactacct tttcaggtac ataccttaaa tagtaataag ttgtataact actgcaggat    9660
agctaggata gcttgtgctt cataaaacat agacaaaaat agaaatttaa gtaggagaca    9720
ctaaagctaa aagcaataca aaattttggt gtttgttaat taatacaaat tttaactaat    9780
gaatcatttt aattttaatt gttaacacaa ttttaattaa caatatacat ttaattaaaa    9840
ttaaatttta atataattta attaagtttg cagtcatgaa aatttgcggt gcaatggact    9900
gttctttggt gttttcaaaa tcatgattta acagttagga atcactgatc taaaggcctg    9960
gtcccaaatt tcgatgaccc ttcatctggt cagtataaat gaagttattg tgtgtgaaga   10020
```

```
aactcacaat cttggtgcgt taaaaatccc agaagtttgt ttttcatttg tatcacatta   10080
tagctctatc gtgggttcag ggtggaggcg tggagttctg cacattggtg gcagcagagt   10140
ccctgggaga ggctgaggtc ctcagaatgt tacgaataag gtgccagaag gaaagataat   10200
gtgaactgtg cgttggcttt taatatttct acctgggagt gactttctaa cttcaaaaat   10260
ttctattttt gtctgtttta tgaagtacaa atgatcctaa ctagtagtta tacaacttat   10320
ttcttttttt cttttttttt tgagatggag tttcgctttt gttgcccagg ctggagtgca   10380
gtggcgcgat cttggctcac tgcaacctcc gccttctggg ttcaagtgat tctcctgcct   10440
cagcctccga agttgctagg attataggtg cccaccacca cgcccagcta attttttgtta  10500 ttttttttta ttttttattt ttagtagaaa tggggtttcg ccatgttggc caggctggcc   10560
tcaaactcct gacctcaggt tttatccacc cgccttggcc tcccaaagtg ctgggataac   10620
aggcgtaagc caccttgccc agccacaact tatttctatt tagggtatgt accccaaaat   10680
ttactcttcc acctgaaaga gcttctgctc acatttcatg ggccaaagtg agccatgtgg   10740
ccaaacctga cccaaggttg gcaaggagat gacgatacca ctgcttgctc agaaaggcaa   10800
agcaccagag agcgtccagg aaatggcaca gatgacacca cgctatcatg attgaagtgt   10860
ctctcacaag attcaaagac agaaatgtgg gaagtaagtt gtggggtgtg ttactgaaac   10920
cagagcttca ttttttcaacc ccacctgtca attatgcaga tattttttgtt gaagctagtg  10980 aactcccatg attgtcagtt ggaatttgca taacaattat aattgtaata tatcttttcc   11040
tgactcccag tgggttcctc ttgcctcctc ccatcttgcg cttcattttg gagactgatg   11100
ttctggaggc ttccatctca ctgaagtact caattggttc aacaacaata acatctcttt   11160
ccattcccac ttgtaaagtg acttcccctgt ttatgacttg tctttcagca aaggcaagct  11220
tcagcttttg tccggttcac tatctagaga attaagaagc attactctgc tcctggctaa   11280
tgaggtgact gctggtgttt ccccggaaga tacaggttat cacttcgcca tgaaatcttg   11340
tccacaatgg aagagctgct tgcttttctct cctgggcctt ggagacattc ctttttcttt  11400
cttctttttt tttttttttt tttttttttt gagatggagt ctctcgctat cccccaggct   11460
ggagtgtagt ggcatgatct ccactcactg caacctccac ctctgggctt caagcaattc   11520
tcctgcctca gcctcctgag tagcagggat tacaggctcc cacaaccacg cccggctaat   11580 ttttgtatttt ttagtagaga cggtgtttca ccatgttggc caggctggtc ttaaacttct  11640
gacctcaagt gatccacctg cctcagcctc caaggtgtt aagattacag gcgtgagcca    11700
ctgcaactgg ccccttagag acatttctta gtccaggcag gatcttgcat aggctgaatc   11760
tagacattaa attcagagac cccttcatca tctaaatgca tcactgaaat ggattgtaga   11820
cctcagaggg ctaagacctt tctgtgtagc agcaatggat tcagagtagc catctttatg   11880
gggccctcat gcagttctct cagtattctg cagggtaagc agtgtcattt ccattttaga   11940
gaggaggatg ctgaagggc ccaaacatgc acagctagga agtgtgggc agatgtgtct     12000 gtccagctct tgctgggtgc agagctgccc attctttcct cctgaacctg tggggtatcg    12060
aataggtagc ggggagcgtg gaggagatga tgttgagacc attaaaacag aagccgagcc    12120
catggccttg actctgtggt cccgtgttct gataagtgac atagagataa gcaggcacac    12180
acctttccct tctgttatcc accctgcttg tgatacctcc cctctcctcg gtctttatgg    12240
tttaaaaata attgtcaggg catagggccc tgagtgcctg tgggggggcac ctacatgtac    12300 cccataaccc ttccatgggg aaattccata gccagccaga gattggtatt ttaatagcaa    12360
```

```
ttcctcaaga tgctgtataa aaaagaccac agaaacagtt ttttttccgta tgtcccagca   12420
tgcctttgtg tacggtctgt agtattgtaa actccccaaa atcaaaatgt gcatgaacag   12480
gggattcgag agagaagcag gtgtagctct gggaggggat atggaatagt cgccccagcg   12540
cagggacttc ttttttgtttt tgtttttttgt tttttttttt ttactgtatc aatgtagact   12600
ggaaacaatg tcagaaggag aaagcaagta gcagaaggat gtttaggatg taaccatttg   12660
ttaattacac acataggcac ccccgccccc aacctcccac acaagggac caactcataa   12720
atgtattgtt tgtgggttca tacacattgc agtaatacca tggacacatg gcaggaagg   12780
actccctacc ttcagggtga gagctgcccg tggggaggag ggaaaggata gttttgatga   12840
gagtttcaaa taaatctcac ctatttctgt caagttttct gtcttttaat aagaagaaac   12900
caaaagaggc tgggcgcggt ggctcacgcc tgtaatccca gcactttggg aggctgaggt   12960
gggtgggtca tctgaggtca ggagttcgag accagcctgg ccaacatggt gaaacccgt   13020
ttctactaaa aatacaaaaa ttagtggggt gtggtggtac acacctttag tcccagctac   13080
ttgggaggct gaggcaagag aatcgcttga acccgggagg cagaggttgc agtaagccga   13140
gatcacatca ctgcactcca gcctgggtga cagagcaact ctgtctcaaa aaaaaaaaa   13200
aaaaaaaaaa aaggaaagaa accaaaagaa aatacaatgt ggtatcctgg actggatctt   13260
aggccagaac aaggacatct gtggaaacac tggtacagtc tgaaacaaat ctggagtcga   13320
gttgacagtt acacagcaat gtgaacgtct cggttttgtc aaatgccctg tggttgtgga   13380
agatgttcac cctggaggca ctgggtgaag ggtactcaag tattctctgt actagctttg   13440
caatgttctt ataagttat tctaaaataa aagtttatt tattttttt aaaggaagca   13500
actatgatgc tacctctcat catttctctg ttatgggtgc atggatgtcc atgagctcat   13560
ccaccagctg ctctttgtgg tggtcctgcc atttccaagg ctgggggcag gagagccagt   13620
cctagagcct gttcagtatg atgccctgaa ggccaataac gaatcaatct acggacccat   13680
taacacgaca gggactcagc aagtaaaaga aaaacccaca ggacagtgcc ctgagaactt   13740
taaaactctc ttttcctcat tcataaggtg cccgatataa agcagctgtt agtttatggt   13800
caagaaagag ggggtagggt gggaggagat ctaaaagatc tttcgatttt cttcttggtc   13860
ctgaattttg taaaatgccc cctactccat tccccaatct tcccacttct caagtttcag   13920
tttttgactg acttgaccta acatttcttg agagagaagc ccttaaaaat ggcagcaggg   13980
cctcagaacc ttccaggcta gtaaatgttt atgggatgga ggcactggtt ggtcatttcc   14040
tttaggagga aacaataaat gaagctactt gccttatgcc tactcaggcc ctgagctcct   14100
aattatctta atatactggt gggaagtggg gatggaaggg ggtgggggac ccagaaatct   14160
ctgcgcctct ggagcttgga agtgcccttt ttagtacgtt tagtgtgcag tttctcagcc   14220
tgggcactat tggtatgttt aaccagatcg ttctctgctg ggagctgtcc tgtgtattat   14280
aggatgtttg gcagcattcc tagccctcc cccaggatct gacaaccaag tgtatctcca   14340
gacattgcta actgtacccct gggggcaaa gttgccccca gttgagaacc actggtttag   14400
agtaacttgc ctcaaccttg ggaattcatc tgggagcctt agcctcaaac gcactgaccc   14460
acagtggtga gtgggaaaaa cagcatttct agatggacgg gttatttct ggctgaaaga   14520
agcacagatt gcaatcaaaa ctcgaggctt ctcctgggaa cacagctcta cctggctttg   14580
aaacaccctg gagactgaaa tggagctcaa gtctctaacg agcaagcatt gtctcctggg   14640
aaccaaaata cttgactgca ccttttgctc gatgatgcta aaagtttatt aaacacacat   14700
cgaggactgg cccctctttt attttatct tcggacgttc ctcaggaaga ataggggcaga   14760
```

```
tctctctctt accttgttcc cctctcttgg caggtaactt actctggggt gggagaggga    14820
aggtgagcac agaagctata ttttcccgtg tctccctgta gcttaaatgc tgcttggagc    14880
agggagacct gcttgcttca gaccccagcc cgcgggccaa ctccagccca caacctgttt    14940
tagtacagcc tgcaggctaa gaatggctgg tacatttttt aaaagtgtga taaatactcg    15000
agaagaatca tatttcatga cactaaaatg acatgaaatt caaatttcaa ggtctgtaaa    15060
taaagttttta ttggaacaca tctatccact tacgcattca ctctgactgc tttactgccg    15120
ctgcgacagg gttgagcagt tgccacagac acgatggtga ccgaggccta caatagtttc    15180
tgtctggctc ttcatggggt ttattgatcc ctgctttcca cacgctatgt cccctacctg    15240
ggaaagtgca aaaagtaaaa aagcctgagt tttgttttgt tttgctttgt ttttttgaga    15300
cagagccttg ctctgtcacc caggctggag tgcggtggcg cgatcccggc tcactgcaac    15360
ctctgcctcc cgggttcaag caattctcct gcctcagcct cccgagtagc tgggattaca    15420
ggcgtgcatc accacgccca gataatttt gtattttag tggagacagg gtttcaacat    15480
gttggccagg ctggactcaa agtcctgacc tcaagggatc tgcctgcctc ggcctcccaa    15540
agtactggga ttacaggcgt gagccactgt gcccggccaa aagcctgagt tttttatctg    15600
tccctttttgt ccttctgcag acagtgactc agccacactt cctgccccccc ctccatgttc    15660
actggagctc ctctgagtct gcgaaagctg taggttaaag gatgtcccct cggaagactc    15720
ctctgcatct ttaacatgag gcatgtgctc tgagtcccca caagggtgat gtcgaacaca    15780
gggaggcttt tcctgcgttt gcttggtccc agcaccctgt tctcctgtgt ttttgaaaaa    15840
attctaaaat gtctcagatg gtagttaaga gtttgggtct gagtcagacc gtcagactgc    15900
agagccccca ccgctctgcc cccacctccc cgactcaggc aggttgttaa accctgggtc    15960
tcctgtttcc tactctgggg ttaatgtggg tgcctgtctc ctgggctgct gtgaagatcc    16020
catgtgggga gacaggaaga gggctgacct cgggccgcct gcagctggtg cctggggatg    16080
tcagtggtag gcagtgatgc tgtcatttgc tacaccatag ccaatcagga acccaccgtg    16140
cacgggacct gcctgtgccc tgagctcagc tgctctgtta cccaccgtgg tgggatgtgc    16200
tgctggtttg tgctggggtc cagagcaggc agtgggcacg gtggccccca agccgtgtct    16260
ccacaggact tggatcaggg cagctggcct tctctttgcg atgataccte agctgaaatg    16320
ggaggcttgt cggtgtcgac tggacacagg caaaacagga aactgggtgt attttgacga    16380
atcctgttat actagaaaat tgcctcctgc tgattaagat ctgtgtttat tggtgcagag    16440
ttttaaggag acaccagat ctgcccaccc ttgccggctg ggggcacagg caacctgctg    16500
ggtttagaca gttgactgtg ggctggccta ctccaaaaaa agcacatcaa taaaactttc    16560
acagtaaagt tatatatttt tcttttattt ctttgaacac cattcatgtc agacttagtg    16620
gggtggcatt tctgtgtttc cctcactttt tgatatgggc aaatgaattt ctccttttt    16680
ttttttttt tgagtcagag tcagggtgac aggttctgtc atccaggctg gagtgtagtg    16740
gtaccatctt ggctcactgc agcctctacc acctgggctc aagtgaccct cccacctcag    16800
cctcctgagc agctggaact acaggcatgt atcaccatgc ctggctaatt ttttgtgtgt    16860
gtatatatat ctatatttaa tatagatata tattatatat tatataaata tatttatatt    16920
aaaataatat atttaataaa aatatactct atatatattt ttgtagaaat tgggtttcac    16980
catgttgcct agactggtct tgaactcctg ggctcaagca gtcctcctgc ctcagcctcc    17040
caaagtgctg ggattatagg tgtgagttac tgcacctggc ccatttcttc attttaagtg    17100
```

| | |
|---|---|
| aggaccagcc catgccagat gttcattaaa tagcatgatt tcaacattta tttttatgta | 17160 |
| tgtgaaaata gggtcaggaa tgacaaatta ctcgccgagc tttggggatg caagtctgt | 17220 |
| ctgtctttgg gtccaggtca ctggtgtgtg tcctcaggca agttactgaa ggggttggag | 17280 |
| tgctctgggc ctcagtttcc ctctctggtg ggtggctcaa ggctcaggac actaggattg | 17340 |
| agtgagatca tggcaggaag gggctcagtc ctcacctgca gggaactctc agtaaacagg | 17400 |
| gctgctcctg gctgccttgg gggtccagtc tcgctgcaga gcctcttcta ggctcatccg | 17460 |
| tgaacatgac agtagaccaa tatcaatgga gaacatgaca atggcctgat gatgttttag | 17520 |
| ttcagcagct gtaattcatt ggagatgcct ggaagtttgt gactaaatac agccctcata | 17580 |
| tccaagacta tacacttccc tgagtacctt cacatttcaa acattatatg tatcttattt | 17640 |
| actcaactcc catcatagat tttgaaaaga atccgggaca tttgaaaaag tgcgatgcag | 17700 |
| tcacccctgc atcaggggta ggctaaagac agcaggtagg acagacattg ggtagagtgg | 17760 |
| gaattacctt tgaatttcca tgggaagctg tttcgttatg cagtatctcc atatggctga | 17820 |
| gttccttctc ccagtttctc tcccagtgtt gcagcagatc actgcttctt ccgttgcaca | 17880 |
| tgggatgaaa taatctgctt gagtgtagga cctgtatcat accaaaacac ttgccttcaa | 17940 |
| acactagaag gtaagaagtt tggtatgata caggtcctac acttaaggac cctctgggtg | 18000 |
| ttatacttac acttaaggac ctataacacc ctctgggaca gcagatacta taagagatac | 18060 |
| acatcctaat ggccactacc tgcttctgtg gagaggaatg gtgtttcatt tagaactcgt | 18120 |
| tcagcagtca gccgggcgtg gtggctcatg cctgtaatcc tagcactttg ggaggccgag | 18180 |
| gcgggcagat catgacatca ggagatcaag accatgctag ctaacacggt gaaacatcgt | 18240 |
| ctctactaaa aatacaaaaa aaaattagct gggcgtggtg gtgggcacct gtagtcccag | 18300 |
| ctactcagga ggctgaggca ggagaatggc gtgaacccag gaggcggagc ttgcagtgag | 18360 |
| ccgagatcac accactgcac tccagcctgg gggacagagt gagactctgt ctcaaaaaaa | 18420 |
| acaaaacaaa acaaaacaaa acaaaaacaa aaaactcatt cagctgcagt tcacagaaca | 18480 |
| cctgcctagc atggcttcag cacaaaaaca tgtcattatc tcccctaata gcaagtcttc | 18540 |
| agggagatga gttcacgttt gcaggggcag ctcagtgata ctgtccaagc atccatgagc | 18600 |
| ttcccacctc cccctaccac catcctcaaa ttcctcatgt ctcttacctc atgcttacaa | 18660 |
| aatggctgct gccgcccag ccagttcatc ctcatgcaat ctcacattca aggcaggagg | 18720 |
| atggggaatg gcacaaagag ctctccttgc ctgcctgcct acctcttggt ttcctagaag | 18780 |
| ttccttggaa gacttctcct tgtctcttgg gctaaactgt gtgtaagccc ctgtcttgtt | 18840 |
| acttcgaggg agggtgtgaa tgtatgcagc tggcatctgg ccagcacagt gggaggcagg | 18900 |
| ggagggaaaa gtgggttggc agtggttgtt gggtggccac attcaaatga ttgaaatggt | 18960 |
| ttctctctcc ctctttgtcg ttgtttcctg tgttgtatac agttagattt acaaaagtta | 19020 |
| tttgtacatg tgatgtggtt ccactgtatg cacatataaa tagaggccct aagcaagctt | 19080 |
| ccaaagcctc cagatgatag tgttccactg tgaatatata cagaaggttg gttgcacatt | 19140 |
| gacattaatt taaccagacc ctctgtagct catagaaaga ttttagttat tctttaaact | 19200 |
| caaacctacc tacaggtagg tacattagct ctaactttga ggactatata gaactctagc | 19260 |
| caacagccag ttgtttgctg aaaacaagct ttgtttttatt aacataaccc tcctgatctc | 19320 |
| ctgagatagg ggcaaaattt cttgaaaatg acccgaggag gtcaggaatt attgtcccct | 19380 |
| gggaggaagc agaggctggg gtggagcttg gtttgagttc tgcttgtggg acaggcggct | 19440 |
| cctgtttccc ctgagtggag gatgaacaga gcaagagact caaagcattt taagaatctg | 19500 |

```
tgtcagtgtt tgttagccaa gggtggagag ctgcttgaaa gaaacgcctg cctgccctgg    19560
tggaatggtg gaacctcatg cttacactgg gagcctgatc aaatgttttc tagtaaaggg    19620
ttctgggcac ctatatgcct tctgcttatt cccgtgggag actaacgtga tagggtctgg    19680
gtgcctcctt aagcccgttg gttggaggag atgattaggg gagaagctga gaggtggttc    19740
tgaaaaatat tttgctttct attaaatggc tgctgagcaa acggaactct ctgttctcgt    19800
ccccattgtc ttgccttgaa tgtggttttg tgaagacatg ttgcttggaa ccacagcagc    19860
catcttgtga ctgtgggaca agaggcctaa gaattaagtc aacatgcaga caatgatgga    19920
gcaaagaaga cagaagaaat tggggttctt agtcatatgt ttgaactact acattcaact    19980
acaattgttg gggggaggct cttaagcagt ttgaatcaca tgttcactca tgaatcagtt    20040
gggtctagag ggtagaccag gctgcatcaa cacagttgct ggagtcagcc tctgcccctt    20100
tgtgcctggg ctggggtgtg gaggtgtgtc tactatctga ttacagctat gttagccatt    20160
gtaataatca tcccagtagt gaacatttgt caaaggctta ctatgtgcca agcacccttt    20220
gtcctctttt ggttttttt tgagatggag tctcgctctg tcacccaggc tggaatgcag    20280
tggtacaatc ttggctcact gcaacttctg ccttctgggt tcaagtgatt ctcctgcctc    20340
agcctcctga gtagctggga gtacaggcac gtgccaccat gcccggctaa ttttgtact    20400 tttagtaggg atgagttttc accgtgttga ccaggctggt cttgaactcc caacctcagg    20460
tgatccgccc acctcggcct cccaaagtgc tgggattaca ggcatgagcc accgcaccca    20520
gcctgtcctc tttagttaat attaacatat ttaatttca tgacagccat ttcaggtggg    20580
gcagttatta tcacccctat tttacagagc agataaatga gcagagagcg gtagttggcc    20640
caagaccaca tacccagtta agcatcattg gatttggaga tccagttcct ggagacttcc    20700
ctcttacact tgatcctgaa ctgcttctca agcctgaagg ataggtttgg agcaggccag    20760
tcaacagcat tgctaattgg agagtctcac atgagggcag gaggaagaca catagggggtt    20820 ttacagttat gtgtgtcagg cctaatgccc tgtatctttg cttatcaaag tttctgaaaa    20880
ccaggatgta tttaaattga ttaagatatt ggtatatttt cccaaagagc ttctgttgaa    20940
ttgattgtgc ctcttagtat ggtgacaagc gtgtgttgag tagacctggc aatgggtaaa    21000
gctaacaaca cttattatga ataaaactgc taattgagtt ttaatgaaac tgcttattga    21060
ggtgtaacgt gtgcagaaca gcacagaaat caagagcact tgtgagtgtt tacaaggcaa    21120
tcacacaggg taaccagtgt gtagatcaag aagcagaagc gaccagaacc ccctcgtact    21180
tgtacccagc ggtaactatt gtcctgtttt ctaatagcat aaattaacct tgcctgtttc    21240
taaactttat ataaatttaa ttgtacaata atactgttaa atcactaacc atggccgggc    21300
atgctggctg acgcctgtaa tcccagcact ttgggaggct gaggcgggca gatcatgagg    21360
tcaggagatc gagaccatcc tggctaacac ggtgaaaccc catctccact aaaaatacaa    21420
aaaatcagct gggcgtggtg gcgggcgcct gtaatcgcag atactcggga ggctgaggca    21480
ggagaatggc gtgaacccag gaggcggagg ttgcagtgaa ccgagatcac gccactgcac    21540
tccagcctgg gtgacagagc aagactctgt ctcaaaaaaa aaaaaaaaa aaaatcacta    21600 atcacaggag caatgatttg gaaagaagac cccaagtaga acttttttgga gtctgtttgc    21660 aactcttcca gttacatttc atataggata caaaatgtaa tttaaaaacc attctctggg    21720
ccccgtaggg tgcctcatgc ctgtaattcc agcactttgg gaggctgagg caggaggatc    21780
acttgagctc aggagtccaa ggcttcagtg agctgtaatt acatcactgc actccagttg    21840
```

```
ggagtgacag agtgagaccc tatctctata aaaaataaaa attaaaaaaa aacaccactt   21900
ttttgttttg atctcatatt ctcctgcttc ccacaccgga aagaggttta aaggacaacc   21960
atgcaatttg aagggtgttt tgatcgttta gcttagggat ttaagtttga gttcttacaa   22020
tgtgaacttg aaatgagtga ggctcttcaa gatttccagt tcccaccaaa tctgccccat   22080
cagcccctgg ggcggctttt gtacgtctct gcaccttcct gttttcagaa atgaagctga   22140
ttactgtggt ccagggacag agtgtggctt taaagaagac tcttattttg aaagggagac   22200
aggggctggg catggaggaa aggcagaacc atcttttcct tcactgcacc tgcatctcct   22260
gggcctaatg agtttaggct gatggaaccc aggcctcagg aaggattata aattctcatt   22320
tgatttgatt tgcctctaaa ataccttaaa ccagctgtgt ctgcccagct gacccaagcc   22380
tctctggctg ctctgggggg aaggtctgag caggctcctc ctgtcctggg aagggaggg    22440 aggacggcag cttcacttcc cccacctggc tgctcttggg gcctgctctg gcctggctgg   22500
gagcaggcaa ggcacaggtc tctgctgccc tccctggtgg ccagcctcca tgtccttgaa   22560
ttctcccaac agccccagaa ctgggggcct ctgcctgtcc ccattttata gagagaaaaa   22620
gttgagcctt ccagaggtgg gttaacttgt cctgggtcac tgctggtgat tggcagagcc   22680
tgcgtgtgaa ccagacctcc aggccccatg gcccacgctc aacccagtt ctctcctgca    22740 tcctgggctg agtaaggcta aggagccggt gtcttcctcc tgatttgctc acggggagag   22800
tttcaaaacc cacttcacta agtctccgga gaagctgctg agtgcccagc aagtgagcgt   22860
gggaggtggt gtgtgaacag tgctaagcaa cagagcaatc agagcgaata gcttccaaga   22920
ctattacatg tgccaggcac tccatggaca ctctccttc ctctggttct caaagtgggg    22980
tttctagacc tgcattatca ccatcacctg gcatgtgtt agacattcat gctcttgggc    23040
ccaccctaga tcacccacct tagacatgct ggaagtgggg cccagtggcc tgtgctgtaa   23100
taagctcgcg tgtgactctg gcatcctga aggtggagca tgcctggtct actttactcc    23160
tgggctttaa ctggcagccc agtggagtca gtgctattac tacacctgca tttcacagaa   23220
gaggagtgac gcgccccagc aagtggcaga gccgagactc gccctctcgc ccggctctgc   23280
tctggaaacc tcctgagtcc tgctcctttg ctcagttctt actttcctgg agttaaaatc   23340
tagaagagag gacagtggag aaacaggtca gcaggtctct caccaaaata atcccagtag   23400
ttaggctatg ggagggaaat gaaaggggct gagagggaag gaggcccagg gagagtgtca   23460 gtggggggtga gaccaactca gccgtgggga ggggctgcgg tgcccgggca ggcctggagc   23520
aaagcctctg cggtcgtgaa cttggcacgt ctaacaatta ccagcaggat accactcgcc   23580
aggtgcttgg tggggagtgt ttgctcccta ggtgacccca tgagcagagt gaggatcctt   23640
gtacctgttc aacagccccc atcccaggcc tcaaacccgt aagtcaggag ttaaattcct   23700
gaatttctca cactgggaac gccatttcat taatttttt aattatttt tttttagggc     23760 agagtcttgc tgtgtcaccc aggagtgcag tggtacgatc tcagctcact gcaacctctg   23820
cctcctgggt tcaagcgatt cttgtgcctc agcctcctga gtagctggga aacaggaat    23880 gcaccaccac gcctagctaa ttttttgtatt tttagtagag acagggtttt ggcatattag   23940
ccaggctggt ctcccggact caagtgatac acctgcctcg acctcccaaa gtgctgggat   24000
tatgggcgtg agccaccaat cccacagttt taaagaaaaa ctttctccta catctctgag   24060
aacatagtcg ggaccctca tttgcagtgg cccctgcaa accttggtg ctacaaagca      24120 gtgtgggcga cagcacctct tcaatgatgg ggacacctgt gatctgggct gtccactagg   24180
aaggccatga gccacataca gctgtttaga ttttattta tttttgaga tggaattttt      24240
```

```
gctctgttgc caggctgga gagcagtggc accatcttgg ctcactgcaa cctccgcctc   24300
ctgggttcaa gtgattcttg tgcctcagcc tcccgagtat ctgggattac aggcacgtgc   24360
caccatgcct ggctaatttt tgtatttta gtagagacga tgtttcagca tattggccag    24420
gctggtctca aactcctgac ctcaagtgat ccacccacct tgccctccca aagtgctggg   24480
attacaggca tgagccactg tgcctggcag ctgtttacat ttaaattaat tacaatgaaa   24540
tacaattaaa cattcagatc tcagtcacgg aagccacatt tcaagtgctc agtagcccca   24600
cgtgtctcag tgtgctttac cagacagcac agatagagcc tccaagctgc cccgaggtgt   24660
tagggtgaac cccatacagg tcaaaactgg tagagtatca gcagcttttt acatggtaca   24720
gtctaatagg cgagaaaagg gacttcagag aaattcagtc ctttccttg ttatgggagg    24780
aaactgaggc ccagtgagcc tggggttata ccagccagct cacagctcag atgaggccaa   24840
accccaggtt tcttgaccct cttgagctct gcctgtctgt cggtccagat caaggactct   24900
caactcagca ctagtcacat ttggggttgg atggggacc atcctgagca ttgtgaaatg    24960
tttagcggtg tccctggtct gtacccagta catgccagga gcaccccctc ctaagttatg   25020
acaaccaaaa atgactccag acaatgccca gggtgccttc atgggagtga ggggaggaca   25080
aagtcagctc tggctgagaa tcactggttc ttttccctca atttcaatga gctgaggatg   25140
gggttggaac ccagacatcc ctggagactg cgttcctccc tctgggaggt gggaagccgt    25200
aggccagggg gctgtctggg tctatagtag aaagagcaac atgtgcttgc ggcccattt    25260
tcttttcagc tctacgggca tctggtctt tttaggcaaa gaactggcct cagctctaga   25320
gataattaaa cccatctttt ttccctctcc ctgcccatc cctaaaccc tttggttcat     25380
tcaattcaca atgataacat tgttcaagca acactgcaca catgttgaca ttgaagtgtt   25440
taatcttgtg gtacaatcat tccctctggc ccctacccca acatctgtgc aggctgcagg   25500
ctcagggctc atgacaagag gatggccaag gagatgcctg cctgtggtct cgcctccagg   25560
tctcatgtct ctggacgcag ccccccagca cctaacaagg aggcagtgtc tccaaagacc   25620
ctcttggaga gccaggcggg taggactcca ggtggtattg ctggcagctg aagcatttgg   25680
tggaaagttc gagagttgaa gcagttcagg aacaggggag acaatgctgc ctgtgtgccc   25740
tttgccaggc agggccctgc cccccaatct ggggcctgg ggaggggtaa tgaggagatg    25800
ggtgaatgct acaaaacctt caggctgtca gcctccctcc ctcaaggact ggcattaggc   25860
aggagcaaaa tttacaagtc tgagagggag ctgagtcgga tgcagaacct tcactttgag   25920
tttagctttg gagatttatg tggcgagtgc atcgagtgtg ccaagagcag agcatggttc   25980
agctcagagc tgtccttatt gaatcgttgc cacagctaag aggtcactgg cagctcccat   26040
gtgaggaaga gagttggtat ggctgagtgg ggaagagtac gggcctttaa agattcagat   26100
cagctgtgtg accctgggca agagtcagtc tgagcctcag tgtcctcatc tggaaagtga   26160
gcacgatgtg tcccctgcc tctgagaggg gttttcataa ggattcagtg agatgatata    26220
tacatgtgaa gtggcagcca ggccagtggg agggcttcta aaatgctggc tgcccacctc   26280
acagccatca ggatggtcac tgatatggtt tggctgtgtc cctaccaaat ctcaacttga   26340
attgtatctc ccagaattcc cacgtgttgt gggaggcacc caggggagg taattgaatc    26400
atggagtcca gtcttttccca tgctgttttg gtgataatga ctaattctca caagatctga   26460
tggtttgatc aggggtttcc acttttgcat cttcctcatt ttctcttgct gctgtcatgt   26520
aagaagtgcc tttcacctct tgccatgatt ctgaggcctc tccagccatg tggaactgta   26580
```

```
agtccaatta aaccttttc ttcccagtct cgggtatgtc ttttttcagca gcatgaaaat    26640 ggactaatac attaattggt accagtaaag tggggcattg ctgagaaaat acccaaaaat    26700
gtggaagtga ctttggaact ggctaacagg tagagattgg aacagtttgg aagactcaga    26760
agaagatagg aaaatgtgga aaagtttgga attgcccaga gacttgttga atggctttgc    26820
ccaaaacgct gatagtgata tggacaataa aatccaggct gaagtggtct cagatagaga    26880
taaggaactt gttgggaact ggagcaaagg tgactcttgt tatgttttag caaagagcct    26940
gacggcattt tttcccacc ctagagattt gtggaacttt gaatttgaga gagctgattt    27000
agggtatctg gtggaagaaa tttctaagca gcaaagcatt caagaggtgc cttgggtgtg    27060
ttaaaggcat tcacttttaa aagggaaaca aagcataaaa gttcagaaaa tttgcagcct    27120
ggctatgcga tagaaaagaa gaatccattt tctggggaga aattcaagct ggctacagaa    27180
atttgcataa gtagcaagaa gcctaatgtt aatcctcaag accatgggga gaatgtctcc    27240
aggccatgtc agagaccttc atggcagccc ctcccatcac aggcctggag gcccaggagg    27300
aaaaagtggt ttcatgggcc agtctctggg tcccctgct gtgtgcaccc tagggacttg    27360
gtggcctgtg tcccagccac tcaagccatg gctgaaaggg gtcaatgtac agcttgggct    27420
gtgatttcag agggtagaag ccccaagcct tggcagcttc catgtggtgt tgagcctgtg    27480
ggtgcacaga agtcaagaat tgaggtttgg gaatctgcac ctagatttca gaaaatgtat    27540
ggaaatgcct ggatgcccag gcaaaagttt gctgcaggag tgggtccctc atggagaacc    27600
tccgctaggg cagtggggaa gggaaatgtg gaattgggac tcccacacag agtccctagt    27660
ggggtgcagc atagtggagc tgtgagaaga gggccactgt cctccagacc ccagaatggt    27720
agatccaaca gcttgaaccg tgtgcctgga aaagccatgg tcactcaacg ttcaatgcca    27780
gcccatgaaa gcagctggga gggaggccgt accctgcaaa gccacagggg tggagctgcc    27840
taagaccatg ggaagccacc tcttgcatca gtgtggcctg gatgtgagac ctggagtcaa    27900
aggagatcat tttggagctt taagtttga gagccctgct gaatttcgaa cttgcatggg    27960
ccctgtaacc cctttatttt ggccaatttc tcccatttgg aatggccgta tttacctgat    28020
acctgtacct ccattgtatc taggaagtaa ctagcttgct tttggtttta gaggctcata    28080
ggcagaaggg acttgctttg tctcagatga gactttggac tgtggacttt tgagttaatg    28140
ctgaaatgag ttaagaattt gggggactat tgggaaggca taggtggctt tgaaatgtga    28200
ggatatgaga tttggagggg ccaggggtga atgggtttg gctgtgtccc caccaaatct    28260
caacttgaat tgtatctccc agaatgccca tgtgttgtgg gagggactcg ggggaggtaa    28320
ttgaatcatg ggggtaggtc tttcctgtgc tattctcatg atagtgaatc tcacaagatc    28380
tgatgggttt atcaggggtt tcagcttttgc ttcttcccca tttctcttg ctgctgccat    28440 gtaagaagtg cctttttgcct cccgccatga ttctgaggcc tccccagcca tgtggagctg    28500
caagtccaat ttaacctctt tttttttttc ctggtctcgg gtatgtcttt gtcagcagca    28560
tgaaaacaga ctaatacagt caccatcaaa caaaacaaaa cagaacagaa atcacaatg    28620 gtggtggaca tgtggagaaa ttggaaccct tcccgactgc cggcgggaag gtaaaatgct    28680
gtagccacta tggaaaacag aatggtgctt cctcaaaaat attgaaaata gagctacaat    28740
gtgacacagc gatttcattt ctgggtatgt ccctgaaaga tttgaaagca ggatctccaa    28800
gagatatttg cacacccata gtcacagcag cattactcgc aatcacaaaa atgtggaagc    28860
tgcataccat tcagggatga ataaacaaaa tgtggcccat ccatcagtg gaatattatt    28920 cagccttaaa aaggaaggac attctgacag gctacagcac ggatgaaact tgaagacatt    28980
```

```
ttgttaagtg aaataagccg gtcacaaaag gacaaatact gtgtgattcc atttataggt  29040
gttgcccaaa gcagtcagat tcatagagac agaaagtaga agggtgggtg cctggagctg  29100
gaggagggag gaagaaaggg gagttagtgt ttaatgggga cagagttttg gcgttgcaag  29160
atgaaaaaag tcctggagac tggatgtgca agaatggtat cccgtgtgtt taaaatgact  29220
gaactgtaca cgtaaaagtg gttaggatgt taaattgtat attctgtgta ttttaccaca  29280
attaaaaata aaagttttaa aaaatggtgg ctgtttacct ggcttaggtg ttccataggt  29340
tgtcagggct gcaatctaag tgagcttcta tgaactactc ttctacagta caactgacgg  29400
ctctcacgtc catgctgggg cagccagaaa gtccttgttg aatgagtaca gtggaggtgt  29460
tatctgaaca atgtgtatca ttgtcaactt ctaggcgatg ttctgtttct ctgggcatag  29520
agcattctcc tcccttctcc caagagctgt gtgtgtcagt gtggcctctc caggctgctc  29580
atgttattaa gagaacattt tcctgttaga gtagtcaggt atgtctgttc cactttccag  29640
aattcccaat ttattgcatg cctctggcgg ctttttcaag ctccttaatc ttgccatgta  29700
aatctttgaa tgaatgaatg aagagccatc atcaaatttc acatccctga aactgtgggt  29760
cgtaaactgc ctcctaacag cagccgggat aagtcagctc cagtgagttc tggtgtgtgc  29820
cagaaccttc cagatgagct gtagccctcc agggaaagag cgagccaggg ttggtagttt  29880
cagagttaaa tgggtaccgg ggacgttccg ggatatgggg ccctgagcag tcctcgggtc  29940
tgtgaaaacc cagttctgac ttctggttat aatgtggact tcgattagtt cttttagccc  30000
cttgagcttc atcctcatta aagtggggtg tgggggtctg tccccggccc ctaactggag  30060
ctgaagaatg ctttggacta gtctgtgctc acagaaacca gactctgagt gaggaacatg  30120
gaattctaat gctggacttg tggttttttgc ctggaaagca tcccttttgct cataaaaatat  30180
ttgttcctgc ctcatagttt agcggcatct ttgggggcag tgagagggcc gcatagtctg  30240
gaaggttaac caaatttttt ctgaagacca taaagttttg gaaggagctg ctgggtgatt  30300
atttactatc catttatcaa ctcttttccag ccctggctgg gagaacgtct tcaggaggaa  30360
atgaaggcgg ctttgcctgg gctgacggtt ccccttttca tggatacaaa tatctttcat  30420
gtgcaactgg ccacagtctt gctcgtcagg tgttttttttt tttttttatgc atggctgtcc  30480
ccatgagagc tgcttcctga ggtctctgag caaccagtga ccaaatccag tgaatggtcc  30540
ctggaagagg ggtctccctg cccccttttct ctgaatctgg ccactgttgc gccatcttgc  30600
cctgccagtc ctctggtcct tcccttcctt tggaccaagt ccttctggtg gcatcgttct  30660
cccccctccca ggtagcccca aatattgatc caaggccatg ctagtctttc tcatcataaa  30720
tgcatttttc gtgcataact ttatccataa acccaattca acagctccca gcttgagcat  30780
tcttgccagg gttatctaaa cctctttttc caactgtcca gttgaacatt ctgcaggtca  30840
tctcaagttt cacctgtctg cagccacacg tgtttcttcc ctaccacttc acctcctgag  30900
cgctctctcc tgtgttgata tctactgatg gtgttatcgc cctcctggca ttccaggccg  30960
gcagtgggca gcatcctcta gttcccctc ttcatatgct tgcttttaat caattgtctt  31020
gttccttccc ctagagaagc acttctggtc cattacactt ctggggtcct gacaagagat  31080
ggaaaatgct gacatctttt ctcttgagcc agtcaagatt gatagtggct gcctgggtgc  31140
cagaattaag aaaggagtgt tgccattgtt tagtgatgcc tacctcgggt gccaggaggg  31200
aggaggaggg tgcatgtact gggtatgcat catctctgat cagagcctcc tctgagctcc  31260
ctgcctctgt cctcactccc tgcctctgtc ctcactccct gcctctgtcc tcactcccta  31320
```

```
taatccactt tccacagggt caccagtcct ctatctaaaa tagatctggt cagggcactg    31380
ctttgtgtct aacaagggac caagccatca tggttgatga catcaatgat caaccccttc    31440
gcttgacatt caagcatttt cccaatgagg aatttgttgc ttttttcttg tcgttctcag    31500
caaacttctt acctaaactc cccagcatgc cctgtttctt gtctgtcgag ccctcgatca    31560
tgctgttgcc tctgcctaca gtgcccttcc ttgtcctctg ggactagtgg gcctccgttc    31620
ttccttaaga gtccattcag cacctctcct ggaagaaccc tcacctgcag agctgcctcg    31680
tacctgaacg caggcactgg gatttgccaa agtcaacaaa aatgaatgat ctctttaggg    31740
actgtgtctc ctttggcctc ataccctgtt tccccaaaat tgttgacatg gaaacagtca    31800
gatgtggaac taaagttgaa cgtgcctacc ctctgaccca gaaatcctgc ttcaagacat    31860
ttacccagtg gacacgtgtt caccaaaagc catgcacaag agtatgcatt gcagcacagc    31920
ttgtctcaaa ctgtaaactc tccaatggct caaactggaa actccccaaa tgactataaa    31980
aaaatgagtt gtgtcctatt catacgatag ggttctagac agcagtggga atgcatggac    32040
cactggtaca cagaaccaca tgagtgaggc tgtggaaggc tgcagacaca gaagagaaca    32100
catctgtgat tccatagtca ggtctcatgg aggcagagcc agtccgtggt attgggtgtt    32160
aggaaggcag tcagccttag gggaggaggg actggtgttt ggggagggacc cctgtcggga    32220 cgacttcgga gctggtaata aatgttttgt gtcctgccct aggtgcattc acgttgtgga    32280
aattcatcac acttcgtgaa tgcttgtctg tgtgccttac tgtgtgtacg ttatcaacaa    32340
agtagtttac ttaaactaga aaggaattgc gtgaagagta atgtgttcaa tgcagaagat    32400
ttatgaggcc ctgctaagca tcaggctgtg gagggcatgc gatccagagc tgagacagtc    32460
atgggccctg ttcttacaga gctcagtcaa gggggatgcc ttacatttgg gaatgatcca    32520
agtctgaaga aagcggtttt catggtgaat ggtcatctgg agagaacaca gctactggga    32580
gtgtttcctg cccatccatt tccacttctg ggtgtgtata caattgggct tgtgtgtgtt    32640
ttgctcagaa ctgccttggt tgcagtcagg cagcagtctg actagagtta gcttaaaggg    32700
gacttctttg aagcatctca acgtaactca tagattggaa gagctgaaac cccaaacttc    32760
aggaagggca gggactacca gaccagggga tcaacccagc aggtctctct cctcaattcc    32820
aacctcagtc ctccgtgctt ggaagcttct ttctcacaga ccagccttcc ctgcaaggtg    32880
ctggcaaggg gcttcccaga gcactggatt acatccttag agatcaaggc ggggagagcg    32940 aacagggct ctttcatacc aggttccaat aaaaataaaa gaaggcctat gtgtggccaa    33000
ggttaaggct ggcttcctcc catccctcaa ctggggagaa gagggtcatg gaacaagatg    33060
gtggctccct tggagtccca tggctcaact gggacagtga tgatggactc tccaagagag    33120
acagatacac gagggatggg agtgggggtg ggggacatg ggcaaggctc cttaacagtt    33180
gtgcattgta atgagccatg ccccaacttt gctcatcctg atgagctatg cccagcacaa    33240
aatcatccct caggaagcag gagaaatata tcttctgtat ctgtttctc gtgtttgtaa    33300 caatgtattg tgttcgttta gttttgtgca ttatgatgta cgactgtaca tatgcatata    33360
tttgggttca taccccctaat ttttaggGtg ttaaatactg tcccacggct ctgaatactg    33420
caggttctgt ttaagcacca gctgcccttt gcaagtctac agagtgggtt gccaatttct    33480
ttggttgtgg ccctccctt gtatcagaca actataactt agtgaggggt ttgcctgagt    33540
atgtctcata actgtaggtg ggaggaagaa ccccagatgt tagggagagg caaggtactc    33600
ctgagtgatg ccggggggcag gtgtgactcc catctgggac agaagtcttc cctggcatgg    33660
cagaggatca tgaagggggg gcgcccaggt gggcagcttc ttgttcctac ctggcctcta    33720
```

```
acccattatt gacaccttcc agcccagaat ttccctctt agggctggtt ttggggctat   33780
ttcgggtttt tgtaaaagga agacactgga cttgtctttg ggacagtgat gggtctgctt   33840
gctgtcagga tggtgttttc tggaatccat tttctttgga cttatctttt ggtcttgggg   33900
atttaggccc ttttaatttt ttgaagatga aagtcctttg ttaatgcctg taagctctct   33960
cagcccttgg ggtgctggga tgtaactgga ggtagaggga ggaaaagctg gaatcctagg   34020
ctctgggctt ccttaggaag cttttctctg tgggcatggg gagatgtcaa ctctagacat   34080
ttagtttaaa actcaagtct tgggtaatca actatataca gtaactttag aagaaagtat   34140
aaagacatat tttcacctga aaatacatg caagcttcta cctcttgtag tggtaacaat   34200
tcaattatct tgatacttga gttgaaatgg tgtagatttc acactgtgga gtggcttcca   34260
tagaaaaggg aaaccttgga aagatgagat ttggaagttg gtttggactt tgaattatcc   34320
actgcttatt tgtgtgtgtg tgtgtgtgtg tgtgtgtgtg tgtgtgtgtg tgtgtgtact   34380
tcatgactgt tctttctttg ataatggata caaaattatt ttcagaacat gtgacaatgt   34440
gggtttcagg gagaatagag taacattgtc gttcctgctt ctcatagtct ccaactaatt   34500
aatgaaggaa atcctctcag aaagccatac caaagagccc acaaatgttt gcaagaaatt   34560
tagttcctca ctttatccct gagtttcttt ttagaaaaga accttgtaac tctgatacct   34620
taacagttaa gatacagttc atcttctata ttaaaaacag ttgtacctgc agctgttgta   34680
acaaaccttg tgtttgtgat tatgtgtcag tgttttcttt cttcattggg catgactcta   34740
atgattgtac ctgtgtttat gtcatgctta ttcaaacgta tctttattgt tcggtctatt   34800
gcactttttt tttcaaatgt aatcataagt gcactgtgta aatgcccaca gcacatgttg   34860
cttcttctgc attgattgtc attcttctgg ctcattgttt tagaggccct gtaacaatgg   34920
cagactcaaa tggctcacct gtggctttct cctgtcagca aatggcttct gtaatcttcc   34980
caacaactcc atgagaaagg gccattgtta ctatctccag ggggagggga acacacaggg   35040
attaagtaga ttggggaagg tcacacagct ggtaagtggc acagccaaga tcaaactcag   35100
gccacctggc tctagagagt gtgaaggtca agagggtgag cttggagtt cagccgctca   35160 cctgatttgt gacctttgaa agttacccgg cctccctgag cctcagtgtc ctcatctgta   35220
aaatggggat cagtcctgtc tcatggggtt ccatcagatg atggcaaaga gtgcttgctc   35280
agtgcaggac tcacagagtt agcactcagc aaacatgtgc tttgtacttc cgggctcttc   35340
agccatcctt agttgtacat cctcagatgt tccccagccc cttttctctgc tcaggctgat   35400 tgcgtatctg ccagtggggc tgctctgaag ctgggttcat ccagcactgg gagcagggaa   35460
ctgaggtttg cggggagcca ctgtgttcaa ggcattggac tttgcacctg tgcatgattg   35520
tgggagcaac cctctctgct gaaagttgaa tcatggcacg actcaagggc tcttcctggt   35580
ctttggaggt ctggctgtgc tgcagtggag aacagagatg gttggaacag gacttcatct   35640
gtgcttcacc gctcctggtc ccctggagaa aagcactcga gaagccatga gttgtcccaa   35700
gactgtgcca cctccttcag ggggcagacc tggtctcttc cacctctctc ctagcatact   35760
catgaaaacc tctcagatgc aatgctttgg gagaacagct tccagggtga ttaaagctgc   35820
aatgcacaat gccacttcta ggcatgaaac acgtgtcctg tgatgttcat agcagcactg   35880
ctttcagagc cccaatctgg aaactccctg aacgcctatg aactgtagaa tggatacatg   35940
gattgcggtc taatacaacg atggactatc atatgacaat gaggatgaat gaacatgcac   36000
ggtgacgtgg atgaattaca caagcactgt gaaatggaag aagccagata cgaaagatga   36060
```

```
tatagtgtat gaggccctgc agcgactgtt caaaaacagg cgaagctaac ctatagtttg    36120
agaagtccag ggtgggaaag ggggttggta atgttctgtc tcttgacctg gaggaatctc    36180
cgtgactggg tttactttgg tttacacaca cgctacacgt atacaacagt gcagttaaaa    36240
agttctggca acggccagg cgtggtggct cacgcctgta atcccagcac tttgtgaggc      36300
cgaggcaggt ggatcacgag gtcaggagat tgagaccatc ctggctaaca tggtgaaaat    36360
cccatctcta ctaaaaatac aaaaaattag ccgagcatgg tgacgggagc ctgtagtccc    36420
agccacttgg gaggctgagg caggagaatg gtgtgggcct gggaggcgga gcttgtagta    36480
agccgagatc gcgccactgc actccagcct gggtgacaga gcgagactct gtctcaaaaa    36540
aaaaaaaaag ttctacaaac aagcagagga acggcccttg ttgagctctt cagctgttca    36600
cgcagccaca gagatgcatg gtggttcagg cctctggttt gggcaggacc tgggcttgaa    36660
tcccaggtct ttggccctgg ggaggtcact ggacacctcc tgggtctcag gtgcatgcct    36720
cacctaccta tgcgggattg tactcacttc ctcgggctgc tcaccttttg gggctggcat    36780
gagggttgac tgagctggaa aggtgacaga ggactggccg ggggcagtcc cacggtgaca    36840
cagtcaggcc cttgtgcccg ccttcccacc tggggtcacc tcccgaggct cacttggttc    36900
ccaagtggct gccctttacg gagactccta ccttctctgt aaatcaaagc agattggtga    36960
catccccatg gccttctctc ccattcatct ggcctgtccc atagattggg tcaggagaga    37020
agggttcctt gtgggcgtga ggggcgtgtt gtgacaagca gagctgtcat ctggaaggac    37080
cccggaacgg tttctggaga gtccttccct cccgccagct ctccatatat ggcccaggat    37140
tctagcagct gtggttcaaa ggtcatcttc ccgaggtctc tccaaagaca gggatgctcc    37200
tgtgcccagc cagagacccc agcctcaggg acttcatctg cccttcttc ctgagaggga     37260 acagcctgag cgggtaattc ccccatgctt cctgccctca cctgctctc tttttggact     37320 gttgttaagg tttaaaccag attgttttta atggagctgc gcagccaggg tcttgggct     37380 gccagtgctg tgaacttctt cctcaatggt gttcccgtcc tgctgtccca cttggaaccg    37440
ggcagccata acccagcctg agagctgaag attgctgatc gtatttctcc tttcttctga    37500
ccaatctgct ggccaaactg gttctgctct ttctccctct ctctccagtt ccccaccccc    37560
agacaggaag tggagatggg cttgtatttt cctgcagatg aaaggtgtct ggaggttctt    37620
ctcactggcc tgagtgtggt cattctgccc cttccagcac tctgtggctc ccattgtcat    37680
tcctgctcca tgttggtcca gagggggcat gatccacagg agccacaggt ccccacccag    37740
aaacaccatt cctgggcttt catcttggtg cttatcatct atgaaatgga catgacatct    37800
tagtctaata ccgctgccag gagaagggag aaaggtggag gccttttgcc ttattttgtc    37860
ctgagtcacg ttcaacctcc accccaactc tgccattcac tccttttagt gctgttagtc    37920
tactgctgtg actgtaaacc ttggcacctc attagaaata tctgggggtg ctttaaagag    37980
atatggattc ccttggttca ggaggggggtc ggagtagctg tgtgctggag cctactgtgt   38040
gcttctcttc ccatgtccag cagcctcacg ttggtagctt gaaatctgcc aagatggcag    38100
tatttacacg gtgtagtcag caggcgcttc agatcaggtc cctgagagcc aattgttaaa    38160
tgtttaccat cccagacttg gccaggaca tcagtatttt ctaaaagttt ccacagtgat     38220
tttcatgtgc attcagggct gagaacccct ggtcctagag atgtctcata ctaggcacag    38280
taaggtttat gcttaccaac aatagctaac agttatccaa ccctagcaga tgttaaacta    38340
tttgtgtgaa tgagatcatt caaccctgac cataacccat gaaggaggat tacaatcccc    38400
attttttaga tgatgaaatt gggttccata gaggttttct gttaccttat ctagggccac    38460
```

```
tctgttggtt agtggctgag gccagattcc aacccaggcc tgagcccctg ggacctgagt   38520
ctggccagga cctcttggat ggctgtggtt agtgccctac ttttcccagc aggttggatg   38580
cagaatcatg ctcttgtcgt tcaggatgac catgggacc atggggtctg agcctgtgac    38640
cctccagtct acagtgtgtt ggtgaggaag gagcagttgt cactggggtc actggcaatg   38700
ggcatgcctc catctagctt aggcaagatg cttggactca gagccagaga gtgaaaccca   38760
gacactaatg agctgtcggt gttggtgtgt gttctcttcc tcttccagtg gaacatgaca   38820
aggaattctt ccacccacgc taccaccatc gagagttccg gtttgatctt ccaagatcc    38880
cagaagggga agctgtcacg gcagccgaat tccggatcta caaggactac atccgggaac   38940
gcttcgacaa tgagacgttc cggatcagcg tttatcaggt gctccaggag cacttgggca   39000
ggtgggtgct atacgggtat ctgggagagg tgctgagttt cctctggggg cagaggaaga   39060
aggtggtgag ggccagagga tgggtcagat tggcacaacc acgtgccagg ccctgtacca   39120
gattatccct tctaaagaag gtgtatgtg tatgtcactt ccttaaaacc atgaccgaca    39180
acaaattcag gaatagtaga aggccaggga gcccagggat gcgtggtgcc ttgtgggttt   39240
ttataggcag tctagatctg gctgggtgct aagggacata aagaaaagg ggaaggggaa    39300
gaaacatttt tgaagggcta cctctctccc gtttctcact ctgaaaccca gtgcacgatg   39360
tcaggcaacc aattaaggtg gccatctaaa ataaaatgtt aggggaagaa aaaacccaa    39420
accaaaaaaa acagagaact cttagccttc caagaatcac taggtcagaa accaaacgtt   39480
tgtgttgaaa gtcttttaatt tatcgagatc cattaatttc aaggtcttgt gagaggtaag   39540
gaggctaaga aaaagggctg gacatttag caggtgcatt ctattcagac agtcccgagg    39600
cagaaatgac caaggtccta ttactcagtg gctgggttgc tggaccccgc aggctgtcag   39660
acatctaccg tccccactgg gcagggaaat tgatggaaga aaggtggtgt gggcacctcc   39720
ttgtgatgtg caggcttagc atcttcagct agaaagggga cttgttacca tagacaggga   39780
cagaagaacc atcacagcta cgtttgccaa gcactgctat ttggtgctgg tgggggtgg    39840
gggtggggat ggtcatctaa gtaccaagaa aacaaaactg ttcttgagcg tttccagagt   39900
gttttgcact tgatatcttg tttcatattc acagtagcct tcagaagtgg tggcttatct   39960
gtaaaatgag gagaactaaa gtgacctgaa gccaaagaat gaggctaccc agagagaatg   40020
tggccacatt aggacgtgag cccaggtttg caaagctgga gcccatgctt atgaaagata   40080
tttctttcca aaatttgttt ttaggccggg tgtggtagct cacgcctgta atcccagcac   40140
tttggaaggc caaggcaggt ggatcatttg aggtcaggag tttgagacca gcctggccaa   40200
cacggtgaaa ccccgtctct actaaaaata gaaaaattag ccaggcatgg tggcgggcgc   40260
ctgtaatccc agctacttgg gaggctgagg caggagaatt gcttgaaccc aggaggagaa   40320
ggttgcagtg agccgagatg gtgccaccgc actccagcct gggtgacaga gtgagactct   40380
ttctcaaaaa aaaaaaaaa aaaaagtttt tgagtaggca agacatgttc atggtataaa    40440
atcaaaagga aagaagagga accacagtga aaatgaaggc ttccagcccc tgctgaggtg   40500
gtccctgatg ccagtttctt gagtctcctg aaatcagcga aggaatctgt gttgctgttt   40560
tcacctgtgg aaccccacag tgcactcact cctgcctctg gctttcatcg ttggatgatg   40620
aaccttggca gccctttcca ggggttcaca cggggtgccc tcatcctctg agtcacctca   40680
ctgttccacg gcttggggtt gctgtgtttt cacgtgtgca cgctggctcc tctgttctat   40740
gatggatggt gccgcagggc aagtaccctc gctgacatac gtgttcatgt ctatcagtca   40800
```

```
gataaagttc tagagataga attgtggggt cagagggccc acacatgggt ggctttggta    40860
gacactgctg agcagctctc ctgggaggtg acatcgacat ctactcccag cagccaggga    40920
gcttcttgct taggatgaaa ccacagcctc tgtgtccagg ctgttatctg gattctccac    40980
tcagctccgg cagctcttgg tccttcctgc tggctttgtg ggcacctggt cccatcatgg    41040
tctgtggtgc ctctgctgtc ttgcctgaga tccatggggt ggatcctgag ggctgcaggg    41100
ttgggcagca ggcctgagca ctgtgtttgg aggaggatg ggcgttccag gcgtcctccc    41160
tgccaggctg ccggcaacag gcaacttggg ctggggtgc ccattctagt gctggggtcc    41220
tgctcctggg ggcttctggg ctgctgagtg actgagtccc tcctcagcac aggtacctgc    41280
tgcatgccat gcctgagggc atcgaccaga acgaaccaga cacgagtccc tgccctctgg    41340
aagctcacgt tccagcagag gagaggacat ggcaggtggg agcattgagc aaggaaggga    41400
atagggtgag aagcagtgga gggcaagacg gagctgcttt ctttaggttt ctacatgttc    41460
ttcctgtgcc tcctgcagca aagcctccat tcttcagaag ttaaatggtt aaatttaaaa    41520
aatatattat ttattcattt ttctggacag gttgttttgt ttttcaacct agaaccaaga    41580
tgcccctatg atgtaattcc ccagctatta agagcatgga ttcaaatcct gccaccagct    41640
acccatgtgg ccttgggaaa gagtcatctc tcagagcctc agttttttccc tctgtaaaat    41700
ggggataata attgaatctc cctcccagag ttgtgctgtg gatgaaaggg ggtgacatac    41760
ttacaacagt gtcttacaca caggaagtgc tcaataaatg gtcacctgcg ttagtatcat    41820
catcatcaca gcaggaagtg gagcaagacc tctttaggaa gacaagagcc ctgggtggtg    41880
gctgtggcac tgccttccca tgtaggtcca ccgagccaat tcccctaatt ctgcaatctt    41940
ccagtaggaa caaagccctg agcttgcaaa tgctcttcaa atcccccacg cttcctccag    42000
ctcgcctgtt cagagatagg ctttttcttt gcatgtcccc aacctggttg catgtccca    42060
acctgggccc gcacagcttc ttccagctga aggcctcctg cagacctcag cccgggggag    42120
cccagagcct gccctgctgt ccccgccatg tggctgcctc tgtctctgtg ccgccagctg    42180
cccagctgtg cagggctggg acatctgacg agctgtgcct gagctccagg aaagccccgg    42240
gggtgccgag gattagccgg cttgggtca gcctcagcgt ctctccctt gtgggagtca    42300
cttccactg actcctcttg atctctcgga atccagatta aattccgata atgagccgag    42360
ctggaggcct tccatagccc tgcggctctg cttaaagcgc ggcccagac agctggaaag    42420
acatgttgga gccgcccttg gcgggctgtg gagcgagtgg gggctcagag gcaggtctgg    42480
ggacagtggc cttggctcca gaggccttgc tggggtgaga gggggctgcg aaaggatcgg    42540
agtcttatcc tcatttctg aaccccaggc ctgaggccag gccagctggg gcctggcttc    42600
caggagctgg acttgctcct gtctccattg gtgcagactt tggttccagg tgaaggtgag    42660
gatatttggg gtaggggttg tgctgtttgc cctgtttctg ctgtggagct gggacctggc    42720
atcttccatc ccagtcttcc ccgtctctcc ttgagcatgt gtcaggcttg ccccactcca    42780
cagcgctgcc ccacatgtag gcgacacact tctgctttgg gagctggcct ctgagaacct    42840
ccctgggagg ccaaggccag ccagggcagc agaatctgct ccaagggagt cggccgccac    42900
caaggtcgag atgatgttgg cagctggatg aaaatgtccc tgggttcatc tcagtgattt    42960
tggctgccag gagggtgacc tcagcgtggt ctcgagggcc aagatttgga tcagctgcag    43020
cctgagtcac tctgaggaag agggagctgc cccctgcctg tccccaccac acaggatgga    43080
ttggcagagg aggcctgggc tcagtttcct gggtcccttc agcccaggca gaggctcttg    43140
ccctcgacta gccctgggat gggggccctg agtttctgcc ttttctgagaa gctccctggg    43200
```

```
gacgccgtga tgattttggt ccataaacct gagaaggtag gtggggctgg atgtggtagg    43260
aggaacgatg cagcccctc acagggcggc cctcgggcag tgggccaagg gctccttgcc    43320
cagtcctctc ctggggatgc tggggtggtg gcaacttatg atgtgcggat tcatgacttg    43380
gtagcaagac tctgggcggg ttttgccctg ccgttagccc ccatgagcgt gtttgggcag    43440
agagccatgg tcacgttcca gagcatgtct ccaccctgtg gttgaggctt cttgttgcgt    43500
ggtgcttact gtttatgact gtgctggaca cttcagcttt gtttcatgcc ttggaaaggt    43560
tcctatgaag atgtatcatc cccattttac aggtgcggag cctggctcag aggtgggaag    43620
taacttgccc aaaagcacac agctacaaag tggcagaggt ggggctcaaa cccaggctct    43680
tagatttcag cagtcaccat cttagccatg ccgtgcctc agtgattccc atagtgctga    43740
ttccctcacc tggggctcag atgggtccat tgatgagtcc tgagctggtt ttcagccttg    43800
gctgtgcaat agaatcacag aggcttttaa aactcctgat ccgtaggggt tgaactgtca    43860
ttggtgtgct ttaaaagctc ccaggtgatt ccctgtgtgc tggggtgtga acaggtggct    43920
aagatctctc taatttctca cccatgagct gtcttacatg cccaagagga aggaaagaga    43980
ttcctttttt ttttttttt gagatggagt ctcactgtgt tgcccaggct ggagtgcagt    44040
ggcacgatcc cagctcactg caacctccac ctctcaagtt caagtgattc tcctgcctca    44100
gcctcccaag tagctgggat tacaagtatg taccaccatg cctggctgat tttttattt    44160
ttagtagaga tgggtttca ccatgtattg gccttctgtg acacattcca tgttcccttc    44220
agcttggtgt ctcagagaag actgttcttc ttcccatgag actgagccca aagtgtagtc    44280
cagaccacaa ttgtcagtct caatggcaca ggaaagggac tggctaaggg tgaagatccc    44340
tttggactct ggctccagag gcttctgaa gcttctggaa gcttccagaa gcctctggag    44400
tttcttgctg ctcctgaagg ctacatgcct gtttcctcgt ctcctggctt ctaccccttg    44460
ccactacacc tcagcccag ggcatgagtt ctggttttga gctgccttct caggatgtgc    44520
caggtcagct tcctgagtag ccttttcaga gggcaaggag gattccttt ggctgctggg    44580
aacttccagg atgtcctgga aggtcagagg agagcagccc tcatcaagga gccttggcat    44640
ttttcctcgc agtcccttc tctgggcctc actccagaac cgagactgaa gctgcctgag    44700
agggagtggc aggcccttaa tgcctttggt tccgcttggg gtcctctcat ggatctgcaa    44760
ggatccctct ggaaaaagcc acccagctgg gcagagatgg caaaccactg tgttcaatcc    44820
agttaatgcc agagacacag ccagtatccc ctactcagca tctgggggcc aaatgcccgt    44880
tggcttcctg tcctgtggcc tgaggccatc tggtgggcct tggtggcttt tttttatctc    44940
tgtccctgtt atttcttccc ataattcatc ccgagcctgg cttcacaggg agcatacggg    45000
tggtggctgg gaatcgatgg caacagattc cgtttgctga gtgtttgcgg cgggcggggg    45060
ctcagcaggt tgcccacatt ttccctgatt ccccgtaggt gttatatcac gttcagtgaa    45120
gccgagcggg tgtccccacg aggtggtcag tcctgcccct cttgtagacc acctgtggga    45180
aaggtctgct ctcttacgt ttccatcgat ttagctgggt ccacaatgcg atcttggagc    45240
ctcctctctc ccatgacact tgtctatgct gggagaaggg atggctgcct ttgggaacag    45300
tcatgatgac aaaagctaat tgcatgcaat ggggctctt tactgcttcc cacaacaacc    45360
ccccatggag acaccttat ccctgcccac cctctttt tttttttt tttttttga    45420
gagatagggt cttgctctgt tgctctgctg gagtgcagtg gagtgatcac agctcactgc    45480
agcctcgacc tcctgggttg gagcaatcgt cccacctgag cctctcaagt agctaggacc    45540
```

```
ataggaacac accactatgt ctggctagtt ttttactttt gtagagatga ggtctcactg   45600
tgttgtccag gctgatctca aactcttggc ctcaagttgt tctcctgcct tggcctccca   45660
gagtgttgtg attacaggca tgaaccaccg tgcctgctcc cacaccctct ttcacagaca   45720
aggaaatgaa ggcacaatac tggggttgggg attaaggatg agaagcttcc atcttttcccc   45780
agtcgcatat gttttcttc cttggctggt ggatacactt ttttctttct cctcgtggca   45840
gtccagtcct gtaaattggg aaatggtggg gcaattcata ttttccacac aaggaaattg   45900
aggcagagac cagtgacctg cccagcctgt cccagtagtg tgtagtgagg ctttgcagac   45960
gcacctggag ccgcctcttt ttccacccct cggaagttgc acggacttgg acagcatgtg   46020
gacacttgct gaaccgtgtg gggctgcata gtgaagatct gagtggggcc cagcagagac   46080
agtgacaggg ggtccacaag gggaggagtt ttgttcgttt tgctcactgt ggtatccatt   46140
ttgcctagag cctggcacat agtaggtgct cagtaagaca ccaaatgcac gaaaggatga   46200
aagcacgacc cagccttccc tttgaagatg tgggctctct gaattcacag accacatggt   46260
ctggtcctgt gtgcctgagc gcatgtacaa cagatgcctg ctggatgagt gagtgccggc   46320
cacagtatct ttgccctgga gctagttcgt cctaccaaat gctccaatgt gctttctctt   46380
ccagaattga aactcgagaa tgccttgctt gcaatctttc ttcagcatct gagcccaatt   46440
tccaaaaagt gaaaattgcc tgtaattatg atactttctg atcctatgga tgtttccctg   46500
tgatgattat aattacgtta tttacagctg tgtgccagtg ggtgcccaag ggtaggtcgg   46560
ttcttgtttg caaatagggg agacatcagc gtgtgtgcgg cagcctgggg ttctttacac   46620
tgggatgcat ttgggaagaa tgggcttccg tggaggcagc tctctggata acttgatttg   46680
gcactttgat tccaaaagca cttcatgctt ggccctgggc ctctgctcgc ctatagaagc   46740
tcattttttcc aaatgtatta acatctatgt ttcgaatcag gatctgtaat tgctttagct   46800
tttttggcag gagacaaaga gaattaatat ttttcaattt ggtcacaagc agtcatctgt   46860
agctgggaag aaaagtgtct gctcaaatac taactctaag ggtggggaat acaggcttac   46920
caggaacatg atgatgtttt aaaggagaca accacagtta atgaagctag ttcaagttca   46980
gattggaagt aggcatgtag gtaaatactc aaggttcttc caaaccctgc ttcttccttt   47040
gtcttcctat tgcaacctct gtcggtgcca tgttcttctt tttcctcaac aatgcccatg   47100
gctttccatt ttgccacccc aagaaaggag gaaggaaagc tgacacctgg tcttgcattc   47160
cagcacgcat gccacccttc tcctcctggg accaaggcag gcattgctaa tggatccctt   47220
tccctccctt tccctggatc cttggtacag gtctctaaat aaggcagcca ctgccagttg   47280
agtgaagctg ccatcaagtg aaacctgttg gccactggtt tcaggtcagg tttctccaaa   47340
gctcaccctc agctgaggat tgtgtggctg tgagagtgaa ggattagaaa gtgtttccag   47400
gaaaggcctt taggagcatc gggcagtggg gagatgggga ggccaggtga gggagcggtg   47460
ctgcgcagag caccccgaag ggtgactttg gctcactctt cctgctagag gttctggaga   47520
caaagttgca ccctcatcct agtcccgtca agagagctga agtgtttata ccctgtcatt   47580
tgaggcaggg tttcggtttc cgagcctccg cagtagtgac ctttgggggt ggctcattct   47640
ctggggttaa gggccatcct gggcatagta gggcattcgg tagcagccct ggcttctgcc   47700
caccagatgc caatgacaca tccccacact cagttgtgaa accaaaaatg tcaccagata   47760
ttgtcagggt cccatctta aaagggcctc taactaggcc ctgactgaga agcacagggt   47820
ggagggaggg agggatgtca agtacctctg ggtgacacag ccgaagttga acatacttaa   47880
gtgggaagtc cctcgcccac cctgtcttct tcccaccttc ccacttacct tgctcactgc   47940
```

```
tacctaccac caaacaccac ctaccagcaa acaccagcta ccagcaaaca ccagctacca    48000
ccaaacacca cctaccaccg aacaaacacc agctaccact gaacaaacac cagctaccac    48060
cgaacagcta ccactgaaca ccagctacca ccgaacagct accaccgaac aaacaccagc    48120
taccaccaaa caccagctac cactgaacaa acgccagcta ccaccaaaca aatgccagct    48180
accaccgaac gccagctacc accaaacaaa caccagctac caccaaacaa acccagctac    48240
caccaaacac cagctatcac tgaacaaaca ccagctacca cctaaccaac cagctacc     48300 actgaacaaa cactagctac caccaaacac cagctaccac caaacaccag ctaccaccaa    48360
acaccagcta ccagcaaaca cataccagct accaccgaac acaccagc taccaccaaa      48420 caaacaccag caccaccaaa caccagctac caccaaacaa acaccagcta ccaccgaaca    48480
aatgccagct accaccgaac aaacaccagc taccaccaaa caaacccagc taccaccaaa    48540
caccagctat cactgaacaa acaccagcta ccaccgaaca aacaccagct accactgaac    48600
aaacaccagc taccactgaa caaacaccag ctaccaccaa acaccagcta ctaccaaaca    48660
ccagctacta ctacaaaaca ccagctacca ccaaacacca gctacctccg aacaccagct    48720
accagcaaac acaccagcgc taccaccgaa cacacaccag ctaccaccaa agaaacacca    48780
gctaccacca acaccagct accaccaaac aaacaccagc taccaccaaa caccagctgt      48840
gcagctcctc acacacatct gtccgaggtg gtgctcaaac ccagctgttg tcagaacctc    48900
ctggaaatat attggaagag aaaaatacag gttcccatgt ttaaccccaa ctagtcaggt    48960
gtaggggcta ggagttttca tcatgaatgt ttaaaaacaa gctcccagga ctggttgtgt    49020
caccttctgg gcccagtgca aaatgaaaat gtgtcaaaaa tgtataaagg atttcaagac    49080
agcaacagca gagcatgaaa ccaagctcgg cgtacttctg tgtgtcgggc cctgtgtgac    49140
tgcacgggtc agatgcccat gaagccggcc ctggccttgc catctccctg gatacagatg    49200
tctgttgata tctgtgttga taggtatctt tatacagata cctttcagcc ccagcctcat    49260
ttccagctgt ctcctgtaca cgtaaacacg tggaaacaca gacagatcca cagaaacaca    49320
gacacagaca cagcacacag atgcgcagac acgcctggtt tcccctgttt taacacctaa    49380
catcaatagg gtacagtttt cataattaag gacccagcat ctgcattttt attaatgaaa    49440
gtcaatcatt tattccggac ccctttgctt ttacttcttg tccttctgtc ctgtccagga    49500
cgccacctac ccttcagtgg ccacattccc tggggctcct cctgcctatg tgtttctcct    49560
gctttgcttg tttctgaaag tgacagtcac ccagcgtttg gagggagttg atgcagagtc    49620
ctctcccact atcgctccgt ctatctcagc cccacctatt ttaaaattca acctgaatcc    49680
ctacactctg gctgtggctc gatgtcttct gaacttgagt gacgtgggtc acagccacac    49740
ggggtcccca gactggagtc cttgtaaccc ctgggctttc agctatggcg acctcagtgc    49800
ctggcacaga gcactccatg tggctttgct tcttgagtgg aaatgagatt ataagagcct    49860
ttttggggta aggggttcttt gtctcctaac tcttccccag gcctagttta ggggcgcttt    49920
aaagatggca cttgaggtgt cctcaatagc aggctctttc ccctccatgc tgtgggctta    49980
gggagcgggc tcagcctctt gctctggggt tgaacccaca ggtcccggaa gtgggagagg    50040
gtgggtgggg tggtttggga gtcaggtttg caagtgggat tgagagctgg aaccaggagc    50100
ctcccaacaa acctgtcatg gtcattctcc ttggaaagct ttctccagct gagtcctgcc    50160
tccatccctt tccccttggg tgttccacat gcggggctc acggtgcagt aggaaaagca    50220
tctctgaggc cctagtctgg ctcctggaca taagagggat cctccagctt ccccagcatc    50280
```

```
actggtgttt gagtctttc tctgcagatg ccaccacagg ttgtcctggc ggggtccct    50340
gccatgaatg tagacagcat ttctcctcca gcccatgtct ggctgctcag gtggtgactc    50400
ccaccatgtc agcctcacca actgccacct tggacagggc ctccactcct cctcggagag    50460
atggacccgc tgagccgcag acctcgaggc ttccctccc cacacacctt cccctatgtg    50520
ggagctctgc ggggaacttt ctctgaccca ctgaggagtc ggagtcaagg tctatggaga    50580
attccccagc cccctcaccc tcaggagaca gtccctcacc ctcaggagac agcccctcgc    50640
cctcaagaga cagcccctca ccctcaggag acagcccctc gccctcagga cagcccccc    50700
tcgccctcag gagacagccc cctcgccctc aggagacagc gccctcgtcc tcaggtgcac    50760
ccctctggag ctgctccagg aggttctgac gggctgaagt cccaggccca cagtgttctg    50820
ttttgacaat ctccaagctt gccttacttc ccgccctct ccaggtggtt cctggggtca    50880
cctctcagac aaactacttg cattcaagtc cttgactcag gacctgcctc tggggtcact    50940
gaagcatgac agaggccaag tgtcaaccac acagggcagc cgggagggct tcctggcaag    51000
gggcagcttt ggcaccggca cagcttctgg gacctggtga gggcctacca agtgcaagct    51060
gatgtcctca gcctgccccc ttcctggacc ccccggctt caggatgcta ccgtgagaat    51120
aagtcttaga cagcccgct ctggccttct ctagatgttc caacccagcc tctgtttttg    51180
agaatcttga atttggaaat tgcgtcactt gtttctgtct gcaaagcact gtcaagtttc    51240
tttccccttg tcgccctgct ttgctgcact ttttctgtct ctgggtttgg aatcttaaaa    51300
cagcctgtgg ttctcttaaa aaaaaaaaaa aatgaggttg gaaagatgac ccagcccgaa    51360
gactgtattt gtggtgcttg tttattcctt gagtgtgctt caggaaaggg gctgaattta    51420
cctcattcta ttttggtctg gacctggagg ctggaggaaa tgcggtcccc aggagaagtc    51480
tagaaagatg agtctcccca tcctccatgg ctgcccgccc acctccacag tgccagatgc    51540
aggcagctgc ccatccgtgt gggatttccc ccagagccgt gtcagaagct ctgcagtgcc    51600
ccccagattt ttctgggggg accccccaga gttcttgatg tttcaccaga gttcttggtg    51660
tgttctgtga gctggaatcc agctcgcggc tcagttccac tgggtttctg gatggatcat    51720
gcctgggttg aatggaacag tagagcctcc agttttccag aaattctggg gctcaaaccc    51780
tgatatctta agcaaagagg gacaagagtc aggtccaaaa ggaaatgtga gatgtgcttt    51840
cttcccagct gttgctttct gcccacctga gtcctcttga ttttttgcctg atgtggggaa    51900
aggaggtggc tccgaagagg tgatggggac agtaaatggg ggcactcaac cggaagccca    51960
tgcagcctgg cagtttccag tgaggggtca atttgaggta atttgacagc cccctggttc    52020
catagccagg cctgtgaagg tggggggtat ggaggtgccc aggggctgat gagggtttcc    52080
cttcaactag gatgtgcagc tgggtgccca tggcctggga gtgtgggtgc ccagtgggac    52140
atagagtggg ctgggtgggc taaggcccca gtgaactgtg agtcagagcc atttctggag    52200
ctacctgaat aatctgaaaa agtatttacc atttctcttt taataatgta aactattgga    52260
agtgaaacca gaaaacctta ctggccataa ggatgcagag gataccagca catttgtcca    52320
gcgtgcatct gaggcctgct ttgtgctaag ctgtgtgcct ggtggagagg ccgctccagg    52380
gctgaataaa atagggctgg ttcttgctga caaaaagctt aaaacctggc aggaaaagag    52440
gagaacccaa aaaactatac aaacaaactg aaactccagc ccagatggcg caggggagag    52500
gacttgggct tggagcgtgt ccgacgtgga tgcaccatta gggcatcagt ggacgcttcc    52560
ctgggatgct caagaacagg caggtgtgag ggaggtgaaa aggcagggaa cagtgttgca    52620
ggcagcggaa acagcatgtg tgagggctg tggtgggctg gagactggca cagatgagga    52680
```

```
gggctgggtg ggaggaggct gtggagacag gggccggacc atccaggggcc ttacaggttg   52740 gatgacctgg agttgacaat aatgcctcct ctctctcccc agtttctcgg tttggactgt   52800
cagttccata gtcttcttta tcacagaaca cattagagag ctttggcttt ttatcctaag   52860
agctgataaa gggtttgagg cagggaagtt aattgctcag cccctgcaag ctgctggggc   52920
agggggagtg cggggtgaga agagtggaag gggaaccccc gggttctctg ggtggtagct   52980
ctccctccac catcaaacca tcaccgtgca ggggtgacac tttgctggaa caaggctctg   53040
gggtggttcc attcactacc tgcatatctc tgagcctcag tctcccacct gtgagagggg   53100
acaacagtgc tcgcctctca ggtaccatac ggttcagagg gctcgctccg caccttgttc   53160
taagatggtt ccatcttgag ttggggtcag ctcactgcag ctgtgatctt actttagagc   53220
caaggcagct tgaatcccat ggtggaagat tcacactgac attgaggttt gctccaacca   53280
gctgcgaacc ttgagtctct ggctttgcgc tggcatcttg agcatatctt tccatttaac   53340
tcattctcag aacaatcctc atggctacct ccatttttaca aacaaaagaa cctgatggac   53400
agagactgac ttgctcaggg ttacttcact gaaatttaac tccaattttc ctcaactcag   53460
agcctggagc cctacagcct acatccctga gcacccactg tgggacccga ggaccactct   53520
ggggatttca tcacaaagag gattccgggc ctctcacccc ctgattgtct ctgctggtgg   53580
ctgtgtctct aatgagggag agccttccat ttgtcgctgt atttctcttc cctcttgacc   53640
cccagcctct gtgatccaca ccttgacaca agtttgaacg gctcgttact gcgctccatt   53700
gccggagcag acatttcttt gcagcaggac ttttcagagc cttaaagag ctaaggtgca   53760 ttatgacatc tctaaggagc aatgtgtcat gtggtgcttc ccaacctcat ttcaccacag   53820
agcattttgg attttttgatc ctctcatttt cctctcttag ctatcctatt aataagttgc   53880
agtttttgag accttgataa actccaaacc ctttgtcttg tggatggaga aactgagggc   53940
tagaacataa gggccactga ctcgccttct gactgtgaca acgctggcct ccgggtgctg   54000
gacgggcatc ttcctgactt tcccatgagt ggctgggttg gtgctgtctg cagtcagctg   54060
gccctgccca gagggagaca gacagccgtg gggtgggtga gagggccgtg ggtggccacc   54120
cgagctctgt ctggggcagg aggatattgt gcctctttgt gtattttttcc accttactcc   54180 ccaaagcttt aatttttagcc ttcctggata tgcaccgtct tcaagaaagt gtattttttaa   54240 aaagccttgg acctccctga cttcctcttc ccgtctgggg gatgccaggg actgttctat   54300
gatttggcag gaaagcaggg cattccctga agctgaggtg ggggagcctg ggccccgggc   54360
tgagtcctcc ccagcctgca gctcagaagg ggcacccctt ggacccggga ctggctgcc   54420 agggtggggc cggcttcctt ctgggctcct ttgatctcct tcccgggctt ccctgcaggc   54480
tggggttgct gctgggctga ctccaggtgc acggcgggtt gcagtttccc ggcctgactc   54540
accgcagccg caagcctgtg ctccctccat gacatcatgc tagcctggga atgctctggc   54600
catgctcgct ggctcgctct cttgctcctt tccttctgag gaatatccctt gcggcccagc   54660 aaccgttcac aacatgcagg ccttcagaat gtccggcctg cagttttcca aagagcagca   54720
gagtgaggcg agggcgaggg tcagactagg ggtcggggag cgagtcagct gggtctgcga   54780
gtggcagagc ccgtcatctc cactcctgct tagaactcct cccggcttcc cagcgctcag   54840
caagacctga cctcccgcgg ccagaggccc tgcagggac atcgtgcacc tgtgccctct   54900
cctcactact ttctcatcat gacttccgca ttcggttctc tctgccggga acgcttttcc   54960 ctgcccttttt agctgtgtta gttctgctca tcctctgacc ccccttcggga gatgtttcta   55020
```

```
taaaacgtcc tccccgcaca ccctcacacc tcacatctag tccttttctt ttgtcttgct    55080
cacccagagg cctcttccct ccttcacgcc acttaattag ggtttgaatg accctcttgt    55140
gtgctacgca cgcccagcct ctggacccgg agctccatct ctggctgccg ctgtgtctct    55200
ggctcctagc agagcacctg tggagaggag gcgtttcagt gtggatctca ggagagaaac    55260
tgtattcatt cctccagctg ctgagcccag tgaccgccaa cttagtggct taagacaaca    55320
cacatttatt ctcttagagt ttgggaggtc tgaagtctga aatgggtttt actaggccca    55380
aatcagggggg tccatagggc tgcatctttt ctggagagcc tggggagga tctgtttcct    55440
tgttgtttct ggcttctagg agacagagcc ccctttcttg gctcaaggtt cccagccgca    55500
gtcacaccac cctgacccct gctttcgctg tcacagctta ttctctggcc tcctgcctcc    55560
cctgttatca ggacccttat gattcctttg gcccatgag gataatccag gataatctcc    55620
caactcaaaa atctttcatc acatctgcaa agtccctgct gctgtggaag gtggcatacc    55680
cacagcttct gggatcaggg cctgggaggt ggcatacccca cagcttcctg ggtcaggacc    55740
tggatgtgtc tgagggggtg ttattctgcc taccacatca tctgaagtgt gttttccttt    55800
ttttgatgg tgggcctggg ccagccccgt cctctcctgc cctgcctcct ctaacttggg    55860
tggggctcct ggagatggct ttctgtgctt cgagtaacct ctggcctggg gcctgttgct    55920
cccagcagag gcgtgtcctg agcctccctg cccctcagtt tttgtacaat ccccatcccc    55980
atgtaatagg tggtattaag gtgatattaa gtggggatgc ggattgtact gacctcattg    56040
gaggagggag gaggaggtgg gagagtgtcc cttaagagcc tagtgtgcag taggtgccca    56100
gtacgaggtg tcagggtgct gagggccccc ggccaccagc cggtgattc cacatgcggc    56160
ccttccaacc ctggcttgcg cctgctccct gaaggtggtg gggggctgtg tctgaaggta    56220
gcagagggg atatcaggct ggctctcagg ctgtgatggc gagaacattt ttcattacac    56280
tgccctaaat tatggcccag aactggtgtc taatcctcgt tcagccacca gctgcccatg    56340
cgcaagacaa aaactctctc atcttttccaa gctgaaaatt aaaatgacca gaatggattt    56400
ccaagggcct gttctgctcc taagaccctg gatggctggg cccaggggca ggaggctgaa    56460
ggagcccga tggtgggcgc agacaggatg gggactgtcc caggtaacga gacagtgtgc    56520
actgtgtggc catgttggaa ttcgtgtttc ctgtggctcc aacgcgtgcc tgggtgcctc    56580
agggccagag agatcctcag actcccaact ccgctctgtt ttgccctggg gcagtttcag    56640
ggccatcttc cctggatctg tgtttgcgct gaggccgggt cctgcatccc acatgggagt    56700
cttactcccc tggaggcgg gtggtgggtg aaggcccatg aggatcagtc tctaaatagc    56760
ctctaggtag gtagccagag gccaaaaaaa ggacttcctg ccttcccacg tttgagattt    56820
taaaatatcc cctttttccat tgtggtagaa ctttccaggg gaaggtgggc tgggagacac    56880
tggaaacgag cctggggatg tgcggttcct cgtcctgctc ccctagaatt agatttcagc    56940
cgattcacct gggcgtcctt ggaggaggc acctgaaagc ccagcagcac gctgtcccca    57000
ggctggtggt taaatattaa cgcctcttag tgcggcggca ttggggtcac cagcggttca    57060
tgccttgcag agcagggcta tgggagaacc cagtttcaga agagaagaga agacgacttt    57120
tggggtcttg ctgtttcttt aatcagaaac agcctgagaa agtggaagga tcatcaagtt    57180
tatagacaac agacgtgtgg cctgtcccct ggctctgctg cctttctctg agattagagg    57240
agtggaaaaa actgtccaaa cccaggaaag aagatgagag ccaggcttgc cccctcacct    57300
aggtttgttc tgctgttcaa gtataacatg gaaatatgtt gccccataca gatctagctt    57360
tttccagaaa tagggcatgc ttactaaatt gagacaatat tgacgtacat gtgttagctt    57420
```

```
gtaaagggaa gcaaaatact tcacagtgaa ttgttgctac cactctggtg tgtatgcgtg    57480
taaatgtttc atgcagctgt gtgtacactt taaaacaatt gttaacataa tggcaccata    57540
ctctatattt ggggcttaga ttggccttat ccattttcaa aaatagctt tattaagatt     57600 tgaagtgtat aattcagtgg tttttggtac attcagagtt gtgcagccaa caccactgtc    57660
taatgttaga atgttttcat caccccgaaa ggaaactcca tacccactaa cagttacccc    57720
cattttccct acctgtctag ctgttggcaa acactaatct actttctttt attttctttt    57780
tgtttgagac agggtctcgc tctgtcactc aggctggagt gcaatagcgt gatcacagct    57840
cactgcaacc tccgcctcct gggctcaagc gattctcctg cctcagcctc tcgagtagct    57900
gggactacag gcatgtacca ccacgcctgg ttaatttata tacatatata tatatatata    57960
tatatatata tatatatata aaatatatata aatctaggta tttgtttatt catttatttt   58020
tgagacagag tttcgccctt gctacccagg ctggagtaca atggtgtgat ttagtagaga    58080
tggggtttct ccatgttggt caggctggtc tcgaactccc gacctcaggg tgatccacac    58140
gcctcagcct cccaaagtgc tgggattata ggcgtgagcc accgtgcctg gccaatttt     58200 atatttttg tagagacggg gttttgccgt cttgcccagt ctggtcttga actcctgggc     58260
tcaagcaatc tgcctacctc tacctcccaa agtgctggga ttacaggtgt gagccaccac    58320
acctggccct actttctgtc tttatggatt tgcctatttg ggacatttca tagaaatgga    58380
ctcatatact atgcaatctt ttaagtctga ctgctttttc ttagcataat gatttcaaga    58440
ttcatctgtg ttgtagcctt tatcagaact tcatttttta atgccaaata atattccatt    58500
gtatcaattg actgtatttt gtttatctgt tcatgagttg atggacactt tggctgtttc    58560
tacctttttg gctgtgaata tcctgctat gaacattggt gtataagatt ttgggtggac     58620
atgtatttta attgcttctg tgggtagctg aattactggg tcacatggta attctacatt    58680
tgaccttttg agacaccact atactgtttt ccagagtggc tgccccattt tccaatccta    58740
ccattagtat atgagagttc cactttctct acatccttgc cagtaacact agttatcatc    58800
tgtggttttg gctctagtca tcctagtggg tgtgaagtgc tgtctcactg tggtttcaat    58860
ttgcgtttcc ctaatggttg ctgatgatgt ttagcatctt ttcatggctc actgccatt    58920 tgtgcatctt cttttaggaaa atgtctgttc aaattagcct tctctatttt gggagtcagt   58980
ggcgtgctag ctttacaata tgggtttcaa acactccttc ttccatgttc ttgatcaaat    59040
tatataagaa agaattatct gttgataatt tgcaaaatct gtggttataa aaccaactgg    59100
gggccgggtc cggtggctca cgcctgtaat cccagcactt tgggaggccg aggcgggtgg    59160
atcatgaggt caggagatcg agaccatcct ggctaacaag gtgaaacccc gtctctacta    59220
aaaatacaaa aaattagccg ggcgcggtgg cgggcgcctg tagtcccagc tactgggag    59280 gctgaggcag gagaatggcg tgaacccggg aagcggagct tgcagtgagc cgagattgcg    59340
ccactgcagt ccgcagtcca gcctgggcga cagagcgaga ctccgtctca aaaaaaaaa    59400 aaaaaaaaa aaaaaaacc aactgggta tggggatggg aaagaccttc ctatttcagt       59460
ttcttttggg caaatcaaaa ttttcatttc ttttttgcacc aattttttgca ttttgcattt  59520 tcccagaagt ttcagtccta caaattctgt ttccttagcac cttcctatca tatttccacc   59580
ttgtcaacaa gtgtagattt atacggtcct ttgaagcggc tgtgcagggc tctgttgcct    59640
tggatgtgcc ataatgtttt taccagtccc tctcactgga tggttagtgc tcagtttttc    59700
tgttataaac aatgtgactg ttgtttgggt tatctgtctc tgaaactaac cactcatatg    59760
```

```
tagtggctta aaacaacatc gttttattgc tcaggaattt aggcagggct tagctgggtg   59820
gttcttctac tctttctggt atctgctgta gtcactgatg gagctaggag cttgactagg   59880
tctggaaggc ctgagatggc acctcactgg ggactggctt ggttttttctc tctctctctg   59940
gtttatagac ccttatcctc catgacctgt gcctccttcc cctccatgtg gtctcttcct   60000
tcagcagtgt agtcagattt ctcgattcag tggcttcctt cccagagggc aaaaatagaa   60060
atgataggct tcttgagtcc tagtcctgag cctggcagga cctcagttcc actgggtcct   60120
actggtcaca gcagatcaca tggtcagtcc agacttcaga ggtggggaac agactccaca   60180
agtttatggg acagcagcat gtgcatacag agacaaggaa ttgttggtgg ctgttatttg   60240
cagaaaatct aacactactg tgaacatagg acacttttct gacaaatttt ggagtccaag   60300
gtaaacattc ttggaatgga caagtggtct gttgactgga gaatcatggg caagtcacat   60360
aacctctggg accaagacat gtaaagtccc catcctagga tttcctgaag tttagcagag   60420
aatagacacc aacactgaca taccttgtaa taagtataga tgctcttcca ggagtgtctt   60480
ggagtttgct gccaggctgg tcttaacctg gctcttccta atcattgaag aagatggcat   60540
tattctcatt ttacataaga ggaaaccaag acacgggaat tatctggcgt aaccttgcct   60600
tatcccttct ccatcacctg ggtttcatcc ccctctagta ttttctctgc cccacacaac   60660
gctgtgatga caacacgtat catacaggat ttgacatctt cctatgtgtc tcttatcccc   60720
aggtgagtga aggaggtggc agggtttaag cgctcaggct cttgagtcag gtttcctgcg   60780
ctgtcgcctg gttctgccac ttatcaggtg tgtccctgga acaactggc ttcatttcac   60840
tgaccccaac ttttctcatc tgtaaaacag taacaggact tgatcatttt catagggctg   60900
gcggggagat tcagagaacc gaggcgtgga agcaccgag attctcagca gtggcgaagg   60960
tgaaagaacg catttaggtt cctcagggcc tttcaccctg agccttcctt acctcttctc   61020
tcacctgggc tgggccgggg aggccagtgt gttcaaggta aataaaaatg tcacaaaggg   61080
ctccttcagt gctctcctgg ttgtaagaac cagtgttctt ttacgatgct caaggtggca   61140
gctagaaatt ccccctctcc gagctgtcag actggacctg gctgctgagt aattccttcc   61200
ttgtcctttc catgaggtcc aacctcatgc ctgggctctc agtctgaaag caaagcccgt   61260
gttagcatct cacactcgac ccatctcagc aaggctcccg tctcccagtg ccttctgatg   61320
aagatttggc tctcctaagt gtgcctggga caaattgcaa actatgactt gaaggagggg   61380
agttgacgca ttcacgttga ttcatggatg agtcagtgct ggcctgtagc atctggcctc   61440
agtgtcatag cctgcaataa gagaatgctc agtatcgttt ggcgaggcgt tctctgttta   61500
aaggtctcac tctgttcctt tggttaccat tcattgtttt actgtcctcg agggcctgtc   61560
cagatatctg gtcacatttt cctgctaata acaattttcc agcaaaatca ccatctgggt   61620
ttgtgacttc tgtgctgagg tgtggatatt tcctacaggg gccttgggag cctgattcag   61680
taggagaagt tgtttcgact tggagtggtg cttcttgtct catctgttaa ttgttgagaa   61740
tcgctaatgg ttcattgaca accttggtag cttttcaaag ccaggaaagt catccaggca   61800
aactggagat aagacagcag gaaattcttg tttataagtt taaaatctgt gtagacatcc   61860
ccgaagccag cctgaaacta cctctaaaag agcatgggga agaagaagta aatgagtcat   61920
gaaaaataat ctcatgactt taattcagtt tggatgtgaa aggtaaactt agggtcttca   61980
aagtcctgtg tggctctaaa aagacttcct tgcttctgtc atctctctgt gcttgagaga   62040
ggaatgagtc ctttacaatc tttaaaaaca aacaaacaaa caaacaaaaa acaaatacct   62100
cattccttat agtcctggag actgggaagt ccaagatcta ggcgctggca gggtcagtgt   62160
```

```
ctggtgaagg ctgccctctg cttcaagatg acacctcgtt gccgtgtcct cacatggccg    62220
aagatggaaa aacagaaagg gtccagactt tctccctcaa acccattcat aaagacacca    62280
atccatcccc aatggcctaa tcacctccta aagggcccac ctcttaataa tgatgcattg    62340
gggattttca acatgagtct tgggaaggac aaaacattga aaccacagca ataacagaat    62400
taagcatttt ctgaatcagg ttctgggggt cattgaatat tacttaaaaa ggagactttg    62460
aggtggcatg ggaggaggtg actcctgcgc ccatctgtgg tcctggtgat gcgtccattg    62520
ctgtggggtg cccacccctcc catggctagg agtgggcaca tagattgact gggccaactg    62580
gattctgtcc cccagagttt tggatggaga gaggcccaga gggaaaagca gctccgattc    62640
gttccttctg tgcttgtgcc tgagaaaatt gcgctgtgcc ctcgcacctg cctcggttcc    62700
tgtctgtttc tgaccctggt tcttcttccc tgtgtaggct tctccgggtc tgttaatctc    62760
ccaatacttg ctaacattac aggtctgttt cccgtgtgtc ttctctgagc cttgttcaca    62820
ttgatgtgcc tgacgaatgt ctaacatatt atggcatgca gcagaagggt gatctagcag    62880
acctcacaaa cctagagttg tccaggtcag acaggaagat aaatagcggt ggctgtctgc    62940
agtgttagta cggagagctg ggggctggag ccaaccggag atgtgtgcct catcaaaggg    63000
gacatgagtg gctcggctcc tgcccgtggc ttagtgggtt acattccaac gaggttgact    63060
ggtgaaaggc tctgaaaagg cagtgtccag aagaactgtc tttgtgtaca gttgcaagct    63120
tgggcttgca ggtagcctgg ttggtttcca gtcctgcctg gactgtccta gtggcataac    63180
cctgggcaca caacttgacc tttcggatcc tgagttttga gttctgcaca atggcatggg    63240
gaatattatc taccctacag agtgttgtaa gaactaagtg acatgagact ggtcaggcat    63300
ttcaacctgg agcctggcat atggtaagtg ctccataaag gatatgcctg acatcttttac   63360 gtgtgagcag acaagattca ctataatcac caggaagatt agataactcc aggtatgata    63420
gagactgttg ttgccctggg gcagggacca gtgtcatgtt gttcatcatt atgccttggt    63480
ttctggtaca acacagaggt ataaatattc tagttgacta ttaaaggact caaagtattg    63540
aaactttgaa ttcttattaa aagtgtgcaa gaaatgttat gaagatcttt catactagaa    63600
ttctactatc cagaaatgta acaatccact tatttacccct cttattcatc tactcatcta    63660
cccattcatc catccatcca cccatttacc catccactca ttcacctacc cgcccaccca    63720
tctactcatc catccatcca tccatccatc caccccaccca ctcatctacc catccattca    63780
cttatccatc caaccatcca tccatccatc cactcattca cccacgtacc catccattca    63840
ctcacctacc catctaccca tccatccaac cacccattca ccctccatcc cctgtcaagt    63900
taattatgat tttacccatt ttgctactgt aaaaagtaag gaagagagaa tgaaaggatt    63960
ttcactatta ataccatcag tccagagatt cacctcctaa ctcttggtgg gctcataaag    64020
atggtgcacg tcctggaaat gaagagtatc tgctctggta cacaggtaaa tgggctgaaa    64080
ccccagcttg gcaacttcct ggttaaatga ccttggacct tgggcaaatc atggcttac    64140 cataaattga gtgaaatga tattcccaca gcttcgggtt gtgggaattg aatgagatag    64200
tgtagtgttg agcccgtggg acagtatctg gcacatggtg aatagttcag tcactatcaa    64260
cttctgctct ctgagactct tccagcaaca cggaggctgc ataatccctg tcttcctata    64320
ctctgtcccg ctgggatgcc cttaacaatt tatgggtga gattgccttg taacagctgc    64380
cttttccctg cgtgtatctc tttgtagctc ttctgcactc tctttcctca ccacagctac    64440
tgaggggtct ttgtgcctgg atcttggtct gatgttccca cttgtcgggg accagtggac    64500
```

| | |
|---|---|
| tctttccctc ccctcccacc ccatgaggct ctgcttccca tctgttgggg tagtggagct | 64560 |
| gtgacctggc taacgcgaag cccgtgtctc tcctcctctc tcgcaggaa tcggatctct | 64620 |
| tcctgctcga cagccgtacc ctctgggcct cggaggaggg ctggctggtg tttgacatca | 64680 |
| cagccaccag caaccactgg gtggtcaatc cgcggcacaa cctgggcctg cagctctcgg | 64740 |
| tggagacgct ggatggtgag tcccccggcc actgccagtc ctaatgcagc ctgtgctcct | 64800 |
| ggacttcagg agggtctcag cagtgctcat gcttgcttca ctacaaacag gcttccccgc | 64860 |
| ccctcccaac cagtactcca tgttcagcct tttgatccaa accagaagca gccccttccc | 64920 |
| ctcttttcac aagaagatta catgtttggt catagcagaa ttgggtaagg cttcattaca | 64980 |
| caaagggtgg tcccatatca gcagggtga gggcagccct cttatgagaa atgcagaatc | 65040 |
| ctgggcccac cccagacctg ctgcatcaga acctgcactt taactagagc cccaaggtga | 65100 |
| caccacagga cacaggacat tctggactgt tccgtgcacg gcagggtgtt tagcagcgtc | 65160 |
| cccggtctct tactcactag atgctagtag catctcccag ttgtgacacc gaaaaatgtc | 65220 |
| tccagacatc gccagattgt gccctgtggg acaaaattgc ccttgtgcaa ggcattggtc | 65280 |
| ccttccacat tagaacctga atgtgcgtct gactctccag ttcctggaga atccattgtg | 65340 |
| agtctgccct ccccaacact tctcattccc actacagttc tgcctccttt gagaagggaa | 65400 |
| gaaggaagga tggtgagtgg agaagtggga atggacttct ctatgctaat ttttccccac | 65460 |
| cccaaacaga taagaaatga tatcttgtag cttgactttg cttaaaattc agtggtgatg | 65520 |
| gtttccagct gtgtagcttc ttccttccac cagttttatg aacaaaacaa ttttttcatt | 65580 |
| tattttgaa taaacacctt cacaatgttt gcctttggag ctatgaacaa tacatgtgta | 65640 |
| acactaaata gtttccctcc cactttcttc tccagctgct gagttccact tcccagggac | 65700 |
| aactgctgtt tctgtctttt cagagatgct ctctgggtat ttcagcaatt acatggagat | 65760 |
| tcggctttct gttttccccc tctcccataa atggtggcct ggcatataca gtgttctcca | 65820 |
| gctgacttat ctcggagact ggtcctgtca gccgttaaag agcttccttg ttccatgtgt | 65880 |
| tttgtgtcca tgtagctctg ccacccacac actgtgtgac gttggacaat ttccctaacc | 65940 |
| tgtcagagcc tgggctttct catccagcat gcaggtgatg agaggatttg gccattggg | 66000 |
| ttgttacaag atgtaatggg ttattatggg aagagttttt aaaaatagtg ccttaatgta | 66060 |
| cgtaggattt tcccaggcat cttggtaaaa tgcagattct gactcagctg gcctgggca | 66120 |
| gaggagtctg tgttctcaga cagccaccag gtgacagaag ctgctggtcc ctggaccgtg | 66180 |
| ctttgagtaa tgaggcttag aacaggacct aactgtaata cacatgtaaa ggagagcagt | 66240 |
| catcatcctc gtcatcatga tcaccaaaac tgacataccc agctctcctg ggatggatgc | 66300 |
| ctaggtgttt tctagtcttt tggtctcaca acagggctt cagtgggaaa ccttggtgtg | 66360 |
| taggtcgttt ttcgtttgag tgtagctcta ggaccaattc ctgaagtggc attgtctatt | 66420 |
| tgtagtttta ttttttttg agatggagtc tctgtcaccc aggctggagt gcaatggcac | 66480 |
| gatctcgatt cactataacc tccgcctccc aggttcaagc gattctcctg cttcagcgct | 66540 |
| tgagtagctg ggactacagg cgcccgccac cacaccggct aattttttcta tttttagtaa | 66600 |
| cacatttctg tggacttgta gatgttgggg aaaccttcca actgggcccc agtgggttct | 66660 |
| gtgcttctct gtcttgcctg ttctgctggc tcaggtgatt ttgtcttaat tgacgccagc | 66720 |
| cctgtggcca gctcctctta ctaccagtcc tgccctcatc attcccccca gacacagtca | 66780 |
| gagtccttt gccccttca cctccagcac ctactccccc attgtccagg ttatggagaa | 66840 |
| aggctcagca ttggtggagg cagtgctgcc tgatggttag agctcgggct cccgagccag | 66900 |

```
gctccccagg ttcaaatcct agccctgcta tttccggcct tgtgacctag ggtgagtcac   66960
ttaatgtgtc tcatctggaa aatggggtta ataatagttt ccatctccaa gggcggttgt   67020
gagggattag atgagctcat gcaagtgaag agtttaattg ctcagtgtgt ggttgctacg   67080
aagcaccact gtctcttgtg atcctcacaa ttacccagca aggtagatgc tgtggctcac   67140
atccccgtgg tgcaggcagg aaatggaggc tcctgagaac ccgccggggc tccatatttc   67200
agagcccacc tgagaccctc tccattcctt gcagcctagt ggctgcaggt tgctatctag   67260
agtcagatca aggattagat gctgtgtccc tgtcccctc tgactccggg acaccatctt    67320
tgctcctcct gggcagggcc ctgggggccg ggtgtggtgc caccgcccag tgacttggct   67380
tgtccaggtg ctgtgcgcgc ccaggcagtg agttttgtgt ggttgcccaa gtcggggag    67440 gatcacccac ttggattgtc agggaggggc aaagtgtata atggccagtt ggctgtgtgg   67500
agttttggac tcttgggggg tgagctaaag agcaagtgag tccgggattt tcgagacatc   67560
atggctgtga aaatgctttg ttttccctac cgtggaggat ctcaagcctg gcgtccttca   67620
gggtcaccct aggggcaaa ctgcacatgc aggtgcctga gctccatttc agacccaccg    67680
tgggggatct cagaggatgc gcccaggaat atgccccttt tccccagtag ctttaggggt   67740
acatgtggtt ttgtttccgt gggcaaatca taaagtctga gattctagtg ctcctgtcag   67800
ccaagtagtg cacgctgcac ccagtatgta gcttttatt ccttagccac cttctaaaag    67860
aagacttggg taacttgagg cctggcccag tgacaacact ctggcaaagt cgtgcacggt   67920
gcctagggca gcctgtttac aagatggtgc ctgggctgac aggtacccct cgggttctgg   67980
gtctcaaccc tccccctgcca gatcctgcac ggggaagggc agcagggcct gtgggaggcg   68040
gtgtgcatcc gacaaatcag tgcacacctg ctttgtgcct ggccccgagc tggctgcaga   68100
gaccctggtc cctaccctgg ggacctctta ctgatattaa ctcagaggat atcctgcctg   68160
caccagcacc cagagaagac aggtgcccag gcagcagcgc ccatgtcatc atccagaagg   68220
ggtagagaca gggtcacctg aaccttgcaa ccactaggca gttacactgt gcgtgggtgg   68280
agaggagccc ccagcagctg ctggaatttg gagcccggac acctcctggg gccttgcttt   68340
tctcatgcac acaatgggca tgtggaggat agtaatttgg gccagcgtgt ttccattcta   68400
gcggggcgca gccatcgcag accttctttc agaaggctgg tgtttaaccc cacatgagcc   68460
cctgcctgcc agtggtctcc aaaactccaa agcccagatg gcgtcctcct tccctcccat   68520
ctggccacgg gtggtggggg gtctcgaggt caaagtgcgg aggtgcccct ctgagaccac   68580
ccaggaagcg tgcgtctttt ccctcttcct cccagctggg cctcctgtg agtcaccatg     68640 cggagcagcc gcagctgggg ctctgctcca ggccagcgtg ccctcgcggg gagaagccta   68700
taaactccca ggcacctgca gctcatcagg aggaggccga gcgggagcc tggtctcatc     68760 tccctgggga tgggctggtg ctacaggaat gagggctgga gtctgtttgt ctttccctta   68820
atacagaaga gaggagaggc agcctctcca cttgttccag cccccaggct gtgcttccca   68880
cccatggact ggctgtgtcc tacagcccat gctggatgct ggtgtcagag acccggggtg   68940
aatctagcac tgcccagagc cctgtgagaa aggagaggat agagaggaga gcgagaggag   69000 aggagggag aggagagtga gaggagagga tagagaggag gggagagga gagcgagagg     69060 agaggataga gaggagggg agaggagagc gagaggagag gaggggagag gagaggagag    69120
caagaggaga gaaggggag aggagagcga ggagagga gggagagga gaggagaggc      69180 aaggcacctt tgagtggagg gaatcctgca gctcggggct cctcccacct tgtggcctta   69240
```

```
aggcagggga accctcccta caagccaggc cctgagcttc cagtgtgggt gcagctttta    69300
gaagcaggat ggactagcaa cccctgcaca ctcatactct ggcacccctg ccctgtcat     69360
agcacagctc ctcagtcacc tttgtgtggt ctcagcagct actccaactt cttggggtct   69420
tgttcctttg tctgttccat gaacataata ccatcacgga ttctgtaggc ggctggaaga   69480
agaaagtgag ttctcagaac atgctgaatc ctgggcccag caccctgtct gtgctcatga   69540
atgttagaag ttctaattgt tgatttattt agttctctca ataatcctgc ccaggtagca   69600
caattgatat caccaacatt ttatagatga ggaaatagaa gctgagaagg ctggggaact   69660
ttctcatgac tcccaggtgt agatctgggc tttggccaga ggattgtgac tccaactccc   69720
ttcctctttg ctggaaaatc ttccaaggaa tgtgttcacc aggctgcagc ctcaggatgg   69780
ggtttggagg ggcagatgag cccctgcagg ggacccagcc tggccatccg gaggtagaga   69840
ccccaggacc ctctaacatg ttaggtctta cctggctttt cacctgggaa ggaaagtgtt   69900
tctaaaaagc actcagaaga cagtaggctt cttgcaggac tcactgtggg agccccttt    69960
gcagaagtga ccagggctgc ccttgacttc tatgggctcc tccctccatt acaaaaaaaa   70020
aaaaaattag gccgggtgc ggtggctcat gcctataatc ccaacacttt gggagactga    70080
ggcgggcaga tcacgaggtc aggagtttga ccagcctg gcaacatgg tgaaaccccg      70140
tctttactaa aaatacaaca gttagccagg tgtggtggtg tgcgcctgta gtcccagcta   70200
ctcgggaggc tgactcagga gaatcacttg aacccgggag gtggaggttg cagtgaaccg   70260
agatcatact accgcactcc agcctgggca acagagtggg actctgtctc aaaaaaaaaa   70320
attaaattaa aaagtatgtt ttatggccat gttgatatca agatgaatat tataattctg   70380
ggtgaattaa aaattaagat tatttttgag atggggtctt gctacgttgc ccaggctgtc   70440
caggctcaag cgatcctcta gcctcagcct cctgagtagc tggaattgca ggtgcccagc   70500
tttgaattaa aaaccaaaac tttcttagac actaaaagtt catgttttat cttccgattt   70560
taagagacat tatagtgttt tcgtgggccc tgcatcccag catggggagt gaatgatgaa   70620
tgatggtctt cccccacccc cgcatctggt tgttagaaca agttcctac agcaaatagc    70680
ctctccacct atgttggaag cacagttatt cactcaacaa acaatgagcc aaggactgtt   70740
gtgcccctac aatgaggcaa ggactgttcg aagcagcagg ggcacagcct tgaacaaaat   70800
gaagatttgg ctgttgtgtt gctcacattc ttctaggagg agtccgacca ggaacgagag   70860
accatgtact gaagggtagg ggtgaagcca tgcagatgag gtctgaggct ctgagtatgg   70920
ttcagaaggg cttcctgctg ctctacaaat caatacgccc attttccttg tgccgtcttc   70980
tacccgcaaa gcctgctgca gagagatgaa gactggtttg gctggggag actgtcgtcc    71040
ttgcagacat ggaagcacca ggtcatttgt cccaagaaag ggactgcagc cttttgtcct   71100
ggttcatggt gtctccctcc tcttccttgt ttgcagaaga aatcactcgc gactcaggag   71160
ggccatgtca atcagccctg cctctcagat ccaagaagat gatcggggag ccccttgtctg  71220
cctcatgtta tactccctcg ttggggaccc ttttctccag ctccagtaag cgctggctgt   71280
ccatacctg agctccaagg tcataggca cctctctccc tcctgcaccc catctttgtt     71340
tcctgaagta agtctgctgg gggtcaggag catgtgcatt ttggctatct gcatgcgag    71400
agccctgagc gtctctcctg tgacacacga gagcacgtgt cttacttcat gctcactcca   71460
gattgaattg gatgggattg cagagcattt aaaggattga agggcatgtg ctgtccaagt   71520
gtgacactca gctgtggcag ctgaggaagg agccaggagg tgagccactc gcctgcggcg   71580
gctgtggaaa ctaagcccca caaagccaag gctggtgagc gatgccgccc acggcgcagc   71640
```

```
tggctccaag gtgccttcgc tccatgcgat tgcttcacat cctgtttgtc cagaagccgg   71700
agagggagag aaaagagaaa gcctgatgac ccagtggcgg ggatcggtcc ttccagggct   71760
gggacggcaa gaatggggag ggcggaattg ggtaattggg gccaggcaga tgtcacaagt   71820
gttaactaag ttctcacttg tcacttgggc cttggtccac ccagagaaat ggctggagtg   71880
aatgtgtttt tcacaattaa tgagaaacat tcttgtgctg tgggtcttgg aagggtagcc   71940
tgtagccctg ggcctggaaa acaaaaaagc cacaaggaaa ccgagatgcc accctgtgc    72000 ggcgtgggtg ggctgcatcc cctcctttac caaggggcct cactgtgctc cctgcctgct   72060
ctccagggtc tttccgcaga gttcgctggg ttcctcgggc tggccatgcc gattttgctc   72120
aagtcgtctg gggtttgcca gcggtgccag gatgcacggc tgggccctgt cctcagctca   72180
ctctgagtcc tatctccacc aggctccttt tagaaggcct ttccctctat gcctcagtga   72240
atccctccta cctttggggt ccccgtaagt cacctacatc tatgcctggg cagtctctct   72300
gaatttgggg ggatcctttt ccctgccatc gcctggactc attggcagat ggtgcagggg   72360
tcgagctcac aggctccagt cggctgggcc agggtgtgga ctccatctct gtactcccta   72420
gcattgggtc cccggtaggt gactttgcgc ctgtgacctt gctttcctcc tttgtaaatg   72480
tggggtcaca gttctacctt gggagattcc agcgaggagc gatgcatgga acgggcttag   72540
cacggtgctt ggtatacatt ggtgggtttt cattttgtt gagaagcaac gatgaatca     72600 actgtaccca gaatacttat actggcaaat aatagaaaat aatgatgtct tatctcatga   72660
ggacactgat ggttttccct acaagtctgg aagtgagtgg atctagggtt ggttagagtc   72720
agggtcagca aggttttca tcttcagtaa agtaccagag agtacatatt ttaggctttg    72780
agcgtcaggc gttcgttttt gcctgctgtt tagtgtgaga gtagccacag atcatgcgtt   72840
cctgactgtg catcgactgt gttccaataa agttttattt gcaagaacag gcagtgggct   72900
ggatatggcc tgcaggctgt agtttgttgg cccctgggct agagtatcaa cagactcgag   72960 gcttttttccc ttccggcccc atcatcttga cagtgttgac attttgtcct gaggctctct   73020
catcatggtt ggcaatgtgg ctgcctccat gtccacaagc atggaaggaa aatgcagtag   73080
gcaaggagga aggatgttta tctcatcatg tgcctgcctt ttttggggag aagacacttc   73140
tgagaagcct gcagcatcca tccccagcag gagctgcagg ggatgctgga aagggtctaa   73200
tgtgcagcgt tcatgacgg aggaaggtca ggcacgaggg ggctgggcat ggctgtgggg    73260
tccgcaccag ccacttctgc ctcacctccc tgcaacgatt gggccttctc caatctgctc   73320
tggaccatcg gagcaaaggt ctggtcagac agctttcctg gcctcttcag acaatagtag   73380
ctgtgatgct ttgtgaacag agggcgccta cagcgtgcaa agggctggtt ttggcaatgt   73440
aaaggactca atttctgctt tacatcagaa aatgccaagg taagttcacc ccaaaacctg   73500
cacatgatgt ctctcattat atgagtaatc accaaagctg gaagccacca gatggatgga   73560
taaacaaatt atgctactta catacagcaa aaaggaatga actattgaaa tgcagctacg   73620
tggatgatct caaaggtatt gtgcaggttg aataagcca atgcaaaaga gtgcaggagt     73680
ccattggtat gaaatatcta gaaaatgcag ttatagtgat gtgagtgggt cagtgtcttg   73740
ccagaggccg gcggtcggag ccatgtgact acaaagcgga gtttcccagc cttggcacta   73800
ctgggtagtt ctcagttggg ggccgtccta tgcatcgtag gatgttgaca gcttccctgg   73860
cctccaccca ctcaatgcca gtagcaactg ctcagttacg acaaccaaaa atgtctcaaa   73920
cattgccaca tgtctcttgg ggagcagcat caccccagtt gggagccact gagctaaaag   73980
```

```
gcagctcaga gagttctttg tggcgtggag ctgctctgta tcccgattga agctgggtac    74040
cggcgtctgt acacgcgcta gtgcttacag atgggcatac caaaaggggt ggattttact    74100
gtatggtaac ttaaaaacta agacttccaa aagcaacaaa acacaccaca gagagacaag    74160
cactgagtcc caatgaagaa accagcaaag ccatgacctc tgggcccctc tacctgcctg    74220
tcaggtaggc cgggccccctt tcccacctgg cagctgcagc ctgcagagag ctcagttatt    74280
ataccgcagg aaagcctttc tatcccaccc ttaaggagaa tctcttggag atagaataca    74340
agatgccgag ttaaatttga atttagacaa acaacaaaga atcgcttagt tcagcatgtc    74400
cctcgtattg caaacattat atgtttatct gaaattcaaa ttcaatcagg caccctgttt    74460
ttgttttttt ttttcaaaat ctgctattct tgggcaaatc tgcaggcttt aaaaaaaaac    74520
tattaaacct ctgctaaaat atattttcaa actttctcaa agatacagat tttatggtta    74580
aaatatgatg caggtcctgc cttcctgcct acatcaattt gttcactcac ctcgcccta    74640 tgccttacag atgcaggctg gctccctagc cagtgtgact tgtccgggac atttaaatac    74700
aaataatcaa agtaaatagt tacgcgcact gactaaatct gatatttat aacataaaat    74760 gaaaggaat tgttctcctg caaaataacc tttctcagcc cttcctgggg tattagaaca    74820
aaatacatgt tacatctgta cacgagcacc tacgttagta tgtgctttat atatatatac    74880
acataaaaaa tacataatat atattaatat gtcttctata ttttatatat aatatatact    74940
atatatatta tagtatatat actatatata ctatagtata tatgctatat actattatat    75000
aatataatag tatataatat gtaatagtat atatactata tataatatat agtatatatt    75060
atatatctat gtataactat atattatata taatataata tatagtataa tatgtatata    75120
ttatataaat ttataaatat aaataaatat ataaatttag atataaatat atattatata    75180
atatactata atatgctata ttatatatta tatataatat atattacata tacaataata    75240
tacaattata taatatacta tattatgtgg tatatactat attatataat atactataat    75300
agaaaatata taatatatag tatgtatact atctatacta tatatactat ataatatata    75360
gtatatgtat atttttatatc tataatatat aaaatatgta taatatataa aaacatatat    75420
atactataat ataaaatat ataatatata gtatattata tatattatat attatagtat    75480
atattatata tatatgttt aggtggagtc tcactctgtc acccaggctg gagcgccgtg    75540
acatgatctc cggctcactg caacctctgt ctcccgggtt caagcgattc ttgtgcctca    75600
gcctcccaag tagctgggat tacaggcgtg caccatgacg tccagctaat tttctttgtg    75660
tttttagtct ctactaacac ggggttttta gtctctacaa cacggggttt ctccatgttg    75720
gccaggctgg tctcaaactc ctgacctcaa gtgatctgcc tgcctcggcc tcccaaagtg    75780 ctggattat aggcgttagc caccacacct ggcctacatt tctttcttcc taggtgtaat    75840
caggctaatt tgcatgctcc tcctcattta gtggctcatg ggagggaact tccttctgt    75900 tggccccacc agagcctgcg cctgtcttgc ctctggagca ccccagagca cacggtagtg    75960
ctgggctcag tacccgaggc atgaacacgt gttcagtaaa tgaatcttca ggcactggtt    76020
gatgcttcat gatgcaccctt ctaagttcat taatctcttc ttgataaagc actacattct    76080
ctcttgggtt ttgtaggtca gactcggctg cgatgactca cctttacaca tcttcctttc    76140
ttggcttgtt tagggagtgt gtttgtacag ccatggctct tgaccaggga tggttttcct    76200
cccaggggac atgtagcaat gtctggagac atatttggtt gtcatgacat ggagaggtgc    76260
tactggcatt agtgagaaga ggccaagggt actgctaaac atcccaccat gcccgaggca    76320
gccccgatgc ccactgcgct ggagtgggca ggcccaccat gctggctgtg gcctgtctgg    76380
```

```
tgaacaagct tggagccag cgttaaagct ggcttctgtg caggagcagt gggtgcagga    76440
gaccatcctt cccctaagtt gttgagcttg ttggaggagg agggtagtat gtgtgaggat    76500
cccagggagg ccggccctga gcgtggtggg gcctggagga ggggcgggca ggagcggacg    76560
cgcttctgga ccaccactct ctctcccagc cttgttggtt ccccacacgg cattcagaat    76620
gggtctccca ccacagaacc ctggccacgt cgcccctgc ccaaatcccc cactgggctg    76680
ggagacccca ggtgacccag ccccataccc acctcggctt caccccttg ggctcctcac    76740 tcactctctc cagcctcacc ccctcgggct cctcactcac gctctccagc ctcacccct    76800 cgggctcctc actcacgctc tccagcctca cccctcggg ctcctcactc acgtctcca    76860 gcctcacccc ctctggttcc tcgctcactg tctccagcct caccccttca agctcctcac    76920
tcactctggc ctcacctcct ctggttcctg gctcactctc tccagcctca cctcctctgg    76980
ttcctcggtc actctctcca gcctcacccc ctctggttcc tcgctcactc tctctggcct    77040
cacctcctct gattcctggc tcactctctc cagcttcacc ccctccggtt cctcgctcac    77100
tatctccagt ctcaacctct ctggttcctg gctcacttct ccagcctcac tggcctcttc    77160
actgtgctga cacacaccgt gtatttctca tgaacctggc atgtgccatt ccctctgcca    77220
ggaacatttc ctccccaaaa cctcccatgg ctcactctgc cctgtacact gtgccccact    77280
gtcatgtccc tgccaccctg tcctaggttc ttcctagtcc ttgccaccat cagacacagc    77340
actgtgcacc cctgagctga tctccctcgc cagtcagctc ccagggtggt cgtgttctca    77400
ttcaccgatg tgccccagcc cctggcacac agtaggtgct caataaacag ttgctgaatg    77460
aattaatgaa aaaacaagtt agttgttcaa gcctgggaca cagaacctac gttaggagag    77520
gaggacgagg caaaggatgc ttctatctca gtgtttccag atgggaagct cctctgtggc    77580
caccagggag aaggtcagtg tgtgtttcat cgacgtggaa atatgtctgc aatatattac    77640
gtaaagggca gagtgatatg aaacaggatt gacggtgcag tcccaatcat gtggaatggc    77700
accctgtctc tgcgtcacgc gtgtgcgatg gggccagcct cacaggtgtg ggtgaactta    77760
gaagggccct gtgctgggtt tgcttctgct gccccacct tgaaatgatg aatcactttt    77820
gaacaagagg ccccacattt tcattttgca ccgggccttg cagattgtat agccggtgct    77880
ggcgcctggg gatggatggg aggtcgctgc ccgcaaatgg gctctgagca agatgttcca    77940
gggcctacgt tcttctctgt gatttcctct gttttgcagtc atcaggtatt gttttcagag    78000
ccccctgtac cccaagaaaa agtcagataa ctgagttcag agtatttcag tccaatttct    78060
tccaaatgac tatagtcagg catttgacat ttcaaggaat aacagggaca aaaagaccta    78120
gctgttggaa gaagttgtcc cctccccacc cctggggtgc tgacctccaa gctcatgtgt    78180
aggtcccacc cccttctggg gagctttgac cctagttgag aactgactgt aaacccagac    78240
ggaagggagg ccttgggtgt gtttgcagca cgagagcttg tggttgtcgt ggcagagaat    78300
gcaggctttg gttttgacag accagggttc gaatcttggc cttgccgtgg accagctcaa    78360
aggccttcct cactcagagt cttgttcctc ctttgcaaag tgaggttgca gcatctgccc    78420
tggggctgtg ttgaggatgg ggtgggccat gagctcccag tctgctgctg gtgaggcagg    78480
catttattgg gtaaacagcc agacactgcg gtaggcatcc ttactgttta tttatacaaa    78540
ctgtccctct aaggcacagt gagtgggtca ttcccacccc tgttttgctt tttagttttt    78600
taaaaaatgt gagatctaat tttcctaaca taaaactcac catttcaaag agtgcaattt    78660
ggtgattttt ttttttttt tttagtatat tctcattgtt gtgcagccat cccattgtct    78720
```

```
gattctagaa cgtttccgta tcactccgaa atatcccttà agagccactc tctgctcccc    78780
caacccctag ctctaggcaa ccagtaagct actttctgtt tctatggatt tacctgttcc    78840
ggacatttca tagaaatagg atcattcaat gtgtggcttt tgtatctggc ttcttccatt    78900
tcgtgtaacg agttgaaggt ttgtccgtgt tgtatcatgg atcagaaaat gactccttt    78960
tatggcaaac aatattccac tatatggatt caccatattt tgtttatcca ttcatttgtt    79020
aatggacatc gggttgtttc cacttttcgg ccatcataaa taatgctgct gccaactctt    79080
gtgtacaagt ttttcatgtg aacccgtgtt ttcagttctc gtgggtacac gcctaggagt    79140
ggaattgttg ggtcacgtga agactacata ttaaactttt tttaggaatt gccagtgtat    79200
tttctgtatc cctttgttgt tgttgttgtt gaaggtgaat aagtgtctgc tgtggtgttg    79260
ttcagccttt aggttaaaaa tctgaacctt tttccaaact tggtgacaaa ggggaagatt    79320
ccatacctgt cctcagagca cctgttccac gtcaggttcc agatggctgg caccatgctc    79380
cctgtcccca gtctctagg aaaggggcaa gaacaaccca aaataccagt tcagactaag    79440
aaatcgaagg gtttttcatc ttagtggctg gggtgagaat gcgggcttca gggctggctt    79500
gatccagtga cttagcaatg tcaggagaga cccggtctct gttctgcctt ctaccagggt    79560
ggcctcttg gaaacatggt cacctgtggt tgccagatgg tggctgtttc tgtggctcca    79620
tctatccctc ctccctcaat cgtgtagaga gagagagaga gagagagaga gagagggcag    79680
gcttccttct ggacactaga gtgggaggct tcttttccag aaacctccag gatacttctc    79740
cttcatttat tggccaaaat gggtcatgtg ctcatccctg aactaatcac tgtagccaga    79800
ggattagttg cctttatta aaccacaggc cccacctcta aggccagggt ggaggctatg    79860
taaggcacaa ctgccttaat gaaaatccgg ttggctatca cggaaagggg ggacagatga    79920
gtctcatggc atcatcccca ttttacagat gaggaaattc aggccccagc atacaacttg    79980
cctctctcag cccacacagg ctggttagtg gcagatgcgg gtttaaacac ccttgagact    80040
cacttcttgc ccctctgtcc tgacatttct cagctgaggc tgtggctccc tggatgtggc    80100
tgtcctgaca gctgcccaag gcaagccaga caccttcact cagaggtaca gagagacttt    80160
ttgcagcgcg tggatttaag gtatctggaa cagcatcagc ttttcaggcc aggcatttt    80220
attttgccct aaaagccttc tagtggggga aacacaattc ctaggggctc agctttaatg    80280
gtttctttta tagaaccatt caaattatag atgggtgaac tccggaaaac cccgctcaag    80340
aatgcaggaa agccaaacgt taagggagt taaggtaaaa tagcggcggg tgggggaaaa    80400
tttgttcttt taaacactag ttgttaaaaa accaaagtga accccctggt gctgatctgg    80460
tcctgggagg ctgggtttct tgacttctgg cccgtctggg ggactccagg tgaagttaat    80520
tccagatgtg aacaggccca tcgcttttgc tggcctctga cccctcccat ctaacttggg    80580
ggcaccgtat ctgcagaggc tcagcctccc aactccccgt catcctcacc tgggttcaga    80640
ttctactttg ttgcttccaa gccgggtatc cctgggcggg ttattcagcc tctctgagct    80700
tgtgctgtca tgagtaaaac aggctttgtt tccactggat gctttatttt tggctttgaa    80760
atactcatca cccccagaca tggtattaca tatatatttg ccaatgacct catcattgtc    80820
aaagccagtg gatagatagt gtgttcttag gtccatctgc agagcaacgg acacggagtt    80880
tgctccctct attttcctcc cctgtttttcc gggaccccat accctgttgg tgtccccatt    80940
cttcctgccc aagcgtcttc cagatccttc cttaccgggt actcctgcac agtctccgtt    81000
gcattcccct gacctctcag tggaacacag aggccaccttt cacattgctt gtcaggctgt    81060
acacactttc cccaggcgag ctcatccagt cttctggctt taaatgccat ctctacactg    81120
```

```
gggacaccca agcttacatt actgtctgga ccactgccct gagctagcat ttattgagca   81180
cttagggtat gcaaagctct gtcctgagct agcatttatt gagtacttag ggtatgcaaa   81240
gctctgccct gagctagcat ttattgagca cttagggtat gcaaagctct gccctgagct   81300
agcatttatt gagcacttag ggtatgcaaa gctctgccct gagctagcat ttattgagta   81360
cttagggtat gcaaagctct gccctgagct agcatttatt gagtacttag ggtatgcaaa   81420
gctctgccct gagctagcat ttattgagca cttagggtgt gcaaagctgt gtcctgagcc   81480
ccagctgtgc attaagtgac agaggcaggg ctttgaacct gcctgggccc tactccctcc   81540
ctcactagcc cagagctcat ctcttccaac tgatcaattg atcaagccta ggccagacct   81600
ctgctgccca cctgacacct tccttttggt gtcaagtagg gatttcatac aatatctgct   81660
aaacgaaact gcattttgtc ttccaccctc tatttcccag cttatgctcc attgcctcag   81720
tttccctacc ttggtaaaca gtccctccct tcttccaggg gcttgggcca agagcatgcc   81780
agtctcatga gactccccctt tttctcacac cttttataat cccttcccaa attcagtcct   81840
aaatctgcca ccttcctggt ttggaggctg tgttcttgtt attcgagaca tcacctttgg   81900
gggaaactgg atgaagggca cttgggacct ccctgtacat cgtctttcaa cttcctgtga   81960
atctataatc atttcacaac aaaaagttaa aaccaaaata aattctaaag attttaaaaa   82020
tgaactcttg aggatctggc cttttctcac cagcctccct ccccactgcc ctgggtccag   82080
tctcacgtca cctcccacgt ggaccattct gttgcctcca cctggtctcc ctgcttccag   82140
gttgacccct gccatcggct ctccaggggc agcctgagtg gccttataaa caccactgaa   82200
agtcccaccc cagtggttct tgcttcttgt agagcgcctt ggtgtcctga ccagggccct   82260
ggatgcgaag tcccactcac tgggtggctt gaaacaatag ggctttattg tctcacagtc   82320
tggaggcgag aagtctaaag tcaaggtgcc acagggttgt cctcttacaa aggctctagg   82380
gaggaatccc tccttgcctc ttctggcttc agaggctcct ggcaatcttt ggcatttcat   82440
ggcctctgtc ttccccaggc tgtctgcatc tgtgtcttta tgtggccttc ttatggggac   82500
actagtcact ggattaaggc tcatcctaat ccaggatgag cttattttaa ctgacgacag   82560
cacatctgca aagaccctgc ttccaaatga ggtcacatcc tgaggctctg tgtgggtgtg   82620
aattttagag gacatcagca acagaggaca ctgggctgag gcaggtgctc gtgttgccca   82680
taggacccga cctgactcgt gccctactg ccctcccag ttgtccctgc tacttgcccc   82740
tgccccttga acacaccctc cttgctcctg cctccgggca ttcacctctg cagttccctc   82800
tgcctggaat gcactcttcc caaacatcca ttgggccccc tcactcactg ttacccagat   82860
ctctgctcag atggccccta tagtcattag ggttgtttgc aattgttccc accttccctg   82920
gcacggagca agattgcccc ccaactccct gaaattaggc agataccacg acctgctttg   82980
gccaatggaa tgtgagtggc acttatgggg ttcgctagct tgccaccttc cgcacccctc   83040
agcctggttc cccaccccctt atatttcctg cctgccttcc ccacttgcat ggaaacccag   83100
agaacaggat gttttcttgg ctgctttcac agttgtgttc caagttcctt aaacagtacc   83160
tggcctagag tgagtactca ataaatactt actggatgga ggaataagga gttcatgaat   83220
gaaccgggag gcatagcatc tctgcagccc tgtcccgctc gtggccctcc tgtaactact   83280
cttctgtgca cttggctgct tcctgtccag ggcagagcat caaccccaag ttggcgggcc   83340
tgattgggcg gcacgggccc cagaacaagc agccttcat ggtggctttc ttcaaggcca   83400
cggaggtcca cttccgcagc atccggtcca cggggagcaa acagcgcagc cagaaccgct   83460
```

```
ccaagacgcc caagaaccag gaagccctgc ggatggccaa cgtggcaggt atgcttaggt    83520
gggagggatc acagacccac cacaggaacc cagcagggcc ccggcgggac ccggcaggag    83580
actgactcaa aatccattca ggtgctcacc agatggctct ggaacaaata tagcaggaag    83640
aaaaccccca aatccacccc tacacaggac atcttaattc tgtaaaaata aactagctta    83700
gaaatgcaag tagcaaaaca ttcgtataac acaacaccaa gcatgtagat atttaaataa    83760
acagaacaat ggcggcactt gcagctacac agagatgaag gaaagaccct gaaacgtgga    83820
tgggaagacc cctggggggg cttaccccat ggaaggaggg ggaggaagaa atggggaggt    83880
agaagagttt gctgtatctt tatttcataa atgaaaaata ttttaaattc atggcaaact    83940
ttaatacttg ataaatatta tatatatata cacacacaca cattttttttt tttttgagat    84000 gaagtctcac tctgtcaccc aggctgcagt gcagtggtgc gatctcggct tactgcaact    84060
tctgcctctc agattcaagt gattcttcag cctcagcctc ccgagtagct gggactacag    84120
gtgtgcacca ctgtgtccag ctaattttg tattttagt agagacgggg tttcaccatg    84180
tcggtcaggc cggtctcaaa ctcctgacct caagtgatcc acctgccttg gcctcccaaa    84240
gtgctgggat tacaggcgtg agccactgca cccggccagg tggtaggtgt tttaagaata    84300
tatgatgtgc ggtactttc agtttgtttg aaatgtttat ttacgatagg ttttaaaaaa    84360
attaaagata atatttttat tgcaagcaaa tcaaacatta acagtaaata taagtaaagt    84420
taacgcattg tgcgaaggag acttccagga ggtcgtgctc tgcaggtcct ctaaagcaga    84480
cagcttttag cccatcatgt tgtgtggttc ttgaggctct gaggtagatg gcctcccact    84540
tcacagaggg gaaaactgag gctcaaagag ggtaagtcgt ttgtctaagg gcacagtgta    84600
ggtaactggc agccctggga ttgggtccct ggggtctggg ttgtcccttg ccccaggccc    84660
tcttccctgt tgggcattgc cggggccatc tacctggcct ggatgagctt cggtgtcccc    84720
agcaatccca ttgggtgctt tctgacaatt caccaggcat tcgtggagcc cccacaggag    84780
cctggctttg tcccgggcac tggggctgtg gctggggtgc aatccctttc cccataggct    84840
gattgggaaa ccgacattga cagcctctgg tggcctgggg gtgctgggat ccccagaagg    84900
tgcattctgg ttttgagctt tggaggtggg ctggcctgga gcagacctgc tggcactgtg    84960
ggcatctgtg gacagccctc ccacacccct tgcctggctc atgcccctg cacatgcagt    85020 gtcaagtccg ccagaagatg catcgggact cctcccagac taaaaccaaa gcttcgaata    85080
atgaacctca caacaaacca ttttccagtg gactggaggg gtgacacctc ccagatccaa    85140
ggagcccagt ttgctcccca tccccaatcc catcccgccg gccaggggag ctgctgcccg    85200
ggggtgccgt ttctctggct cttcaggaag ccatttgcaa tgagcagggc aatagcctct    85260
ccaagatgcc agtgtcttaa tctctggaac ccgtgaatgt gtcaccctcc agggcaaagg    85320
ggagttacga ctgcccttgg aatcacaggt gctaatcagc tggccttcca atacgcgggc    85380
tctgtgtagc agggtggtcc catcggtcct tataggagag agccttttg agctgtggtt    85440 ggagccatgt aagcacagag cacagagggg tggagatgag tggggccacc agccctggga    85500
tgtgggtggc ctggagaagc tgcacaaggc aaggaaggga tcctcccta gagcccccag    85560 ttgcatttac ctgctaagac tggtgttgga cttcagagcc acagagctat aatccgcttg    85620
tattgttttg ataatttgct tggttaattt gttaaagcag cgataggaaa gaatacatct    85680
ttgttggcaa agtgattttc ttttctttt ttcttttctt tttttttttt tttagagaca    85740
gggtctcacg ccattgccca ggctggcgtg cagtggtgtg agcatggctt actgtagcct    85800
tgacctcctg ggctcaagca atcctcctgc ctgagcctcc caggtagctg ggactataga    85860
```

```
tggatgccac cacacctggc tattttttgt agagacaggg cctccctata ttgcctaggc    85920
tggtgtcgag ctcttgggct caagctatcc ttccactttg gcctcccaaa gtactgagat    85980
tacaggcatg agctactgcc cccagcctcc tcagagtgct tccctcatcc tgctaaggag    86040
ctgggacaca accatctggg ggccggctca ggagttgcag ccttcttggc tccaggttga    86100
tcacaaggca gaaaaaggtc tgaggtgcaa acctgccctg ccaccatgtg ggaagctatt    86160
agctgcttat cacctccggg gcctgcggtt ggtcccagga agcacccaag gggagcaagg    86220
ggctattgag aaaggtcctg gcgaggggat agcagcagcc ccaccccaa attaaccctc     86280 tagtgccaat agcttcttcc tccttaccta gcctagcttg aaatttatgt tcattttact    86340
tttcaaggga gaaggcaggt cagtggggtt ggtggccttt ttaagacaag gcttcctgac    86400
ccctggcggg tgtcctgggg ccccggatg acctcagtg ggtctgtgtg cccagagtg       86460 tgtagggatt ccgtatattt tcttttctga cagtggatcc attttccag gtttctcaaa     86520 ggggtctttg atctcccaag tcaaaaacca accaaattcc ttcatttgta ttcgaagcct    86580
cttttatgct ggactcttga aggctaggat tcaatgtcga acacccacac aaaggctgcc    86640 cttggggtg ttaatttagg acaggaagga ggggttgcc attcacatcc atacatagta      86700
acagacccag agtcagggtg gtgcctaggg aacgcagccc atcccgaggg ctgcagacaa    86760
catttcgtgg cgagcgagct gagagctctg ggtccagtgg gtgcccacga ggccaggctg    86820
gtccggagag gatgctctgg gctgtgggac ctgcaggggc agaggcctgt gctgtggggt    86880
ttcctggcgc ctttgggag tggggaggag gctgtggggg ctgaagcagg ggagggagt      86940 gagggtgggc gggtcaggca ttctcttggg agtcacgtct tgagtttgaa cttcatgcca    87000
agcatgttca gaagtctttg cagagattca agctgtggtg tggggtgcag gtgataagat    87060
cattctggct gctctaagaa aggtgaggaa cagggtgggt gccgaggggg tgctcagagg    87120
ccggagactc cttagaggat gtggcagatc atccaggcag gaagtgtagg caaactgcat    87180
cccggcagag acttccgtgt cttggagctc catcgggtgc acctgggtaa tgaggggag     87240 aggaactagg catcgcgggc ttagaattca ctctgatttt ccccaccgcc tcctcatcaa    87300
agccccacca agtctccatt tacacagccc ccaggacggg gctctcactg tttcccgtgg    87360
cagaaattca ttgctgggaa cctgcctcct tcccgcggat ggctcgtggc cctgtttgca    87420
gctcttctaa aacctgcctg gaagttaaga aaaaataaa ataaaaatac cgaggcctgg     87480
gccccaccct aggcttaggc cagagtcctt gagtgtgagt gtgtacgcct gtgtgcctgc    87540 cccctttgaat cgctcgtccc cccggttttg ggctggagcc ctgccgtgga ccacacaag    87600 ttgaatctct cggcagccct gtgtgtgctg gggcggggc acatgctccg gcacgctacc     87660
ccacgcggag ctcgctttcc tgcccgccag ccccctcccc cggggcttca cgtgctcttc    87720
agatggtgcg gtttggggtt gagaaactgg gtccctgcac ttccttctcc ccacccacgt    87780
ttggacccag ctccctggta agcagccgcc tttgccagat gacccgtgga ggcgggagct    87840
gagcctaagc accagtcctg acttgtctgc ggcccaagca gggggttgag gaggtggatg    87900
aatcccggtg ctggcgtcag ggctgtctcc tgctcacttt ctgttgcttg ggggcgggtg    87960
gggcaggctt ggacggacag gggagctggg agtccctcct tcgtttcctt tccttgtttt    88020
cctgctaata agtcctaagg atacacagga gctccggcca cttttctgctg ggacagccgt   88080 gatcaaagag ccctggaagc acagagcagg gtctggagtc cctggtggca gggccagtgc    88140
ccacgcctca ctcgtacacc ataactagct tcatgagctg tgctcggcct tggtctgttt    88200
```

```
ggccttgggt ttgaactaag ttatgccaaa tgtcgtggct ttactttaag acagggttgg    88260
ggaaagtagc actcaggcca ctccttgtcc cttctgtgct catgacagac attgctaata    88320
gatcatggcc tctcctgtgc tcatgacaga cattgctaat agatcatggg acttccttct    88380
gacggagcct gaacacagct tcagaatcct ccttgactca ggacaccaag gagtcagcaa    88440
tgtccctggc tcgagctagc agcttcacct gacacatccc tgagctgagg ggatgttcct    88500
tctcctccac cctgccttct accccccac agggaagagg gaggaggctc gtggaggggc    88560
atggctacct gtggccctgg gcattgccac agccatgaag gccatcttag gtttctgctt    88620
ggcatcgtgt gctctagagg gcaggctgta gagtccagct gtttgggctc ctcccagatg    88680
gttccttgac cttgaccttc ctgtgttgag gacaccctgg ccctggggag gttcctgctg    88740
ccccagagct ggttctctct ctcccagccc tgctactccc ccacggaggg tgggaccag    88800 gggcctctgg gctcccctg gctgcctcca tccactctga gcacccctt gcagcattga    88860 gccttggggc tggttccagc cacgcagatc ttccctccgc ccacactgtc tgctgaccca    88920
ggccccagct tcctcattcc ttgccaggct cagtgcctgc ctctgatcct ctatccgatg    88980
ctactccagc ggcctcagac atggagggcg cctcgtcccc actgctcagc atcgtcatgc    89040
aggaatgcct cgcccttgga tgcctcccca ccctcctatc tcacttcctt ttggttctta    89100
cccacatgtc acctcctcag aagagcgcct gctggcaccc gcggcagcat gcccgctcac    89160
tccagcttct cctgccttgt tttcctctgt agccctcatc tccatgtaag tcatgtgcac    89220
tcacttatct atgacccgcc tctcgttctg gaaaagcccc tgagtggcag ggctttgctg    89280
tcttacacct gggactcatc tcatgcctgc acaccaggaa gcagcccta gcaatggctg    89340 aatgaatgag tgactccaca aggcatgcag gccgcgaggg cagggcaccc aggggcaagc    89400
gctcctgccc caaagcctgg agcccaccag ccccgcccca gccttcagca gttcacttc    89460 accgaaagtc tcaagtgtct cctcaggaat cacacatgtg attcggttat aatcaattaa    89520
atgtaatttc gttattggtg tgcatatctt tccacattgc ttttctgaac tgtagataaa    89580
ttttatatct gtataaatag atatattcaa aaatggcatt tgggaggcc aaggcgggtg    89640 gattacctga ggtcaggagt ttgtgaccag cctggccaac atggtgaaac cccgtctcta    89700
ctaaaaatac aaaaattagc tgggcatggt gatgagtgcc tatagtctca gctactcagg    89760
aggctgaggc aggagaattg cttgaaccca ggaggcagag gttgcagtga ccaagattg    89820 caccactgta ctccagcctg ggcaacagag caagactctg tctcaaaaaa aaaattgctg    89880
atgaaaataa aagcagcctg cttttcagtc cccagcaggg agcatggtgc tcctgtctca    89940
gcctgagcct tggaggccag ttcctgactc ctgtgctctc catgctgttc tcctctctcc    90000
tgcctccttc ctcctcaacc ctcttctttc tcctttctgc tttccactct ggcttgctg    90060 cttctagccc atttcattcc acaattgttc tcagccatgg ggtagctaag gcacactgaa    90120
ggtttccagg accaacagaa tgtccagtct gtgtctgagg aggtgtccta atttgcagtg    90180
tgtggtccat gggaggctag cttactgcac cactcctgtc ccacccattt tacagatgaa    90240
gaaagtaagg cttagggaag ggagttcggc gatgtccttc ttatcttacc atttctcatt    90300
atcctagaag ctatgcagat agaattctca tgaatcagag aaaagccaaa aattgagtgg    90360
tgttccactc tttgacatat accctaatgg catgtagtgg gtgtggagga aagagccatg    90420
cattcaaaca gttaacaggt gtgtgtgtgt gtgtgtgtgt gtgtgtgtgt gtgtgtgtga    90480
atggagaatg tgcgtagttt caaatttccc taacaagtgg gctagaagaa gaagaagaaa    90540
atatgaaact gccatgaaca ctcaagccta ccccaggagt tataggagct ctcttcattt    90600
```

```
tgcaaaccag gagtccaaga tctaggagag ctggggtttg actccagagc tagagcagtc   90660
cccaagacct ggtcttgact cacgagttag actccactca gaggctgact gtgctccagg   90720
gtctacacct ctaagggcga cacctgggct caagcagact gccgttttct atatgggatg   90780
agccttcaca gggcagccag ttgggatggg ttgaggtttg gctgtagaca tcagaaaccc   90840
aagtcaaatg cgcttcaacc agtagaaaat tcaccagccc gcagagctaa ggttgggtgg   90900
acattagggt tggttgatcc aggagctcaa cagtgtcctc tgagcccagc tccttctgc    90960 cccaccccac catcttcagt gctgcttcct ctcaaggcca cagctgtagt tggccagggg   91020
ggcttcatta ttttttgctc ctgggcagta ggaggaagag aatgaatgtc tctccatggg   91080
tctttcttag gaatgtggga acttttttcca gaagtctcta tgtcttttag tttgtgttgg  91140
gtcacttgcc cttcctgaac cacttcctga ctcctggaca ggatgtgcac tgatgagctt   91200
agctttgggg atctaatagt gactttacaa agcctctttg agaaggtgac attggaacca   91260
aggcttgagc cagacacaac aaagattgca gggaggggca ttgcaggtgg aggaaacggc   91320
acatgcaaga gccctgcggt gggagtgagc ttggtgtttg gtcaatcagt tgtcagagca   91380
caccgggcct gtgggccaca ggcacagcct gggccctgct ctgagtatga cagagagccc   91440
ctgggaagtt gtaggtggag gaaagacagg tcatgactag gaaaaaagca atccctctgt   91500
tgtggggtgg aaggaaggtt gcagtgtgtg tgagagagag acaagacaga cagacagaca   91560
cttctgcaat gtttacaagt gctcaggccc tgacccgaat gcttccaaat ttacgtagtt   91620
ctggaaaacc ccctgtatca ttttcactac tcaaagaaac ctcgggagtg ttttcttctg   91680
aaaggtcatc aggttttgac tctctgctgt ctcatttctt cttgctggtg gtggtgatgg   91740
ttgcttgtcc caggccctgt cccgcatcct cttgccctg cagagggatg agtgtgttgg    91800
ggcctcacga gttgaggttg ttcataagca gatctctttg agcagggtgc ctgcagtggc   91860
cttgtgtgag gtggatgggg tttgattccc ttatggaatc caggcagatg tcagcattta   91920
aacaacacac gtgtataaaa gaaaccagtg tccgcagaag gttccagaaa gtattatggg   91980
ataagactac atgagagagg aatggggcat tggcacctcc cttagtaggg cctttgctgg   92040
gggtagaaat gagttttaag gcagttagac cctcgaactg cttttgaat cgggaaattt     92100 accccccagc cgtctgtgct tcattgctgt tcacatcact gcctaagatg gagggaactt   92160
tgatgtgtgt gtgtttcttt ctcctcactg ggctctgctt cttcacttcc ttgtcaatgc   92220
agagaacagc agcagcgacc agaggcaggc ctgtaagaag cacgagctgt atgtcagctt   92280
ccgagacctg ggctggcagg taaggggctg gctgggtctg tcttgggtgt gggccctctg   92340
gcgtgggctc ccacgaggca gcgggtctgt gctcagtctt gtttctcatc tctgccagtt   92400
aagactccag tatcaagtgg cctcgctagg aagggact tgggctaagg atacagggag     92460
gcctcatgaa atccgagagc agaaatgtgg ttgagacttg aacttgaacc aggaacccaa   92520
acactttgga ctctgaaccc cattctctgc atgcacctca ttcccatccc ttggctggct   92580
gcttctcaag atgatgccgg gccgtgtgtt tgaatgtaga tacctgggga gccatctccc   92640
cctctgccct ctgacttcat ttaccccatt cccattccca cgggagggac ggatctgccc   92700
agcttggttc aggcacttgt tcctgaacca gtcaactgtt tcaggggtgg ggtcatgtta   92760
ctggcacatg gctgccccct ctggagccat ttgcatggag tgaggcaaaa ggcaggggat   92820
gaatcctagg agaggagtga gggtcatgtg atccacctgc cgtgagctct ggtgtgattc   92880
tcattcagca gtcatgcagc atctgcagcg ttctgggccc tgttctaggt actggattgg   92940
```

```
agatgcagcg atgaacactg caatgtgtct gccctgtggg gctcaaatat ccctggagag    93000
ggtattgtca tgaggtcatc agggcaactg gtggtattct accctcaggg agcttgtagt    93060
tcagtgggag agtccagaat cttccctggg gattatgccc agacacactc agggcgtacg    93120
tgcacacagc cagctctgag ccctcctgtg agcctgccct caggactgat gaccacatcc    93180
acctgcagct gggacagaac ccaaactcca ggggcctctg ctggaagatt ccatgtgctt    93240
aagcatcact gaggagtata ttgattattg ggcaacattt ctgtgccacc cagaccctag    93300
aggcaaggat ggcacatgga tcccttactg accagtgcac ccggagccag catgggtgat    93360
gccattatga gttattagcc tctctggcag gtgggcaaac cgaggcatgg aggtttgttt    93420
aaggtgaact gccagtgtgt gaccacctag tgggggtaga gctgatgatt gcctcacacc    93480
ggaggctcct tcctgtgccg cgttctgtcc agaagacaca gccatggatg tccattttag    93540
gatcagccaa gccccgtggg gctttccttc atttttattt tatgttttt tagaaatggg     93600 gtcttgctct gtcacccagg ctggggtgca gtggtgtgat catagctcac cgcagctttg    93660
agccgtcttc ccactcagtc tactaagctt ggactatagg ccaagactat agagtggtcc    93720
ttctttccat tcttttggga ccatgagagg ccacccatgt ttcctgcccc tgctgggccc    93780
cctgctgctc agaaggcatg gtctgaggct tccaccttgg gtcgtgagcc tggcgtggtg    93840
gtttctggcc agcatggggg ttgggatgct gtggctcagg ccttctgcat ggtttcccac    93900
actctcttct cctcctcagg actggatcat cgcgcctgaa ggctacgccg cctactactg    93960 tgaggggag tgtgccttcc ctctgaactc ctacatgaac gccaccaacc acgccatcgt     94020
gcagacgctg gtgggtgtca cgccatcttg gggtgtggtc acctgggccg ggcaggctgc    94080
ggggccacca gatcctgctg cctccaagct ggggcctgag tagatgtcag cccattgcca    94140
tgtcatgact tttgggggcc ccttgcgccg ttaaaaaaaa atcaaaaatt gtactttatg    94200
actggtttgg tataaagagg agtataatct tcgaccctgg agttcattta tttctcctaa    94260
tttttaaagt aactaaaagt tgtatgggct ccttttgagga tgcttgtagt attgtgggtg    94320
ctggttacgg tgcctaagag cactgggccc tgcttcattt tccagtagag gaaacaggta    94380
aacagatgag aaatttcagt gagggggcaca gtgatcagaa gctggccagc aggataatgg    94440
gatggagaga tgagtgggga cccatggggc catttcaagt taaatttcag tggggtcacc    94500
aggaagattc catgtgataa tgagattaac gtgcccagca cgtggcgaca ctcagtaggt    94560
gttattcctg ctctgccaac agcaaccata gtgataagag ctgtagggat tttgttcttt    94620
tgcttagaat ccaaggttca aggacccttgg ttatgtagct ccctgtcatg aacatcatct   94680
gagcctttcc tgcctactga tcatccaccc tgccttgaat gcttctagtg acagagagct    94740
cactaccagg actactccct cctttcattt agtaatctgc ctccttcttt tcttgtccct    94800
gtcctgtgtg ttaagtcctg gagaaaaatc tcatctatcc ctttcatttg attctgctct    94860
ttgagggcag gggttttgt ttctttgttt gttttttaa gtgttggttt tccaaagccc      94920
ttgctcccct cctcaattgt aaacttcaaa gccctacttg ggattgaagg tccttaggct    94980
ggaaacagaa gagtcctccc caacctgttc cctggcctgg atgtgctgtg ctgtgccagt    95040
atccctggaa aggtgccagg catgtctccc cggctgccag gggacacatc tctatccttc    95100
tccaacccct gccttcatgg cccatggaac aggagtgcca tcgccctgtg tgcacctact    95160
tccatcagta tttcaccaga gatctgcagg atcaaagtga attctccagg gattgtgaaa    95220
tgatgcgatt gtggtcatgt ttaaaagggg gcaactgtct tctagagagt cctgatgaaa    95280
tgcttccaga ggaaatgagc tgatggctgg aatttgcttt aaaatcattc aaggtggagc    95340
```

```
aggtggggaa gggtatggat gtgtaagagt ttgaaattgt ccatcataaa atgtgtaaaa    95400
agcatgctgg cctatgtcag cagtcacagc ctggaggctg tgaacagagt gccagtcact    95460
gatgctcttg cctggcacct acagttgctg gaaacccaga agtttcacgt tgaaaacaac    95520
aggacagtgg aatctctggc ctgtcttgaa cacgtggcag atctgctaac actgatcttg    95580
gttggctgcc gtcagcttag gttgagtggc ggcctcttcc cttagtttgc cttagtcccc    95640
actattccct attgtcttac ctcggtctat tttgcttatc agtggcactc acgtggcact    95700
cataggcatt tgagtctatg tgtccctgtc ccacatcctc tgtaaggtgc agagaagtcc    95760
atgagcaaga tggagcactt ctagtgggtc caagtcaggg acactattca gcaatctaca    95820
gtgcacaggg cagttcccca acagagaatt acctggtcct gaatgtcgga tctggcccct    95880
tccttcccca ctgtataatg tgaaaacctc tatgctttgg ttcccttgtc tgcaaaacag    95940
ggataatccc agaactgagt tgtccatgta aagtgcttag aacagggagt gcttggcttg    96000
gggagtgtca cctgcagtca ttcattatgc ccagacagga tgtttcttta tagaaacgtg    96060
gaggccagtt agaacgactc accgcttctc accactgccc atgttttggt gtgtgtttca    96120
ggtccacttc atcaacccgg aaacggtgcc caagccctgc tgtgcgccca cgcagctcaa    96180
tgccatctcc gtcctctact tcgatgacag ctccaacgtc atcctgaaga aatacagaaa    96240
catggtggtc cgggcctgtg gctgccacta gctcctccga gaattcagac cctttggggc    96300
caagtttttc tggatcctcc attgctcgcc ttggccagga accagcagac caactgcctt    96360
ttgtgagacc ttcccctccc tatccccaac tttaaaggtg tgagagtatt aggaaacatg    96420
agcagcatat ggcttttgat cagttttttca gtggcagcat ccaatgaaca agatcctaca    96480
agctgtgcag gcaaaaccta gcaggaaaaa aaacaacgc ataagaaaa atggccgggc    96540
caggtcattg gctgggaagt ctcagccatg cacggactcg tttccagagg taattatgag    96600
cgcctaccag ccaggccacc cagccgtggg aggaagggg cgtggcaagg ggtgggcaca    96660
ttggtgtctg tgcgaaagga aaattgaccc ggaagttcct gtaataaatg tcacaataaa    96720
acgaatgaat gaaaatggtt aggacgttac agatatattt tcctaaacaa tttatcccca    96780
tttctcggtt tatcctgatg cgtaaacaga agctgtgtca agtggagggc ggggaggtcc    96840
ctctccattc cctacagttt tcatcctgag gcttgcagag gcccagtgtt taccgaggtt    96900
tgcccaaatc caagatctag tgggagggga aagagcaaat gtctgctccg aggagggcgg    96960
tgtgttgatc tttggaggaa aaatatgttc tgttgttcag ctggatttgc cgtggcagaa    97020
atgaaactag gtgtgtgaaa tacccgcaga catttggat tggcttttca cctcgcccca    97080
gtggtagtaa atccatgtga aattgcagag gggacaagga cagcaagtag gatggaactt    97140
gcaactcaac cctgttgtta agaagcacca atgggccggg cacagtagct cccacctgta    97200
atcccagcac tttgggaggc tgaggtgggc ggatcatttg aggtcaggag ttcgagacca    97260
gcctggccaa catggtgaaa ccccatctct actaaaaata caaaattag ccgggcatgg    97320
tggcacgcac ctgtaatccc agctactctg gaggctgagg caggagaatt gcttgaaccc    97380
cagaggtgga ggttgcagtg agccaagatc gtcccactgc actccagctt gggtgacaaa    97440
acaagactcc atctcaaaag aaaaaaaaaa cagcaccaat gaagcctagt tctccacggg    97500
agtggggtga gcaggagcac tgcacatcgc cccagtggac cctctggtct ttgtctgcag    97560
tggcattcca aggctgggcc ctggcaaggg cacccgtggc tgtctcttca tttgcagacc    97620
ctgatcagaa gtctctgcaa acaaatttgc tccttgaatt aagggggaga tggcataata    97680
```

| | | | | |
|---|---|---|---|---|
| ggaggtctga | tgggtgcagg | atgtgctgga | cttacattgc | aaatagaagc | cttgttgagg | 97740 |
| gtgacatcct | aaccaagtgt | cccgatttgg | aggtggcatt | tctgacgtgg | ctcttggtgt | 97800 |
| aagcctgcct | tgccttggct | ggtgagtccc | ataaatagta | tgcactcagc | ctccggccac | 97860 |
| aaacacaagg | cctaggggag | ggctagactg | tctgcaaacg | ttttctgcat | ctgtaaagaa | 97920 |
| aacaaggtga | tcgaaaactg | tggccatgtg | gaacccggtc | ttgtggggga | ctgtttctcc | 97980 |
| atcttgactc | agacagttcc | tggaaacacc | ggggctctgt | tttttatttt | tttgatgttt | 98040 |
| ttcttcttta | gtagcttggg | ctgcagcctc | cactctctag | tcactgggga | ggagtatttt | 98100 |
| ttgttatgtt | tggtttcatt | tgctggcaga | gctgggcctt | tttgtgtgat | ccctcttggt | 98160 |
| gtgagttttc | tgacccaacc | agcctctggt | tagcatcatt | tgtacattta | aacctgtaaa | 98220 |
| tagttgttac | aaagcaaaga | gattatttat | ttccatccaa | agctcttttg | aacacccccc | 98280 |
| cccctttaat | ccctcgttca | ggacgatgag | cttgctttcc | ttcaacctgt | ttgttttctt | 98340 |
| atttaagact | atttattaat | ggttggacca | atgtactcac | agctgttgcg | tcgagcagtc | 98400 |
| cttagtgaaa | attctgtata | aatagacaaa | atgaaaaggg | tttgaccttg | caataaaagg | 98460 |
| agacgtttgg | ttctggctct | ttggcctgtg | tctgtctgtg | tgtgttgtgt | ttttctctca | 98520 |
| gttcttggac | actgaagttc | tctcacactg | ctaagagctc | cctgccttcg | tctccaccgt | 98580 |
| gaacgctctg | tttagcatcc | aggccttgcg | gggaagtggc | cgctcgtcaa | tatttggtgc | 98640 |
| agctgtgtgg | ggctccgggc | aggagagatg | gaaccaagca | acacatgtga | atttggtagg | 98700 |
| ctcgactaca | aaggtccttg | attgaattac | agtgcagctg | tcagcagctg | tttcaaagag | 98760 |
| gcaggggggta | aattagctgt | gtttactgct | aacatagttg | aaagatttag | tcatcccaat | 98820 |
| aaaatagagg | caccacagag | agaaaaaggg | caggaggtgc | acgcccaaaa | ctttaaagcg | 98880 |
| gtgccggccc | cagagctgac | actgtccagt | gcaaatgatt | gggcagttg | ctggagcgcg | 98940 |
| actgtggacg | tggatggccc | ccagcaggcc | tggcgaaggc | ggccagggcc | cagtgtctcg | 99000 |
| ccgagcatgg | agcagcactt | ggctgcgtag | cgtggagcag | cagtttggac | gccttccctc | 99060 |
| tttgaagtgc | acactcaggt | ca | | | | 99082 |

<210> SEQ ID NO 10
<211> LENGTH: 27767
<212> TYPE: DNA
<213> ORGANISM: Human

<400> SEQUENCE: 10

| | | | | | | |
|---|---|---|---|---|---|---|
| aaagccagga | agaagttctg | ttttcctctg | ccctcttgct | agccaccaca | cagccactgt | 60 |
| tcttggagaa | ttaaaaaaaa | aaacaaacaa | aaacaaaaca | aacaaaaca | aaaaaccgt | 120 |
| ccctcctacc | atttctttag | tcctgaatct | ccttttccct | tcctctcccc | agccatcccc | 180 |
| accccctactt | cctcttctct | ccctcccgct | gccagttctc | tggttactcc | cccctccct | 240 |
| tgcttctatc | ccagcctggt | gcaagctaag | agggcgagga | cgagggagtg | ggagagattg | 300 |
| gctgaggact | ctacagatca | gctagagagc | gaaagaacta | agtctctctc | tctcatacac | 360 |
| acacacacac | gcacacacgc | gcgcgcgcgc | gcgcacacac | acacacacgt | acactaaaaa | 420 |
| actcggacca | gccgcgccgc | agctgctcca | atccctggaa | aaggcaatcg | agcgccctcc | 480 |
| ggaccgctgc | gcacagcccc | ggctccgacc | tggcgcccaa | aacagagcta | gtcctagtcc | 540 |
| ctcgcgcggc | cagtttggcc | gggtgttccc | aaaaataaag | cgaggaggga | aggtacagac | 600 |
| agatcttgaa | aacacccggg | ccacacacgc | cgcgacctac | agctctttct | cagcgttgga | 660 |
| gtggagacgg | cgcccgcagc | gccctgcgcg | ggtgaggtcc | gcgcagctgc | tggggaagag | 720 |

```
cccacctgtc aggctgcgct gggtcagcgc agcaagtggg gctggccgct atctcgctgc    780
acccggccgc gtcccgggct ccgtgcgccc tcgccccagc tggtttggag ttcaaccctc    840
ggctccgccg ccggctcctt gcgccttcgg agtgtcccgc agcgacgccg ggagccgacg    900 cgccgcgcg gtacctagcc atggctgggg cgagcaggct gctctttctg tggctgggct    960
gcttctgcgt gagcctggcg cagggagaga gaccgaagcc acctttcccg gagctccgca   1020
aagctgtgcc aggtgaccgc acggcaggtg gtgcccgga ctccgagctg cagccgcaag   1080
acaaggtctc tgaacacatg ctgcggctct atgacaggta cagcacggtc caggcggccc   1140
ggacaccggc tccctggag ggaggctcgc agccctggcg ccctcggctc ctgcgcgaag   1200
gcaacacggt tcgcagcttt cgggcggcag cagcaggtga gtgcgcgagg tgagactccc   1260
ttcccgcggt cccgccccag ctttctcccg ggaccccca cagcttcctt gtctgcccct   1320
tgcttggtgg cgctgcctag ggacctttct ccgccctcct cagctgccct ctggattcct   1380
ccgtccagtc acacccgcg tgtcgccagc tgcatctcct gtaagcccag ttttcaaatc   1440
caaagtgaga gggggaaata aatgaaggc gcggagcagt ggagggtag gctggaggag   1500 cttcgtggaa aaagggaagg ggcgacaccc catgcctgtg aggcctcctg ccctgagtga   1560
ctggagcacc tctagggtac cttattctgt tgattcctaa atcggccagc ggaaattcct   1620
ttggactggg ctttagccat gtttactaag aggcagatgc cattttatgc caatgccagg   1680
acccgagaga aatcatactt gaataagacg ccttcccctc tccttttctc cttccccagt   1740
cgcttctcca gatattgcac ccgctcctaa ttcgcgccct ttgtgttact gtactatatt   1800 tgacactta cttgatagtt ccttagtggc aaaaaaaaa aaaaaaaaa aaaaacagg   1860 tgcttgggtg tttcgattat taaaacgcat ctgggtaaac agggggttgta ccatccatcc   1920 tgggaggagc tgggagacaa ggggagggag caaccctgga tgtaaacacc tcttggaatc   1980
tgcccaagaa aatctgctca tcccattttt cagcacagat cacttcggac tgaaattcat   2040
ggcttaacaa ggtttctcct agcccctgtg gtgaagggaa taacttatgc taacagcctc   2100
cctcccttgt gttaacagct tgagggaaag cttcctggac actaactctg tttttatgct   2160
ttgaggattc accaggcttt tttgttcact acattcatga taaggggaaa tgtaactgca   2220
aagcctgtct tcagtgaaca gttgaacaat agccaagaat cttcaagaaa atgaggccat   2280
gcctcagtca atactgtcag aatcactaga aagaaatctc ccaaagtttt gatatgcaag   2340
actcctggaa aaagggaaaa ctaaggcatt catcaaggaa agccctgcat tgtctgtgta   2400
aatatattct agagcttaca ggcatgatga catttacaat agatgtgaat tatgcttcct   2460
aatacagaag tctttagcta gagactgaac tgaaccagat tttactttct tcttaaaacc   2520
atgagcatga tctgtgagga gagcgccacc agtaaggaaa aagaaacctg ctctgtgtta   2580
tccacagtat cctagccatt ggaggaggct gtcctgacag ctgactacac cagtgaatac   2640
tctgtttact ttagtgcaac tctaggggca taactcagtg agtaactcat gtgggagttg   2700
caaggattga aaggaagttg ggtgagctag gcaggtggca aaaatgaagg tactcaaatg   2760
actcttatct tgatatttgt tttcttggtt atattgctag ggagtagctg aggcccctaa   2820
gataaaaaac aatatgtttg ggattaacaa gtttcattta tagaatgaac cacatggttt   2880
ggaggtagaa tttgaatttg tttcattcac gtattgtata gctttatttt gtttttaggcc   2940 aagttaacca tggataaaga ttttaacaac tcaggcacca tattcttttt ggcttcaact   3000
cattccttgc agtattccag agtgtgcctt atcagcctca ctgtagtctc atagcatcaa   3060
```

```
ataataaact ctgatatgga ggccagacat tcccttgaaa cgatgagttg cagcttgatg    3120
catatataca aggctgtgtg ccctgataag aaaagtaatc cctttagcat cctagagact    3180
gtcttaatga cttattcatc aaatgtagac actggttttt gtggaagctt aagtgtcatg    3240
ttacctcatt gaggctcctg gtgaggtggt tcgtgttggg ccccttccaa gagtgtttag    3300
ttactaacac actaaaaaga ctattataag gcagttctgg ctctaataag gcaggactct    3360
aggaaggtgc taaggttttc atgtgtgtcc ctctctcgtc atccatatca gcatttccat    3420
aacacccttt caccttgtga catatgttcc cttgtaggtg aaagatgctg tctaaattaa    3480
tatagtagat atgttttcca gtccagagtt tttaagtttt agaacatatg gtttctctg     3540 tactgaagac gttagaaatt ttaatggaag atcaggtggt gtgctgtgta tggggcagct    3600
gctgatccgg cagcctctga gtgcttattc aggctgagtt atagctttag agtcctgttt    3660
gtgccttggt acatacctga ttaaaattat ttattgttct aaacctagaa tatcttcgat    3720
tgaaatttag ctgctgtggt ctccctctga ttactttcta cttaaaccat tacttgatgg    3780
tgggtggcat tcatcctaaa tacactttct gctaaaccct tttctcctcc ctgaatgcta    3840
tgtagttggt gtgccaaaac cgtaagtttg gagtgcttgt aagttttttt gtcatgtgga    3900
agggtttaca taaagatagg ttttatcttt ccctttgcaa aaggtaattc acaaaatcta    3960
ttagtgacag agaaggtcag cttcataaaa atacaccatg tgaaggaaga cagaaggata    4020
tgaaattagc atttattttg atttggttt aagttgtctc tggctactat atgataaaga     4080
agaatatttt acatgaattt ttcttctgtc ttgatctttt aagatacttt aggatcatca    4140
ctttctcatg actcccatag tcacttaatc ttccttttct taatgacaaa tataatctct    4200
ttaggaaaaa caattaaagc acacatgttg ttaggaaact ttcactattc atgacatgca    4260
cccaccaaaa tagcacattt tagtgagtac ttatcacctt ttaaaaaatc tcacatactt    4320
catagattta aaaaaataac tgaggcaatc cagccccaca agtgaatatt ttcctgcaat    4380
gaggaagagg agattcttc ctcctatgac caaagtactt ttaagataag taattataat     4440
attgaaatgt ttctgaagta taaggctaaa atataaggct tcggcaaaga tagtatataa    4500
ctaagtgttg aatgatcatc ccaataggag ccattccttc aaaatatatg gaaccagtgg    4560
gaaaacatca tttttgatag gtttgatgct aagggactag aaaaactatt aaaatgtagt    4620
taccttgaag tgcctggcac ctagaaacta ggcttgaaat ttaaaagtac ttggataatc    4680
tgatgttttc atttaaagga caatagtaca tctggggaag aggagatggg tgtgcagctg    4740
ctttgaatta cacactactc tgaatacatg atagccttta atgaagtttt tactgtaaca    4800
agcaagacag cttcataatc tctgacattt aaaacatcat aatgtcatga attcttcatt    4860
attcatgcta atgcaaagga gaagggaat gaattacata taaaaaaatt taagtttaac     4920
tttgttgttt agctagaaac acttgaagag accaagtgtt tcattgacca tgggggtcaa    4980
tgaaaaaaaa atctcctaag caaataattc actcaaggaa tatttgtaca ctagaaatag    5040
ataaataatt cagaatgaat tagaaggtta catacatttt acctaagtag tggaagctcg    5100
taagcatttg attgaatgag ttcagatttt tctaaaaatt aaatagggac atgaatatca    5160
aatctgcttt taagcatttt tgcatcatat aattttatat ttggaagaag cattcaagaa    5220
aacaagtcct tcctttaatg gaagcagaag caagtactat gatgtatttg ccagataatt    5280
tttcaaacat actgagctca tctcaaaacc tattattttt aatagccaaa tctaattttg    5340
taggagaaca tgtcacaaaa acaggtcttt gcaagatgtt aacaggtatt atataaaatt    5400
gggcctcatg gtcaaacttg gaaaacgtga tcaatttct ttgctgtggg acctttcaag     5460
```

| | | | | |
|---|---|---|---|---|
| acctttaaat | gctaatgagt | ccccataaaa | ggcgaatact | ttctcctgga gaaagcattt | 5520 |
| tacagaaatg | tccttctaag | atgtctagtt | gggaaaacag | tggttcaacg gaacactgtc | 5580 |
| tcatttttca | tttcccatgc | agtacctatc | tcagtatgtt | aacttatatt attacatttt | 5640 |
| ggacttgggt | tcaattggca | ttgtaccatc | ttcctgcttt | tatgtcataa acgtctctga | 5700 |
| atgtaatttt | agatatcttc | tgtcattaaa | ttttatttt | tcctatatct ttatgagttc | 5760 |
| tccttcatta | ttttcatcta | taagattaat | attcattgtt | tcacacaggt attatgcttt | 5820 |
| aaaaagaaaa | gctagtttat | ttgtggaaaa | attcactaat | gatcatatat atcactttat | 5880 |
| taatgtttta | tcaccattac | taccttgatg | aaagacacat | ttacttaaga tgtcaatcaa | 5940 |
| attccttata | ttataaatcc | ccagtgtttg | ttatatttaa | taggcataat aaaaatatca | 6000 |
| cacctatcaa | aaaaccttat | gaaaatgctt | gagcaacttg | ttatatattt tcttttggct | 6060 |
| agtcaggatt | tttgtgcttc | agtaacagaa | catctctccc | caaatttttga tgattctccc | 6120 |
| atatgctaaa | tttgtatata | ctaataatca | gttagtgtct | taatgtcttt attttggggg | 6180 |
| tagtagtgga | aagacatttg | gcatcacaaa | taaccttaag | tcggactttt ctatgccatg | 6240 |
| tttcagttga | gtaaatttttt | atgattatgt | tatgaatcca | tgaaaataga atttgtaata | 6300 |
| gaaatattga | ctttatatta | atcaagtaat | acaagtatac | ctggatcata tctacttttg | 6360 |
| acagtagtga | aagatgaaat | gtaacccaaa | aagctttcat | atatggaata tatgtaacag | 6420 |
| ccaataaaat | tactagttta | tctacatgtt | agcagtggtt | gtgtcttagc atgatggcat | 6480 |
| atacagcagt | actcctggat | aacacacatt | ttaagggatg | atactttaaa ggcatgaatt | 6540 |
| cctctttgtt | tatctaaaac | atcagcatgt | agatcataga | atcaaatgac cacggtggtt | 6600 |
| ttattgactc | tttcaatgat | ctatatttct | ttaaaagcca | tcttttcatg gctatagaac | 6660 |
| catggtaaat | gcagtacctt | gattgtattt | gggcatacca | tgaatatgtg tgtgtgcaaa | 6720 |
| atgatctcac | tttattacta | gcttcagtta | gttcttttta | ctttactaag gtactgttaa | 6780 |
| atatctcttt | tataaaataa | ttacattcaa | taaatttaaa | aatataaggt tgtttgttca | 6840 |
| gcccctcat | tttacagtta | aaccaactgt | ccaacatact | attatttgct tttccttcaa | 6900 |
| aaacctttct | ctttagttgc | atgaaattaa | tttaaagatg | aattaagggt aattgctgta | 6960 |
| cttggtgtta | agtgaaatgg | ttttcaagta | gagaaaagat | tattagtgtt ttgttttttc | 7020 |
| tattacctaa | agctaagtgt | taggtgatct | aacttccatg | gttggctgaa ccgctaagaa | 7080 |
| gtaaagtcat | ctaatattgc | tattctcagt | ttcttcatct | atcaaatggg ttaagttata | 7140 |
| cctcctgtgc | ctgtctcaca | gaaagatggt | gaaactcaat | tgacaaagtg aatgcaaaga | 7200 |
| tgctttaaaa | gttttgaagt | cctatataaa | ttaggtattc | taacattctt aatattttga | 7260 |
| gattatttcc | ctctggcttt | ccacaaagca | ttaaacatat | ctcaaatgtt gataatatgt | 7320 |
| acttgtctgt | agcacagatg | atgatgtaaa | aatagttagt | aatcatctgt gcaatctatg | 7380 |
| atatcccaaa | cctatattca | acaaatgtac | tattttctgt | cctgaccatg gtggctgagg | 7440 |
| ggtgtagggt | tatgcttttt | tagagagatt | tcttgaagtt | aattgttctc aaagtatagt | 7500 |
| tcgtggacta | gctgcatcag | tattacttag | aaccttgtta | gaaattctct agcccatact | 7560 |
| agacccgcgg | aatcaaactc | tggtgacgga | gctcagaaat | atgtgtttta aaagccatc | 7620 |
| tacaagattc | tgatccatat | ttgagaaaca | ctgctctaag | cttctgtccc tagagttttg | 7680 |
| agtatttat | atcaaaacca | gcctcttaaa | atctagaatt | gattatcatg ttattcctga | 7740 |
| tctcatctgg | cccttttagt | gggcctatcc | ataaacaaat | ggtttattga cttatataat | 7800 |

```
ggtaagcttt ttaaaatata taccttagaa ggtatattac tgcctttatg atggttttgc    7860
cataaagaag tcttcaaaat aagttaatca agactgctta cccttcactc atagctgcag    7920
agagtttatg atataataaa tttgctagaa gaaaaatatg gtatgagcag gggcctacaa    7980
agcaagtccc tggaggacat ggagtctatc tcaattcatc tttgtgttct gaggacctag    8040
cacagtttgc catgtagttg acactcacta aatacttcag ttgagttgag ttacatattc    8100
aggagaaaag atgagatagt tcaaaagcta tcagccaggc aaatatcctt taaaataaaa    8160
cttgccttga aggaatttct tatggggcat tttaccattt atatattaaa tggcaatact    8220
attctacttc atatacaatg attataataa ttcttttcta atgaactgaa aggaaatatc    8280
atatggtatt tatacccaag aagggctctt gctgattttg ggaacttgaa attacttgaa    8340 agttttatg ctttggtgtt aagtaggaaa cacttttaaa tctgttaagt ttagagagtt    8400
gttcattcaa cacacctaac aaatacccttt tgggacttaa gtgctccagg ctgtgtgaag    8460
tactaggaat tcaaagatct atagaacata ggtctgccct ctcagcactc acagtctagg    8520
aatgcctttg ggcagaggct aagagtagat aaactgatta atgaacattt tactattcta    8580
gaaaaacata catcatatca tctttggctg ttttacttt ggacatagag aatggttgtt    8640
ttgaggtccc ataaagcaca gtcatttgac tgggactatg aaggagaaac acaattctat    8700
gactttgtgt tctttgtaga attcttcctt ttgcctgtgc ctgaaagtta aaggcagcac    8760
agggatgctg caatcttgac taagtaatct gcagcaaata ttcagccagt gactgagggt    8820
ggatgtgtcc ctgtcctagg caccctggc atttctagca gctgtatttt gtttgaagaa    8880
agaagttggg gcagcgggag gtggttgttc tttgtcacat attttctgta tgactaaaat    8940
gttttccctg cttcctgggg atttagctaa tcatcaagat ttcatttagt ctatttgttt    9000
taaaatcaga cttttacatag aaagctttcc attgtatgtt ctaattcccc ttgcaaacgt    9060
tctgtgtggg ccagcacaaa ggtgaacttc cccttaccac tccctggaca cagcctcagc    9120
tactcctgga gaggcactga agtgttgcaa tagcatggct ggccttaagt cccgaagtca    9180
gaacccgact tcctgaaatg agtccttggt ttcatcaggt tcaagtgctt tgttttttaga    9240 taaaaacaga aataaatctt ctaccttttat ataataatca aactccttttt aaaacgccta    9300 tctgactttc tctccaaagt caattgctag ctagcttgct aactcctagg gtccttcatg    9360
tttgcatttc tctaatgagt aggttgaact aaatttgctc atgcatataa aaaaagcttt    9420
agggtcaagc cctgtgttgg aggctgaaga gtctgatata atttagagcc ttgtctttaa    9480
ggaacttatg gccttaagaa ggagcaaagg tgtaatgaaa atggtaatag aggcaggatc    9540
ctagccaagg aaatgggttg tcatgacaag cttgcatcca ggaatggtat ctctgccttg    9600
ccttaaaaaa caaatctgga ttatcaagga gaaaaatcgt gggtagagac attgcagaga    9660
gaagcagcaa caggtgcaaa gtcccaacaa gtgtgtaaaa gagagtatag cttgttcaga    9720
aactcacctg acttccaacc tccttttcaa ttctcaggtg ttaaaactct agaaaattca    9780
aaatataaga ttataatgct aatggtaaac cctaactagg ctgcaataaa tacattccca    9840
tgtgccagtg ccagcaaaca gtaagaaaat agcaccacct attggtagtc acattttggc    9900
atcaaaatat ttctttgggg aaagctagaa aacaaagccg gttatagtta cttgcaaggg    9960
atgagacgtt ctctcgttca ctttcacact ctactctacc ataaaaacat cctcctgtaa   10020
tagtcttgac ttacctccag ttgccccagt cccacagatg gatctcacta agtaaaacag   10080
tttgaaagtc atgacttata ttggcttgga tttggcctcc atttaactat caccgttaga   10140
ctgcattctc atctttgaca ctggaaagaa aaaccctgat ctctccacag tcccttaaat   10200
```

```
attggaaaat aattctcata tcattgctaa acttttttt ctccctccag gcaatgtttt   10260
cttatttatt caactcaaat ctatgagata gtttccagac ccctcaacat ctgggttact   10320
ttccaagttg ctctcttctg cattaataaa ctggttacaa tgagagcacc caaaatgagg   10380
catgcaattc cagatatatt tagatgatca gtgtagcata caattaatat tttctagtac   10440
cgaatactat ccacagccta aaaacgcata agtatttttt gtaacctgaa aaaatccacc   10500
cttttttta tcattattat atcggtttgc tcttattaat caggaagtac acttcaggtt   10560
tttgattcaa tcattcccaa tagataagta tctgaatatt tcagaagact agaaaaggtg   10620
aatattaagg tattttttat ttactgatat tcaaacgtag atatttgtgt gcatagataa   10680
agctgtgcta caactcatgg ggaagagaga gacaatgcaa atcttctgtt cataagtatg   10740
gaaagttact caccttacaa gttaatataa aatctaaaaa gtaaaagagc atgaaagtaa   10800
ttgagtagat attatcatgc actgctattt gcaggaagcc gtttacctca ctcttattta   10860
cttctctata tacattcact tgaccccatg ctgctcgctt attacaattt ttttcatcca   10920
ttgtaaatgc tcagcaacta tttgttaagt tgctttggag agaagatcat taacttacac   10980
aaaaataaag tgttttagaa tcagagaagg caaaaataaa gtatgggtta gaaaagtcaa   11040
agtcaatgaa tgctttgtga aatggctgat aattctagct tattgttttg cttcttggtt   11100
tttttttaaac ccaggaggga gaggacctag aacaggcaga gatccctagc ctaggtggaa   11160
ataacaagag caaacacatc aagtgttggg cataacataa tgcctttggt tagccttcag   11220
attggccatt ccttgctcaa cttggatgac ttagacattc actagaactt caattctata   11280
gaactactag aacttcaata actaagttaa ttgtaagtat ttttatattt tctatttaaa   11340
acattggcaa catttctttt gcaaaagctt ccagacatac agcattgcat actgctagaa   11400
tgtgttcctt ccatcccctc accaagattt ctttcttcct tcatctttaa aagtctggtc   11460
caaagattac ttcctacctg tgtgtttctt tgcctctacc tgggtaaagt taatggctcc   11520
caattctgct ccaagcatag ctaacacctt cggcagcttg tattatcatc atggcatagt   11580
cttttttttt tccttttccat tttgactaca aaactagtga ttattctaga ccacaaccat   11640
ccaatagaga tataagggga gccacaaatg ttagtcacat atgtaattta aaaattttag   11700
tagccacatt tcaaagtgtg aaaagcaaca agtgagatta atttaataa tatatttaat   11760
gcaatatagt tcaataaagt cactttaaca cacactggct taatataaaa tgtattgcta   11820
cgatatctta tattcatttt cttaccaagt cttcaaaatt cagtatgtat tttatactta   11880
cagcacatct caatttgaat gtaagtggct acatactatc atactggaaa ccacagttct   11940
agttagctaa catttattga atactttctg tgtgctttat gtgccttctc tcaattaatc   12000
ctcgcaacaa ctctatagtt gctactacta gacccacttt atagataagc acaccaaaac   12060
ttaaagagct taggttattt gtctgagggc tgctattggt tgtagtgaaa ttgcaactgg   12120
accaacaggc tttgacttca taagaaagca ctggtttaaa atgagagcca ttggaagagg   12180
cagtaagaca gattctgaga cttttacaaa acgatgttgt agattagaca cagaggtaga   12240
ggctaattaa cagcaggtca caaggtgact agaaggaaac atgtttgaaa gaagaaaata   12300
ttttgaagca aaatgtgggg caagggcag gattggttta cccattaagt tactgccact   12360
catatccctt ggagatcatt tattccctgc cagcatgttt gtttggcaac cattggattg   12420
ccacatacct agaacagagt ggcttctctt ccttccactt taaacttcta gctactacac   12480
gaaatttggg taaaagtata tgctccggtg actggtatga attaaggctc aagtctctga   12540
```

```
acagtcctga tgccatggct tgttataaa  ggtctgtaaa atattatcct ggtgtcatgg  12600
attatacaaa tgtgcaccaa tggcagtttc ctccttttcc ttcacacagt gttaaaaatg  12660
aatagaatat gtttcccatt gcacttccct tgtgcttggg gactcaatga actcatttta  12720
agtttccaca tctttataaa aatgttttgt ttttactgaa acatgttttt gatcaagaac  12780
ataatttcac gattgcgtgt gtgtttctga aacaaatatg tatatgaaac aagtgcatgg  12840
agaagggctt aggctctggt gactgatccc aggatgggag attccagagt tctaacctca  12900
gtcctgtgga tctcggttta tgagctaaag gagaggaatc aaattctgca cctattaata  12960
aatctctcat tctcttcttc tctctcattt ctggatttga agaattggaa gtatgggtga  13020
acaattttaa tcattttgt  tgcactatat agaaagttaa ctcttaaatt tatggaatgt  13080
cataaacttc aaacaagctc cacaacagca ttcttttttt ttcttttttg acattttgc   13140
agtatgcctt atttttcag atgtattatt tgaatattga gatgcgttgg atcctgctta  13200
cccaatgctt atcaagcata ctacaatttt tttttttttt tgagacagcg tctcactctg  13260
ttgcccaggc tggtgtgcag tagtgtcatc tcggctcact gcaacctcca cctcccagac  13320
tcaagcgatt ctcctgcctc agcctcccga gtagctggga ttacaggtgt gtgccactac  13380
cgccttgcta atttttgtat ttttagtaga cagggttt  cactatggtg gccaggctgg   13440
tcttgaactc ctgacctcaa atgatccacc tgccttggcc tcccaaagtg ctggcataac  13500
agtcatgagc cactgcacct ggcctcatcc tacatttttt gaagtaggta gaagaagatg  13560
taatccctgt aagactgtta ataccagaac taataacaat aataattgat atttaagaaa  13620
cacttcacag acactttatg gactgcttta tacatgtctc atttaattct gatgacatgg  13680
gaggtagata ttgtctcatt ttgtgaatga gaatattagc ttgtataatg ttgtgaagtt  13740
ggtaagtggc tgagcgagta ctcgaatcaa ggtgagtgta attccaaacc ctgtgtttgt  13800
agcccgtagg ctatacgtgc ctcagataaa aagctattac aatacattgc caaatttgta  13860
ggaataagtc ttgacaatcc tccataactc tgagctttca ccccttttaag tttatttctc  13920
cgttaaaatt ttcacacatt tatggtgctt cagtaaagga aagagcaaag taattaaaat  13980
ggctgatcct tgctaacctt ttttttgtctt ttaaaattat tcctgtttat tactctcttt  14040
ttattccact tccaggaagc ctccaaagca agagactgca taattgtttt gctttgtttt  14100
aattgaggtg aaattcacat agtataaatt taactaattt taagtaaaca atataatgac  14160
agttaatacc ctcacaatgt tgtgctatca ccaagtctat atagttccaa atatttcca   14220
caattttaaa acaaaaccct gtaaccatta aggagtttct tttcattagc ccctcccttt  14280
ggcttctggc aaacaccgat ctgattctgt ctctatggat tttactattc tggatattcc  14340
atataaatgg aatcaaacaa tatgtgatct tccatgtctt gctttcattt agcatagttt  14400
tttcaaggtt catccacatt gtagcatgtg tcagtacttc attctttttc atggaagaat  14460
aatatttgat tgtatgggta taccacaatt tctttatcca ttcatccatt ggtagtcatt  14520
tgagctgttc taacttttgg ctattgtgac tagtgctgct ataaccatgt aattatttga  14580
gtgcctgttt caattctttg gcgtgtatac ataggagagc aattgcggaa tcataataat  14640
tctatgttta acttttgag  gaactgccaa agagtattcc acagcaggtg aaccattttg   14700
cattcccacc agcaatttga gagtgttcca atttctccac cttctcagta accttctggg  14760
ttttttcgtt tatttgttat agtcatccta gtgtgtatca agtagtactt cactgtgatt  14820
ttgattgtgt ttccctgatg gctaatgatg ttgagcatct tgtcatgtgc ttcttggcca  14880
tttatatatc ttctttgaag aaatgtctat tcaaggcatt ttcccatttt tatttggttt  14940
```

```
cttggtctgt ttattgctga gttgtaactg ttatttatat gttctggata ctagatttat   15000
caaatgtatg atttgcaatt attttatctt attatggaag ttgtcttttc actttcttga   15060
caatgtcttt tgatatacaa aagttttta ttttaatgaa gtccagttta ttttataaat    15120
ttaccgattt tattgatgta tctacttttt cttttattgc ttacacttat ggtgtcatat   15180
ctaagaatgg cttcatatct aagaagtcat tgccaaattc aaagtcatga agatttaccc   15240
ctaggtttct ttccaaaaat ttcatggatt tagttcttat ataggtttt ctgattcatt    15300 ttgagttaat tgtcatatag tgaagtaatg gtcttgtttt ctcctgttta ctctctttct   15360
ttttccttcc tagaaactct tgaaagaaaa ggactgtata tcttcaatct gacatcgcta   15420
accaagtctg aaaacatttt gtctgccaca ctgtatttct gtattggaga gctaggaaac   15480
atcagcctga gttgtccagt gtctggagga tgctcccatc atgctcagag gaaacacatt   15540
cagattgatc tttctgcatg gaccctcaaa ttcagcagaa accaaagtca actccttggc   15600
catctgtcag tggatatggc caaatctcat cgagatatta tgtcctggct gtctaaagat   15660
atcactcaac tcttgaggaa ggccaaagaa aatgaagagt tcctcatagg atttaacatt   15720
acgtccaagg gacgccagct gccaaagagg aggttacctt ttccagagcc ttatatcttg   15780
gtatatgcca atgatgccgc catttctgag ccagaaagtg tggtatcaag cttacaggga   15840
caccggaatt ttcccactgg aactgttccc aaatgggata gccacatcag agctgccctt   15900
tccattgagc ggaggaagaa gcgctctact ggggtcttgc tgcctctgca gaacaacgag   15960
cttcctgggg cagaatacca gtataaaaag gatgaggtgt gggaggagag aaagccttac   16020
aagacccttc aggctcaggc ccctgaaaag agtaagaata aaaagaaaca gagaaagggg   16080
cctcatcgga agagccagac gctccaattt gatgagcaga ccctgaaaaa ggcaaggaga   16140
aagcagtgga ttgaacctcg gaattgcgcc aggagatacc tcaaggtaga ctttgcagat   16200
attggctgga gtgaatggat tatctccccc aagtcctttg atgcctatta ttgctctgga   16260
gcatgccagt tccccatgcc aaaggtagcc attgttctct gtcctgtact tacttcctat   16320
ttccattagt agaaagacac attgactaag ttagtgtgca tatagggggt ttgtgtaagt   16380
gtttgtgttt ccatttgcaa aatccattgg gaccttatt tactacattc taaaccataa    16440
taggtaatat ggttattctt ggtttctctt taatggttgt taaagtcata tgaagtcagt   16500
attggtataa agaaggatat gagaaaaaaa catgtgtgaa acatacttgt tgtgttgctt   16560
ctcaacatgg tgcatattca gccacatggt tgtgtgtgaa cctgcacctg tccatgtaag   16620
caagccccaa atggtagaag gctgaccttg gaagagtatt caaggaataa gtgaatgtca   16680
tgggagcaca gagaagagct gatgggattg atgccctaat gcagaacatg ttttaataaa   16740
taccctcttg tgagctaagt tgtccccaca gaggtcagga tcaggattga ctcaggtaaa   16800
ctggcctcat gaaatccact acgtgcttat ttcatttgct tcattgctaa acatcagaaa   16860
aggaaagcaa catagaatat gatgactctg taaactttg ccaagactaa tttcaacctt    16920
tcggagctta cctgtatctc ctcgaaaatc cataaggtct gaacttcatc atatcagttc   16980
tcagtctcct gacaaatata tttgcagaag tctctccaac ccccacctcc aacttgcacg   17040
gcaagttcaa gtgactgttc tctttgaatt tacagtttaa gtagtaccct ctatagtaaa   17100
atatagtggc actcttcagc cttcagttaa gcttattggt gcacttccat tctcagcttg   17160
tagcagttta tatctctgtt ataccaaaaa aaaaaaaagt tgctgaagga acagaattca   17220
gaggaagaat acagtttttt ctttcaaaat ttgaaacaag tccattttg ctattgtatg    17280
```

```
ataatgaaga aaaaatcctt tgtctcaaca aatgaccaac ttctgcttat gcatctctaa    17340
aatagcgttt tcatgttcta gccaagtgta gcacttggtt ataatcattg ggatgacaag    17400
cataacaaac ataaatgcaa agggctttag tctggcacag tggcatgccc ctgtagttcc    17460
agctactctg gaggctgagg caggaggatc acttgagtcc aagagttgga gtaagctctg    17520
attgcactac tgcactccag cctgggtgac agagtgagac agcgagaccc tgactctgaa    17580
gagaaaaaaa aaaaaaaaaa aaaagcaaag ggctgacagc acaaggctgg gttagccttt    17640
tcagggccac aaacttgatt gaaattttat tttcttgtaa aatacttct ctaagacccc     17700 ttctttccca aggattttg atcattttat gtttcataaa cccaaacaca aagtacgaat     17760
tctatacact tgcaattata taaagagcct tatcttgtct aaatattcat aaaggatatt    17820
ttactgatca aacaaagttg ttcaaatgag ataacatgaa aaaacacaca cacaacaaag    17880
atgacaaatg taacaagcag tgatgagtct ttattttaca gtgtggcttg ccttgtggca    17940
ttgagaggca agaatggttt caatatctgt ctttaaaccc aggatgactg actttagttg    18000
ggtctcgaag ttttccaaat aatccctctc acttataaag ggtaatatat tctgggtagc    18060
ctggggaagt agttttccc ttttctcctg actacaatct tcaggactca ggaagccatg     18120
ataatgcaga gatactctgt tagtttgctt ttgaacctct agctctggag aattgatttg    18180
gtatccaccc caccacaatt acttccaatt tgtccctctc atttattggt tctacctgct    18240
tttactgttc cgaaacctgc tgttacttca gaagagctcc atcatgtttc tcagtgatct    18300
aaagaataat aatttaagaa ttgatgagga ataaggtaaa aatagcagaa ataaatttaa    18360
ggagagaagt atgttagtgc agaagaataa ttaaatgtac acgcttggtc atagcagggc    18420
atcttaaacc ttaatgtcct ggcaaattgc cctggattta gttaatatgt aggttctgat    18480
ccagtggata taggagtaga gcctaagatt ctgcatatct aacaagttcc taggtgatgc    18540
agatgctgct gattcacaaa ttgcactttg agtagcaaaa ataaaagtca aatccttta     18600 acttgaatct tgattctacc acttacctgc tatgactctt tggagaagtt attcagactc    18660
tctacaagtt attttacag tctgaaatgg gtcaaatagt aaatagtaaa aataatagtt     18720
tctatataac aaaaacagtg gaaaaatgag acagtagagc accttgcaca tagtaggtta    18780
tcaataaata cctgttattg gcattattat tcacggccat ttctgagact gaggagaaag    18840
aaaagcaaac gtaggactct gaagaaagac tacataggaa acgagatcaa gagaataaaa    18900
gttgtaaggc aggaaaatgt tttctaaatg tttctagtcc cttttcaaac atcacaaagc    18960
tgaaaatagg tttctcccct tgcattcaac cgcccgtgag ctcttccagg gaggtttatt    19020
tggagagtaa gagaatcagg agagcatcag ttgcagcaac tgaactcatc ataatatttg    19080
tcaaaacttg gaagggcatc agaactccag ggagacataa cagggataag tgtggagctt    19140
tctctctgag cttcagattt cctttttgcca agttgagagt ggaagtttgg ctgttacata    19200
gagttctcaa tctctcatca ccttgtgtgt atctgtttaa cttttaaagc tttctagtgg    19260 ttcccttta gccttccacg ccttgtgtct ttcaagtggt acggtgacca aaaagatggg     19320
aaacatgcag ccaaatgaag ctgctacatt aggggtaatt aataaacatc cctgttatct    19380
gcaccgtgtc caatactgca accagagtga actttgtaaa taaaaatata gtctaagcaa    19440
cagaggagaa tcaaggccac tggtcagatc agtacaaaac atgtggaata actgaggtgc    19500
caaagacctt tcagacttta gatatagttt ttgccccaga gaaagttccc ccaggctaga    19560
ctgctttgtt ggccctcctt tcttttggcc tcctgagcca aagagtgttc tatatgcag    19620 ggctttttgt ctgcaaaagt tgacaacctg ttctctaatt cagaacagct gtgttctttc    19680
```

```
tgcctttccc aaattccagg ctttgccctt tcactgattc caattagata gtttctgggc   19740
tatcacaccc atgtgggctg gactggaaga attgtggagt aaaactccat ggcccaggtc   19800
aggaatgaag gctcttagct gatgacatgc tctccctgc taatgcattt gtaatcaaat    19860
tcaactcgag gacatcatac acggcttggc aggtgcaggc ctgaccattg tagatttcat   19920
tcacagacac ggcagtttgg attttctga tttctagccc ttacagccaa tctgttctcc    19980
cagagagaga ttcttggaat tctgccatga gatgaaaaat acccatacag ttaatgccaa   20040
gttctatacc tttgcctctc ctcatcacct tagaagagat ggaaaacaga aatttcaaat   20100
gaaagtgatt gagctgttgt cactgacaaa gatccaagag aagttagttt tgcttttttt   20160
ttttcaagga attttgcaaa agctataaat agcaaacaca tagaattagg cagcaaagaa   20220
tctaaacact ttgaaccaag tattccatac aaagaagaaa ttcacattta atgcgttcaa   20280
aatgatacaa cctcaattaa tttcctgaat cttccaattc taatctctgg tcataaaaat   20340
gaactccaaa aacattaaat cttgatgtgc taagttactt aagcaaaaaa ttacctaact   20400
gctattgaag tcgtgcttca ccctcattag aaagagctgg taaggcaaat accacagata   20460
tgcattagta attgatatat taatttttta acttgtttaa taaagagtca tgagaaacat   20520
gacctgaact cagaaacaaa cagaaattcc ggactggcaa tatgctttac accagcaaat   20580
taccggatgg atcttttgtg cacgatgtaa ttatttctgt taatggcagg ttgatcagag   20640
gatttcatag tgagaaaaaa aaagcaggg gaaacttcct agtaatctga gaggttcctg     20700
ataagataca ccaatgcaga atcagggct tctgtccaaa ttccagtgag cccactagag     20760
actactcata tactcatagt ttctgaatct atcatttgtt acttgaagct gtaaaaaaaa   20820
ggacaggaat tttcctagga aacacccatg aatattatcc atatctacac caggtcattt   20880
gcacagaaac ttgtatttgt gttgatagga actatttcca cagaaatgga taaaaatgga   20940
gggtatgttg tttcttttaa gtatttcatc catttaacaa gcatttgttc catgcctaga   21000
ttatactagg tgctcaggaa cagcaatgca caggagaatt tagcacccaa ggtctcatct    21060
aattaagttg atccactttg tataaaattc aaatattata ggagtcatta acattaaaa    21120 taacagaata attttggaaa atctagttta aaagttttcg ctttatgaca agctatttag   21180
attattgagt cataaaaata actttaaatc agtagagaaa agtggatggc tgcaaaagct   21240
ttctttagaa attaccaata gcaataacaa gcaatggcta ctgacatttg ttgtacaata   21300
ctgattgtag tttgtgtaag ttacacagat attattggtg atgcagggca tacaatgtgc   21360
aaaataaaac agcatggact tcctctcctc aagggaggaa taacttgctt tgtaatgaat   21420
taaagctaat taattcaaag ttaaccagtc ttttaacat atactgaaaa tctctaggaa     21480 aaaaagtaa gaacagttgc ccatcattaa gtctaattat ttagttactt atgcctaatc    21540
acaataaagt tgaagtctga tgtatggatt ttatttcatt gatattaaaa gatgggatga   21600
gatttaacct ttctctgcca aaaataatcc ttttttttctt tttttttta agagtatgcc    21660 tgctttctat attattgtct tctcccttgg tttgtatata cccttaaagt tttaacttgt   21720
tccagtttcc catgctggga gctttaggag tttgaaatta aaataccaat ccactggggc   21780
ggggttcctc tgagccatga gaaacatggc tcaagttct gaaattaaaa agcgaaagtt     21840
ttggtcaaag tcctactcct gaattggtct ctggcaagtt accaaacttc tgtttctcaa   21900
tgtgtttaaa acaaaactac tttcacctgc ctaaaagagg aatcgagaaa cacaggtgtt   21960
gcacagtggg gcatctctta ggaagttctt accactctgg caatacctaa cattctggac   22020
```

```
ttgcaaaaat gactgttcct ttagtacttt tagctagagc agagctgtat ggggttctct    22080
aaataaaacc acatgcttca catgaatgtt agtggtccca tttggcattt tctcagggaa    22140
aagattctta ctcaggcttc tttggtgaaa gttctggtat ccataggata actttaggcc    22200
ctcataattc ccagagggaa ttcccagagg acgtggccca ctcttagaac acaactccat    22260
gcctaattct aaaccagtgg agcaacagtg accccagtg gccaatggtg tggtcttctt     22320
accccccagt ttgtacttct aaggagagtt gaataattac atagtggaat agtaaccatc    22380
caatccatct tggcaactat taaattaaat aaatcaatac ccctctgacc tgcttggttt    22440
tattttaaca acaatgccta aatatcaata tagcagtggc aataatgtat ctctgttaaa    22500
tagagtgctt gttaggattt tgattaatgt agggtcaata acgaatcatt ttttgtttca    22560
atcctgttat tgaaaacacc gtagagtgta ttaattccat gtttgggggc taagttgttt    22620
gtaattaaat gattcttgct gagataactt ggtttaaatc ctctaccatt tacaagctat    22680
ttgaacttag ataagtcgtt taagcttttt gagcctttgt aaaatgtaag aaatgttagc    22740
tttgttgtga gaattagaga tactacatat aatatgcctg gaatgcagca ggcacttaat    22800
aaataataac cattttggta gtggtgggat aggcgattgg gcttaatgta taatgatgcc    22860
agaggtttta ttaaattgtt gaaacaaatt cattagataa gcattttgtg taatgaggac    22920
tgaggagtgg aaacgcagtt ccacctaaca tatgtgttct tctttcattt ctttctctag    22980
tctttgaagc catcaaatca tgctaccatc cagagtatag tgagagctgt ggggtcgtt    23040 cctgggattc ctgagccttg ctgtgtacca gaaaagatgt cctcactcag tatttattc     23100 tttgatgaaa ataagaatgt agtgcttaaa gtataccta acatgacagt agagtcttgc     23160
gcttgcagat aacctggcaa agaactcatt tgaatgctta attcaatcat tagtttattt    23220
ttatggactt cttcctgttt tttttttttt ttttttgca ctgccaatgc atttgtttc      23280 aaaagattat ttctatagtc agagggaat gagcaaatag actgaagatt gccaccaagg     23340
aaaagaactg tatttgtttc tgaatgtaac ttaaagcaag atttttagta aatatggaca    23400
tctatttctc ttttttgtaat caaacacaac aacttatcaa actgttttta gaactgttag    23460
agaacacact ggtttatttt tgtaatgttc tttgaaaaca gaatggagaa gcagcaatag    23520
cttgtcattt atctcatttta atgactaatg ggaaatagag aacaatttcg cgttttgaat    23580
taggcttatt gccttagaat cctgagaaag tgctaaataa tcaactctga tgttttttctt   23640 aagttcttga gactcttgtt tatccttgtt tttcctccac aagtcattgt ctaagtgtaa    23700
tggaaagttt atgctgagcg ttagtgtgta tgtatgtgcg tacatgcgcc aggtgcctgt    23760
gccctctgta ggatggtttg cttaatatgg ttttataatt cagtttacac aggattcttt    23820 attttttta attttgtatt ttggcaaaca ccattcagtt ataagaactt tgccaaatat     23880
gatagaataa ttcaagagca tatacagaga gttaccactt gacccagcta tttaattgca    23940
aatacagttg ttttcatttc atttcctacc agaaaaagga atcagaaacc tagttttga     24000 aaacacaagt gtaattcctc ttttgtactt cttttcaca aatgctttta tttattctaa     24060
attgaattta aaaatccttc ctaaagccat taactctta attctcctga tatgccttta    24120
cttcctatga agttattggt agatgttgag gcccaaaaac tggtagaata ttgaagatct    24180
tcttaaatga ccaatttaac cataaccaaa tattgaatat cattcttcag tcacatctaa    24240
gtcaggcact ttttcacata gatcagggct tttggctcag tcacgaaatc tacaagttag    24300
caaagcttac aaaacattat tcgtcaggta tgggaatcaa atatagacac ttgtttgtct    24360
ttgctttcca tttctatgtg tcacatacat atatgtgtcc tcttataact ttagtcttca    24420
```

```
aaattatttc aatatccttc ttctcactat atttatttgt gtgatggaaa tgctttcagg   24480
ccgtagatca ttgttggtgt taatctgtgg ttaatcctca ttttagttcc gtcttatctg   24540
atacttagaa atatctcagc cattttggag gctgtgcagt atcagaagac gtggagtttg   24600
ttctgtctct gcctgtagct aattatggtg gttcagtcat ttaataaata tgttttgagc   24660
atctattttg tgaaaggcac tgtgttacct gtgtgtcttt agtgtcctca ctggtaaaat   24720
gaagaggctg gccatgagct ggaagggtta agtttataat tccagctatt tcacacccgt   24780
cttccttgaa ggaatgatag tgatagatat aaaaacactg taagtccctc ttttaataaa   24840
ctaaatgaaa gaacatccta tacttcgctg tttgtaaatt agtatggcat tcgctttggt   24900
ttaagtggta ttttattgca aacccattaa aagaataact catgaaaaga agctctttga   24960 cacccttgggg tacacaaatg ttggtgtggg tgtgtgttaa ttctgtgagt gagacacacc   25020
agttctaaaa aaaatgagtg aagttctggt gcctgagtta ccatgctttc ttctagttct   25080
tacagtagca taaaattaaa gattcaaagt gagatggagg ataaaattac tttttaatac   25140
atgttctcaa acatttgaaa ataaaagtat atgatagaag ggggccagag tgtggccacc   25200
atcctgatcg tactgttttt caataaagaa aacttttttca ttggtagatt tggtgaaatt   25260
ctaaatttag gttttttttct agagctgtat caaccaaaac ttctggcaat tcccagtatc   25320
acttcttagc cttcttatat ccaaatgcct gtttattacc tttcttaatt tgaatcaatg   25380
cctagttatt acagattgca ccccacaatg gccaaaaacc cactacataa taaaatttac   25440
aggtactaac tagttaagat tatattttaa gtagcaattg atataaaatt acaacacaat   25500
gaaagaactt gggtaatctc ttagcaatgg aaataggttt taaccagcag ttttctctggg   25560 tgctttgtaa ctatcatttt actaatgaat tgaggatgta ttatggttta aattggaaga   25620
gttttattcc caaagaataa agcaagatta tctttcagta gtagagattg aagtaaatgt   25680
attaatattt taattaatac agatttacta agagtagtta gaaaatttag taagtgcctg   25740
ttttacaaat tgttaggtac tagtttctgt ataattccta cacagaagct ttagaaatct   25800
cctgatatta aattattaaa ttggcattca tgaaaagaga agctacaatt ataaactcca   25860
tttgctaaat catgcataat actctctctc tctcttcccc cacaagtaat ctctctaccc   25920
catgcagtgt gcacacacac acacacacag tcagttactg aaaaaaataa ttctttttct   25980 ttttttttt aaatggagtt tcactcttgt cgcccaggct ggagtgcagt ggcgtgatct   26040
cggcccactg caacctccac ctcccaggtt caagcagttc tcctgcctca gcctcctgag   26100
tagctgggat tacaggtgtc cgccaccatg cctggctaat ttttttattt gataaaaaga   26160 attcttttc tcaataactg ttctcttgaa ttcaaattaa gggactgcca aagtcaatta   26220
gaatatttta aaaatacttt gttgtaacct gtgtaaataa tatacaattt acaggatttg   26280
ggattgtaga acttaaactg gaagactgga ttcctcagat ctcaggacta taacattcca   26340
gataaatttt tacattccct ttgctgtata ttaactgatg atcatttata tgttaagatt   26400
ttttacctta atatttctga ataaaactct tattgcccat ttaatatttt cataggcaat   26460
caaatgtgag taatactgct aagagtctga tttattaaaa atatttgtat aattcattca   26520
gtttagtttt tcagtttagt ctttctgctt tcacttttct ctgtgctaac aagtaactaa   26580
tgtctgggca ttgacttctt attgaatcaa agttgggtta ggcatagcta tgcacacctg   26640
atgtgtaaga ttaagaaga gattaaataa gaaatcttgg gtaagttgga cttttctgta   26700
tagctctttt ttcctctgag ttgtatttta atgtagttta taagtgataa aatgatcctt   26760
```

```
gttttctaaa agccagtcct tcccttcagc tttccacagt ttctgtaaat gtttaatact    26820
tgtacagtca atggcaattt taaatatata tatatatata atatatgtat atggaaaagg    26880
ttcaaagatg cttttaattt atttaatgac tattgccttc ctataataat aattttcatc    26940
cttaattatg ataatacttt tagcaagaaa aattcctttt tactacagtt tttagatgca    27000
aaatgcagtt tggttcttta gtcaaatcca cttagagggt atattgcagt gaaactgtga    27060
aggatacttc actaccaatg tataagcttt gttgaatttg tatcattttc tttcagtaat    27120
gaaaagctat tcattataca gtatggaaat aaaaattgct tcattgacca ttcattttta    27180
cttattggga aatactatat ttccagacat tttcaagtgt gctgcattta aagaggtaa     27240
taaagcttaa gcatagagtt gaacattttc aaatggtatt ctaaatggag catcgtaact    27300
tactcttaac ataacatgat tatcgttgta aacaagatt  gaaatatacc catcaggaaa    27360
aatatatctt tcaagcttga gaaactcaac ttaaattgtt tcatattttc ttttcttttt    27420
taaccaaaaa ctccacattt tatagttgga gacttttgtt tctttctgga tgtctgactc    27480
actattttga caataacttt atttcatcta tcattcttac catgtcctgt tcttttagaa    27540
tgataactat ctaaatttaa ttaatcttat cattgagata tattctagcc atttttttgtt   27600
taggccatag ttttttcttt aaggaaaaaa aatgacctga aattaagaaa taaaatatgc    27660
ttttatatta tttttattat tttaatccat ctttgtaaca ctgtgtatgt ttgcattttg    27720
gaactacaag gaaattttaa agatcatctt gaacaagttc cttaact                  27767
```

<210> SEQ ID NO 11
<211> LENGTH: 117
<212> TYPE: PRT
<213> ORGANISM: Human

<400> SEQUENCE: 11

```
Val His Pro Glu Pro Thr Ala Cys Arg Glu Lys Gln Tyr Leu Ile
1               5                  10                  15

Asn Ser Gln Cys Cys Ser Leu Cys Gln Pro Gly Gln Lys Leu Val Ser
            20                  25                  30

Asp Cys Thr Glu Phe Thr Glu Thr Glu Cys Leu Pro Cys Gly Glu Ser
        35                  40                  45

Glu Phe Leu Asp Thr Trp Asn Arg Glu Thr His Cys His Gln His Lys
    50                  55                  60

Tyr Cys Asp Pro Asn Leu Gly Leu Arg Val Gln Gln Lys Gly Thr Ser
65                  70                  75                  80

Glu Thr Asp Thr Ile Cys Thr Cys Glu Glu Gly Trp His Cys Thr Ser
                85                  90                  95

Glu Ala Cys Glu Ser Cys Val Leu His Arg Ser Cys Ser Pro Gly Phe
            100                 105                 110

Gly Val Lys Gln Ile
        115
```

<210> SEQ ID NO 12
<211> LENGTH: 376
<212> TYPE: PRT
<213> ORGANISM: Human

<400> SEQUENCE: 12

```
Met Gln Trp Ala Ser Val Leu Leu Leu Ala Gly Leu Cys Ser Leu Ser
1               5                  10                  15

Gln Gly Gln Tyr Asp Glu Asp Ser His Trp Trp Ile Gln Tyr Leu Arg
            20                  25                  30
```

```
Asn Gln Gln Ser Thr Tyr Tyr Asp Pro Tyr Asp Pro Tyr Glu
            35                  40                  45

Pro Ser Glu Pro Tyr Pro Tyr Gly Val Glu Glu Gly Pro Ala Tyr Ala
 50                  55                  60

Tyr Gly Ala Pro Pro Pro Glu Pro Arg Asp Cys Pro Gln Glu Cys
 65                  70                  75                  80

Asp Cys Pro Pro Asn Phe Pro Thr Ala Met Tyr Cys Asp Asn Arg Asn
                 85                  90                  95

Leu Lys Tyr Leu Pro Phe Val Pro Ser Arg Met Lys Tyr Val Tyr Phe
            100                 105                 110

Gln Asn Asn Gln Ile Ser Ala Ile Gln Glu Gly Val Phe Asp Asn Ala
            115                 120                 125

Thr Gly Leu Leu Trp Val Ala Leu His Gly Asn Gln Ile Thr Ser Asp
 130                 135                 140

Lys Val Gly Arg Lys Val Phe Ser Lys Leu Arg His Leu Glu Arg Leu
145                 150                 155                 160

Tyr Leu Asp His Asn Asn Leu Thr Arg Met Pro Gly Pro Leu Pro Arg
                165                 170                 175

Ser Leu Arg Glu Leu His Leu Asp His Asn Gln Ile Ser Arg Val Pro
            180                 185                 190

Asn Asn Ala Leu Glu Gly Leu Glu Asn Leu Thr Ala Leu Tyr Leu His
            195                 200                 205

His Asn Glu Ile Gln Glu Val Gly Ser Ser Met Arg Gly Leu Arg Ser
 210                 215                 220

Leu Ile Leu Leu Asp Leu Ser Tyr Asn His Leu Arg Arg Val Pro Asp
225                 230                 235                 240

Gly Leu Pro Ser Ala Leu Glu Gln Leu Tyr Leu Glu His Asn Asn Val
                245                 250                 255

Tyr Thr Val Pro Asp Ser Tyr Phe Arg Gly Ser Pro Lys Leu Leu Tyr
            260                 265                 270

Val Arg Leu Ser His Asn Ser Leu Thr Asn Asn Gly Leu Ala Thr Asn
            275                 280                 285

Thr Phe Asn Ser Ser Ser Leu Leu Glu Leu Asp Leu Ser Tyr Asn Gln
 290                 295                 300

Leu Gln Lys Ile Pro Pro Val Asn Thr Asn Leu Glu Asn Leu Tyr Leu
305                 310                 315                 320

Gln Gly Asn Arg Ile Asn Glu Phe Ser Ile Ser Ser Phe Cys Thr Val
                325                 330                 335

Val Asp Val Met Asn Phe Ser Lys Leu Gln Val Leu Arg Leu Asp Gly
            340                 345                 350

Asn Glu Ile Lys Arg Ser Ala Met Pro Val Asp Ala Pro Leu Cys Leu
            355                 360                 365

Arg Leu Ala Asn Leu Ile Glu Ile
 370                 375

<210> SEQ ID NO 13
<211> LENGTH: 423
<212> TYPE: PRT
<213> ORGANISM: Human

<400> SEQUENCE: 13

Met Gly Phe Leu Ser Pro Ile Tyr Val Leu Phe Phe Cys Phe Gly Val
 1               5                  10                  15

Arg Val Tyr Cys Gln Tyr Glu Ala Tyr Arg Trp Asp Asp Asp Tyr Asp
```

```
            20                  25                  30
Gln Glu Pro Asn Glu Asp Tyr Asp Pro Glu Phe Gln Phe His Gln Asn
        35                  40                  45

Ile Glu Tyr Gly Val Pro Phe Tyr Asn Asn Ile Leu Gly Cys Ala Lys
 50                  55                  60

Glu Cys Phe Cys Pro Thr Asn Phe Pro Thr Ser Met Tyr Cys Asp Asn
 65                  70                  75                  80

Arg Lys Leu Lys Thr Ile Pro Ile Ile Pro Met His Ile Gln Gln Leu
                 85                  90                  95

Asn Leu Gln Phe Asn Asp Ile Glu Ala Val Thr Ala Asn Ser Phe Ile
                100                 105                 110

Asn Ala Thr His Leu Lys Glu Ile Asn Leu Ser His Asn Lys Ile Lys
                115                 120                 125

Ser Gln Lys Ile Asp Tyr Gly Val Phe Ala Lys Leu Ser Asn Leu Gln
                130                 135                 140

Gln Leu His Leu Glu His Asn Asn Leu Glu Glu Phe Pro Phe Pro Leu
145                 150                 155                 160

Pro Lys Ser Leu Glu Arg Leu Leu Gly Tyr Asn Glu Ile Ser Ile
                165                 170                 175

Leu Pro Thr Asn Ala Met Asp Gly Leu Val Asn Val Thr Met Leu Asp
                180                 185                 190

Leu Cys Tyr Asn His Leu Ser Asp Ser Met Leu Lys Glu Lys Thr Leu
                195                 200                 205

Ser Lys Met Glu Lys Leu Met Gln Leu Asn Leu Cys Asn Asn Arg Leu
                210                 215                 220

Glu Ser Met Pro Leu Gly Leu Pro Ser Ser Leu Met Tyr Leu Ser Leu
225                 230                 235                 240

Glu Asn Asn Ser Ile Ser Ser Ile Pro Asp Asn Tyr Phe Asp Lys Leu
                245                 250                 255

Pro Lys Leu His Ala Leu Arg Ile Ser His Asn Lys Leu Glu Asp Ile
                260                 265                 270

Pro Tyr Asp Ile Phe Asn Leu Ser Asn Leu Ile Glu Leu Asn Val Gly
                275                 280                 285

His Asn Lys Leu Lys Gln Ala Phe Tyr Ile Pro Arg Asn Leu Glu His
                290                 295                 300

Leu Tyr Leu Gln Asn Asn Glu Ile Glu Ser Ile Asn Val Thr Met Ile
305                 310                 315                 320

Cys Pro Ser Pro Asp Pro Val His His His Leu Thr Tyr Leu Arg
                325                 330                 335

Val Asp Gln Asn Lys Leu Lys Glu Pro Ile Ser Ser Tyr Ile Phe Phe
                340                 345                 350

Cys Phe Pro Arg Ile His Ser Ile Tyr Tyr Gly Glu Gln Arg Ser Thr
                355                 360                 365

Asn Gly Glu Thr Ile Gln Leu Lys Thr Gln Val Phe Arg Ser Tyr Gln
                370                 375                 380

Glu Glu Glu Glu Glu Asp Asp His Asp Ser Gln Asp Asn Thr Leu Glu
385                 390                 395                 400

Gly Gln Glu Val Ser Asp Glu His Tyr Asn Ser His Tyr Tyr Glu Met
                405                 410                 415

Gln Glu Trp Gln Asp Thr Ile
                420

<210> SEQ ID NO 14
```

<211> LENGTH: 1751
<212> TYPE: DNA
<213> ORGANISM: Human

<400> SEQUENCE: 14

```
aggcatttct gattcagtta aaggattgcc aattcatcag tccctgaaac tagagcaatc      60
tcaacaggtt tatttattta ttatatgtaa tacactgtag ctgtcttcag acactccaga     120
agagggagtc agatctcgtt acggatggtt gtgagccacc atgtggttgc tgggatttga     180
actcctgacc ttcggaagag cagtcgggtg ctcttacaca ctgagccatc tcaccagccc     240
gaggacaaga aaagaaaatg ggcttttaa gtccaatata tgtccttttc ttctgttttg      300
gagttagagt atactgccaa tatgaagctt accgatggga tgacgattat gaccaagagc     360
caaatgagga ttatgatcca gaattccaat ttcatcaaaa tattgaatat ggagttccct     420
tttataataa tattttaggt tgtgctaagg aatgcttctg tccaactaac tttccaacat     480
caatgtactg tgacaatcgt aaactcaaga ctatcccaat tattccaatg cacattcagc     540
aactcaacct tcagttcaat gacattgagg ctgtgactgc aaattcattc atcaatgcaa     600
ctcatcttaa agaaattaac cttagccaca acaaaattaa atctcaaaag attgattatg     660
gtgtattcgc taaactttca aatctacaac aacttcatct agagcacaat aacctagaag     720
aatttccatt tccacttcca aaatctttgg aaagactcct tcttggttat aatgaaatct     780
ccatacttcc aacaaatgcc atggacgggc tggtgaatgt gactatgctt gacctctgct     840
ataatcatct ttctgattcg atgttaaaag aaaagaccct ttccaaaatg gaaaaattaa     900
tgcagctcaa cctatgtaat aacagattag aatcaatgcc ccttggattg ccttcatcac     960
ttatgtatct atctttagaa aataattcaa tttcatctat accagacaat tattttgaca    1020
aacttccaaa acttcatgct ctaagaatat cacacaacaa actggaagac attccatatg    1080
acatctttaa tctttccaat cttatagaac tcaacgttgg acacaataaa ttgaagcaag    1140
cattctacat tccaaggaat ttggaacatc tatacctaca aaataatgaa atagaaagca    1200
tcaatgtgac aatgatatgt ccttctcctg atccagtaca ccatcaccat ttaacatacc    1260
ttcgtgtgga ccaaaataag ctgaaagaac caataagttc atacatcttc ttctgcttcc    1320
ctcgtataca cagtatttat tatggtgagc agaggagtac taacggtgaa acaattcaac    1380
tgaagaccca gttttcagg agctaccaag aggaggaaga ggaagacgac catgacagtc     1440
aggacaacac tcttgagggt caagaagtat cagatgagca ctataattct cattactatg    1500
agatgcaaga gtggcaagat actatatagg tacacattta tgcctccata aagccttact    1560
aattacaaat gtaaacatgt aactgctcat aataatatat ctacaagtat gtgttagtat    1620
aaagatcaga actgcgttta agatgttggt gaaaatggct ttacttcata agcttagagc    1680
ttactaaaaa tgatgcaaat cttaagaaat ataaaataga atggtaagtg ggaataaaaa    1740
aaactaagct c                                                          1751
```

<210> SEQ ID NO 15
<211> LENGTH: 7355
<212> TYPE: DNA
<213> ORGANISM: Huiman

<400> SEQUENCE: 15

```
ccccccgcgc agagcatccc tgctgcagcg cagcaagacc cggggctggc agcccccagg      60
aatccctagc tgcttcgcag ggataaagga ctgaagttct tggaggagcg agtccaactc     120
ttcaagctga actatgacca ctttactctt ggtctttgtg actctgaggg tcatcgctgc     180
```

```
agtgatctca gaagaagttc cagaccatga caactcactg agcgtgagca tccctcaacc     240
atccccattg aaggtcctcc tagggtcttc cctcaccatc ccctgctact tcatcgaccc     300
catgcatcct gtgaccactg ccccctccac tgcccccctc accccaagaa tcaagtggag     360
ccgtgtttcc aaggaaaagg aggtggtact gctggtggcc actgaaggac aggttcgagt     420
caacagcatc taccaagaca aggtgtcgct ccccaactat ccagccatcc ccagcgatgc     480
taccttggag atccagaacc ttcgctccaa tgactctggg atctaccgct gtgaagtgat     540
gcacggcatc gaggacagcg aagccaccct ggaggtcata gtgaaaggta ttgtgttcca     600
ctacagagct atttccacac gctacaccct ggactttgat cgagcacagc gggcttgcct     660
acagaacagc gccatcatcg ccaccccaga caactgcag gctgcctatg aggatggctt     720
ccaccagtgc gatgcaggct ggctggctga ccagacagtc agatacccca tccacacgcc     780
ccgggaaggt tgctatggtg acaaggacga gttccctgga gtgagaacct acggaatccg     840
ggacaccaat gagacctatg atgtgtactg cttcgctgag gagatggagg tgaggtcttt     900 tatgcgaca tccccagaga aattcacctt ccaggaggca gccaacgagt gccggaggct     960
gggggcacgc ttggccacca caggccagct ctacctggcc tggcagggcg gtatggacat    1020
gtgcagcgct ggctggctgg cggaccgcag cgtgcgctac cccatctcca aggctcggcc    1080
caactgcggg ggcaacctcc tgggtgtaag gactgtctat ctacacgcca accagacagg    1140
ctatcctgat ccctcatccc gatatgacgc catctgttac acaggtgaag attttgtaga    1200
catcccagaa aacttcttcg gggtgggtgg tgaagacgac atcaccatcc agacggtgac    1260
ctggccagac ctggagctgc ccctgccccg taatgtcaca gagggagagg ccctgggcag    1320
cgtgatcctt acagcaaagc ccatctttga cctgtccccc actatctcag gccggggga    1380 ggccctcaca cttgcccctg aagtggggag cacagccttc ccagaggctg aggagagaac    1440
tggagaagcc accagaccct ggggctttcc tgcagaagtc acacgtgggc cggactctgc    1500
cactgccttc gccagtgagg acctggtagt gcgagtgacc atctctccag gtgcagctga    1560
agtccctggt cagccccgct tgccaggggg agttgtattc cactatcgcc caggctccac    1620
cagatactct ctgacatttg aggaggcaca gcaggcctgc atgcacaccg ggccgtcat    1680 tgcctctcct gagcagctcc aagctgccta tgaggcaggc tatgagcagt gtgatgctgg    1740
ctggctgcag gaccagaccg tcagataccc cattgtgagc ccacgaaccc catgtgtggg    1800
tgacaaagac agcagcccag gagtcaggac ctacggcgtg cgcccatcat cagaaaccta    1860
tgatgtctac tgctacgtgg acaagcttga gggggaagtt ttcttcgcca cacgcctcga    1920
gcagttcacc ttccaggaag cgcgggcctt ctgtgcggct caaaatgcca ccctggcctc    1980
caccggccag ctctatgctg cctggagcca gggtctggac aagtgctatg ctggctggct    2040
ggcagatggc accctccgat acccatcat accccctcgg cctgcctgtg gtggggacaa    2100
acctggcgtg agaactgtct acctctaccc caaccaaacc ggcctccctg acccactgtc    2160 aaaagcaccat gccttctgct tccgaggtgt gtcagtggcg ccctctccag gagaagaagg    2220
gggtagtaca cccacatcac cctctgacat agaggactgg atcgtcactc aggtggggcc    2280
tggtgtggat gctgtcccct tggagccaaa gacaacagaa gtgccatatt tcaccactga    2340
gccaagaaaa cagactgaat gggagccagc ctacacccca gtgggcacat cccacagcc    2400 agggatccct cccacatggc ttcccacct cccagcagca gaggaacaca cagaaagccc    2460
ctctgcctct gaagagccct ctgcctcagc agtcccttcc acctcagagg agccatacac    2520
```

```
atcttcattt gcagtgccga gcatgacaga gctgccaggc tctggggagg cgtcgggcgc    2580
acctgacctc agtggtgact tcacaggcag tggagatgct tcaggacgcc ttgactccag    2640
tgggcagcct tcaggggca ttgaaagtgg ccttccctca ggtgaccttg actccagtgg     2700
cctcagcccc acagtgagct caggcctgcc tgtagaaagt ggttctgcct caggagatgg    2760
agaagtcccc tggtcccata ctcccacagt tggcaggttg ccctctggag gtgagagccc    2820
cgaaggctct gcctctgcct ctggaacagg agaccttagt gggctgcctt caggaggaga    2880
aattacagaa acttctactt ctggggcaga agaaaccagt ggacttcctt ctggaggaga    2940
cggtctagaa acttctacct ctggagtaga tgatgtcagt ggaattccta ctggaagaga    3000
aggtctagag acttctgcct ctggagtaga ggacctcagt ggacttcctt ctggaagaga    3060
aggttcagaa acatctacct ctggaataga ggacatcagt gtacttccaa ctggaggaga    3120
aagtctagaa acctctgctt ctggagtggg agacttgagt ggacttccct caggaggaga    3180
aagtctagaa acatctgctt caggtgcaga ggatgtcact cagcttccta ctgaaagagg    3240
aggtctagag acttctgcct ctggagtaga agacatcact gttcttccta ctggaagaga    3300
aagtctagaa acttctgcct ctggagtaga ggatgtcagt ggacttcctt ctggaagaga    3360
aggtctagag acttctgcct ctggaataga ggacattagt gtgtttccta ctgaagcaga    3420
aggtctggac acttctgcct ctgggggata tgttagtggg attccttctg gaggagatgg    3480
tacagaaacc tctgcttctg agtagagga tgtgagtggt cttccatctg gaggagaggg    3540
tctagaaact tctgcctctg gagtggaaga tcttggtcct tctactagag atagtctaga    3600
gacatctgct tcaggagtag atgttactgg gtttccttct ggaagagggg acccagagac    3660
ctctgtttct ggggtaggtg atgacttcag tggacttcct tctggaaaag aaggcctgga    3720
gacctcagct tctggagctg aggacctcag tggcttgccc tctggaaaag aagacttggt    3780
agggtctgct tctggggcct tggactttgg caaactacct cctggaactc taggaagtgg    3840
tcaaactcca gaagtaaatg ctttccctc tggatttagt ggtgagtatt ctggagcaga    3900
cattggaagt ggcccatcct ctggcctgcc tgactttagt ggacttccat ctggctttcc    3960
aactgtctcc cttgtggaca gtaccttagt ggaagtgatc acagccacca cttccagtga    4020
actgaaagga aggggaccca ttggcatcag tggttcagga gaagtatcag gctgcccct    4080
gggtgaattg gacagtagtg cggacattag tggtctccct tcaggaactg aactcagtgg    4140
ccaagcatct ggatctcctg atagcagtgg agaaacatct ggattttttg atgttagtgg    4200
acagccattt gggtcttctg gcgtcagcga ggaaacatct gggattcctg aaatcagtgg    4260
gcagccatca gggactcctg acaccactgc gacatctgga gtgactgagc ttaatgaact    4320
gtcctctgga caaccagatg tcagtggaga tgggtctgga attctctttg gcagtggaca    4380
gtcctctggt ataacatctg tgagtggaga aacctctggg atttctgatc tcagtgggca    4440
gccctcaggg ttcccagtgt tcagtggaac agcaaccaga acccctgacc tggcttctgg    4500
caccataagt ggcagtggag agtcttctgg cattacattt gtggacacca gttttgttga    4560
agtgacccct accacattta gggaagaaga agggttagga tctgtggaac tcagtggctt    4620
tccttctggg gagacggaac tgtctggcac atctgggacg gtggacgtca gtgaacaatc    4680
ttctggagca attgattcca gtggactcac atcccccact ccagagttca gtggcctccc    4740
aagtggagta gctgaggtca gtggtgaatt ctctggagtt gagactggga gcagcttgcc    4800
ctcaggagca tttgatggca gtggacttgt ctcaggtttc cccactgtgt ctcttgtaga    4860
cagaactttg gtggaatcta taactcaggc tcctactgct caagaagctg gagaaggacc    4920
```

-continued

| | |
|---|---|
| ttcgggcatt ttggaattca gtggtgccca ttctgggaca ccagacatat ctggggagct | 4980 |
| ttctgggtct ctggacctaa gcacattgca gtctgggcag atggaaacca gcacggagac | 5040 |
| accaagctct ccatatttta gtggagactt ttccagcacc actgatgtaa gtggagaatc | 5100 |
| catagctgcc acaactggca gtggggaaag ctctgggctt ccggaagtta ctttaaacac | 5160 |
| ctcagagtta gtggagggtg tgactgaacc cactgtttcc caggaacttg ccatggtcc | 5220 |
| ttctatgaca tacactcccc ggctctttga ggccagtggg gacgcctcag catccgggga | 5280 |
| ccttggtggc gctgtaacaa acttcccagg gtctgggata gaagcttcag tcccagaagc | 5340 |
| cagcagtgac ctgtctgctt accctgaggc tggtgtggga gtgtctgctg ccctgaggc | 5400 |
| cagcagtaaa ctgtctgagt tcccagatct gcatggaatc acttctgcct tccatgaaac | 5460 |
| agatctggaa atgacaaccc caagcacaga ggtaaacagc aacccatgga cctttcagga | 5520 |
| aggcaccagg gagggatcgg ccgctccgga agtgagtgga gaatctagca ctacctccga | 5580 |
| catagacaca ggcacttcag gggtgccttc tgccacaccc atggcttctg agacaggac | 5640 |
| tgaaatcagc ggagaatggt ctgatcacac ctcagaggtg aatgttgcca tcagcagcac | 5700 |
| catcacagag tccgagtggg cccagcctac ccggtaccct acagagacac ttcaagaaat | 5760 |
| cgaatcccca aatccctcat actcaggaga ggagacccag acagcagaaa caaccatgtc | 5820 |
| cctgacagat gccccaccc tctcttcttc agaagggtca ggggagacgg agtcaaccgt | 5880 |
| tgcagaccag gagcaatgtg aggaggggtg gactaagttc cagggtcact gttaccgcca | 5940 |
| ctttcatgac cgagagacct gggtggatgc ggagagacgg tgtcgggagc agcagtcaca | 6000 |
| tctgagcagc attgtcactc ctgaggaaca ggagttcgtc aacaaaaatg ctcaagacta | 6060 |
| ccagtggatc ggtctgaatg acaggactat cgaaggggac ttccgctggt ctgacggaca | 6120 |
| ctctctgcaa tttgagaagt ggcgtccaaa ccagcctgac aacttctttg ccaccggaga | 6180 |
| ggactgtgtg gtgatgatct ggcatgagag aggcgaatgg aacgacgtcc cctgcaatta | 6240 |
| ccagctgccc ttcacgtgta aaaagggcac cgtggcctgt ggagacccc cagtggtgga | 6300 |
| gcatgctaga accctcgggc agaagaaaga tcgctacgag atcagctccc tggtgcggta | 6360 |
| ccagtgcact gagggctttg tccagcgcca cgtgcccacc atccggtgcc agcccagcgg | 6420 |
| gcactgggaa gagcctcgaa tcacctgcac agaccccaac acctacaagc acaggctaca | 6480 |
| gaagcggagc atgagaccca cacggaggag ccgcccagc atggcccact gagaggagct | 6540 |
| tccataatgt gcccaggatg ctgagcccag cggccagcca ggctgaccgt gcatcccacc | 6600 |
| cacatggtgt cttcttgtcg ctttttgtca tataaggaat ccattaaaga aggaaaaaaa | 6660 |
| acccacattg tgtgtgcccc actccccgca tcacccaaac tgcatctaat ttatcccctt | 6720 |
| ctccccccc cccaaaaaaa aagaaaaatg ccaaagcaat tcactgtaac ccgtggactg | 6780 |
| agtttagaga cttttttttga tttcccaccg tgcctttcca gggaccagtg cagggacagg | 6840 |
| gtgagaagta aggggttaaa ttaaataaag aagattcttt tttgttgttg ttcctgact | 6900 |
| ttgcccaaga acagtacaat ggttggttac ttcgcctcca gggagagcta ggggaccaga | 6960 |
| ggaggagctg aaagaagaca ggaccaggaa gggaggagta gggcggtcac agagcttgga | 7020 |
| ggactcagaa gaggcaaagt acagcttagt gtgttggaca aaaggaattg aggtctgtgc | 7080 |
| catctgtgag ggaaggagcc tggggtaggg acaggctggc tgaagagaag gcagagccct | 7140 |
| ctcctaggga ccttcatct gggtcaacca acctagcagg tgtcatttct cggctggact | 7200 |
| gggtaggggc acttccttcc caggggtgct ccgccgtccc cttccctctc cccaccccgg | 7260 |

```
gacggtgcag gcaccagtgt tccgtgcacc tatttatatt tttgaaaact aaagattatg      7320
ataattataa taataaagac attggaagag atcta                                 7355
```

<210> SEQ ID NO 16
<211> LENGTH: 1498
<212> TYPE: DNA
<213> ORGANISM: Human

<400> SEQUENCE: 16

```
gggagctgct ggagtcccca tatcctatgg gatctttggg aagaggaatg actcaggcat        60
caagccccaa ggaattctgt tctgttcaga gaatattgtg agtttacagt accattgctt       120
tgtaaaaata ccagaatgat tctctgggtg cgattataat cagctcagtt gacaatttac       180
ttgaaaacaa acatgccaaa tatcatgcag gttccacttt ctgttttgac ttgcacttca       240
gtttgcagcc tctgtcctgg atgactttta cctttctgct gaagaagttg caacggagat       300
ttcaagatcc cttcaaattg cacaattctg ttttaggtc catccagaac cacccactgc        360
atgcagagaa aaacagtacc taataaacag tcagtgctgt tctttgtgcc agccaggtga       420
gatgccaacc tctagcccc atcatggagt ccccctttgc tttggtggca gacgcagacc        480
ccatatgtta actgtaaact caaatctgaa acgacccatt tcccagccct gcttcactgt       540
cagaatgttc tggttccctc tctaccaggt aaaactctgt ctaccctgaa ctagggatcc       600
cagcttctcc atcttcctcg cctgattatg aaggatccaa gactttcatc tttgaatccc       660
ctaccctaaa gcctggcctg atcattgtgt ggttagtgtc tgactcatgg agttggccag       720
agccctccct catttcctga tgttttccag gacagaaact ggtgagtgac tgcacagagt       780
tcactgaaac ggaatgcctt ccttgcggtg aaagcgaatt cctagacacc tggaacagag       840
agacacactg ccaccagcac aaatactgcg accccagtgc gtgcgctgtt gggaaaggga       900
cgcttgggaa ccgggctgat attcccgaca atgcagccat tctaatttta tgtagccagg       960
gtctgctctg attggttgga gtccgggctg tactgatcat taaatgattt gattgccatc      1020
tctacttgga agagggtctg aggaagaaag agcaggcaat gtgggagtg aggctcagag       1080 catggcccag caggggttc ccatccttcc tgcccttctc ttctcagacc tagggcttcg       1140
ggtccagcag aagggcacct cagaaacaga caccatctgc acctgtgaag aaggctggca      1200
ctgtacgagt gaggcctgtg agagctgtgt cctgcaccgc tcatgctcgc ccggcttttgg     1260 ggtcaagcag attggtaagt ggctcatctg gaatcagtt ttggagggg acagaggagc       1320 ttagggccca aggtgagggg ctgggcagtg ggcacttagc cccagaggca gaggaagcag      1380
aggctccaac ctatgtcggt atccccactg gagtgagctg cagacgggac cttgttcatt      1440
ctgccttctg ccatggggat ctgcctttga agggcaatgg gagaagtcct cctgggga        1498
```

<210> SEQ ID NO 17
<211> LENGTH: 2859
<212> TYPE: DNA
<213> ORGANISM: Human

<400> SEQUENCE: 17

```
ctgccacatt ctccaaccca aggagaccag acagaaggac gtggtcactc tgaacagttc        60
aacccaagag acaaaaatgc agtgggcctc cgtcctgctg ctggctgggc tctgctcact       120
ttcccagggc cagtatgatg aagactctca ctggtggatc caatacctcc gaaaccagca       180
gtccacctac tacgacccct atgacccctta ccctgatgag ccctctgagc ttacccccta     240
tggagtggaa gaaggcccag cctatgccta tggtgcacca cctccaccag agccccgtga      300
```

```
ttgtccccaa gaatgcgact gtcccccaa  cttccccaca gccatgtact gtgacaaccg    360
caacctcaag tacctgcctt ttgtgccctc ccgcatgaag tacgtctact tccagaacaa    420
ccagatctct gccatccagg aaggtgtctt tgacaatgcc actgggctcc tctgggtcgc    480
tctacatggc aaccagatta ccagtgacaa ggtaggcagg aaagtcttct ccaagctgag    540
gcacttggag aggctgtact tggaccacaa caacctgacc cggatgcccg gccgctgcc     600 ccgatccctg agagagctcc acctggacca caaccagatc tcacgggtcc caacaatgc     660 tttggagggc ctggagaacc tcacggcctt atatctccac cacaatgaga tccaggaagt    720
ggggagttcc atgagaggcc tccggtccct gatcctacta gacctgagtt ataaccacct    780
tcggagggta cccgacggtc tgccctcagc cctggagcag ctgtacctag aacacaacaa    840
tgtctacacc gtccctgaca gctacttccg ggggtcaccc aagctgctgt acgtccggtt    900
gtctcacaac agtctcacta caacggcct  tgctaccaac accttcaact ccagcagcct    960
tcttgagcta gacttgtctt acaatcagct gcagaagatc cctcctgtca acaccaacct   1020
ggagaatctt tacctccagg gcaacaggat caatgagttc tccatcagca gcttctgcac   1080
ggtggtggac gtcatgaact ctccaagct  gcaggtgcta cgcctggatg gaacgagat    1140 caagcgcagc gcaatgccgg tggacgcccc actctgcctg cgcctcgcca acctcatcga   1200
gatctgaggg gcctcgcctt gggctcctgg ctccgggctc cgagtaccgt gcaccgtgca   1260
ccgggctcgg ggtacatgcc ctgccacccc gctgcatgtt tggcttttgc tggatggtct   1320
gggacacgca tgtgacagaa gtccacagga tcttattcaa tctccttcca acaggcagag   1380
ttaggtggga tcaggggcca ggccagtttc tgcaggggga tgaatttggt ggtaaaagaa   1440
atatagctat agagtctagc cccaaaatct tcttgcttgg acagtagcat ataaccagtt   1500
ccaatttgac cttttttgag ctgtgctcaa cagcatggcc agctgcttct gcagttgctc   1560
tgggctcctg ctctttgctc ctcaaaacat cacaacacac ctcttgccca gtcacctcct   1620
cccagcccca gctcaccctc tctgccctct ttcactgggg cctcttctaa tgtcttaggc   1680
agtcaggaga cacccacacc ctaagggcac actcttatct gaggctaaac ggatggctaa   1740
aatcacacac ttaccccac  ctcacctgtt taaagtcacc atattgaaca ccataatgat   1800
gagctgttaa catagggggat aaccgactct ataatggagg atctatcaga ggagggaagt   1860
gtccagtggt cattatcagt atccatagta agatggggaa gagacacacc tcaggatagc   1920
agaactgaag gggcagcccc ctttccagtt tcatctgaca caacatgatc tgcaccccctt  1980 cttgggcttt tagtatcgaa ggggcaagcg tggttttcaa aacatgagaa agagcctctg   2040 ctcatcctt  ggtctagtat gaagggttgt tacgcaaatg gcagaggcag actccacccg   2100
ccgaggacct acccactaac ccagactagg gggtgatctc aatagctcgt ttgtccataa   2160
tgctagagca tcaggaacca gccctgtgga gatgctcact ggggtgcaag aagccctgcc   2220
aggcccaagt cctgccgaca ctagacctgg cttcctctgc attcacacta tgcagtccgc   2280
cttatgccca gtggtgcctg tgatttgtag tttgtctaag aacagcccca tcttctcctt   2340
tttaaaggtg atattgccta ggtacaacca acagcttctt ctagacccca ctgggataga   2400
gccaccaggg tagcgagtgg caagaagcag ttgtaagatg ctagcctgag gtgggtccct   2460
gccttagacc cctgactctg tgtgcacttg ggagcaagct tctctggaaa ggacagggtg   2520
gggcggggtg cttagactgt gctacgggtt ccagaactgc aatccacaaa agccaaacca   2580
gcttgtttca accggggagt gccacctgcg gagcaaggct gccctggcca gggttcttgg   2640
```

| | |
|---|---:|
| gaagcacctg catgtatcac catcctgcct ctgaagagcc ctcagcatga agcaagcatg | 2700 |
| aatggcggcc aacctaacca ataaagttat tttataagtg catctgcaag gatggaatgg | 2760 |
| ttggtggcag ccctcggcat cgcctcgggg tacctagaca cacaggcctt gaaccgtgtc | 2820 |
| agctctttat aaagagtagc ctatataaaa actcaagtt | 2859 |

<210> SEQ ID NO 18
<211> LENGTH: 4936
<212> TYPE: DNA
<213> ORGANISM: Human

<400> SEQUENCE: 18

| | |
|---|---:|
| aaactcatct atcctttacg gcaagggtac ctacggtacc tgaaaacaac gatggcatgg | 60 |
| aaaacacttc ccatttacct gttgttgctg ctgtctgttt tcgtgattca gcaagtttca | 120 |
| tctcaagagc tttcctgtaa aggccgctgc tttgagtcct tcgagagagg gagggagtgt | 180 |
| gactgcgacg cccaatgtaa gaagtatgac aagtgctgtc ccgattatga gagtttctgt | 240 |
| gcagaagtgc ataatcccac atcaccacca tcttcaaaga aagcacctcc accttcagga | 300 |
| gcatctcaaa ccatcaaatc aacaaccaaa cgttcaccca accaccaaa caagaagaag | 360 |
| actaagaaag ttatagaatc agaggaaata acagaagaac attctgtttc tgaaaatcaa | 420 |
| gagtcctcct cctcctcctc ctcttcctct tcttcttcaa caattcggaa aatcaagtct | 480 |
| tccaaaaatt cagctgctaa tagagaatta cagaagaaac tcaaagtaaa agataacaag | 540 |
| aagaacagaa ctaaaaagaa acctaccccc aaaccaccag ttgtagatga agctggaagt | 600 |
| ggattggaca atggtgactt caaggtcaca actcctgaca cgtctaccac ccaacacaat | 660 |
| aaagtcagca catctcccaa gatcacaaca gcaaaaccaa taaatcccag acccagtctt | 720 |
| ccacctaatt ctgatacatc taaagagacg tctttgacag tgaataaaga acaacagtt | 780 |
| gaaactaaag aaactactac aacaaataaa cagacttcaa ctgatggaaa agagaagact | 840 |
| acttccgcta agagacacaa agtatagag aaaacatctg ctaaagattt agcacccaca | 900 |
| tctaaagtgc tggctaaacc tacacccaaa gctgaaacta caaccaaagg ccctgctctc | 960 |
| accactccca aggagcccac gcccaccact cccaaggagc ctgcatctac cacacccaaa | 1020 |
| gagcccacac ctaccaccat caagtctgca cccaccaccc ccaaggagcc tgcacccacc | 1080 |
| accaccaagt ctgcacccac cactcccaag gagcctgcac ccaccaccac caaggagcct | 1140 |
| gcacccacca ctcccaagga gcctgcaccc accaccacca aggagcctgc acccaccacc | 1200 |
| accaagtctg cacccaccac tcccaaggag cctgcaccca ccaccccaa gaagcctgcc | 1260 |
| ccaactaccc ccaaggagcc tgcacccacc actcccaagg agcctacacc caccactccc | 1320 |
| aaggagcctg cacccaccac caaggagcct gcacccacca ctcccaaaga gcctgcaccc | 1380 |
| actgccccca gaagcctgc cccaactacc cccaaggagc ctgcacccac cactcccaag | 1440 |
| gagcctgcac caccaccac caaggagcct tcacccacca ctcccaagga gcctgcaccc | 1500 |
| accaccacca agtctgcacc caccactacc aaggagcctg cacccaccac taccaagtct | 1560 |
| gcacccacca ctcccaagga gccttcaccc accaccacca aggagcctgc acccaccact | 1620 |
| cccaaggagc tgcacccac caccccaag aagcctgccc caactacccc caaggagcct | 1680 |
| gcacccacca ctcccaagga acctgcaccc accaccacca agaagcctgc acccaccact | 1740 |
| cccaagagc ctgccccaac taccccaag gagactgcac ccaccacccc caagaagctc | 1800 |
| acgcccacca cccccgagaa gctcgcaccc accacccctg agaagcccgc acccaccacc | 1860 |
| cctgaggagc tcgcacccac caccccctgag gagcccacac ccaccacccc tgaggagcct | 1920 |

```
gctcccacca ctcccaaggc agcggctccc aacaccccta aggagcctgc tccaactacc   1980
cctaaggagc ctgctccaac taccectaag gagcctgctc caactacccc taaggagact   2040
gctccaacta ccctaaagg gactgctcca actaccctca aggaacctgc acccactact    2100
cccaagaagc ctgcccccaa ggagcttgca cccaccacca ccaaggagcc acatccacc    2160 acctgtgaca agcccgctcc aactacccct aaggggactg ctccaactac ccctaaggag   2220
cctgctccaa ctacccctaa ggagcctgct ccaactaccc taaggggac tgctccaact    2280 accctcaagg aacctgcacc cactactccc aagaagcctg ccccaagga gcttgcaccc    2340 accaccacca aggggcccac atccaccacc tctgacaagc ctgctccaac tacacctaag   2400
gagactgctc caactacccc caaggagcct gcacccacta ccccaagaa gcctgctcca    2460 actactcctg agacacctcc tccaaccact tcagaggtct ctactccaac taccaccaag   2520
gagcctacca ctatccacaa aagccctgat gaatcaactc ctgagctttc tgcagaaccc   2580
acaccaaaag ctcttgaaaa cagtcccaag gaacctggtg tacctacaac taagactcct   2640
gcagcgacta aacctgaaat gactacaaca gctaaagaca agacaacaga aagagactta   2700
cgtactacac ctgaaactac aactgctgca cctaagatga caaaagagac agcaactaca   2760
acagaaaaaa ctaccgaatc caaaataaca gctacaacca cacaagtaac atctaccaca   2820
actcaagata ccacaccatt caaaattact actcttaaaa caactactct tgcacccaaa   2880
gtaactacaa caaaaaagac aattactacc actgagatta tgaacaaacc tgaagaaaca   2940
gctaaaccaa agacagagc tactaattct aaagcgacaa ctcctaaacc tcaaaagcca   3000
accaaagcac ccaaaaaacc cacttctacc aaaaagccaa aacaatgcc tagagtgaga   3060 aaaccaaaga cgacaccaac tccccgcaag atgacatcaa caatgccaga attgaaccct   3120
acctcaagaa tagcagaagc catgctccaa accaccacca gacctaacca aactccaaac   3180
tccaaactag ttgaagtaaa tccaaagagt gaagatgcag gtggtgctga aggagaaaca   3240
cctcatatgc ttctcaggcc ccatgtgttc atgcctgaag ttactcccga catggattac   3300
ttaccgagag tacccaatca aggcattatc atcaatccca tgcttccga tgagaccaat    3360 atatgcaatg gtaagccagt agatggactg actactttgc gcaatgggac attagttgca   3420
ttccgaggtc attatttctg gatgctaagt ccattcagtc caccatctcc agctcgcaga   3480
attactgaag tttggggtat tccttccccc attgatactg tttttactag gtgcaactgt   3540
gaaggaaaaa ctttcttctt taaggattct cagtactggc gttttaccaa tgatataaaa   3600
gatgcagggt accccaaacc aattttcaaa ggatttggag gactaactgg acaaatagtg   3660
gcagcgcttt caacagctaa atataagaac tggcctgaat ctgtgtattt tttcaagaga   3720
ggtggcagca ttcagcagta tatttataaa caggaacctg tacagaagtg ccctggaaga   3780
aggcctgctc taaattatcc agtgtatgga gaaacgacac aggttaggag acgtcgcttt   3840
gaacgtgcta taggaccttc tcaaacacac accatcagaa ttcaatattc acctgccaga   3900
ctggcttatc aagacaaagg tgtccttcat aatgaagtta agtgagtat actgtggaga    3960 ggacttccaa atgtggttac ctcagctata tcactgccca acatcagaaa acctgacggc   4020
tatgattact atgccttttc taaagatcaa tactataaca ttgatgtgcc tagtagaaca   4080
gcaagagcaa ttactactcg ttctgggcag accttatcca agtctggta caactgtcct   4140 tagactgatg agcaaaggag gagtcaacta atgaagaaat gaataataaa ttttgacact   4200
gaaaaacatt ttattaataa agaatattga catgagtata ccagtttata tataaaaatg   4260
```

-continued

| | |
|---|---|
| tttttaaact tgacaatcat tacactaaaa cagatttgat aatcttattc acagttgtta | 4320 |
| ttgtttacag accatttaat taatatttcc tctgtttatt cctcctctcc ctcccattgc | 4380 |
| atggctcaca cctgtaaaag aaaaagaat caaattgaat atatctttta agaattcaaa | 4440 |
| actagtgtat tcacttaccc tagttcatta taaaaaatat ctaggcattg tggatataaa | 4500 |
| actgttgggt attctacaac ttcaatggaa attattacaa gcagattaat ccctcttttt | 4560 |
| gtgacacaag tacaatctaa aagttatatt ggaaaacatg gaaatattaa aattttacac | 4620 |
| ttttactagc taaaacataa tcacaaagct ttatcgtgtt gtataaaaaa attaacaata | 4680 |
| taatggcaat aggtagagat acaacaaatg aatataacac tataacactt catatttcc | 4740 |
| aaatcttaat ttggatttaa ggaagaaatc aataaatata aaatataagc acatatttat | 4800 |
| tatatatcta aggtatacaa atctgtctac atgaagttta cagattggta aatatcacct | 4860 |
| gctcaacatg taattattta ataaaacttt ggaacattaa aaaaataaat tggaggctta | 4920 |
| aaaaaaaaaa aaaaaa | 4936 |

<210> SEQ ID NO 19
<211> LENGTH: 2206
<212> TYPE: DNA
<213> ORGANISM: Human

<400> SEQUENCE: 19

| | |
|---|---|
| actatattca caggcttgga gccagtgcca ttcacacttc cccctcttct gcagcagacg | 60 |
| gactgagttc ctctaatccc tgtgttcctt ctcccccatc tttctaaaac ccttctctga | 120 |
| gagaggaata actatagctt cagggataat atagctttaa ggaaactttt ggcagatgtg | 180 |
| gacgtcgtaa catctgggca gtgttaacag aatcccggag gccgggacag accaggagcc | 240 |
| actcgttcta ggaatgttaa agtagaaggt ttttccaat tgatgagagg agcagagagg | 300 |
| aaggagaaag aggaggagag agaaaaaggg cacaaaatac cataaaacag atcccatatt | 360 |
| tctgcttccc ctcacttta gaagttaatt gatggctgac ttctgaaagt cacttttcctt | 420 |
| tgccctggta cttcaggcca tatacatctt ttcttgtctc cataatcctc cctttcaagg | 480 |
| atggccagtc agctaactca aagaggagct ctctttctgc tgttcttcct aactccggca | 540 |
| gtgacaccaa catggtatgc aggttctggc tactatccgg atgaaagcta caatgaagta | 600 |
| tatgcagagg aggtccccaca ggctcctgcc ctggactacc gagtccccg atggtgttat | 660 |
| acattaaata tccaggatgg agaagccaca tgctactcac cgaagggagg aaattatcac | 720 |
| agcagcctgg gcacgcgttg tgagctctcc tgtgaccggg gctttcgatt gattggaagg | 780 |
| aggtcggtgc aatgcctgcc aagccgtcgt tggtctggaa ctgcctactg caggcagatg | 840 |
| agatgccacg cactaccatt catcactagt ggcacttaca cctgcacaaa tggagtgctt | 900 |
| cttgactctc gctgtgacta cagctgttcc agtggctacc acctggaagg tgatcgcagc | 960 |
| cgaatctgca tggaagatgg gagatggagt ggaggcgagc ctgtatgtgt agacatagat | 1020 |
| ccccccaaga tccgctgtcc ccactcacgt gagaagatgg cagagccaga gaaattgact | 1080 |
| gctcgagtat actgggaccc accgttggtg aaagattctg ctgatggtac catcaccagg | 1140 |
| gtgacacttc ggggccctga gcctggctct cactttcccg aaggagagca tgtgattcgt | 1200 |
| tacactgcct atgaccgagc ctacaaccgg gccagctgca agttcattgt gaaagtacaa | 1260 |
| gtgagacgct gcccaactct gaaacctccg cagcacggct acctcacctg cacctcagcg | 1320 |
| ggggacaact atggtccac ctgtgaatac cactgtgatg gcggttatga tcgccagggg | 1380 |
| acaccctccc gggtctgtca gtccagccgc cagtggtcag gttcaccacc aatctgtgct | 1440 |

-continued

```
cctatgaaga ttaacgtcaa cgtcaactca gctgctggtc tcttggatca attctatgag    1500
aaacagcgac tcctcatcat ctcagctcct gatccttcca accgatatta taaaatgcag    1560
atctctatgc tacagcaatc cacctgtgga ctggatttgc ggcatgtgac catcattgaa    1620
ctggtgggac agccacctca ggaggtgggg cgcatccggg agcaacagct gtcagccaac    1680
atcatcgagg agctcaggca atttcagcgc ctcactcgct cctacttcaa catggtgttg    1740
attgacaaga agggtattga ccgagaccgc tacatggaac tgtcacccc cgaggaaatc     1800
ttcacattca ttgatgacta cctactgagc aatcaggagt tgacccagcg tcgggagcaa    1860
aggacatat gcgagtgaac ttgagccagg gcatggttaa agtcaaggga aaagctcctc     1920
tagttagctg aaactgggac ctaataaaag gaggaaatgt tttcccacag ttctagggac    1980
aggactctga ggtgggtgag tttgacaaat cctgcagtgt ttccaggcat cctttagga    2040
ctgtgtaata gtttccctag aagctaggta gggactgagg acaggccttg ggcagtgggt    2100
tgggggtaga agttcttcct ttcctaaccc gggcccctgc ccagctctcc aaagtctttc    2160
agaaaagtaa atcctaaatt cagtgatgaa aaaaaaaaaa aaaaaa                   2206
```

<210> SEQ ID NO 20
<211> LENGTH: 465
<212> TYPE: PRT
<213> ORGANISM: Human

<400> SEQUENCE: 20

```
Met Ala Ser Gln Leu Thr Gln Arg Gly Ala Leu Phe Leu Leu Phe Phe
1               5                  10                  15

Leu Thr Pro Ala Val Thr Pro Thr Trp Tyr Ala Gly Ser Gly Tyr Tyr
            20                  25                  30

Pro Asp Glu Ser Tyr Asn Glu Val Tyr Ala Glu Val Pro Gln Ala
        35                  40                  45

Pro Ala Leu Asp Tyr Arg Val Pro Arg Trp Cys Tyr Thr Leu Asn Ile
    50                  55                  60

Gln Asp Gly Glu Ala Thr Cys Tyr Ser Pro Lys Gly Gly Asn Tyr His
65                  70                  75                  80

Ser Ser Leu Gly Thr Arg Cys Glu Leu Ser Cys Asp Arg Gly Phe Arg
                85                  90                  95

Leu Ile Gly Arg Arg Ser Val Gln Cys Leu Pro Ser Arg Trp Ser
            100                 105                 110

Gly Thr Ala Tyr Cys Arg Gln Met Arg Cys His Ala Leu Pro Phe Ile
        115                 120                 125

Thr Ser Gly Thr Tyr Thr Cys Thr Asn Gly Val Leu Leu Asp Ser Arg
    130                 135                 140

Cys Asp Tyr Ser Cys Ser Ser Gly Tyr His Leu Glu Gly Asp Arg Ser
145                 150                 155                 160

Arg Ile Cys Met Glu Asp Gly Arg Trp Ser Gly Gly Glu Pro Val Cys
                165                 170                 175

Val Asp Ile Asp Pro Pro Lys Ile Arg Cys Pro His Ser Arg Glu Lys
            180                 185                 190

Met Ala Glu Pro Glu Lys Leu Thr Ala Arg Val Tyr Trp Asp Pro Pro
        195                 200                 205

Leu Val Lys Asp Ser Ala Asp Gly Thr Ile Thr Arg Val Thr Leu Arg
    210                 215                 220

Gly Pro Glu Pro Gly Ser His Phe Pro Glu Gly Glu His Val Ile Arg
225                 230                 235                 240
```

Tyr Thr Ala Tyr Asp Arg Ala Tyr Asn Arg Ala Ser Cys Lys Phe Ile
                245                 250                 255

Val Lys Val Gln Val Arg Arg Cys Pro Thr Leu Lys Pro Pro Gln His
            260                 265                 270

Gly Tyr Leu Thr Cys Thr Ser Ala Gly Asp Asn Tyr Gly Ala Thr Cys
        275                 280                 285

Glu Tyr His Cys Asp Gly Gly Tyr Asp Arg Gln Gly Thr Pro Ser Arg
    290                 295                 300

Val Cys Gln Ser Ser Arg Gln Trp Ser Gly Ser Pro Pro Ile Cys Ala
305                 310                 315                 320

Pro Met Lys Ile Asn Val Asn Val Asn Ser Ala Ala Gly Leu Leu Asp
                325                 330                 335

Gln Phe Tyr Glu Lys Gln Arg Leu Leu Ile Ile Ser Ala Pro Asp Pro
            340                 345                 350

Ser Asn Arg Tyr Tyr Lys Met Gln Ile Ser Met Leu Gln Gln Ser Thr
        355                 360                 365

Cys Gly Leu Asp Leu Arg His Val Thr Ile Ile Glu Leu Val Gly Gln
    370                 375                 380

Pro Pro Gln Glu Val Gly Arg Ile Arg Glu Gln Gln Leu Ser Ala Asn
385                 390                 395                 400

Ile Ile Glu Glu Leu Arg Gln Phe Gln Arg Leu Thr Arg Ser Tyr Phe
                405                 410                 415

Asn Met Val Leu Ile Asp Lys Gln Gly Ile Asp Arg Asp Arg Tyr Met
            420                 425                 430

Glu Pro Val Thr Pro Glu Glu Ile Phe Thr Phe Ile Asp Asp Tyr Leu
        435                 440                 445

Leu Ser Asn Gln Glu Leu Thr Gln Arg Arg Glu Gln Arg Asp Ile Cys
    450                 455                 460

Glu
465

<210> SEQ ID NO 21
<211> LENGTH: 646
<212> TYPE: PRT
<213> ORGANISM: Human

<400> SEQUENCE: 21

Met Ala Pro Ser Ala Asp Pro Gly Met Val Arg Met Ala Leu Leu Leu
1               5                   10                  15

Leu Pro Pro Leu Trp Leu Leu Pro Leu Thr Gly Gly Ser Gln Arg Ala
            20                  25                  30

Glu Pro Met Phe Thr Ala Val Thr Asn Ser Val Leu Pro Pro Asp Tyr
        35                  40                  45

Asp Ser Asn Pro Thr Gln Leu Asn Tyr Gly Val Ala Val Thr Asp Val
    50                  55                  60

Asp His Asp Gly Asp Phe Glu Ile Val Val Ala Gly Tyr Thr Gly Pro
65                  70                  75                  80

Asn Leu Val Leu Lys Tyr Asn Arg Ala Gln Asn Arg Leu Val Asn Ile
                85                  90                  95

Ala Val Asp Glu Arg Ser Ser Pro Tyr Tyr Ala Leu Arg Asp Arg Gln
            100                 105                 110

Gly Asn Ala Ile Gly Val Thr Ala Cys Asp Ile Asp Gly Asp Gly Arg
        115                 120                 125

Glu Glu Ile Tyr Phe Leu Asn Thr Asn Asn Ala Phe Ser Gly Val Ala

```
            130                 135                 140
Thr Tyr Thr Asp Lys Leu Phe Lys Phe Arg Asn Asn Arg Trp Glu Asp
145                 150                 155                 160

Ile Leu Ser Asp Asp Val Asn Val Ala Arg Gly Val Ala Ser Leu Phe
                165                 170                 175

Ala Gly Arg Ser Val Ala Cys Val Asp Arg Thr Gly Ser Gly Arg Tyr
            180                 185                 190

Ser Ile Tyr Ile Ala Asn Tyr Ala Tyr Gly Asp Val Gly Pro Asp Ala
        195                 200                 205

Leu Ile Glu Met Asp Pro Glu Ala Ser Asp Leu Ser Arg Gly Ile Leu
    210                 215                 220

Ala Leu Arg Asp Val Ala Ala Glu Ala Gly Val Ser Lys Tyr Thr Ala
225                 230                 235                 240

Gly Arg Gly Val Ser Val Gly Pro Ile Leu Ser Ser Ala Ser Asp
                245                 250                 255

Ile Phe Cys Asp Asn Glu Asn Gly Pro Asn Phe Leu Phe His Asn Gln
                260                 265                 270

Gly Asn Gly Thr Phe Val Asp Thr Ala Ala Ser Ala Gly Val Asp Asp
            275                 280                 285

Pro His Gln His Gly Arg Gly Val Ala Leu Ala Asp Phe Asn Arg Asp
        290                 295                 300

Gly Lys Val Asp Ile Val Tyr Gly Asn Trp Asn Gly Pro His Arg Leu
305                 310                 315                 320

Tyr Leu Gln Met Ser Ala His Gly Lys Val Arg Phe Arg Asp Ile Ala
                325                 330                 335

Ser Pro Lys Phe Ser Thr Pro Ser Pro Val Arg Thr Val Ile Ala Ala
            340                 345                 350

Asp Phe Asp Asn Asp Gln Glu Leu Glu Val Phe Phe Asn Asn Ile Ala
        355                 360                 365

Tyr Arg Ser Ser Ser Ala Asn Arg Leu Phe Arg Val Ile Arg Arg Glu
    370                 375                 380

His Gly Asp Pro Leu Ile Glu Glu Leu Asn Pro Gly Asp Ala Leu Glu
385                 390                 395                 400

Pro Glu Gly Arg Gly Thr Gly Val Val Thr Asp Phe Asp Gly Asp
                405                 410                 415

Gly Met Leu Asp Leu Ile Leu Ser His Gly Glu Ser Met Ala Gln Pro
            420                 425                 430

Leu Ser Val Phe Arg Gly Asn Gln Gly Phe Ser Asn Asn Trp Leu Arg
        435                 440                 445

Val Val Pro Arg Thr Arg Phe Gly Ala Phe Ala Arg Gly Ala Lys Val
    450                 455                 460

Val Leu Tyr Thr Lys Lys Ser Gly Ala His Leu Arg Ile Ile Asp Gly
465                 470                 475                 480

Gly Ser Gly Tyr Leu Cys Glu Met Glu Pro Val Ala His Phe Gly Leu
                485                 490                 495

Gly Arg Asp Glu Ala Ser Ser Val Glu Val Thr Trp Pro Asp Gly Lys
            500                 505                 510

Met Val Ser Arg Ser Val Ala Ser Glu Glu Met Asn Ser Val Leu Glu
        515                 520                 525

Ile Leu Tyr Pro Gln Asp Glu Asp Lys Leu Gln Asn Thr Ala Pro Leu
    530                 535                 540

Glu Cys Gly Gln Gly Phe Ser Gln Gln Asp Asn Gly His Cys Met Asp
545                 550                 555                 560
```

```
            Thr Asn Glu Cys Ile Gln Phe Pro Phe Val Cys Pro Arg Asp Lys Pro
                            565                 570                 575

Val Cys Val Asn Thr Tyr Gly Ser Tyr Arg Cys Arg Thr Asn Lys Arg
                        580                 585                 590

Cys Asn Arg Gly Tyr Glu Pro Asn Glu Asp Gly Thr Ala Cys Val Ala
                    595                 600                 605

Gln Val Ala Phe Leu Gly Gly Tyr Ser Ser Ala Phe Arg Leu Ser
                610                 615                 620

Glu Pro Leu Ser Gln Ala Ser Tyr Leu Ser Leu Gly Leu Gly Leu Cys
            625                 630                 635                 640

Leu Gln Leu Tyr Ala Leu
                        645

<210> SEQ ID NO 22
<211> LENGTH: 2616
<212> TYPE: DNA
<213> ORGANISM: Human

<400> SEQUENCE: 22
```

| | | | | | |
|---|---|---|---|---|---|
| ataaagcgag | cgcgcggcgt | cggggcggga | ggctcgaggc | cagcccggga | ccagggctgg | 60 |
| gcgctgcaag | gcggcggcgc | cagcggcaga | ggcagcatcg | agcgcccgcg | ctccgacgcc | 120 |
| cccaagcggt | ggggctgaga | gagccagagg | atggctccga | cgctgacccc | gggcatggtc | 180 |
| aggatggctt | tgctcctgct | gccgccctg | tggcttctgc | ctctcactgg | gggatcccag | 240 |
| agggctgagc | ccatgttcac | tgcagtcacc | aactcagtcc | tgcccctga | ctatgacagc | 300 |
| aaccccaccc | agctcaacta | tggagtggca | gtgacagatg | tggaccatga | tgggacttc | 360 |
| gagatcgttg | tggcggggta | caccggcccc | aacctggttc | tgaagtacaa | tcgagcccag | 420 |
| aatcggctgg | tgaatattgc | ggtggacgag | cgcagctcac | cctactatgc | tctgagggac | 480 |
| cgtcagggga | cgccatcgg | ggtcacagcc | tgtgacatcg | atgggacgg | ccgtgaggag | 540 |
| atctactttc | tcaacaccaa | taacgccttc | tcaggtgtgg | ccacatacac | agacaagttg | 600 |
| ttcaaattcc | gaaataaccg | gtgggaagac | atcctgagtg | atgacgtcaa | tgtggcccgt | 660 |
| ggagtggcca | gcctctttgc | gggacgctcc | gtggcctgtg | tagacaggac | gggctctgga | 720 |
| agatactcta | tctacatagc | caactatgcc | tatggtgatg | tggggcctga | tgccctcatc | 780 |
| gaaatggacc | ctgaggccag | tgacctgtcc | cggggggatcc | tggcactcag | ggacgtggcg | 840 |
| gctgaggctg | ggtcagcaa | gtacacagcg | ggccggggtg | tcagcgtagg | ccccattctc | 900 |
| agcagcagtg | cctcagatat | cttctgtgac | aacgagaacg | ggcccaactt | cctcttccac | 960 |
| aaccaaggca | acggtacctt | tgtggatact | gcggccagtg | ccggcgtaga | cgaccctcat | 1020 |
| cagcatggcc | gaggtgtggc | cctggcagat | ttcaaccgtg | acggcaaagt | agacatcgtc | 1080 |
| tatggcaact | ggaacggccc | acatcgcctc | tatctacaga | tgagtgctca | cgggaaggtc | 1140 |
| cggtttcggg | acattgcttc | gcccaagttc | tccacgccct | ccctgtccg | gactgtcatt | 1200 |
| gctgccgact | ttgacaatga | ccaggaactg | gaagtcttct | tcaacaacat | tgcctacaga | 1260 |
| agctcctcag | ccaatcgcct | cttccgtgtc | atccgcaggg | agcacgggga | ccctctcatc | 1320 |
| gaggagctca | atcctggtga | cgccctagag | cctgagggcc | ggggtacagg | gggcgtagtg | 1380 |
| accgacttcg | atggtgatgg | gatgctggat | ctcatcttgt | cacatggaga | gtccatggct | 1440 |
| cagccactgt | ctgtcttccg | ggaaatcag | ggcttcagca | acaactggtt | gcgtgtggta | 1500 |
| cctcgcaccc | ggttcgggc | ctttgccagg | ggcgccaagg | ttgtactcta | caccaagaag | 1560 |

| | |
|---|---|
| agtgggcgc acctacggat cattgatggg ggttccggct acctgtgtga aatggagcct | 1620 |
| gtggcacatt ttggcctggg acgggatgaa gccagcagtg tggaggtgac gtggccagat | 1680 |
| ggcaagatgg tgagccgaag tgtggccagc gaggagatga actcggtgtt ggagatcctc | 1740 |
| taccccagg atgaggacaa acttcagaac acagccccac tagagtgcgg ccaaggattc | 1800 |
| tcccagcagg acaatggcca ttgcatggac accaatgaat gcatccagtt cccatttgtg | 1860 |
| tgccctcgag acaaacccgt atgtgtcaac acctatggaa gctacaggtg ccggaccaat | 1920 |
| aaaagatgca atcggggcta tgaacccaat gaagacggca cagcctgtgt ggctcaagtg | 1980 |
| gccttttag gtgggtactc atcggctgcc tttagactct ctgagcctct ctctcaggcc | 2040 |
| tcgtatcttt ctctaggcct gggactttgc cttcagttat atgcacttta aatcccatca | 2100 |
| ataaaggaaa aaaaaatcta acaacctttg tggaaaacta tatctctcct gctgcctacc | 2160 |
| tctctccaca ccccatagat cccgccatgt gctccttcga acggacagca ggggtggcca | 2220 |
| tctttgaaaa gggaagtttg ggagatactg atgggacctt agttgttggt gaagcctttc | 2280 |
| tttgcatgtt ttctgagaaa acagaaaaag gaaaactatc tcctctaccc cacccctcct | 2340 |
| tccgtgagaa gaaccaagag agtccagtca tttctgtatc ttcgtgagct tcttcttgtt | 2400 |
| ttgcccttga caaagatggc tcctgggtgg ttgctggctc ggttgattca gtaatgtatc | 2460 |
| ctgtgcctgc tgatccggcc tgtgctgctg ctgctgcttt gtacaacctg atttcctatg | 2520 |
| attacgaag ccttattgga ttggtggtgg cgacggaaag ggaaagggtg cccctttggg | 2580 |
| actgttgata aaaaaaaaat gcttaagttt gaactt | 2616 |

<210> SEQ ID NO 23
<211> LENGTH: 2447
<212> TYPE: DNA
<213> ORGANISM: Human

<400> SEQUENCE: 23

| | |
|---|---|
| gacagcagct gcagctccgc cgccatgggc cccactgcct gcgttctagt gctcgccctg | 60 |
| gctatcctgc gggcgacagg ccagggccag atcccgctgg gtggagacct ggccccacag | 120 |
| atgctgcgag aacttcagga gactaatgcg gcgctgcaag acgtgagaga gctgttgcga | 180 |
| cagcaggtca aggagatcac cttcctgaag aatacggtga tggaatgtga tgcttgcgga | 240 |
| atgcagcccg cacgcactcc aggcctgagc gtgcggccag tgccgctctg cgcacccggc | 300 |
| tcctgcttcc ccggcgtagt ctgctccgag acagctacgg gcgcgcgctg cggcccctgc | 360 |
| cctcctggct acaccggcaa cggctcgcac tgcaccgacg ttaatgagtg caatgctcac | 420 |
| ccctgtttcc cgcgggtgcg gtgcatcaat accagccctg gctttcactg cgaagcctgt | 480 |
| cccccctgggt tcagcggacc cacccacgag ggcgtgggac tgaccttcgc taagtccaac | 540 |
| aaacaagttt gcacggatat taatgagtgt gagaccgggc agcacaattg cgttcccaac | 600 |
| tccgtgtgcg tcaacacccg gggctccttc cagtgcggcc cctgccagcc cggtttcgtg | 660 |
| ggcgaccaga cgtcaggctg ccagcggcgt gggcagcact tctgccccga tgggtcaccc | 720 |
| agcccgtgcc atgagaaagc aaactgcgtc ctggagcggg atggctcgag gtcttgcgtg | 780 |
| tgtgcagttg gctgggccgg caacgggctc tgtgcggcc gcgacacgga cctggacggt | 840 |
| tttcctgacg agaagcttcg ctgctcagag cgccagtgtc gcaaggacaa ctgcgtgacg | 900 |
| gtgcccaatt cggggcagga ggatgtggac cgggacggca tcggagatgc ttgtgacccg | 960 |
| gatgcggacg gggatggagt ccctaacgag caagacaatt gcccgctggt tcgaaaccca | 1020 |
| gaccagcgta actcggacag tgataagtgg ggagatgcct gcgacaactg ccggtccaag | 1080 |

```
aagaatgacg atcagaaaga tacagacctg gatggccggg gcgatgcctg cgacgacgac   1140
atagatggcg accgaatacg aaatgtagct gacaactgtc cccgggtgcc caactttgac   1200
cagagtgaca gtgatggtga tggtgttggg gatgcctgtg acaactgtcc ccagaaagat   1260
aacccagacc agagggatgt ggaccacgac tttgtgggtg atgcctgtga tagtgaccaa   1320
gaccaggatg gggatggtca ccaggactcc cgggacaact gccccacagt acccaacagt   1380
gcccagcagg actcagatca tgatggcaag ggcgatgcct gtgatgacga tgatgacaat   1440
gacggagttc ctgatagccg ggacaactgc cgcttggtgc ctaaccctgg ccaagaggac   1500
aatgaccggg atggcgtggg tgacgcgtgt caggqtgact cgatgctga caaggttata   1560 gacaagatcg atgtgtgccc cgagaacgcc gaggtcaccc tcaccgactt cagggccttc   1620
cagacggttg tgttggaccc cgagggtgat gcgcagatcg atcccaactg ggtggtgctc   1680
aatcagggaa tggagatcgt tcagaccatg aacagtgacc ctggcctggc tgtgggttac   1740
acagccttca acggcgtgga cttcgaggqc acattccatg taaacaccgc cactgatgat   1800
gactatgctg gtttcatctt cggctaccaa gacagctcca gtttctacgt agtcatgtgg   1860
aaacagatgg agcagacgta ctggcaggcc aatcccttcc gggctgtggc tgagccaggg   1920
attcagctca aggctgtcaa gtcctctaca ggtcccgggg aacagctccg aaacgcactg   1980
tggcacacgg gggacacagc atcccaggtg cggctgctgt ggaaggatcc tcgaaacgtg   2040
ggctggaagg ataaaacatc ctaccgctgg ttcctgcagc accggcctca gttggctac    2100 atcagggtgc ggttctatga gggtcctgag ctagtagctg acagcaatgt ggtgttggac   2160
acggccatgc gtggtggccg cctgggtgtc ttctgcttct cccaagagaa catcatctgg   2220
gctaacctgc gctaccgttg caatgataca atccctgagg actacgagag tcaccggctg   2280
cagagagtct agggaccagt ggggtcccgc tgcctgatgg actgtggtgg cacaagctac   2340
gggtgtgtgt gtgggggggt ctggcatccc tctgaagggg tgtctggcct ggggaggaga   2400
ggcaaataaa gtacgtatgt gggggaaaaa aaaaaaaaaa aaaaaaa                 2447
```

<210> SEQ ID NO 24
<211> LENGTH: 755
<212> TYPE: PRT
<213> ORGANISM: Human

<400> SEQUENCE: 24

```
Met Gly Pro Thr Ala Cys Val Leu Val Leu Ala Leu Ala Ile Leu Arg
1               5                   10                  15

Ala Thr Gly Gln Gly Gln Ile Pro Leu Gly Gly Asp Leu Ala Pro Gln
            20                  25                  30

Met Leu Arg Glu Leu Gln Glu Thr Asn Ala Ala Leu Gln Asp Val Arg
        35                  40                  45

Glu Leu Leu Arg Gln Gln Val Lys Glu Ile Thr Phe Leu Lys Asn Thr
    50                  55                  60

Val Met Glu Cys Asp Ala Cys Gly Met Gln Pro Ala Arg Thr Pro Gly
65                  70                  75                  80

Leu Ser Val Arg Pro Val Pro Leu Cys Ala Pro Gly Ser Cys Phe Pro
                85                  90                  95

Gly Val Val Cys Ser Glu Thr Ala Thr Gly Ala Arg Cys Gly Pro Cys
            100                 105                 110

Pro Pro Gly Tyr Thr Gly Asn Gly Ser His Cys Thr Asp Val Asn Glu
        115                 120                 125
```

```
Cys Asn Ala His Pro Cys Phe Pro Arg Val Arg Cys Ile Asn Thr Ser
    130                 135                 140

Pro Gly Phe His Cys Glu Ala Cys Pro Pro Gly Phe Ser Gly Pro Thr
145                 150                 155                 160

His Glu Gly Val Gly Leu Thr Phe Ala Lys Ser Asn Lys Gln Val Cys
                165                 170                 175

Thr Asp Ile Asn Glu Cys Glu Thr Gly Gln His Asn Cys Val Pro Asn
            180                 185                 190

Ser Val Cys Val Asn Thr Arg Gly Ser Phe Gln Cys Gly Pro Cys Gln
        195                 200                 205

Pro Gly Phe Val Gly Asp Gln Thr Ser Gly Cys Gln Arg Arg Gly Gln
210                 215                 220

His Phe Cys Pro Asp Gly Ser Pro Ser Pro Cys His Glu Lys Ala Asn
225                 230                 235                 240

Cys Val Leu Glu Arg Asp Gly Ser Arg Ser Cys Val Cys Ala Val Gly
                245                 250                 255

Trp Ala Gly Asn Gly Leu Leu Cys Gly Arg Asp Thr Asp Leu Asp Gly
            260                 265                 270

Phe Pro Asp Glu Lys Leu Arg Cys Ser Glu Arg Gln Cys Arg Lys Asp
        275                 280                 285

Asn Cys Val Thr Val Pro Asn Ser Gly Gln Glu Asp Val Asp Arg Asp
290                 295                 300

Gly Ile Gly Asp Ala Cys Asp Pro Asp Ala Asp Gly Asp Gly Val Pro
305                 310                 315                 320

Asn Glu Gln Asp Asn Cys Pro Leu Val Arg Asn Pro Asp Gln Arg Asn
                325                 330                 335

Ser Asp Ser Asp Lys Trp Gly Asp Ala Cys Asp Asn Cys Arg Ser Lys
            340                 345                 350

Lys Asn Asp Asp Gln Lys Asp Thr Asp Leu Asp Gly Arg Gly Asp Ala
        355                 360                 365

Cys Asp Asp Asp Ile Asp Gly Asp Arg Ile Arg Asn Val Ala Asp Asn
370                 375                 380

Cys Pro Arg Val Pro Asn Phe Asp Gln Ser Asp Ser Asp Gly Asp Gly
385                 390                 395                 400

Val Gly Asp Ala Cys Asp Asn Cys Pro Gln Lys Asp Asn Pro Asp Gln
                405                 410                 415

Arg Asp Val Asp His Asp Phe Val Gly Asp Ala Cys Asp Ser Asp Gln
            420                 425                 430

Asp Gln Asp Gly Asp Gly His Gln Asp Ser Arg Asp Asn Cys Pro Thr
        435                 440                 445

Val Pro Asn Ser Ala Gln Gln Asp Ser Asp His Asp Gly Lys Gly Asp
450                 455                 460

Ala Cys Asp Asp Asp Asp Asn Asp Gly Val Pro Asp Ser Arg Asp
465                 470                 475                 480

Asn Cys Arg Leu Val Pro Asn Pro Gly Gln Glu Asp Asn Asp Arg Asp
                485                 490                 495

Gly Val Gly Asp Ala Cys Gln Gly Asp Phe Asp Ala Asp Lys Val Ile
            500                 505                 510

Asp Lys Ile Asp Val Cys Pro Glu Asn Ala Glu Val Thr Leu Thr Asp
        515                 520                 525

Phe Arg Ala Phe Gln Thr Val Val Leu Asp Pro Glu Gly Asp Ala Gln
530                 535                 540

Ile Asp Pro Asn Trp Val Val Leu Asn Gln Gly Met Glu Ile Val Gln
```

```
                545                 550                 555                 560
Thr Met Asn Ser Asp Pro Gly Leu Ala Val Gly Tyr Thr Ala Phe Asn
                    565                 570                 575
Gly Val Asp Phe Glu Gly Thr Phe His Val Asn Thr Ala Thr Asp Asp
                580                 585                 590
Asp Tyr Ala Gly Phe Ile Phe Gly Tyr Gln Asp Ser Ser Ser Phe Tyr
                595                 600                 605
Val Val Met Trp Lys Gln Met Glu Gln Thr Tyr Trp Gln Ala Asn Pro
            610                 615                 620
Phe Arg Ala Val Ala Glu Pro Gly Ile Gln Leu Lys Ala Val Lys Ser
625                 630                 635                 640
Ser Thr Gly Pro Gly Glu Gln Leu Arg Asn Ala Leu Trp His Thr Gly
                    645                 650                 655
Asp Thr Ala Ser Gln Val Arg Leu Leu Trp Lys Asp Pro Arg Asn Val
                660                 665                 670
Gly Trp Lys Asp Lys Thr Ser Tyr Arg Trp Phe Leu Gln His Arg Pro
            675                 680                 685
Gln Val Gly Tyr Ile Arg Val Arg Phe Tyr Glu Gly Pro Glu Leu Val
        690                 695                 700
Ala Asp Ser Asn Val Val Leu Asp Thr Ala Met Arg Gly Gly Arg Leu
705                 710                 715                 720
Gly Val Phe Cys Phe Ser Gln Glu Asn Ile Ile Trp Ala Asn Leu Arg
                    725                 730                 735
Tyr Arg Cys Asn Asp Thr Ile Pro Glu Asp Tyr Glu Ser His Arg Leu
                740                 745                 750
Gln Arg Val
        755

<210> SEQ ID NO 25
<211> LENGTH: 1653
<212> TYPE: DNA
<213> ORGANISM: Human

<400> SEQUENCE: 25
gcccaggctc aaggcgttcc aaccatggcc cgcgcgctct tattcagtct ggtcttcctt     60
gccatcctcc tgcctgcgct agccgcctgc ccccaaaact gccactgcca tggagatctg    120
cagcatgtca tctgcgacaa ggtggggctg cagaagatcc ccaaggtatc agagacaacc    180
aaactgctca atctccagcg caacaacttc ccggtgctgg ctgccaactc gtttcggacc    240
atgccgaacc tggtctccct gcacctgcaa cactgcaaca tccgcgaggt ggcggctggt    300
gccttccgag gcctgaagca gcttatctac ctgtacctgt cccacaacga catccgggta    360
ttgcgagctg agccttcga cgacctgact gaactcactt acctctatct agaccacaac    420
aaagtgtcgg aactgccccg ggggttgctc tctcctctgg tcaacctctt catcttgcaa    480
ctcaacaaca caaaatccg agagctgcgt gctggagctt ccaggggggc caaggacctg    540
cgctggctct acctgtcaga aaatgccctc agttccctgc agcctggttc cctggatgat    600
gtggagaacc tagccaagtt ccacctggac aagaaccagc tgtctagcta cccctcagcc    660
gccctgagca acttcgggt ggtggaggag ctgaagctgc tcacaacccc tctgaagagc    720
atcccagaca tgccttcca gtccttcggt agatatctgg agaccctctg ctggataac    780 accaacctgg agaagttctc agatgctgcc ttctcgggtg tgaccacact gaaacacgtc    840
catctggaca caaccgcct gaaccaactg ccttcctcct tccccttga caacctggag    900
```

-continued

```
accctcactc tcaccaacaa cccatggaaa tgcacctgcc agctccgtgg ccttcggcgg    960
tggttggaag ccaaggcttc tcgaccggat gctacctgct cctcgccagc caagttcaag   1020
ggtcagcgga ttcgtgacac agatgccctt cgcagctgca atccccgac caagaggtcc    1080 aagaaagctg ccgccatta acaggtcct gatccagcca gtcctggcga ctgccttccg     1140
ctggagagac tactgacgtt ccctcccatt atccacacct tctcctacag cctctgcgga  1200
tgcacagcgc tgccccgccc ccgcccccac ctaggtacat cctggcaggg gcactgggct   1260
ctctatcacc atcccagctc cacccagtgg ggtcctagga agacacaga atccctcccc    1320 agccactgtg tctgggctct gccatggctc ctttgagaga agctattgta gaacctccta   1380
ccctctgtcc atcggagcta aagcgcagtg gtcattggga tgaccacgtt attaccacct   1440
tcctcggttc cctctgtccc tgccatttgg aaacaaacat caggcccctg acccaccctg   1500
attgccagaa agaatttcag gcccatgccc caactctgcc agttcctgcc tgccaggaca   1560
tgctaccagg ataccagtag cgcttggctg catatccttc ctgtttgcgc tccagatttc   1620
tataaacata aatgtatgtg tgttcaacat tca                                1653
```

<210> SEQ ID NO 26
<211> LENGTH: 358
<212> TYPE: PRT
<213> ORGANISM: Human

<400> SEQUENCE: 26

```
Met Ala Arg Ala Leu Leu Phe Ser Leu Val Phe Leu Ala Ile Leu Leu
1               5                   10                  15

Pro Ala Leu Ala Ala Cys Pro Gln Asn Cys His Cys His Gly Asp Leu
                20                  25                  30

Gln His Val Ile Cys Asp Lys Val Gly Leu Gln Lys Ile Pro Lys Val
            35                  40                  45

Ser Glu Thr Thr Lys Leu Leu Asn Leu Gln Arg Asn Asn Phe Pro Val
        50                  55                  60

Leu Ala Ala Asn Ser Phe Arg Thr Met Pro Asn Leu Val Ser Leu His
    65                  70                  75                  80

Leu Gln His Cys Asn Ile Arg Glu Val Ala Ala Gly Ala Phe Arg Gly
                85                  90                  95

Leu Lys Gln Leu Ile Tyr Leu Tyr Leu Ser His Asn Asp Ile Arg Val
                100                 105                 110

Leu Arg Ala Gly Ala Phe Asp Asp Leu Thr Glu Leu Thr Tyr Leu Tyr
            115                 120                 125

Leu Asp His Asn Lys Val Ser Glu Leu Pro Arg Gly Leu Leu Ser Pro
        130                 135                 140

Leu Val Asn Leu Phe Ile Leu Gln Leu Asn Asn Lys Ile Arg Glu
    145                 150                 155                 160

Leu Arg Ala Gly Ala Phe Gln Gly Ala Lys Asp Leu Arg Trp Leu Tyr
                165                 170                 175

Leu Ser Glu Asn Ala Leu Ser Ser Leu Gln Pro Gly Ser Leu Asp Asp
                180                 185                 190

Val Glu Asn Leu Ala Lys Phe His Leu Asp Lys Asn Gln Leu Ser Ser
            195                 200                 205

Tyr Pro Ser Ala Ala Leu Ser Lys Leu Arg Val Val Glu Glu Leu Lys
        210                 215                 220

Leu Ser His Asn Pro Leu Lys Ser Ile Pro Asp Asn Ala Phe Gln Ser
    225                 230                 235                 240
```

```
Phe Gly Arg Tyr Leu Glu Thr Leu Trp Leu Asp Asn Thr Asn Leu Glu
                245                 250                 255

Lys Phe Ser Asp Ala Ala Phe Ser Gly Val Thr Thr Leu Lys His Val
            260                 265                 270

His Leu Asp Asn Asn Arg Leu Asn Gln Leu Pro Ser Ser Phe Pro Phe
        275                 280                 285

Asp Asn Leu Glu Thr Leu Thr Leu Thr Asn Asn Pro Trp Lys Cys Thr
    290                 295                 300

Cys Gln Leu Arg Gly Leu Arg Arg Trp Leu Glu Ala Lys Ala Ser Arg
305                 310                 315                 320

Pro Asp Ala Thr Cys Ser Ser Pro Ala Lys Phe Lys Gly Gln Arg Ile
                325                 330                 335

Arg Asp Thr Asp Ala Leu Arg Ser Cys Lys Ser Pro Thr Lys Arg Ser
            340                 345                 350

Lys Lys Ala Gly Arg His
        355

<210> SEQ ID NO 27
<211> LENGTH: 3014
<212> TYPE: DNA
<213> ORGANISM: Human

<400> SEQUENCE: 27
agaagcggga cctttaaatt ggttgccaat gtgaggccct atggctgaga cctctgaccc      60
tgtgtacccc agttacctcg cggctcacag accccggcag gtcgtcaagc ccatcatgtt     120
gctctcagcc cccttacgcc acctcccggg gcttctgctg ctgctctggc cgctgttgct     180
cctgccttcc ctggctgctc tggacgtttt ggcccgcgcg agcgtccgcc ggctggggac     240
acgagtcccc ggaggcagcc ctgggcatct ctctgctctg gctacttcca cccgcgcgcc     300
atattccggg ggccgcggcg caggtgtttg caagagcagg cctttggact tggtgttcat     360
cattgatagt tctcgtagcg tccggcctct ggaattcacc aaggtgaaga cctttgtctc     420
ccgcatcatc gacactctgg acatcgggc cacagacacg agggtggctg tggtgaacta     480
tgccagcact gtgaagatag agttccagct caacacctat tccgacaagc aggccctgaa     540
acaggctgtg gcacggatca caccttgtc aacaggcacc atgtcagggc tagctatcca     600
gacagcgatg gaggaagcct tcactgtgga ggccgggggct cggggggccca tgtctaacat     660 ccccaaggta gctattatcg tgacagatgg gaggccgcag gaccaggtga atgaggtggc     720
tgctcgagcc cgtgcatctg gcattgagct gtatgctgtg ggtgtggacc gggcagatat     780
ggagtccctc aagatgatgg ctagcaagcc cctggaagag cacgtcttct acgtggagac     840
ctacggggtc attgagaagc tttctgctag attccaggaa accttttgtg ctctggatca     900
gtgcatgctt ggcacacacc agtgtcagca cgtgtgtgtc agcgatggtg acggcaagca     960
tcactgcgag tgcagccaag gctacaccct tgaacgctgat gggaaaacgt gttcagccat    1020
tgataagtgt gcccttagca ctcatggatg tgaacagatc tgtgtcaacg acagaaatgg    1080
ctcttaccac tgcgagtgct atggaggtta cgccttgaat gcagacagga gaacgtgtgc    1140
agctctggac aaatgcgcct ctggtacaca tggttgccag cacatctgtg tgaatgatgg    1200
agccgggtcc catcactgtg aatgttttga aggctacact ctgaatgcag ataagaaaac    1260
atgttcagtc cggaacaagt gtgctctagg cactcatggc tgccagcaca tctgtgtgag    1320
tgatggagca gtggctacc actgtgactg cttccctggc tacaccttga atgatgacaa    1380
gaagacatgt tcagacattg aagaagcccg aagcctcatt tccatagaag acgcctgcgg    1440
```

-continued

```
ctgtggggcc acgctggcat tccaggagaa ggtcagctcc catctccaga agctgaacac    1500
caaacttgac aacattttga agaagttgaa agtaacagaa tatggacaag tacatcgtta    1560
aactgtgtaa aactctcgcc tggaaatgtg gagggcttga tatatgcgat tctcattctc    1620
ttgtcacgct atctgatgtg cctgctaata atctgccatt ataaatgctt aacattattt    1680
ggtaaacagt gtgaggggtt tctggagaac catattgttt tccaaggaga taaatgtgta    1740
gacccttatt aaaagcaagt ttaatgtctc atagctatga ctgtgaaatc attaataaga    1800
tagagagtga aaagtttaag gttttgttat ctactgtttg agccatttaa gtttaaattg    1860
tttatattag taagatgatc ttactcataa aactttaggt ctattttctc ttggtcatat    1920
ttataatacg aaccagcctt actaccaaga gtgcaaattt tatgaaatat ttacacatac    1980
aaagataaac taattaaact gagatttaga attgcttact attttgtttt ttttttttg     2040
ctggaatatt attaaagcta caaacaaggg attataatac atgtacctaa aaataattta    2100
cacagactaa gtggatgtta tatgacactt ttaattcatt aatgtcatgg aaatgaacaa    2160
ctaaagagta ctggctatga acttatggtg ctaagatttt tgctaagaga aaaaattttg    2220
aattctatca ttttgtttta gcatgcaatt ggcaaaatta catatttata gaattaatat    2280
aataagtaac aagttataat attatcttaa aaactgtcaa taagcctgat ttttcactca    2340
aaatatactg aatgcataca cttttttaagc gcagctcata acttttagaa cgaaacaatt    2400
ctgtaaattt tgtgctactt gatctgtttt ggtttgtatt gttctaata tattaaaagt     2460
tcccgtcttt ctacattaac ggcatggttg atgtttttat gattcttgtt attttttct     2520
atcaagcata ttatgttgaa tggaatgaat aattttgaa tatgtaacag ctgagaaact     2580
gaaagaatga aatggtgatg atactctttc aataatttaa tctcatgcct ctgttgaggc    2640
ataaaatgtt agtaagttca gggtaaacag aaagaagttc ctaaataaaa ccagtggggg    2700
aaaatgtgat tacagaagtg tgcatgtgct tgagctagtg tttgtgcgca tgcgtgtgct    2760
tatgtctgca tgggtgcaca cgcaccacag cacatgtgga cgtgtgtggg tggacggttt    2820
gtggaatggc ttctctcctt ccgccactgt gttctagtga tccggttggt catcaggctt    2880
ggaggtgggt gcctctgcct gccgagccat cttgccagcc cctcactgtg acattttcag    2940
aatcccaatc atgtctggat attatcttct gtttcttctt gatagttgaa taataatcct    3000
ctgtgtatac atgc                                                      3014
```

<210> SEQ ID NO 28
<211> LENGTH: 481
<212> TYPE: PRT
<213> ORGANISM: Human

<400> SEQUENCE: 28

```
Met Leu Leu Ser Ala Pro Leu Arg His Leu Pro Gly Leu Leu Leu Leu
1               5                   10                  15

Leu Trp Pro Leu Leu Leu Leu Pro Ser Leu Ala Ala Pro Gly Arg Leu
            20                  25                  30

Ala Arg Ala Ser Val Arg Arg Leu Gly Thr Arg Val Pro Gly Gly Ser
        35                  40                  45

Pro Gly His Leu Ser Ala Leu Ala Thr Ser Thr Arg Ala Pro Tyr Ser
    50                  55                  60

Gly Gly Arg Gly Ala Gly Val Cys Lys Ser Arg Pro Leu Asp Leu Val
65                  70                  75                  80

Phe Ile Ile Asp Ser Ser Arg Ser Val Arg Pro Leu Glu Phe Thr Lys
```

```
                    85                  90                  95
Val Lys Thr Phe Val Ser Arg Ile Ile Asp Thr Leu Asp Ile Gly Ala
                100                 105                 110

Thr Asp Thr Arg Val Ala Val Asn Tyr Ala Ser Thr Val Lys Ile
                115                 120             125

Glu Phe Gln Leu Asn Thr Tyr Ser Asp Lys Gln Ala Leu Lys Gln Ala
            130                 135                 140

Val Ala Arg Ile Thr Pro Leu Ser Thr Gly Thr Met Ser Gly Leu Ala
145                 150                 155                 160

Ile Gln Thr Ala Met Glu Glu Ala Phe Thr Val Glu Ala Gly Ala Arg
                165                 170                 175

Gly Pro Met Ser Asn Ile Pro Lys Val Ala Ile Val Thr Asp Gly
                180                 185                 190

Arg Pro Gln Asp Gln Val Asn Glu Val Ala Ala Arg Ala Arg Ala Ser
                195                 200                 205

Gly Ile Glu Leu Tyr Ala Val Gly Val Asp Arg Ala Asp Met Glu Ser
            210                 215                 220

Leu Lys Met Met Ala Ser Lys Pro Leu Glu Glu His Val Phe Tyr Val
225                 230                 235                 240

Glu Thr Tyr Gly Val Ile Glu Lys Leu Ser Ala Arg Phe Gln Glu Thr
                245                 250                 255

Phe Cys Ala Leu Asp Gln Cys Met Leu Gly Thr His Gln Cys Gln His
                260                 265                 270

Val Cys Val Ser Asp Gly Asp Gly Lys His His Cys Glu Cys Ser Gln
            275                 280                 285

Gly Tyr Thr Leu Asn Ala Asp Gly Lys Thr Cys Ser Ala Ile Asp Lys
            290                 295                 300

Cys Ala Leu Ser Thr His Gly Cys Glu Gln Ile Cys Val Asn Asp Arg
305                 310                 315                 320

Asn Gly Ser Tyr His Cys Glu Cys Tyr Gly Tyr Ala Leu Asn Ala
                325                 330                 335

Asp Arg Arg Thr Cys Ala Ala Leu Asp Lys Cys Ala Ser Gly Thr His
                340                 345                 350

Gly Cys Gln His Ile Cys Val Asn Asp Gly Ala Gly Ser His His Cys
            355                 360                 365

Glu Cys Phe Glu Gly Tyr Thr Leu Asn Ala Asp Lys Lys Thr Cys Ser
            370                 375                 380

Val Arg Asn Lys Cys Ala Leu Gly Thr His Gly Cys Gln His Ile Cys
385                 390                 395                 400

Val Ser Asp Gly Ala Val Ala Tyr His Cys Asp Cys Phe Pro Gly Tyr
                405                 410                 415

Thr Leu Asn Asp Asp Lys Lys Thr Cys Ser Asp Ile Glu Glu Ala Arg
                420                 425                 430

Ser Leu Ile Ser Ile Glu Asp Ala Cys Gly Cys Gly Ala Thr Leu Ala
            435                 440                 445

Phe Gln Glu Lys Val Ser Ser His Leu Gln Lys Leu Asn Thr Lys Leu
            450                 455                 460

Asp Asn Ile Leu Lys Lys Leu Lys Val Thr Glu Tyr Gly Gln Val His
465                 470                 475                 480

Arg

<210> SEQ ID NO 29
<211> LENGTH: 3888
```

<212> TYPE: DNA
<213> ORGANISM: Human

<400> SEQUENCE: 29

```
cccctggctg ggcctgggtt acaggctgcc tctccccacc cctttccttt gcttcagctt      60
aaagggttat tgcatgcctc caattcactc tttttgcctt tagccctgag aggggcaaga     120
aggagcaagc ttggggccaa aactcgaagt ccgagaaggg tagagagggg gtcttaggga     180
gtagtgaccc cccctccaaa ccctttacgg tgactcttat aaaccacaga gaacccactg     240
ggaaaatgaa gaacttctgg aaaatctcag ttttcttctg tgtgtgcagt tgtctgggac     300
cctgggtatc cgcaactctt aagcgtcgtg caagatttcc tgccaattcc atttctaatg     360
gtggaagtga actgtgtccc aagatcagga ttggccaaga tgacttacca gggtttgacc     420
tgatttctca gttccaaatt gagaaggctg catctcgaag gactatccag agggtggtgg     480
gatccacagc cttacaagtg gcttacaagc tgggaagtaa tgtagacttc aggattccaa     540
caaggcattt gtatcccagt ggactgcctg aagaatattc cttttaact actttccgga     600
tgactggaag cacacttgaa aagcactgga acatttggca gatccaggat tccgcaggga     660
gagagcaagt tggcgtgaag ataaatggcc aaacaaagtc tgtcgcattt tcatacaagg     720
gactggatgg gagtctccaa acggctgcct tcttgaattt gccgtccttg tttgactccc     780
ggtggcataa gctcatgatt ggcgtggaaa gaacaagcgc cactcttttt attgactgca     840
tcaggatcga atctttacct ataaagccaa gaggccagat tgatgcggat ggctttgcag     900
tgctgggaaa acttgtggac aatcctcagg tttctgttcc ttttgaactc cagtggatgc     960
tgattcattg tgacccctg agacccagga gagaaacctg tcatgagctg ccaatcagaa    1020
tcacaaccag ccagaccact gatgagagag gtcctccggg tgagcagggg cctccagggc    1080
ctcctgggcc tcctggagtt ccgggcatag atggcattga tggtgaccga ggtccaaagg    1140
gtccccagg acctccgggt cctcctggag acccaggcaa gccaggagca ccaggcaagc    1200
caggcacacc aggagctgat ggattaacag gacctgatgg atcccctggc tctgttggac    1260
caaggggaca aaaaggagaa cctggtgtac ctgggtctcg tggatttcca ggccgtggta    1320
ttccaggacc ccctggtcct cctgggacca caggacttcc tggagaactt ggccgagtag    1380
gccctattgg agaccctggg aaaagaggac cacctggccc tcctggacct ccaggaccca    1440
gtggaacaat tggatttcat gatggagacc cattgtgccc caattcctgc ccaccaggtc    1500
gctctggata tccaggccta ccaggcatga ggggccataa aggggcgaaa ggagaaatcg    1560
gcgagccagg aagacaagga cacaagggtg aagagggtga ccaggggaa ctgggagaag    1620
ttggcgatca aggacctcca ggacctcagg gtctgagagg catcactggc atagttggag    1680
acaaaggaga aaagggtgct cgggatttg atggagagcc tggacctcag gcattccag    1740
gtgcagctgg tgatcaagga cagcgaggcc ctccaggaga aacaggtcct gagggagaca    1800
gaggcattca aggttcccga ggaattcctg gatcccagg gccaaaagga gacacgggct    1860
tgccaggtgt agatggccga gatggaatac aggaatgcc cgggacaaag ggtgaagcag    1920
ggaagcctgg accccgggg gacgtgggat tgcaggggctt accaggtgtc cctggaatcc    1980
ctggtgcaaa aggtgttgcc ggtgaaaagg gtaacacggg tgctccagga aagcccggtc    2040
agttgggaag ttcagggaaa ccaggccaac aagggccccc aggagaggtt ggacctcggg    2100
gacccagggg ccttccaggc agtagaggcc cggtaggacc agaagggtct ccaggcatac    2160
cagggaaact gggatctgtt ggcagccctg gccttcctgg cttgcctggg ccccctggac    2220
```

```
ttcctggaat gaaaggagac agggtgtat ttggtgaacc gggtcccaag ggtgaacagg    2280
gtgcctctgg tgaagaaggt gaagcaggag caagggtga ccttggagat atgggacaac    2340
ctggcccaaa gggatctgtg ggtaaccccg gggagccggg tctgagggg cctgaaggaa    2400 tcagagggct tcctggagtg gaaggaccaa gaggaccacc tggaccccgg ggcatgcagg    2460
gagatcaggg tgccactggg ctgcctggta tccagggccc tccgggcaga gcgccgaccg    2520
accagcacat caagcaggtt tgcatggagtcgtgcaaga gcattttgcg gaaatggcag    2580
ccagcctcaa gagaccagac acaggagcct ctggtcttcc tgggaggcct ggccccctg    2640 ggcctccggg cccccctgga gagaatggtt tccctggtca gatgggaatc cgtggtctcc    2700
caggcattaa gggtccccct ggtgctcttg gcttaagagg acctaaagga gacttgggag    2760
aaaaaggaga acgtggtcct ccaggaagag gtcctaaggg tttgcctgga gcgataggtc    2820
tcccaggtga cccaggccct gccagctatg ggaaaaatgg ccgtgacgga gagcaaggtc    2880
cccggggagt ggcaggaatt cctggtgtgc ctggacccc aggtcctcca ggccctcctg    2940
ggttctgtga gccagcctct tgcaccctgc agtctggtca aagagcattt agcaaagggc    3000
cggacaagtg aaatccgtag cgttgtaggc tccctgcaca agcacacct gttagcagag    3060 tgtgggggga gaaacgatac caaaactggg gcaaagcctc aaaggtttca cctctgacat    3120
cattacataa gtgctacttg acaatcagat ttagcaac tggtgctatt cagtaagtct    3180
tgttccttgt ccatggaagg aaggtaggag agtcaacaga caagagtcaa attcaatttc    3240
tctttagcca aatttatata tcctcttccc aggagtttga attttagtgt gctatgaatg    3300
gatatatgat gtgttgtggg tcactgtgcc aacaacaaca caacaacaa gctgttcaca    3360 ttacctcagt tgctgtcatt atttttattt caattaagat attgatctca gattattcat    3420
tcagttatat caagtattgc taggatacta aggaacagac cccactacat tcaataaat    3480 tggtgcttaa atcttcatc agggctgtgt cccaaaagtg gtctctatac atcgcatggt    3540
ggttttgata tttactatga atttgtgaat agtgtgtact gcatccaatc ccatttgtat    3600
tctaaaatcc acgtgaaagc aaagaagtaa taccctgaca cacatatgtt ttgtggctga    3660
cattatttat tttaaaagtt tgaggtaaca tgtctggttg taccaaagaa aaataaaca    3720 cggtttccta gtcttttgtg tgttctaaaa taagtagtca tgttaaatgt ggttacatgt    3780
taattgaact ggtttagagt cattaaaatt ttgacttact gctacttcta aaaatgtatt    3840
tattttactg gtttattcta tctgaagaaa tctgaagagt tcccactg               3888
```

<210> SEQ ID NO 30
<211> LENGTH: 921
<212> TYPE: PRT
<213> ORGANISM: Human

<400> SEQUENCE: 30

```
Met Lys Asn Phe Trp Lys Ile Ser Val Phe Phe Cys Val Cys Ser Cys
1               5                   10                  15

Leu Gly Pro Trp Val Ser Ala Thr Leu Lys Arg Arg Ala Arg Phe Pro
            20                  25                  30

Ala Asn Ser Ile Ser Asn Gly Gly Ser Glu Leu Cys Pro Lys Ile Arg
        35                  40                  45

Ile Gly Gln Asp Asp Leu Pro Gly Phe Asp Leu Ile Ser Gln Phe Gln
    50                  55                  60

Ile Glu Lys Ala Ala Ser Arg Arg Thr Ile Gln Arg Val Val Gly Ser
65                  70                  75                  80
```

```
Thr Ala Leu Gln Val Ala Tyr Lys Leu Gly Ser Asn Val Asp Phe Arg
                85                  90                  95

Ile Pro Thr Arg His Leu Tyr Pro Ser Gly Leu Pro Glu Glu Tyr Ser
            100                 105                 110

Phe Leu Thr Thr Phe Arg Met Thr Gly Ser Thr Leu Glu Lys His Trp
        115                 120                 125

Asn Ile Trp Gln Ile Gln Asp Ser Ala Gly Arg Glu Gln Val Gly Val
    130                 135                 140

Lys Ile Asn Gly Gln Thr Lys Ser Val Ala Phe Ser Tyr Lys Gly Leu
145                 150                 155                 160

Asp Gly Ser Leu Gln Thr Ala Ala Phe Leu Asn Leu Pro Ser Leu Phe
                165                 170                 175

Asp Ser Arg Trp His Lys Leu Met Ile Gly Val Glu Arg Thr Ser Ala
            180                 185                 190

Thr Leu Phe Ile Asp Cys Ile Arg Ile Glu Ser Leu Pro Ile Lys Pro
        195                 200                 205

Arg Gly Gln Ile Asp Ala Asp Gly Phe Ala Val Leu Gly Lys Leu Val
    210                 215                 220

Asp Asn Pro Gln Val Ser Val Pro Phe Glu Leu Gln Trp Met Leu Ile
225                 230                 235                 240

His Cys Asp Pro Leu Arg Pro Arg Arg Glu Thr Cys His Glu Leu Pro
                245                 250                 255

Ile Arg Ile Thr Thr Ser Gln Thr Thr Asp Glu Arg Gly Pro Pro Gly
            260                 265                 270

Glu Gln Gly Pro Pro Gly Pro Pro Gly Pro Pro Gly Val Pro Gly Ile
        275                 280                 285

Asp Gly Ile Asp Gly Asp Arg Gly Pro Lys Gly Pro Pro Gly Pro Pro
    290                 295                 300

Gly Pro Pro Gly Asp Pro Gly Lys Pro Gly Ala Pro Gly Lys Pro Gly
305                 310                 315                 320

Thr Pro Gly Ala Asp Gly Leu Thr Gly Pro Asp Gly Ser Pro Gly Ser
                325                 330                 335

Val Gly Pro Arg Gly Gln Lys Gly Glu Pro Gly Val Pro Gly Ser Arg
            340                 345                 350

Gly Phe Pro Gly Arg Gly Ile Pro Gly Pro Pro Gly Pro Pro Gly Thr
        355                 360                 365

Thr Gly Leu Pro Gly Glu Leu Gly Arg Val Gly Pro Ile Gly Asp Pro
    370                 375                 380

Gly Lys Arg Gly Pro Pro Gly Pro Pro Gly Pro Pro Gly Pro Ser Gly
385                 390                 395                 400

Thr Ile Gly Phe His Asp Gly Asp Pro Leu Cys Pro Asn Ser Cys Pro
                405                 410                 415

Pro Gly Arg Ser Gly Tyr Pro Gly Leu Pro Gly Met Arg Gly His Lys
            420                 425                 430

Gly Ala Lys Gly Glu Ile Gly Glu Pro Gly Arg Gln Gly His Lys Gly
        435                 440                 445

Glu Glu Gly Asp Gln Gly Glu Leu Gly Glu Val Gly Asp Gln Gly Pro
    450                 455                 460

Pro Gly Pro Gln Gly Leu Arg Gly Ile Thr Gly Ile Val Gly Asp Lys
465                 470                 475                 480

Gly Glu Lys Gly Ala Arg Gly Phe Asp Gly Glu Pro Gly Pro Gln Gly
                485                 490                 495

Ile Pro Gly Ala Ala Gly Asp Gln Gly Gln Arg Gly Pro Pro Gly Glu
```

```
                500             505             510
Thr Gly Pro Glu Gly Asp Arg Gly Ile Gln Gly Ser Arg Gly Ile Pro
            515             520             525
Gly Ser Pro Gly Pro Lys Gly Asp Thr Gly Leu Pro Gly Val Asp Gly
            530             535             540
Arg Asp Gly Ile Pro Gly Met Pro Gly Thr Lys Gly Glu Ala Gly Lys
545             550             555             560
Pro Gly Pro Pro Gly Asp Val Gly Leu Gln Gly Leu Pro Gly Val Pro
            565             570             575
Gly Ile Pro Gly Ala Lys Gly Val Ala Gly Glu Lys Gly Asn Thr Gly
            580             585             590
Ala Pro Gly Lys Pro Gly Gln Leu Gly Ser Ser Gly Lys Pro Gly Gln
            595             600             605
Gln Gly Pro Pro Gly Glu Val Gly Pro Arg Gly Pro Arg Gly Leu Pro
            610             615             620
Gly Ser Arg Gly Pro Val Gly Pro Glu Gly Ser Pro Gly Ile Pro Gly
625             630             635             640
Lys Leu Gly Ser Val Gly Ser Pro Gly Leu Pro Gly Leu Pro Gly Pro
            645             650             655
Pro Gly Leu Pro Gly Met Lys Gly Asp Arg Gly Val Phe Gly Glu Pro
            660             665             670
Gly Pro Lys Gly Glu Gln Gly Ala Ser Gly Glu Glu Gly Glu Ala Gly
            675             680             685
Ala Arg Gly Asp Leu Gly Asp Met Gly Gln Pro Gly Pro Lys Gly Ser
            690             695             700
Val Gly Asn Pro Gly Glu Pro Gly Leu Arg Gly Pro Glu Gly Ile Arg
705             710             715             720
Gly Leu Pro Gly Val Glu Gly Pro Arg Gly Pro Pro Gly Pro Arg Gly
            725             730             735
Met Gln Gly Asp Gln Gly Ala Thr Gly Leu Pro Gly Ile Gln Gly Pro
            740             745             750
Pro Gly Arg Ala Pro Thr Asp Gln His Ile Lys Gln Val Cys Met Arg
            755             760             765
Val Val Gln Glu His Phe Ala Glu Met Ala Ala Ser Leu Lys Arg Pro
            770             775             780
Asp Thr Gly Ala Ser Gly Leu Pro Gly Arg Pro Gly Pro Pro Gly Pro
785             790             795             800
Pro Gly Pro Pro Gly Glu Asn Gly Phe Pro Gly Gln Met Gly Ile Arg
            805             810             815
Gly Leu Pro Gly Ile Lys Gly Pro Pro Gly Ala Leu Gly Leu Arg Gly
            820             825             830
Pro Lys Gly Asp Leu Gly Glu Lys Gly Glu Arg Gly Pro Pro Gly Arg
            835             840             845
Gly Pro Lys Gly Leu Pro Gly Ala Ile Gly Leu Pro Gly Asp Pro Gly
            850             855             860
Pro Ala Ser Tyr Gly Lys Asn Gly Arg Asp Gly Glu Gln Gly Pro Pro
865             870             875             880
Gly Val Ala Gly Ile Pro Gly Val Pro Gly Pro Pro Gly Pro Pro Gly
            885             890             895
Pro Pro Gly Phe Cys Glu Pro Ala Ser Cys Thr Leu Gln Ser Gly Gln
            900             905             910
Arg Ala Phe Ser Lys Gly Pro Asp Lys
            915             920
```

<210> SEQ ID NO 31
<211> LENGTH: 688
<212> TYPE: PRT
<213> ORGANISM: Human

<400> SEQUENCE: 31

```
Met Thr Ala Val Pro Ala Pro Arg Ser Leu Phe Val Leu Leu Gln Val
1               5                   10                  15

Leu Trp Leu Ala Leu Ala Gln Ile Arg Gly Pro Pro Gly Glu Pro Gly
            20                  25                  30

Pro Pro Gly Pro Pro Gly Pro Pro Gly Val Pro Gly Ser Asp Gly Ile
        35                  40                  45

Asp Gly Asp Lys Gly Pro Pro Gly Lys Val Gly Pro Pro Gly Ser Lys
    50                  55                  60

Gly Glu Pro Gly Lys Pro Gly Pro Asp Gly Pro Asp Gly Lys Pro Gly
65                  70                  75                  80

Ile Asp Gly Leu Met Gly Ala Lys Gly Glu Pro Gly Pro Val Gly Thr
                85                  90                  95

Pro Gly Val Lys Gly Gln Pro Gly Leu Pro Gly Pro Pro Gly Leu Pro
            100                 105                 110

Gly Pro Gly Phe Ala Gly Pro Pro Gly Pro Pro Gly Pro Val Gly Leu
        115                 120                 125

Pro Gly Glu Ile Gly Thr Pro Gly Pro Lys Gly Asp Pro Gly Pro Glu
    130                 135                 140

Gly Pro Ser Gly Pro Pro Gly Pro Pro Gly Lys Pro Gly Arg Pro Gly
145                 150                 155                 160

Thr Ile Gln Gly Leu Glu Gly Ser Ala Asp Phe Leu Cys Pro Thr Asn
                165                 170                 175

Cys Pro Ala Gly Val Lys Gly Pro Gln Gly Leu Gln Gly Val Lys Gly
            180                 185                 190

His Pro Gly Lys Arg Gly Ile Leu Gly Asp Pro Gly Arg Gln Gly Lys
        195                 200                 205

Pro Gly Pro Lys Gly Asp Val Gly Ala Ser Gly Glu Gln Gly Ile Pro
    210                 215                 220

Gly Pro Pro Gly Pro Gln Gly Ile Arg Gly Tyr Pro Gly Met Ala Gly
225                 230                 235                 240

Pro Lys Gly Glu Met Gly Pro Arg Gly Tyr Lys Gly Met Val Gly Ser
                245                 250                 255

Ile Gly Ala Ala Gly Pro Pro Gly Glu Glu Gly Pro Arg Gly Pro Pro
            260                 265                 270

Gly Arg Ala Gly Glu Lys Gly Asp Val Gly Ser Gln Gly Ala Arg Gly
        275                 280                 285

Pro Gln Gly Ile Thr Gly Pro Lys Gly Thr Thr Gly Pro Pro Gly Ile
    290                 295                 300

Asp Gly Lys Asp Gly Thr Pro Gly Ile Pro Gly Met Lys Gly Ser Ala
305                 310                 315                 320

Gly Gln Val Gly Arg Pro Gly Ser Pro Gly His Gln Gly Leu Ala Gly
                325                 330                 335

Val Pro Gly Gln Pro Gly Thr Lys Gly Pro Gly Asp Lys Gly Glu
            340                 345                 350

Pro Gly Gln Gln Gly Leu Pro Gly Val Ser Gly Pro Pro Gly Lys Glu
        355                 360                 365

Gly Glu Pro Gly Pro Arg Gly Glu Ile Gly Pro Gln Gly Ile Met Gly
```

```
                370             375             380
Gln Lys Gly Asp Gln Gly Glu Arg Gly Pro Val Gly Gln Pro Gly Pro
385                 390                 395                 400

Gln Gly Arg Gln Gly Pro Lys Gly Glu Gln Gly Pro Pro Gly Ile Pro
            405                 410                 415

Gly Pro Gln Gly Leu Pro Gly Ile Lys Gly Asp Lys Gly Ser Pro Gly
        420                 425                 430

Lys Thr Gly Pro Arg Gly Val Gly Asp Pro Gly Val Ala Gly Leu
            435                 440                 445

Pro Gly Glu Lys Gly Glu Lys Gly Gln Ser Gly Glu Pro Gly Leu Lys
        450                 455                 460

Gly Gln Gln Gly Val Arg Gly Glu Thr Gly Tyr Pro Gly Pro Ser Gly
465                 470                 475                 480

Asp Ala Gly Ala Pro Gly Val Gln Gly Tyr Pro Gly Leu Pro Gly Pro
                485                 490                 495

Arg Gly Leu Val Gly Asp Arg Gly Val Pro Gly Gln Pro Gly Arg Gln
            500                 505                 510

Gly Val Val Gly Arg Ala Ala Ser Asp Gln His Ile Val Asp Val Val
        515                 520                 525

Leu Lys Met Ile Gln Glu Gln Leu Ala Glu Val Ala Val Ser Ala Lys
530                 535                 540

Arg Glu Ala Leu Gly Ala Ala Gly Met Val Gly Leu Pro Gly Pro Pro
545                 550                 555                 560

Gly Pro Pro Gly Tyr Pro Gly Lys Gln Gly Pro Asn Gly His Pro Gly
                565                 570                 575

Pro Arg Gly Ile Pro Gly Ile Val Gly Ala Val Gly Gln Ile Gly Asn
            580                 585                 590

Thr Gly Pro Lys Gly Lys Arg Gly Glu Lys Gly Asp Arg Gly Glu Met
        595                 600                 605

Gly Arg Gly His Pro Gly Met Pro Gly Pro Pro Gly Ile Pro Gly Leu
            610                 615                 620

Pro Gly Arg Pro Gly Gln Ala Ile Asn Gly Lys Asp Gly Asp Arg Gly
625                 630                 635                 640

Ser Pro Gly Ala Pro Gly Glu Ala Gly Arg Pro Gly Arg Pro Gly Pro
                645                 650                 655

Val Gly Leu Pro Gly Phe Cys Glu Pro Ala Ala Cys Leu Gly Ala Ser
            660                 665                 670

Ala Tyr Thr Ser Ala Arg Leu Thr Glu Pro Gly Ser Ile Lys Gly Pro
        675                 680                 685

<210> SEQ ID NO 32
<211> LENGTH: 2746
<212> TYPE: DNA
<213> ORGANISM: Human

<400> SEQUENCE: 32
agttcctccc cacagtgctc tcaggtgaca ggcctgcagg tccccgcccc ggcccgtcta        60
gctgcgtttt cgggagatcc agtccgaggc tccgaaagca gccccgccca tcggtgcttg       120 gaccccgct ccagaacccg ctgttcgcca tgaccgccgt gcccgcgccc cgcagcctgt       180
tcgttctcct ccaggtgctg tggctcgccc tggctcagat cagaggtcca ccaggggagc       240
cgggtcctcc aggccaccca gggccaccag gagtgcctgg ttcagatggc atcgacggtg       300 acaagggggcc tccaggtaaa gttggtcctc cgggatccaa aggagagcct ggcaaacctg       360
```

```
gcccagatgg tccagatggg aaacctggca ttgatggttt aatgggagcc aagggagagc   420
ctggtcccgt ggggacccct ggagtcaagg gccagcctgg gctcccaggg cccctggcc   480
tgccgggccc tggttttgct ggacctcccg accccctgg acctgttggc ctccctggtg    540
agattggaac cccaggcccc aaggggatc caggaccaga gggaccatca gggcccccag    600
ggcccctgg gaaaccaggc cgaccaggaa ccatccaggg cttggaaggg agtgcggatt    660
tcttgtgtcc aaccaactgt ccagctggtg tgaagggtcc tcagggtttg caaggagtga    720
agggtcatcc aggcaaacgg gggattctgg gtgatcctgg tcgccagggg aagccaggtc    780
ccaagggaga tgtgggtgcc tctggagagc aaggcatccc tggaccaccg gccccccaag    840
gcatcagggg ctacccgggc atggcaggac ccaagggaga gatgggtcct cgtggctata    900
aaggcatggt gggctccatc ggggctgctg ggccaccggg tgaagaaggc ccaagagggc    960
caccaggccg agccggtgag aagggggatg tggggagcca aggtgccaga ggaccccagg   1020
ggataacagg cccaaaggga caaccggtc caccaggcat tgatggcaag gatgggaccc   1080
caggcattcc tggcatgaag ggcagtgcag gacaagtggg acggcagga agcccaggcc    1140
accagggctt agcgggtgtg ccgggtcagc ctggaacaaa aggaggtcct ggagacaagg    1200
gtgaaccagg ccagcagggc ttgccggag tctctggtcc ccctgggaaa gaaggggagc    1260
cagggcctcg aggagaaatt ggtccacagg gcatcatggg acagaagggt gaccagggcg   1320
agaggggcc agtgggacag ccaggccctc aaggacgaca gggcccccaaa ggagagcagg   1380
gccctccagg aattccagga ccccaaggct tgccaggcat caaaggagat aagggttccc    1440
cagggaagac cgggccccga ggcggagtgg gtgaccgggg ggtggccggc ctcccgggag   1500
agaaaggaga aagggccaa tcaggcgagc cagggcttaa gggacagcaa ggagtccgtg    1560
gagagaccgg ctacccggc cccagcgag atgccggtgc cccaggagtg cagggctacc    1620
ccgggcttcc cgggcccga ggactggtgg gagatcgagg cgtgccagga caacccggga    1680
gacagggtgt ggtgggccga ccgccagtg accagcacat cgtggatgtg gtgctgaaga    1740
tgattcaaga gcaacttgct gaggtagctg tgagtgccaa gcgagaagcc ctgggtgcag   1800
cagggatggg gggccttcca ggacctcctg ggccccctgg atatccaggc aaacaggggc   1860
ccaatgggca tcccggcccc cgaggcattc ctggcatcgt gggagcagtg ggtcagattg   1920
gcaacactgg acccaaggga aagcgtggag agaaggggga tcgaggagaa atgggtcgtg   1980
gccatcccgg gatgcctggg ccccaggga tcccaggtct tcctggccgg cctggccagg    2040
caatcaatgg caaggatggg gaccgaggat ccccagggc tccaggagag ctgggagac    2100
ctggccggcc aggcccagtg gggctaccag gtttctgtga gcctgccgca tgcctggggg   2160
cttcagccta tacctctgct cgcctcacag agcctgggtc catcaagggg ccatgagcaa    2220
ccagccagga cagagcctat tagtgtctag ggtcacttct gggtggacat gtactccaga   2280
cccaggaggc tagatttctc aggatcttct ggaaacccaa gatccagggg ttctgaagac   2340
aagttcagtg agggagggt tggggagggg agagcacggg agtaaaggtg aggccaacag   2400
agccaagtat tggagagcca ccctcccaa gggaagaggg tagcttctct tcctggagta   2460
ccaactaccc ctcacccatg cctttcagca ctggccatc ccaccctcgg gcagggggg    2520
actgaggctt ctggtggtcc ttaccctatt cttattctct ggacttattt ttattgggta    2580
tcttttgggg gagaatacct tgaggtggca gttcttaggc cagccctgct attgcctgtc   2640
tcccatccca gtatttaaac atccatcttc cctgttcccc agtctctttt gcccacacca   2700
ctctggcctt tgtgtaaata aagttcctc agttggttac aaagtg             2746
```

<210> SEQ ID NO 33
<211> LENGTH: 5605
<212> TYPE: DNA
<213> ORGANISM: Human

<400> SEQUENCE: 33

```
gctgggtct  ctgagctgcc  agggtggcca  ggggcacaca  gtagcggcca  ccgaagagca      60
agcagcactg  acaagaagag  gtgcccccac  aacggcacct  tgctgcatgg  agctgggcca     120
ctgaaagctg  ctgacatccc  ggggtcctgg  ttccgaggct  cagctggctt  ctgtctgctg     180
tcagcaccag  gactgcctgg  gatctggcat  tctgagccat  ggagcggtgc  agccgctgcc     240
accgcctcct  tctgttccta  cctctggtgc  tgggtctgag  cgctgccccg  ggatgggcag     300
gtgctccctc  tgtggatgtg  cttcgtgccc  tgaggttccc  ctcccttccc  gatggtgttc     360
ggagatcaaa  aggggtctgt  ccgggtgatg  tggcttaccg  tgtggcacgg  cctgcccagc     420
tcagcgcacc  cacgcgccag  ctcttcccag  gaggctttcc  caaagacttc  tctctgctga     480
cggttgtccg  gacccgccct  ggcctccagg  ctcccctctt  gactctatac  agcgcccagg     540
gagtccagca  gctgggcttg  gagctcggcc  gccctgtccg  ctttctctat  gaggaccaga     600
ggggacggcc  acaagcctcc  gctcagccca  tcttccgagg  cctcagccta  gcagatggca     660
aatggcacca  cgtggctgtg  gctgtgaagg  gtcagtctgt  cactctcatt  gtggactgta     720
agaagcgagt  taccggccc   cttccagaa   gtgtgcatcc  ggtgttggac  acccacgggg     780
tggtgatctt  tggtgcccac  atcctcgacg  atgaagtctt  tgaaggcgat  gttcaggagc     840
tcctcgttgt  cccaggcgtc  caagctgcct  atcagtcttg  tgggcagaag  gatctggaat     900
gtgagagaga  acagagggac  ggccctcaga  ctcagaagcc  tcacagagcc  cagagatctc     960
caaagaagga  accagcaaga  cttcataagc  cacagagcca  ggagcccag   aagcagtacc    1020
ccaccccagg  tgaagaggaa  ggagtcctgg  agtccagtcc  cttgccattc  cttgaagagg    1080
ttgcccacgg  accccggggg  ctaaagggag  agaagggaga  gcctgcagtg  ctggagcctg    1140
gtatgtttgt  agagggaccc  ccaggcccag  aaggcccagc  gggattagct  ggaccccctg    1200
gcatccaggg  gaacccaggc  ccggttggag  acccggtga   gagggcccc   cctggccgag    1260
cagggctccc  cggatcagat  ggaccccctg  gtcctcccgg  cacatctctg  atgcttccat    1320
tccggttttgg  cagtagtggg  ggtgacaagg  gcccgtggt   ggcagcccag  gaggcccagg    1380
cccaggcgat  tctgcagcag  gcacggctgg  cactccgtgg  gccccctggc  cccatgggtt    1440
acacgggccg  ccctggacca  ttgggtcagc  ctggagcccc  tggcttgaag  ggagaatctg    1500
gagatctggg  cccacagggc  cccagaggac  ctcagggcct  cacaggtcct  cctggcaagg    1560
ctggacgaag  gggccgagca  ggtgctgatg  gagcccgtgg  gatgccggga  gaacctggca    1620
tgaagggtga  ccgaggttc   gacggacttc  cagggctacc  tggcgagaag  ggacaaaggg    1680
gtgatacagg  tgctcagggc  cttcctggcc  ctcctggtga  ggacgagag   aggggtgatg    1740
atggagagat  tgggccacgg  gggctgcctg  gagagtcggg  acctagagga  ctccttggcc    1800
ctaaaggccc  gcctggtatt  ctgggccgc   cgggagtccg  aggcatggac  ggtccccacg    1860
gccccaaagg  gagcttggga  cctcaaggag  agccaggacc  tcctgacaa   cagggtactc    1920
ctgggccca   gggcctcccc  ggacctcagg  gagccatcgg  tcctcatgga  gagaagggtg    1980
ctcgtgggaa  accaggcctc  cctggcatgc  ctggatcaga  tggactcccg  ggtcacccag    2040
ggaaggaagg  tcccctgga   accaaaggga  accagggcc   gtccggacca  cagggtcctc    2100
```

-continued

```
taggataccc aggccctcga ggcgtcaagg gtgtggatgg aattcggggc ctgaagggcc    2160
acaagggtga aaagggcgag gacggctttc ctgggttcaa aggtgacata ggagtgaaag    2220
gagacagggg cgaggttgga gtccctggtt ccagggcgga agacggccct gaagggccaa    2280
aagggcgcac tggacctaca ggagaccctg gacccactgg gctcatgggc gagaagggca    2340
agctaggtgt tcctggtctg cctggctatc ctggacgcca gggccccaag ggatctctgg    2400
gtttccctgg ttttcctgga gccagtggag agaagggagc tcgggccctg tctgggaaat    2460
caggacctcg gggagaacgg ggccccacgg gtccaagggg tcagcgggga cctcgaggtg    2520
ccactgggaa atctggagct aagggaacat caggtggtga cggtccccac gggccacccg    2580
gagagagggg tcttcctgga cctcaaggcc ccaatggatt tcctggcccc aaaggccctc    2640
cgggccctgc agggaaggat gggctgccgg gacaccccgg ccagagagga gaagtgggat    2700
tccaaggaaa gaccggccca ccaggcccgc ccggagtggt gggacctcag ggaacagctg    2760
gagaaagtgg tcccatggga gagagaggtc actctggccc ccaggaccct cctggagagc    2820
aaggattgcc tggaacatct gggaaagaag ggaccaaggg tgaccctggt cctcctgggg    2880
ccccagggaa ggatggtcct gctggtctga gaggcttccc aggagagcga ggccttccag    2940
gcactgctgg tggaccccgg ttgaaaggaa atgaaggtcc agctggccct cctggccctg    3000
caggctctcc tggcgagcga ggtgcagcag gatcagggg ccccattggt ccccgggac    3060
gtccaggccc acaaggtccc cctggagcag caggagagaa aggcgtaccg ggcgagaaag    3120
gccctattgg tcccactggt cgtgatgggg tgcagggccc cgtgggtt cctggtcctg    3180
caggacccc aggcgtggct ggagaggatg gagacaaggg tgaagtggga gaccctggac    3240
agaagggaac caaggaaac aagggtgaac atggccctcc tggacctcct ggtcccatcg    3300
ggcctgtggg gcaacctgga gctgcggag ctgatggtga gcctggagct cggggacccc    3360
agggacactt tggagccaaa ggtgatgaag gaacaagagg gttcaatgga ccccgggac    3420
ccatcggcct acagggcctg ccaggaccct ctggggagaa aggagaaaca ggagacgggg    3480
ggcctatggg acccctggc cctccaggac ctcgaggccc cgctggaccc aatggtgctg    3540
atggcccaca aggttcccct ggaggtgttg gaaacttggg tccccctgga gaaaagggtg    3600
aaccggggga gtcagggtct ccaggcgtcc agggcgagcc gggcgtcaag ggaccacgtg    3660
gagagcgtgg tgagaaagga gagtctggcc aggcgggaga ggctgaccca ccggggcca    3720
aaggccctac aggcgacaat ggccccaagg ggaaccctgg tcctgttggc tttcctgggg    3780
accctggccc ccctggagaa gctggcccac ggggccagga tggtgctaag ggagaccgag    3840
gcgaggatgg cgagccagga caacctggat cccctggtcc caccggggag aatgggcccc    3900
ctggaccct tggaaagcgg ggacctgctg gcactcctgg tccagaagga cggcaaggag    3960
agaagggagc taagggggac cctggtgctg tgggggcccc gggaaagaca ggccctgtgg    4020
gtcctgcagg cctagcagga aagcccggcc ccgatggtct tcggggctc ccgggttcag    4080
tgggtcagca aggccgccct ggagccacag gccaggctgg gccccaggt cctgtgggac    4140
ccccagggct tcctggcctc cggggtgatg ctggagccaa gggggaaaag ggtcacccag    4200
gtctcatcgg actgattggg ccgactggag agcaaggcga aaggcgac cgtgcctcc    4260
ctggacctca gggctcaccc ggacagaagg gagagacggg tatcccagga gcatctggcc    4320
ccatcggtcc tggagggcct cctggcctgc ctggaccctc tggccccaaa ggagccaaag    4380
gagccacagg cccagctgga cccaaggag agaagggtgt ccaggccct ccaggacacc    4440
cgggccccc gggagaggtg atccagccac tgcccatcca gatgcccaag aagacccgcc    4500
```

```
gttccgtgga cggaagcaaa ctgatacagg atgaggaggc tgtgcccact ggcggtgctc    4560
cgggcagtcc tgcggggctg gaggagatct ttggctcact ggactctctg cgggaggaga    4620
tcgagcagat gaggaggccg gcggggaccc aggacagccc tgctcgcacc tgccaggact    4680
tgaagctgtg ccaccggag cttcctgatg gagagtactg ggttgaccct aaccagggct    4740
gtgctcggga tgccttccgg gtgttctgca acttcacagc aggaggggag acgtgtgtca    4800
cacccaggga tgacgtcaca cagttctcct acgtggactc cgagggctcc ccagtgggcg    4860
tggtccagct caccttcctg cggctgctca gcgtctctgc ccaccaggat gtctcctacc    4920
cttgctctgg agtatcccag gatggtcccc tgaaactccg aggggccaac gaggatgagc    4980
tgagccctga ccagccct tatgtcaagg agttcagaga tggctgtcag acccagcaag    5040 gccgacggt gttggaggtg cgcacgcctg tactggagca gctgcccgtg ctggatgcct    5100
ccttcgcaga cctgggggcc cccacaagac ggggagggt gcttctgggg cctgtctgct    5160
tcatgggcta ggcctgtctc tgacgctgtc aaccaaaacc aggtctagct ggagtcacac    5220
agcacggact ccatgtcacc tctcgtgagg atctctcatc gtctagaggg ccttgggcca    5280
ggcaggcatc tcaagcctca agtcaggcag cacgggc tggggtgaac caggggtgc    5340 cgggatagcc caggggagg gtggtacctg gcctccagc tctcccactt atgacccatt    5400
agagagctga gacctttatt taaaacactt ccctgtcacc ccaaataagt ggaagagaaa    5460
ggacactgtg tattttgtat ttaaaaaaat aattatatta attatttaaa gagtggaaga    5520
acaaagtaac aaagaagata aagagagaaa tgccaaaaat cccagcagat attgggggca    5580
ggtgctgcaa gggtgggcgg gcagt                                         5605

<210> SEQ ID NO 34
<211> LENGTH: 1650
<212> TYPE: PRT
<213> ORGANISM: Human

<400> SEQUENCE: 34

Met Glu Arg Cys Ser Arg Cys His Arg Leu Leu Phe Leu Pro Leu
1               5                   10                  15

Val Leu Gly Leu Ser Ala Ala Pro Gly Trp Ala Gly Ala Pro Ser Val
                20                  25                  30

Asp Val Leu Arg Ala Leu Arg Phe Pro Ser Leu Pro Asp Gly Val Arg
            35                  40                  45

Arg Ser Lys Gly Val Cys Pro Gly Asp Val Ala Tyr Arg Val Ala Arg
        50                  55                  60

Pro Ala Gln Leu Ser Ala Pro Thr Arg Gln Leu Phe Pro Gly Gly Phe
65                  70                  75                  80

Pro Lys Asp Phe Ser Leu Leu Thr Val Val Arg Thr Arg Pro Gly Leu
                85                  90                  95

Gln Ala Pro Leu Leu Thr Leu Tyr Ser Ala Gln Gly Val Gln Gln Leu
            100                 105                 110

Gly Leu Glu Leu Gly Arg Pro Val Arg Phe Leu Tyr Glu Asp Gln Arg
        115                 120                 125

Gly Arg Pro Gln Ala Ser Ala Gln Pro Ile Phe Arg Gly Leu Ser Leu
    130                 135                 140

Ala Asp Gly Lys Trp His His Val Ala Ala Val Lys Gly Gln Ser
145                 150                 155                 160

Val Thr Leu Ile Val Asp Cys Lys Lys Arg Val Thr Arg Pro Leu Pro
                165                 170                 175
```

```
Arg Ser Val His Pro Val Leu Asp Thr His Gly Val Val Ile Phe Gly
            180                 185                 190

Ala His Ile Leu Asp Asp Glu Val Phe Glu Gly Asp Val Gln Glu Leu
            195                 200                 205

Leu Val Val Pro Gly Val Gln Ala Ala Tyr Gln Ser Cys Gly Gln Lys
            210                 215                 220

Asp Leu Glu Cys Glu Arg Glu Gln Arg Asp Gly Pro Gln Thr Gln Lys
225                 230                 235                 240

Pro His Arg Ala Gln Arg Ser Pro Lys Lys Glu Pro Ala Arg Leu His
                245                 250                 255

Lys Pro Gln Ser Gln Glu Pro Gln Lys Gln Tyr Pro Thr Pro Gly Glu
            260                 265                 270

Glu Glu Gly Val Leu Glu Ser Ser Pro Leu Pro Phe Leu Glu Glu Val
            275                 280                 285

Ala His Gly Pro Arg Gly Leu Lys Gly Glu Lys Gly Glu Pro Ala Val
            290                 295                 300

Leu Glu Pro Gly Met Phe Val Glu Gly Pro Pro Gly Pro Glu Gly Pro
305                 310                 315                 320

Ala Gly Leu Ala Gly Pro Pro Gly Ile Gln Gly Asn Pro Gly Pro Val
                325                 330                 335

Gly Asp Pro Gly Glu Arg Gly Pro Pro Gly Arg Ala Gly Leu Pro Gly
            340                 345                 350

Ser Asp Gly Pro Pro Gly Pro Pro Gly Thr Ser Leu Met Leu Pro Phe
            355                 360                 365

Arg Phe Gly Ser Ser Gly Gly Asp Lys Gly Pro Val Val Ala Ala Gln
            370                 375                 380

Glu Ala Gln Ala Gln Ala Ile Leu Gln Gln Ala Arg Leu Ala Leu Arg
385                 390                 395                 400

Gly Pro Pro Gly Pro Met Gly Tyr Thr Gly Arg Pro Gly Pro Leu Gly
                405                 410                 415

Gln Pro Gly Ser Pro Gly Leu Lys Gly Glu Ser Gly Asp Leu Gly Pro
            420                 425                 430

Gln Gly Pro Arg Gly Pro Gln Gly Leu Thr Gly Pro Pro Gly Lys Ala
            435                 440                 445

Gly Arg Arg Gly Arg Ala Gly Ala Asp Gly Ala Arg Gly Met Pro Gly
            450                 455                 460

Glu Pro Gly Met Lys Gly Asp Arg Gly Phe Asp Gly Leu Pro Gly Leu
465                 470                 475                 480

Pro Gly Glu Lys Gly Gln Arg Gly Asp Thr Gly Ala Gln Gly Leu Pro
                485                 490                 495

Gly Pro Pro Gly Glu Asp Gly Glu Arg Gly Asp Asp Gly Glu Ile Gly
            500                 505                 510

Pro Arg Gly Leu Pro Gly Glu Ser Gly Pro Arg Gly Leu Leu Gly Pro
            515                 520                 525

Lys Gly Pro Pro Gly Ile Pro Gly Pro Pro Gly Val Arg Gly Met Asp
            530                 535                 540

Gly Pro His Gly Pro Lys Gly Ser Leu Gly Pro Gln Gly Glu Pro Gly
545                 550                 555                 560

Pro Pro Gly Gln Gln Gly Thr Pro Gly Ala Gln Gly Leu Pro Gly Pro
                565                 570                 575

Gln Gly Ala Ile Gly Pro His Gly Glu Lys Gly Ala Arg Gly Lys Pro
            580                 585                 590
```

```
Gly Leu Pro Gly Met Pro Gly Ser Asp Gly Leu Pro Gly His Pro Gly
            595                 600                 605

Lys Glu Gly Pro Pro Gly Thr Lys Gly Asn Gln Gly Pro Ser Gly Pro
610                 615                 620

Gln Gly Pro Leu Gly Tyr Pro Gly Pro Arg Gly Val Lys Gly Val Asp
625                 630                 635                 640

Gly Ile Arg Gly Leu Lys Gly His Lys Gly Glu Lys Gly Glu Asp Gly
                645                 650                 655

Phe Pro Gly Phe Lys Gly Asp Ile Gly Val Lys Gly Asp Arg Gly Glu
                660                 665                 670

Val Gly Val Pro Gly Ser Arg Gly Glu Asp Gly Pro Glu Gly Pro Lys
            675                 680                 685

Gly Arg Thr Gly Pro Thr Gly Asp Pro Gly Pro Thr Gly Leu Met Gly
            690                 695                 700

Glu Lys Gly Lys Leu Gly Val Pro Gly Leu Pro Gly Tyr Pro Gly Arg
705                 710                 715                 720

Gln Gly Pro Lys Gly Ser Leu Gly Phe Pro Gly Phe Pro Gly Ala Ser
                725                 730                 735

Gly Glu Lys Gly Ala Arg Gly Leu Ser Gly Lys Ser Gly Pro Arg Gly
            740                 745                 750

Glu Arg Gly Pro Thr Gly Pro Arg Gly Gln Arg Gly Pro Arg Gly Ala
            755                 760                 765

Thr Gly Lys Ser Gly Ala Lys Gly Thr Ser Gly Gly Asp Gly Pro His
            770                 775                 780

Gly Pro Pro Gly Glu Arg Gly Leu Pro Gly Pro Gln Gly Pro Asn Gly
785                 790                 795                 800

Phe Pro Gly Pro Lys Gly Pro Pro Gly Pro Ala Gly Lys Asp Gly Leu
                805                 810                 815

Pro Gly His Pro Gly Gln Arg Gly Glu Val Gly Phe Gln Gly Lys Thr
            820                 825                 830

Gly Pro Pro Gly Pro Pro Gly Val Val Gly Pro Gln Gly Thr Ala Gly
            835                 840                 845

Glu Ser Gly Pro Met Gly Glu Arg Gly His Ser Gly Pro Pro Gly Pro
850                 855                 860

Pro Gly Glu Gln Gly Leu Pro Gly Thr Ser Gly Lys Glu Gly Thr Lys
865                 870                 875                 880

Gly Asp Pro Gly Pro Pro Gly Ala Pro Gly Lys Asp Gly Pro Ala Gly
                885                 890                 895

Leu Arg Gly Phe Pro Gly Glu Arg Gly Leu Pro Gly Thr Ala Gly Gly
            900                 905                 910

Pro Gly Leu Lys Gly Asn Glu Gly Pro Ala Gly Pro Pro Gly Pro Ala
            915                 920                 925

Gly Ser Pro Gly Glu Arg Gly Ala Ala Gly Ser Gly Gly Pro Ile Gly
            930                 935                 940

Pro Pro Gly Arg Pro Gly Pro Gln Gly Pro Pro Gly Ala Ala Gly Glu
945                 950                 955                 960

Lys Gly Val Pro Gly Glu Lys Gly Pro Ile Gly Pro Thr Gly Arg Asp
                965                 970                 975

Gly Val Gln Gly Pro Val Gly Leu Pro Gly Pro Ala Gly Pro Pro Gly
            980                 985                 990

Val Ala Gly Glu Asp Asp Lys  Gly Glu Val Gly Asp  Pro Gly Gln
            995                 1000                1005

Lys Gly  Thr Lys Gly Asn Lys  Gly Glu His Gly Pro  Pro Gly Pro
```

```
            1010                1015                1020

Pro Gly Pro Ile Gly Pro Val Gly Gln Pro Gly Ala Ala Gly Ala
    1025                1030                1035

Asp Gly Glu Pro Gly Ala Arg Gly Pro Gln Gly His Phe Gly Ala
    1040                1045                1050

Lys Gly Asp Glu Gly Thr Arg Gly Phe Asn Gly Pro Pro Gly Pro
    1055                1060                1065

Ile Gly Leu Gln Gly Leu Pro Gly Pro Ser Gly Glu Lys Gly Glu
    1070                1075                1080

Thr Gly Asp Gly Gly Pro Met Gly Pro Pro Gly Pro Pro Gly Pro
    1085                1090                1095

Arg Gly Pro Ala Gly Pro Asn Gly Ala Asp Gly Pro Gln Gly Ser
    1100                1105                1110

Pro Gly Gly Val Gly Asn Leu Gly Pro Pro Gly Glu Lys Gly Glu
    1115                1120                1125

Pro Gly Glu Ser Gly Ser Pro Gly Val Gln Gly Glu Pro Gly Val
    1130                1135                1140

Lys Gly Pro Arg Gly Glu Arg Gly Glu Lys Gly Glu Ser Gly Gln
    1145                1150                1155

Ala Gly Glu Ala Gly Pro Pro Gly Pro Lys Gly Pro Thr Gly Asp
    1160                1165                1170

Asn Gly Pro Lys Gly Asn Pro Gly Pro Val Gly Phe Pro Gly Asp
    1175                1180                1185

Pro Gly Pro Pro Gly Glu Ala Gly Pro Arg Gly Gln Asp Gly Ala
    1190                1195                1200

Lys Gly Asp Arg Gly Glu Asp Gly Glu Pro Gly Gln Pro Gly Ser
    1205                1210                1215

Pro Gly Pro Thr Gly Glu Asn Gly Pro Pro Gly Pro Leu Gly Lys
    1220                1225                1230

Arg Gly Pro Ala Gly Thr Pro Gly Pro Glu Gly Arg Gln Gly Glu
    1235                1240                1245

Lys Gly Ala Lys Gly Asp Pro Gly Ala Val Gly Ala Pro Gly Lys
    1250                1255                1260

Thr Gly Pro Val Gly Pro Ala Gly Leu Ala Gly Lys Pro Gly Pro
    1265                1270                1275

Asp Gly Leu Arg Gly Leu Pro Gly Ser Val Gly Gln Gln Gly Arg
    1280                1285                1290

Pro Gly Ala Thr Gly Gln Ala Gly Pro Pro Gly Pro Val Gly Pro
    1295                1300                1305

Pro Gly Leu Pro Gly Leu Arg Gly Asp Ala Gly Ala Lys Gly Glu
    1310                1315                1320

Lys Gly His Pro Gly Leu Ile Gly Leu Ile Gly Pro Thr Gly Glu
    1325                1330                1335

Gln Gly Glu Lys Gly Asp Arg Gly Leu Pro Gly Pro Gln Gly Ser
    1340                1345                1350

Pro Gly Gln Lys Gly Glu Thr Gly Ile Pro Gly Ala Ser Gly Pro
    1355                1360                1365

Ile Gly Pro Gly Gly Pro Pro Gly Leu Pro Gly Pro Ser Gly Pro
    1370                1375                1380

Lys Gly Ala Lys Gly Ala Thr Gly Pro Ala Gly Pro Lys Gly Glu
    1385                1390                1395

Lys Gly Val Gln Gly Pro Pro Gly His Pro Gly Pro Pro Gly Glu
    1400                1405                1410
```

Val Ile Gln Pro Leu Pro Ile Gln Met Pro Lys Lys Thr Arg Arg
    1415                1420                1425

Ser Val Asp Gly Ser Lys Leu Ile Gln Asp Glu Glu Ala Val Pro
    1430                1435                1440

Thr Gly Gly Ala Pro Gly Ser Pro Ala Gly Leu Glu Glu Ile Phe
    1445                1450                1455

Gly Ser Leu Asp Ser Leu Arg Glu Glu Ile Glu Gln Met Arg Arg
    1460                1465                1470

Pro Ala Gly Thr Gln Asp Ser Pro Ala Arg Thr Cys Gln Asp Leu
    1475                1480                1485

Lys Leu Cys His Pro Glu Leu Pro Asp Gly Glu Tyr Trp Val Asp
    1490                1495                1500

Pro Asn Gln Gly Cys Ala Arg Asp Ala Phe Arg Val Phe Cys Asn
    1505                1510                1515

Phe Thr Ala Gly Gly Glu Thr Cys Val Thr Pro Arg Asp Asp Val
    1520                1525                1530

Thr Gln Phe Ser Tyr Val Asp Ser Glu Gly Ser Pro Val Gly Val
    1535                1540                1545

Val Gln Leu Thr Phe Leu Arg Leu Leu Ser Val Ser Ala His Gln
    1550                1555                1560

Asp Val Ser Tyr Pro Cys Ser Gly Val Ser Gln Asp Gly Pro Leu
    1565                1570                1575

Lys Leu Arg Gly Ala Asn Glu Asp Glu Leu Ser Pro Glu Thr Ser
    1580                1585                1590

Pro Tyr Val Lys Glu Phe Arg Asp Gly Cys Gln Thr Gln Gln Gly
    1595                1600                1605

Arg Thr Val Leu Glu Val Arg Thr Pro Val Leu Glu Gln Leu Pro
    1610                1615                1620

Val Leu Asp Ala Ser Phe Ala Asp Leu Gly Ala Pro Thr Arg Arg
    1625                1630                1635

Gly Gly Val Leu Leu Gly Pro Val Cys Phe Met Gly
    1640                1645                1650

<210> SEQ ID NO 35
<211> LENGTH: 2846
<212> TYPE: DNA
<213> ORGANISM: Human

<400> SEQUENCE: 35
cgtcgctcgg cgcctgccgc tcagagcgcc tgccagccat gaccggagcg cctgccctag     60
ccctgctgct gctggggcag ctcctgacgg ccacctccgc gcagaaagtg ggaccccgag    120 gccccctgg tccccaaggg cctcctggaa aacccggcaa ggatggcatt gatggagaag    180
ctggccctcc aggtctgcct ggccttccag acccaaagg gacctcaggg aagccaggga    240
agccgggaga ggcaggactg ccaggactgc ctggtgtaga tggtctgaca gggagagatg    300
gacccgcagg acccaaaggt gcccctggag aacggggaag tctaggaccc ccagggccac    360
caggacttgg gggcaaaggc ctccctggac ctcctggaga ggcaggagtg agtggcctcc    420
caggtgggat tggtctacgt ggccccccgg gaccctctgg acttccagga ctgcctggcc    480
tcccaggacc tcctggacct cctggaaacc ctggagtcct ccctgaaggt gctactgatc    540
tgcagtgtcc cgccatctgc ccgccaggcc ctccgggacc cccaggaatg ccggggttca    600 agggggcctac tggctacaaa ggggaacaag gagaagttgg caaagatggt gagaagggta    660

```
gtcctggccc ccccgggcct cctggaatcc caggcaccgt ggggctacag ggcccacgag    720
gattaagagg acttccaggg ccactcgggc cccctgggga ccggggtccc attgggtttc    780
ggggcccccc tgggacccca ggagcacctg ggaaagtggg tgacagggt gaaaggggac    840 cagaagggtt ccgtggccct aagggtgacc tgggcaggcc tggtcccaaa ggaatccctg    900
gaatggctgg gccaggcgga gaaccaggca tgccaggcaa ggatggcaaa gatggtgtgc    960
cgggacttga tggtgagaag ggagaggctg gtcgcaatgg tggccaagga gagaaaggcc   1020
ccaatgggct gccggggctc cctggacgag cagggtccaa aggcgagaag ggagaaccgg   1080
gtagaactgg cgagctgggt gaggctggcc cctctggaga gccaggtatc ctggagatg    1140 ttggtgttcc aggggagcgt ggtgaggctg gtcacagggg ctccgtggga gctcttggcc   1200
cacaaggtcc tcctggtgct cctggcatcc gtggctttca gggacaaaaa ggcagcacag   1260
gagaccctgg ccttccgggc ccccaaggcc tacgggagag tgtgggtgac cggggtccag   1320
gaggtgccac aggccctaag ggagaccagg gcattgcagg ttccgatggt cttccagggg   1380
acaaaggcga gctgggtcct aatggccccg ttggacaaaa aggagagtct ggcagccgag   1440
gggaactggg ccccaaaggc atccagggcc caatggcac cagtggagtc cagggtgtac   1500
ctggtccccc aggtccactg ggcctccaag gtgtgcaggg tgtcccaggc atcaccggga   1560
agcctggagt tccgggcaag gaagccagtg aacagcgcat cagggagcta tgcggggta   1620 tgatcagtga gcaaattgca cagttggctg cacacctgag gaagccctta gcaccaggct   1680
ccatcggcag gcctggtcca gctggccccc caggccctcc aggccctcca ggctctattg   1740
gccaccctgg cgctcggggt ccccctggat accgtggtcc cactggggaa ctaggagatc   1800
ctggaccaag agggagccag ggtgacagag gggacaaggg agcaacaggt gcagggctgg   1860
atgggcctgc tggggaccag ggctaccaag ggcctcaagg tgtacctggc atcagcaaag   1920
atggtcgaga tggtgctcat ggtgagcctg gccttcccgg tgatcctggc cttcctggag   1980
ctgctggtgc tcagggtacc ccagggatct gcgacacttc agcctgccaa ggagctgtgt   2040 taggggagg tggggaaaag tcgggtcctc ggagctcata aaacaaggac ttcagtagga   2100
aatggctcca tatttcctac tgaaatacga gagcactcca gcaggcagca gggatgagcg   2160
gtgtggctat ggacagaaat ggacagtggc tggctacagt tggtccttca tggcctgctg   2220
cttggcccca agaacatcta ttggcagcac tgtcactgtc ccatctccaa gatttatggc   2280
agcccaatac ctcagacaca ggccttaggg atggagactt taaacccagc atctgggagg   2340
gatggtgtta tctaagagtt ttgtacaatt ccatgagata aaacactcca agagacttgt   2400
ttacataaca tttatataaa gcctatgata gactaccaat aaagtgatct tctaacccttt  2460 cagattagta ctggttatag tgtgatgaag gcaaggaact taatgtctac tttgcctgct   2520
ttctattgca aacttagtat ctctgatgcc tagtgtttat tcaaggaact acactgcacc   2580
atctgttaaa ataaataaag cgactcactg ggaaccttg ttccaaacat acagtttatt   2640
acacataaag cactgcctca caatatgaa atgtgggcat taaagcaatg tactgcgaaa   2700
atgtttatgg gcaaaaggag ctttaaaaga agtctctgga aaattcttag caaagtttta   2760
aaatggcact gcatttttcca atagagtacc atgagactgg aaatagggg gacagaacaa   2820 atgaaataaa gtttccaaac ctcttc                                        2846
```

<210> SEQ ID NO 36
<211> LENGTH: 680
<212> TYPE: PRT
<213> ORGANISM: Human

<400> SEQUENCE: 36

```
Met Thr Gly Ala Pro Ala Leu Ala Leu Leu Leu Gly Gln Leu Leu
1               5                   10                  15

Thr Ala Thr Ser Ala Gln Lys Val Gly Pro Arg Gly Pro Gly Pro
                20                  25                  30

Gln Gly Pro Pro Gly Lys Pro Gly Lys Asp Gly Ile Asp Gly Glu Ala
            35                  40                  45

Gly Pro Pro Gly Leu Pro Gly Leu Pro Gly Pro Lys Gly Thr Ser Gly
    50                  55                      60

Lys Pro Gly Lys Pro Gly Glu Ala Gly Leu Pro Gly Leu Pro Gly Val
65                  70                  75                  80

Asp Gly Leu Thr Gly Arg Asp Gly Pro Ala Gly Pro Lys Gly Ala Pro
                85                  90                  95

Gly Glu Arg Gly Ser Leu Gly Pro Pro Gly Pro Pro Gly Leu Gly Gly
            100                 105                 110

Lys Gly Leu Pro Gly Pro Pro Gly Glu Ala Gly Val Ser Gly Leu Pro
            115                 120                 125

Gly Gly Ile Gly Leu Arg Gly Pro Pro Gly Pro Ser Gly Leu Pro Gly
    130                 135                 140

Leu Pro Gly Leu Pro Gly Pro Pro Gly Pro Pro Gly Asn Pro Gly Val
145                 150                 155                 160

Leu Pro Glu Gly Ala Thr Asp Leu Gln Cys Pro Ala Ile Cys Pro Pro
                165                 170                 175

Gly Pro Pro Gly Pro Pro Gly Met Pro Gly Phe Lys Gly Pro Thr Gly
            180                 185                 190

Tyr Lys Gly Glu Gln Gly Glu Val Gly Lys Asp Gly Glu Lys Gly Ser
            195                 200                 205

Pro Gly Pro Pro Gly Pro Pro Gly Ile Pro Gly Thr Val Gly Leu Gln
            210                 215                 220

Gly Pro Arg Gly Leu Arg Gly Leu Pro Gly Pro Leu Gly Pro Pro Gly
225                 230                 235                 240

Asp Arg Gly Pro Ile Gly Phe Arg Gly Pro Pro Gly Thr Pro Gly Ala
                245                 250                 255

Pro Gly Lys Val Gly Asp Arg Gly Glu Arg Gly Pro Glu Gly Phe Arg
            260                 265                 270

Gly Pro Lys Gly Asp Leu Gly Arg Pro Gly Pro Lys Gly Ile Pro Gly
            275                 280                 285

Met Ala Gly Pro Gly Gly Glu Pro Gly Met Pro Gly Lys Asp Gly Lys
            290                 295                 300

Asp Gly Val Pro Gly Leu Asp Gly Glu Lys Gly Glu Ala Gly Arg Asn
305                 310                 315                 320

Gly Gly Gln Gly Glu Lys Gly Pro Asn Gly Leu Pro Gly Leu Pro Gly
                325                 330                 335

Arg Ala Gly Ser Lys Gly Glu Lys Gly Glu Pro Gly Arg Thr Gly Glu
            340                 345                 350

Leu Gly Glu Ala Gly Pro Ser Gly Pro Gly Ile Pro Gly Asp Val
            355                 360                 365

Gly Val Pro Gly Glu Arg Gly Glu Ala Gly His Arg Gly Ser Val Gly
            370                 375                 380

Ala Leu Gly Pro Gln Gly Pro Pro Gly Ala Pro Gly Ile Arg Gly Phe
385                 390                 395                 400

Gln Gly Gln Lys Gly Ser Thr Gly Asp Pro Gly Leu Pro Gly Pro Gln
```

```
            405                 410                 415
Gly Leu Arg Gly Asp Val Gly Asp Arg Gly Pro Gly Ala Thr Gly
            420                 425                 430

Pro Lys Gly Asp Gln Gly Ile Ala Gly Ser Asp Gly Leu Pro Gly Asp
        435                 440                 445

Lys Gly Glu Leu Gly Pro Asn Gly Pro Val Gly Gln Lys Gly Glu Ser
    450                 455                 460

Gly Ser Arg Gly Glu Leu Gly Pro Lys Gly Ile Gln Gly Pro Asn Gly
465                 470                 475                 480

Thr Ser Gly Val Gln Gly Val Pro Gly Pro Pro Gly Pro Leu Gly Leu
                485                 490                 495

Gln Gly Val Gln Gly Val Pro Gly Ile Thr Gly Lys Pro Gly Val Pro
            500                 505                 510

Gly Lys Glu Ala Ser Glu Gln Arg Ile Arg Glu Leu Cys Gly Gly Met
        515                 520                 525

Ile Ser Glu Gln Ile Ala Gln Leu Ala Ala His Leu Arg Lys Pro Leu
    530                 535                 540

Ala Pro Gly Ser Ile Gly Arg Pro Gly Pro Ala Gly Pro Pro Gly Pro
545                 550                 555                 560

Pro Gly Pro Pro Gly Ser Ile Gly His Pro Gly Ala Arg Gly Pro Pro
                565                 570                 575

Gly Tyr Arg Gly Pro Thr Gly Glu Leu Gly Asp Pro Gly Pro Arg Gly
            580                 585                 590

Ser Gln Gly Asp Arg Gly Asp Lys Gly Ala Thr Gly Ala Gly Leu Asp
        595                 600                 605

Gly Pro Ala Gly Asp Gln Gly Tyr Gln Gly Pro Gln Gly Val Pro Gly
    610                 615                 620

Ile Ser Lys Asp Gly Arg Asp Gly Ala His Gly Glu Pro Gly Leu Pro
625                 630                 635                 640

Gly Asp Pro Gly Leu Pro Gly Ala Ala Gly Gln Gly Thr Pro Gly
                645                 650                 655

Ile Cys Asp Thr Ser Ala Cys Gln Gly Ala Val Leu Gly Gly Gly
        660                 665                 670

Glu Lys Ser Gly Pro Arg Ser Ser
    675                 680

<210> SEQ ID NO 37
<211> LENGTH: 700
<212> TYPE: DNA
<213> ORGANISM: Human

<400> SEQUENCE: 37
caagagaggc agctcctgtc tccttccact ccccttctcc cctcctttct ggctggagca    60
gagtctgtca atcccaggca gagacaaggc agacaaagct tcacttgtaa ggagcctcct   120
cgcttctcct tgcccagac tgccccagtg agctggagca ttgaagaaga gtctcctgcc   180
aataacactg aaaagaaaga aaaggagca agagccatga tgaaatctgt ggtacttgtc   240
atccttgggc taactttgct gttagaaaca caagccatgc cttcaagtcg cctctcctgc   300
tacagaaagt tgctaaagga tcgcaattgt cacaaccttc cggagggcag agccgacctg   360
aagctgatag atgcaaatgt ccagcatcat ttctgggatg ggaagggatg cgagatgatc   420
tgctactgca acttcagcga actgctctgc tgcccaaaag atgtcttctt ggaccaaag    480 atctcctttg tgatcccctg caacaaccac tgaggatctg ccttgcactc tggagaacat   540
```

-continued

```
ggtcctgaag gccttcacgt ccccctaattt cccacaaact ctgtcagttc agcgccattt      600
ctgatatcca tccagtatat ccaatcttgc atagattcta taaagtctta cttgctagag      660
tatacttggg ctaaagtggt aataaaagtt gtttccattt                             700
```

```
<210> SEQ ID NO 38
<211> LENGTH: 98
<212> TYPE: PRT
<213> ORGANISM: Human

<400> SEQUENCE: 38
```

Met Met Lys Ser Val Val Leu Val Ile Leu Gly Leu Thr Leu Leu
1               5                   10                  15

Glu Thr Gln Ala Met Pro Ser Ser Arg Leu Ser Cys Tyr Arg Lys Leu
            20                  25                  30

Leu Lys Asp Arg Asn Cys His Asn Leu Pro Glu Gly Arg Ala Asp Leu
        35                  40                  45

Lys Leu Ile Asp Ala Asn Val Gln His His Phe Trp Asp Gly Lys Gly
    50                  55                  60

Cys Glu Met Ile Cys Tyr Cys Asn Phe Ser Glu Leu Leu Cys Cys Pro
65                  70                  75                  80

Lys Asp Val Phe Phe Gly Pro Lys Ile Ser Phe Val Ile Pro Cys Asn
                85                  90                  95

Asn His

```
<210> SEQ ID NO 39
<211> LENGTH: 356
<212> TYPE: PRT
<213> ORGANISM: Human

<400> SEQUENCE: 39
```

Met Arg Ser Leu Leu Leu Val Leu Ile Ser Val Cys Trp Ala Asp
1               5                   10                  15

His His Leu Ser Asp Ser Tyr Thr Pro Pro Gln Asp Arg Val Ile
            20                  25                  30

His Ile Gln Ala Glu Asn Gly Pro Arg Leu Leu Val Glu Ala Glu Gln
        35                  40                  45

Ala Lys Val Phe Ser His Arg Gly Gly Asn Val Thr Leu Pro Cys Lys
    50                  55                  60

Phe Tyr Arg Asp Pro Thr Ala Phe Gly Ser Gly Ile His Lys Ile Arg
65                  70                  75                  80

Ile Lys Trp Thr Lys Leu Thr Ser Asp Tyr Leu Arg Glu Val Asp Val
            85                  90                  95

Phe Val Ser Met Gly Tyr His Lys Lys Thr Tyr Gly Gly Tyr Gln Gly
                100                 105                 110

Arg Val Phe Leu Lys Gly Gly Ser Asp Asn Asp Ala Ser Leu Val Ile
            115                 120                 125

Thr Asp Leu Thr Leu Glu Asp Tyr Gly Arg Tyr Lys Cys Glu Val Ile
        130                 135                 140

Glu Gly Leu Glu Asp Asp Thr Ala Val Ala Leu Glu Leu Gln Gly
145                 150                 155                 160

Val Val Phe Pro Tyr Phe Pro Arg Leu Gly Arg Tyr Asn Leu Asn Phe
                165                 170                 175

His Glu Ala Arg Gln Ala Cys Leu Asp Gln Asp Ala Val Ile Ala Ser
            180                 185                 190

Phe Asp Gln Leu Tyr Asp Ala Trp Arg Gly Gly Leu Asp Trp Cys Asn

```
               195                 200                 205
Ala Gly Trp Leu Ser Asp Gly Ser Val Gln Tyr Pro Ile Thr Lys Pro
    210                 215                 220

Arg Glu Pro Cys Gly Gly Gln Asn Thr Val Pro Gly Val Arg Asn Tyr
225                 230                 235                 240

Gly Phe Trp Asp Lys Asp Lys Ser Arg Tyr Asp Val Phe Cys Phe Thr
                245                 250                 255

Ser Asn Phe Asn Gly Arg Phe Tyr Tyr Leu Ile His Pro Thr Lys Leu
            260                 265                 270

Thr Tyr Asp Glu Ala Val Gln Ala Cys Leu Asn Asp Gly Ala Gln Ile
        275                 280                 285

Ala Lys Val Gly Gln Ile Phe Ala Ala Trp Lys Leu Leu Gly Tyr Asp
    290                 295                 300

Arg Cys Asp Ala Gly Trp Leu Ala Asp Gly Ser Val Arg Tyr Pro Ile
305                 310                 315                 320

Ser Arg Pro Arg Arg Cys Ser Pro Thr Glu Ala Ala Val Arg Phe
                325                 330                 335

Val Gly Phe Pro Asp Lys Lys His Lys Leu Tyr Gly Val Tyr Cys Phe
                340                 345                 350

Arg Ala Tyr Asn
        355

<210> SEQ ID NO 40
<211> LENGTH: 5055
<212> TYPE: DNA
<213> ORGANISM: Human

<400> SEQUENCE: 40
agaggatctg ggaggagaag tctcctggtg acgctttgcc tttcttctgc tcttggtgag     60
aagtggctcc tttatcctcg gatcaggacc tctgccatcc aacaccacaa agagacattc    120
tgcacacacg cgctcggaca cacacaccca tacccacacc cacacccaca ccgcactcgc    180
ccagagacaa acttaaggtc aggacgagca ctagctcact tcatctccag ctcccagcta    240
agtgggactc agcttctgaa ctggaattca ggacaagcag agaagagtct gagctacaag    300
gatgagaagt ctgcttctcc tggtgctgat ttcagtctgt tgggctgacc accacctttc    360
agacagctac actcctccag atcaagacag agttattcac atccaagcag aaaatgcccc    420
ccgtctactt gtggaagcag aacaagccaa ggtcttctct caccgaggtg gcaacgtgac    480
actgccatgc aaattttatc gagaccctac agcatttggc tcaggaatcc acaaaatccg    540
catcaagtgg accaagctaa cttcagatta cctcagggaa gtagatgtct tcgtttccat    600
gggctatcac aagaagacct atggaggcta tcaaggtcga gtgttttctga agggaggcag    660 tgataatgat gcctccctgg tcatcacgga tcttaccctg gaggattatg ggagatataa    720
atgtgaggtg attgaaggc tagaagatga tactgctgtg gtggcattgg agttacaagg    780
tgtggtgttc ccttactttc cacgactggg acgctacaat cttaactttc acgaggcacg    840
ccaggcttgt ctggaccagg acgcagtgat tgcttccttt gaccagctgt acgatgcctg    900
gcggggtggg ctggactggt gcaatgctgc tggctcagt gatggatctg tgcagtaccc    960
aatcaccaaa ccacgagagc cctgcggggg ccaaaacacg gtgcctggag tcaggaacta   1020
cgggttttgg acaaggata aaagcagata tgacgttttc tgttttacat ccaacttcaa   1080
cggccgattt tactacctga tccaccccac caaactcacc tacgatgagg cggtgcaagc   1140
ttgtctcaat gacggtgctc agatcgcgaa agtgggccag atatttgctg cctggaagct   1200
```

```
tctgggctat gaccgctgcg atgccggctg gctagcggat ggcagcgtcc gctatcctat      1260
ttctcgacca agaaggcgct gcagtccgac tgaggctgca gtgcgctttg taggtttccc      1320
agataaaaag cataagctat acggggtcta ttgcttcaga gcatacaact gagtgtgccc      1380
taggaagagt cagttcttga gttacgtgaa agttttgttt gtttgtttgt ttttgttgtt      1440
gttgttttta atatgaactc atgcaagtta ccaaaactgt gataacccctt tttcacttac     1500 tgtaaagagt cgttttcata aaggccaatt cattcatttg ttttgtaaag ctatcagtcg      1560
atatatatat tataaagtaa tgtaagcgga aggcattcta aaatagggggt gtggcggggg     1620 gtgctttaga gcctaaactg gttcatgcta catcatccca acaagatgcc atttcatgaa      1680
tgggatatgt tgtaggctga gaatcaccag gattgtagta agggaagtaa tgctacttgc      1740
cgcagtaatt tccacaagca caaattttac atatttctac aattttgaaa tgcacttcgg      1800
taaacaaatt agaacaacaa atttgaaata caggcttctt tacataaacc aggattctgg      1860
gaggtgcaaa aactcactat cataaggaaa caacagagac tttttctaaa agttaatact      1920
ttaagtctcc agtatacaga atagtttact ctttacaatt ctaccttttt gaccaaaaaa      1980
ttcatataga ctcagatgca gaataataaa gccacagtta gaactcctag gtcaactcat      2040
ttatatgaaa tatctactta agtacacaga taatacttta gcaatgaaag agtcctacct      2100
tctaattaca attacctatc tgagaagact tgtttttatta ttttgagta gcttactga      2160 atcatattta aattctaaga acctttgcta agcagtattt agaatctact cagggcagtt      2220
aaaacgacaa actgctggac agaaaatgtg taaaatgtag cagcttgatt ttatgttagc      2280
ttatgaaaca ttattgtcct ataaaaataa ttttaatcta tttaatattt cttatttaca      2340
ttacatgaca aaaaccatca aatgaatgaa taactctaca cttgcctaag aaataaagac      2400
tcaacttcca aagttgttct tgtttgtatc cacaatacag tgcccaaata agacctttat      2460
ttatagaaga aagggaaaaa tacatttcta aatagtctct caagtaggaa atacagtcac      2520
tgtcagtttc cttttctggtt agaatttggc aaaaataaaa tactggcatt ctcatagcag      2580
actttacacc tccaggtttt aagtgaaaag ttaagcccag gttcagaaaa gtgactttca      2640
gtattagcaa ctccagtctt aaattaaagt ttcttgttat gattgcagag accccagagg      2700
gaccaatatt tatattcaag taatatttct ggtttcccat tatttcacag tgaattcttg      2760
tgagtaggcc ttagcataat aatccaagta caacatggct agtatgctgt catcaatgtt      2820
tttatgtaga tttcccccca tgaacataac ataaataaat ctgtttcctg aattgaccat      2880
ggttgcattt aaagctctgt aataactata ataaaaaatg ctctataaat atagagttat      2940
gtgtgtggaa agtatagagc agatggaagt ccatgaaacc ataactatca tgatatatta      3000
cctagataaa atattagaag taaaaataga acctttcttt caggtactta agccatgaca      3060
atgcatgaag ttataagtta ggatatgcaa attacacaaa agtatacatc caaagaaaat      3120
gtggggtttc actcaaacag tgctgttgta aattgaattc agacttctaa gctaaacaca      3180
aattaaagag aatgaatggt ctataatata atgactgtat tacttaagga ggagactcca      3240
aactagcccc tcaaacacct acaggctag gctaatctct ttggaggaag atcatacttg       3300
aacaatcatt acgtatattg taagaatttt gtctgcaatg caagtagata aattttatac      3360
cgaattaggt gcactccatc cagttattgt catagaactc cacattacag tgcagtagca      3420
tttcttaact tttgaatact tagtatagga aatggtgctg atcaaaatct ccaaagtgac      3480
tgttagctga catatgtcta taccaattgt gcaccatttg tccattcttg acaacatcct      3540
```

```
agaatgaaca ctgctgggca gagtttttaa cttctaattt cacacaaagg accagaatcg    3600
tcatgccctc cctttgaact cctaattgaa aggggtcttt taatgttccc atcttgctgt    3660
tttcactcca ccaaataatc tattttccta cttcatatct cattataaat gtcttcaaaa    3720
gaaaaaaagt tgtcttagca caattcctag cagaaagttg acataacact gtctaattca    3780
gaaatcccct tcgagacttc aagattacca gagtatcaag gtgatgagag acagacttt     3840 aaaaaaatga aaacatttta tagtatggcc cacatataaa aacataata aatctataaa     3900 ttttactgaa atgccttgat ttgaaacctc taagcaaaaa gaaccaatat atttaaaaat    3960
acatataagg atgaagataa tttgtcatat taacactgga agccatcttt taatgactgc    4020
tgccatattt tgtcacagca acttttagcc aaatatagta tttgtaaatt taaattttct    4080
ttcatataaa gagggccggt acctgtcaaa gtgctatttt atgcagtaag atggtcgctt    4140
gttattttgg caattagtag actcaaataa gataccaatt tggttgctgg cagccatact    4200
ggatttcttg atttcagtac tcctaaaagc atgctggtgt catggagtag ctgaccacta    4260
aaaaagggag gattcaaagg gaatcagttg tcaggtttgg tttagtctta gtttttttt     4320 ttgttgttgt tttgttttgc tttgtttttt gcttttttt tccatttagt ttgtttcatt     4380
ttggttttgc atagaatgct tagagaaaac actgacaacc ttttttgagaa gtatgtcatt    4440 gctcaagact gccagcacag tgtacagcaa aagctatgaa taatacagac atcagtaagc    4500
cacccaatta gaagaaggtc aatatttaaa tgcatttaat agctactaag tacaagtttg    4560
aggagaaaca atgtgtatta caaaaagaa tgttttcatt ttctgtaaga tacaatgaac      4620
tgatgaacaa atattaaaag tcaatttgc tttactatag tatcatttga ttcttatgac      4680
ttgtagaatc agtcatttt tccccttggg tcaaacttga caaatacacc atgcattctt      4740
ctgttgctag caatgctttg aatgaatacc cacccaaatg agttagagct ttgacattca    4800
aacaagaaag tatacttcag aaatttccct taattatttg gaataaatta acaaccttg     4860 aagaaaaaa aaaactccc aatagtgaga tcaattaaat tttgttttag ttgtaaactc      4920
tttcaaaatg agggatatca tattcatttt gtcatcattt ttcatatatt tttattcttg    4980
tcatacaaag tctatgaggc agggtgaaag attctgtgga ggttcttagt ccccaaataa    5040
aagtaatgaa accat                                                     5055

<210> SEQ ID NO 41
<211> LENGTH: 1520
<212> TYPE: DNA
<213> ORGANISM: Human

<400> SEQUENCE: 41
tcatcctcac cttagacctc tcctgtcctt ggctcctctt catctttgct tttccgactc     60
ctcaagcagc ggtcctactt ggtcctctga ggacttactt gtgtccttat ctcactttct    120
cccggctcat cccggggttg tctgaccttg ggacaaggaa ggatggttcc cggggtgagg    180
atcatcccct ctttgctggg actcgtgatg ttctggctcc cgttggactc gcaagcacta    240
tcccgctcgg gcaaagtctg cctttttcggt gaaaagatat ataccccccgg ccagagctgg    300 cacccctact tggaaccaca aggcacgata tactgcgtgc gctgtacctg ctctgagaat    360
ggacatgtga attgttaccg cctccgctgc ccacccttc actgctcaca gctgtgatg      420 gagccacagc aatgctgtcc caggtgtgtg atcctcatg tcccctctgg cctccgagtt     480
cccctaaagt cctgccagct caatgagacc acataccaac atggagagat cttcagtgcc    540
caggagctgt tccctgcccg cctgtccaac cagtgtgtcc tgtgtagctg tattgaaggc    600
```

```
cacacttact gtggtctcat gacctgtcct gaacccagct gccccaccac actccctctg    660
cctgattcct gctgtcagac ctgcaaagac aggacaactg agagttccac agaagaaaac    720
ttgacacagc tgcagcatgg agagagacat tcccaggatc catgctcgga gaggagaggc    780
cccagcacgc cagcccccac cagcctcagc tcccctctgg gcttcatccc tcgccacttc    840
cagtcagtag gaatgggcag cacaaccatc aagattatct tgaaggagaa acataaaaaa    900
gcttgcacac acaatgggaa gacatactcc catggggagg tgtggcaccc cactgtgctc    960
tcctttggcc ccatgccctg catcctgtgc acatgtatcg atggctacca ggactgccac   1020
cgtgtgacct gccccaccca atatccctgc agtcaaccca agaaagtggc tgggaagtgc   1080
tgcaagatct gcccagagga cgaggcggaa gatgaccaca gtgaggtcat ttccacccgg   1140
tgtcccaagg taccaggcca gttccaggtg tacacgttgg catctccaag cccagacagc   1200
ctacaccgct ttgtcctgga gcatgaagcc tctgaccagg tagagatgta catttggaag   1260
ctggtgaaag gaatctacca cttggttcag atcaagagag tcaggaagca agatttccag   1320
aaagaggctc agaacttccg gctgctcacc ggcacccatg aaggttactg gaccgtcttc   1380
ctagcccaga ctccagagct gaaagttaca gccagcccag acaaagtgac caagacatta   1440
tagcaaggac ctaaagagtt gcagatacga gttttattgg ttttgttatt atatattaat   1500
aaagaagtcg cattaccctc                                               1520

<210> SEQ ID NO 42
<211> LENGTH: 426
<212> TYPE: PRT
<213> ORGANISM: Human

<400> SEQUENCE: 42

Met Val Pro Gly Val Arg Ile Ile Pro Ser Leu Leu Gly Leu Val Met
1               5                   10                  15

Phe Trp Leu Pro Leu Asp Ser Gln Ala Leu Ser Arg Ser Gly Lys Val
                20                  25                  30

Cys Leu Phe Gly Glu Lys Ile Tyr Thr Pro Gly Gln Ser Trp His Pro
            35                  40                  45

Tyr Leu Glu Pro Gln Gly Thr Ile Tyr Cys Val Arg Cys Thr Cys Ser
        50                  55                  60

Glu Asn Gly His Val Asn Cys Tyr Arg Leu Arg Cys Pro Pro Leu His
65                  70                  75                  80

Cys Ser Gln Pro Val Met Glu Pro Gln Gln Cys Cys Pro Arg Cys Val
                85                  90                  95

Asp Pro His Val Pro Ser Gly Leu Arg Val Pro Leu Lys Ser Cys Gln
            100                 105                 110

Leu Asn Glu Thr Thr Tyr Gln His Gly Glu Ile Phe Ser Ala Gln Glu
        115                 120                 125

Leu Phe Pro Ala Arg Leu Ser Asn Gln Cys Val Leu Cys Ser Cys Ile
    130                 135                 140

Glu Gly His Thr Tyr Cys Gly Leu Met Thr Cys Pro Glu Pro Ser Cys
145                 150                 155                 160

Pro Thr Thr Leu Pro Leu Pro Asp Ser Cys Cys Gln Thr Cys Lys Asp
                165                 170                 175

Arg Thr Thr Glu Ser Ser Thr Glu Glu Asn Leu Thr Gln Leu Gln His
            180                 185                 190

Gly Glu Arg His Ser Gln Asp Pro Cys Ser Glu Arg Arg Gly Pro Ser
        195                 200                 205
```

```
Thr Pro Ala Pro Thr Ser Leu Ser Ser Pro Leu Gly Phe Ile Pro Arg
    210                 215                 220

His Phe Gln Ser Val Gly Met Gly Ser Thr Thr Ile Lys Ile Ile Leu
225                 230                 235                 240

Lys Glu Lys His Lys Lys Ala Cys Thr His Asn Gly Lys Thr Tyr Ser
                245                 250                 255

His Gly Glu Val Trp His Pro Thr Val Leu Ser Phe Gly Pro Met Pro
            260                 265                 270

Cys Ile Leu Cys Thr Cys Ile Asp Gly Tyr Gln Asp Cys His Arg Val
        275                 280                 285

Thr Cys Pro Thr Gln Tyr Pro Cys Ser Gln Pro Lys Lys Val Ala Gly
    290                 295                 300

Lys Cys Cys Lys Ile Cys Pro Glu Asp Glu Ala Glu Asp Asp His Ser
305                 310                 315                 320

Glu Val Ile Ser Thr Arg Cys Pro Lys Val Pro Gly Gln Phe Gln Val
                325                 330                 335

Tyr Thr Leu Ala Ser Pro Ser Pro Asp Ser Leu His Arg Phe Val Leu
            340                 345                 350

Glu His Glu Ala Ser Asp Gln Val Glu Met Tyr Ile Trp Lys Leu Val
        355                 360                 365

Lys Gly Ile Tyr His Leu Val Gln Ile Lys Arg Val Arg Lys Gln Asp
    370                 375                 380

Phe Gln Lys Glu Ala Gln Asn Phe Arg Leu Leu Thr Gly Thr His Glu
385                 390                 395                 400

Gly Tyr Trp Thr Val Phe Leu Ala Gln Thr Pro Glu Leu Lys Val Thr
                405                 410                 415

Ala Ser Pro Asp Lys Val Thr Lys Thr Leu
            420                 425

<210> SEQ ID NO 43
<211> LENGTH: 3080
<212> TYPE: DNA
<213> ORGANISM: Human

<400> SEQUENCE: 43
ccccaggtcc ggacaggccg agatgacgcc gagcccctg ttgctgctcc tgctgccgcc      60
gctgctgctg gggccttcc accggccgc cgccgcccga ggcccccaa agatggcgga     120
caaggtggtc ccacggcagg tggcccggct gggccgcact gtgcggctgc agtgcccagt     180
ggaggggac ccgccgccgc tgaccatgtg accaaggat ggccgcacca tccacagcgg     240
ctggagccgc ttccgcgtgc tgccgcaggg gctgaaggtg aagcaggtgg agcgggagga     300
tgccggcgtg tacgtgtgca aggccaccaa cggcttcggc agccttagcg tcaactacac     360
cctcgtcgtg ctggatgaca ttagcccagg gaaggagagc ctggggcccg acagctcctc     420
tgggggtcaa gaggacccg ccagccagca gtgggcacga ccgcgcttca cacagccctc     480
caagatgagg cgccgggtga tcgcacggcc cgtgggtagc tccgtgcggc tcaagtgcgt     540
ggccagcggg caccctcggc ccgacatcac gtggatgaag gacgaccagg ccttgacgcg     600
cccagaggcc gctgagccca ggaagaagaa gtggacactg agcctgaaga acctgcggcc     660
ggaggacagc ggcaaataca cctgccgcgt gtcgaaccgc gcgggcgcca tcaacgccac     720
ctacaaggtg gatgtgatcc agcggacccg ttccaagccc gtgctcacag gcacgcaccc     780
cgtgaacacg acggtggact cgggggggac cacgtcctc cagtgcaagg tgcgcagcga     840
```

```
cgtgaagccg gtgatccagt ggctgaagcg cgtggagtac ggcgccgagg gccgccacaa    900
ctccaccatc gatgtgggcg ccagaagtt tgtggtgctg cccacgggtg acgtgtggtc    960
gcggcccgac ggctcctacc tcaataagct gctcatcacc cgtgcccgcc aggacgatgc   1020
gggcatgtac atctgccttg cgccaacac catgggctac agcttccgca cgcccttcct   1080
caccgtgctg ccagacccaa aaccgcaagg gccacctgtg gcctcctcgt cctcggccac   1140
tagcctgccg tggcccgtgg tcatcggcat cccagccggc gctgtcttca tcctgggcac   1200
cctgctcctg tggctttgcc aggcccagaa gaagccgtgc acccccgcgc ctgccctcc    1260
cctgcctggg caccgcccgc cggggacggc ccgcgaccgc agcggagaca aggaccttcc   1320
ctcgttggcc gccctcagcg ctggccctgg tgtggggctg tgtgaggagc atgggtctcc   1380
ggcagccccc cagcacttac tgggcccagg cccagttgct ggccctaagt tgtaccccaa   1440
actctacaca gacatccaca cacacacaca cacacactct cacacacact cacacgtgga   1500
gggcaaggtc caccagcaca tccactatca gtgctagacg gcaccgtatc tgcagtgggc   1560
acgggggggc cggccagaca ggcagactgg gaggatggag gacggagctg cagacgaagg   1620
caggggaccc atggcgagga ggaatggcca gcacccccagg cagtctgtgt gtgaggcata   1680
gcccctggac acacacacac agacacacac actacctgga tgcatgtatg cacacacatg   1740
cgcgcacacg tgctccctga aggcacacgt acgcacacac gcacatgcac agatatgccg   1800
cctgggcaca cagataagct gcccaaatgc acgcacacgc acagagacat gccagaacat   1860
acaaggacat gctgcctgaa catacacacg cacacccatg cgcagatgtg ctgcctggac   1920
acacacacac acacgagatat gctgtctgga cgcacacacg tgcagatatg gtatccggac   1980
acacacgtgc acagatatgc tgcctggaca cacagataat gctgccttga cacacacatg   2040
cacggatatt gcctggacac acacacacac acgcgtgcac agatatgctg tctggacagg   2100
cacacacatg cagatatgct gcctggacac acacttccag acacacgtgc acaggcgcag   2160
atatgctgcc tggacacacg cagatatgct gtcagtcac acacacacgc agacatgctg   2220
tccggacaca cacgcatg cacagatatg ctgtccggac acacacacgc acgcagatat   2280
gctgcctgga cacacacaca gataatgctg cctcaacact cacacacgtg cagatattgc   2340
ctggacacac acatgtgcac agatatgctg tctggacatg cacacgtga cagatatgct   2400
gtccggatac acacgcacgc acacatgcag atatgctgcc tgggcacaca cttccggaca   2460
cacatgcaca cacaggtgca gatatgctgc ctggacacac gcagactgac gtgcttttgg   2520
gagggtgtgc cgtgaagcct gcagtacgtg tgccgtgagg ctcatagttg atgagggact   2580
ttccctgctc caccgtcact cccccaactc tgcccgcctc tgtccccgcc tcagtccccg   2640
cctccatccc cgcctctgtc ccctggcctt ggcggctatt tttgccacct gccttgggtg   2700
cccaggagtc ccctactgct gtgggctggg gttgggggca cagcagcccc aagcctgaga   2760
ggctggagcc catggctagt ggctcatccc cactgcattc tcccccctgac acagagaagg   2820
ggccttggta tttatattta agaaatgaag ataatattaa taatgatgga aggaagactg   2880
ggttgcaggg actgtggtct ctcctggggc ccgggacccg cctggtcttt cagccatgct   2940
gatgaccaca cccgtccag gccagacacc aaccccccacc ccactgtcgt ggtggccca   3000
gatctctgta attttatgta gagtttgagc tgaagcccg tatatttaat ttatttttgtt  3060
aaacatgaaa gtgcatcctt                                              3080
```

<210> SEQ ID NO 44
<211> LENGTH: 504

<212> TYPE: PRT
<213> ORGANISM: Human

<400> SEQUENCE: 44

```
Met Thr Pro Ser Pro Leu Leu Leu Leu Leu Pro Pro Leu Leu Leu
1               5                   10                  15

Gly Ala Phe Pro Pro Ala Ala Ala Arg Gly Pro Pro Lys Met Ala
                20                  25                  30

Asp Lys Val Val Pro Arg Gln Val Ala Arg Leu Gly Arg Thr Val Arg
            35                  40                  45

Leu Gln Cys Pro Val Glu Gly Asp Pro Pro Leu Thr Met Trp Thr
        50                  55                  60

Lys Asp Gly Arg Thr Ile His Ser Gly Trp Ser Arg Phe Arg Val Leu
65                  70                  75                  80

Pro Gln Gly Leu Lys Val Lys Gln Val Glu Arg Glu Asp Ala Gly Val
                85                  90                  95

Tyr Val Cys Lys Ala Thr Asn Gly Phe Gly Ser Leu Ser Val Asn Tyr
                100                 105                 110

Thr Leu Val Val Leu Asp Asp Ile Ser Pro Gly Lys Glu Ser Leu Gly
            115                 120                 125

Pro Asp Ser Ser Gly Gly Gln Glu Asp Pro Ala Ser Gln Gln Trp
    130                 135                 140

Ala Arg Pro Arg Phe Thr Gln Pro Ser Lys Met Arg Arg Val Ile
145                 150                 155                 160

Ala Arg Pro Val Gly Ser Ser Val Arg Leu Lys Cys Val Ala Ser Gly
                165                 170                 175

His Pro Arg Pro Asp Ile Thr Trp Met Lys Asp Asp Gln Ala Leu Thr
                180                 185                 190

Arg Pro Glu Ala Ala Glu Pro Arg Lys Lys Trp Thr Leu Ser Leu
        195                 200                 205

Lys Asn Leu Arg Pro Glu Asp Ser Gly Lys Tyr Thr Cys Arg Val Ser
210                 215                 220

Asn Arg Ala Gly Ala Ile Asn Ala Thr Tyr Lys Val Asp Val Ile Gln
225                 230                 235                 240

Arg Thr Arg Ser Lys Pro Val Leu Thr Gly Thr His Pro Val Asn Thr
                245                 250                 255

Thr Val Asp Phe Gly Gly Thr Ser Phe Gln Cys Lys Val Arg Ser
                260                 265                 270

Asp Val Lys Pro Val Ile Gln Trp Leu Lys Arg Val Glu Tyr Gly Ala
            275                 280                 285

Glu Gly Arg His Asn Ser Thr Ile Asp Val Gly Gly Gln Lys Phe Val
290                 295                 300

Val Leu Pro Thr Gly Asp Val Trp Ser Arg Pro Asp Gly Ser Tyr Leu
305                 310                 315                 320

Asn Lys Leu Leu Ile Thr Arg Ala Arg Gln Asp Asp Ala Gly Met Tyr
                325                 330                 335

Ile Cys Leu Gly Ala Asn Thr Met Gly Tyr Ser Phe Arg Ser Ala Phe
                340                 345                 350

Leu Thr Val Leu Pro Asp Pro Lys Pro Gln Gly Pro Val Ala Ser
        355                 360                 365

Ser Ser Ser Ala Thr Ser Leu Pro Trp Pro Val Val Ile Gly Ile Pro
    370                 375                 380

Ala Gly Ala Val Phe Ile Leu Gly Thr Leu Leu Leu Trp Leu Cys Gln
385                 390                 395                 400
```

```
Ala Gln Lys Lys Pro Cys Thr Pro Ala Pro Ala Pro Pro Leu Pro Gly
            405                 410                 415

His Arg Pro Pro Gly Thr Ala Arg Asp Arg Ser Gly Asp Lys Asp Leu
            420                 425                 430

Pro Ser Leu Ala Ala Leu Ser Ala Gly Pro Gly Val Gly Leu Cys Glu
            435                 440                 445

Glu His Gly Ser Pro Ala Ala Pro Gln His Leu Leu Gly Pro Gly Pro
        450                 455                 460

Val Ala Gly Pro Lys Leu Tyr Pro Lys Leu Tyr Thr Asp Ile His Thr
465                 470                 475                 480

His Thr His Thr His Ser His Thr His Ser Val Glu Gly Lys Val
                485                 490                 495

His Gln His Ile His Tyr Gln Cys
            500
```

```
<210> SEQ ID NO 45
<211> LENGTH: 4972
<212> TYPE: DNA
<213> ORGANISM: Human

<400> SEQUENCE: 45
```

| | | | | | |
|---|---|---|---|---|---|
| cggcgacgct | tcctgcgggc | gcggccgctg | tgggcgcgga | gccgcgagcg | agcgaacgaa | 60 |
| cgagcgaggc | ggagccggcg | gccgaggagc | cgagcgcagg | tcccgcgcag | cccgcgccgc | 120 |
| gaacaaaggc | cgccatgaag | cccgggccgc | cgcgccgcgg | gaccgcacag | gggcagcgcg | 180 |
| tggacaccgc | cacccatgcg | cccggggccc | gcgggctgtt | gctgccaccg | ctgctgctgc | 240 |
| tgctgctggc | cggccgcgcc | gcggggctc | aacgctggcg | caatgagaac | ttcgagaggc | 300 |
| cggtggatct | tgagggctca | ggggatgacg | actcgtttcc | tgatgatgaa | ctagacgacc | 360 |
| tctactcggg | gtcaggctct | ggctacttcg | agcaggagtc | cggccttgag | acggccatgc | 420 |
| ggttcatccc | tgatatggcc | ctggctcgcg | ccactgcacc | tgccatgcta | cccacaaccg | 480 |
| ttatccagcc | cgtggacacc | ccatttgagg | aactcctttc | tgagcacccc | agccctgaac | 540 |
| cagtcaccag | tcccccgctg | gtgacagagg | tgacagaggt | cgtagaagag | tccagccaga | 600 |
| aagctaccac | catctctacc | accacatcta | ccaccgcggc | caccaccaca | ggggcccaa | 660 |
| ctatggccac | agcacctgcc | acagcagcca | ccactgcccc | tagcactccc | gaggcgcccc | 720 |
| ctgccacggc | taccgtggct | gacgtaagga | ccaccggcat | acaggggatg | ctgcctcttc | 780 |
| ccctgaccac | agctgccaca | gccaagatca | ctacccccagc | agcaccctca | ccacccacta | 840 |
| ctgtggctac | cttggacaca | gaggccccga | cacctaggct | ggtcaacaca | gctacctcga | 900 |
| ggccacgagc | ccttcctcgg | ccagtcacca | cccaggagcc | tgatgttgct | gagaggagta | 960 |
| ccctgccgtt | ggggaccacg | gctcctggac | ccacggagat | ggctcagacc | ccaactccag | 1020 |
| agtcccttct | gaccaccatc | caggatgagc | cagaggtgcc | agtaagtggg | gggcccagcg | 1080 |
| gggactttga | gcttcaagaa | gagaccacgc | agccggacac | ggccaatgag | gtggtggctg | 1140 |
| tggaaggagc | cgcggccaag | ccgtcacctc | cactggggac | actgcccaag | ggtgccgcc | 1200 |
| caggccctgg | cctccacgac | aatgccatcg | attcgggcag | ctcggccgcc | cagctccctc | 1260 |
| agaagagcat | actggagcgg | aaggaggtgc | tcgtagccgt | gatcgtgggt | gggggtggtgg | 1320 |
| gcgccctctt | cgctgccttc | ctggtcacgc | tgctcatcta | ccgcatgaag | aagaaggacg | 1380 |
| aaggcagcta | caccttggaa | gaacccaagc | aggcaagcgt | cacgtaccag | aaacctgaca | 1440 |
| agcaggagga | gttctacgct | tagcagagcc | acagtgcctc | ctgcagcctc | cactccgcct | 1500 |

```
cgcccagtcc ctggccccag cagcagccca ggcctgatcc tgggcctggg cctgggcctg    1560
ggatggagcc tggccctgct tctttctgct caggctgcta gcgtaacaca gactgtccta    1620
aggagcagag gtgctgccat ctgccccaga ctgtgtcctt atgacccctt ctttggtccc    1680
attccctcca gcccggggct tcaggacctt gtgtcccatg acaagagga aggaagccct    1740 gggttgctgg ttgaaacagg ggcagggca gggttaagat ggcccacagt gcttgctgat     1800
gtcctcttct tgctccagag gccaccatgc tggcttctag aaccaataat acatggtaca    1860
tctagccctc caattcaaaa tcacccagat gctgtggcct cgagctgctg tcccaaggcc    1920
tctctcttga caggagggtg ccctttgtca ccagcctgag ctcatgatgg ggtcaccgcc    1980
ccctccccct gccaaatgca caggtcccca ggctgcacct cttcctgcat gcctcccag    2040 ggaaagggct tccttcagtg tacagggcag ccagtggtaa gtgaggccag tctagcatcc    2100
ctcctgagag gggatgccac atagcctccg tcaaccacta ctagaatcct aaaatgcatt    2160
cacacaggag acaaaaacat acccagtcct gaccacccag ccagcgagac atcacacaga    2220
tgcaccacct tcacgcagtg ctcagccatc ctgatgcttc tgctacatcg taggccactg    2280
tcattgtcac cagtggcgac cacaccacct tcctcccaat ctattctctt tacacacatt    2340
ggtcctgcat ctggctcctc taaccatcca ggtcactgag gaaggcagga ccgagttgta    2400
ggcatcagcc catattgggt cccccagagt cactctattc cacttggtcc ccaccatgac    2460
acctatacca gccacactga tgctgatccc agctgacgtc agtcacaagc ccacacagtt    2520
aatgcaggct ctccctcccc cactgtggct catagagaag tttggggcta gcctccacca    2580
gccaagtttg aagcaagaag ggagctaggg cctcccagga ccaaggcgct gtgtgggttg    2640
tccctggtct ccatgtatct cctttctgct ctgagccagg agctgtctct gcctcccagg    2700
acacgtgtct ccaaagtgcc tgtgagggtg ggctccgccc aggccctctg tgtccctgc    2760 cctgccctgg cctggtgagg ccaacctcag gcctacctac cctgggtcct ttctgtggac    2820
acaactgacc aggcaacttg gcagttctgg ctatatccag atgaacccat agcccaccag    2880
gctcatccca atgctatagg ctctgagaat cattgatggg gacaagggtg tcacaggcct    2940
caagtctacc atcctgtctc tgttatcctt agaagtgggg ctatttcaga ggtatttaaa    3000
atgtgggggg tcaccattct ctttgtgaaa gggccatgcc gaaggagctc tcagcaccaa    3060
agggacacag cttgggtagt gactggccgg caccccctcca ccatctctca catgtcccag    3120
gttcagtcag gtgaccacat ggtttctttc tgtttcattt taaagaatcc ctgacagcag    3180
agttgggcag actgaagaac cacatctggg taatggacag gatctaggca gttggcacag    3240
cttgtctttc tggggtgggg gtggaggggg tgtcccctg tcaggctctg ttctgtcttc    3300
cagacctcca tgactccctt gatgggactt tagagttttg taagccagtc ggcctggtct    3360
ttaagtgggg gggaaggaat gagaggcgtc ctaaacccat gagatgtgga ggaggggagct    3420 tggccaagat cttccctgca gcaggggctg ggtaggggcgt agaggagagc cagtgtccca    3480
gaccctccca ctcctccctg gtaagctgca gtcttgggga ctagagcttt ggaaagagag    3540
gctcagcagc tgggcgaggc aacctccagg tactcagccc aagggacac cacgaccagg    3600 gcaggaggcc ccagcttctg tgtgttgggcta gggttcactt ctcacatctc agggtggctc   3660
tggccctggg gctatgggtt tggcatcctg ataccagcat ccttaatgtg tcagcatctg    3720
agagaagagg cagtgggtct taagtatggg gtccgggctc caaggccaac gcctaggctt    3780
catggccatg gcgtttgacc tgaaggttaa tggtgtgagc agcccagata aactgggcta    3840
```

-continued

```
gcctggtgag gccaggacga tttaagagaa ctcagttcca agggtgaact gaattcttcc   3900
tagtgcaatg tgggtgcggg gttcccaccc tgccccagaa acagtgcggt acatacagag   3960
cctgtccaaa ggagtccaga gacacctcag tgctcctggg aaggtattca ggacaccggc   4020
ttgcctggag acacaatgca ttctgaatca gaggtggtga tgtgtcctgg acttctctgg   4080
gccctggttt ccctagagag taagacatgc tggggccaga gcactgaaga gctaagcttc   4140
atctctcttg ggggccagac tagggactct atgtgtaagg ttgattctcc ttgattgcca   4200
gaggcatgtg ggtgacagcc aggactggct gagcagatct gcagcaagag cttaggatgc   4260
tggggccaga cccctgggc ttggcttagc tactcatcag gcctcctggc tggggctcga   4320
gcttcagaga gcagagccaa cgctgctctc agggcagttg tggctccctg gctgtcctg    4380
gctttctcct gggatgtgcc tcccagcctt ggtgtctgta aatagaagcc cacactgtac   4440
agatctacag agaggcccaa actgggctct ggtgtcacca tctgaggggc tgatggcctg   4500
gcttccccca ggtgccctgt gggtgcttgg gtatgcctgg cccggcgtg gtgaatgcat    4560
gtaaatactt cgtagacagt gtggctccag agagcccct gagacagtgt ccccccacc    4620
ttactggttc atcctctctc ctgtacagag ccctcccagc ccctgggcca ccaggatcag   4680
gggttacctc ccttccccag acctttccta cccgttctct ccctataacc tgtttattaa   4740
ccaaccctgt cctgagttca tggccaaaac ttaaataaga aaggaggag agggtcagat     4800
ggataaagat aaagatacca aggcctggtc catccttacc atgggcgctc gtacacccct   4860
ggcttgggaa ggacagggct tgctttgttt tgttttctgt tagttttgt ttttaacat     4920
ttccctgtgc tgtgcccatt tataagagga aataaaatta agctgaaaga tg           4972
```

<210> SEQ ID NO 46
<211> LENGTH: 442
<212> TYPE: PRT
<213> ORGANISM: Human

<400> SEQUENCE: 46

```
Met Lys Pro Gly Pro Pro Arg Arg Gly Thr Ala Gln Gly Gln Arg Val
1               5                   10                  15

Asp Thr Ala Thr His Ala Pro Gly Ala Arg Gly Leu Leu Leu Pro Pro
            20                  25                  30

Leu Leu Leu Leu Leu Leu Ala Gly Arg Ala Ala Gly Ala Gln Arg Trp
        35                  40                  45

Arg Asn Glu Asn Phe Glu Arg Pro Val Asp Leu Glu Gly Ser Gly Asp
    50                  55                  60

Asp Asp Ser Phe Pro Asp Glu Leu Asp Asp Leu Tyr Ser Gly Ser
65                  70                  75                  80

Gly Ser Gly Tyr Phe Glu Gln Glu Ser Gly Leu Glu Thr Ala Met Arg
                85                  90                  95

Phe Ile Pro Asp Met Ala Leu Ala Ala Pro Thr Ala Pro Ala Met Leu
            100                 105                 110

Pro Thr Thr Val Ile Gln Pro Val Asp Thr Pro Phe Glu Glu Leu Leu
        115                 120                 125

Ser Glu His Pro Ser Pro Glu Pro Val Thr Ser Pro Pro Leu Val Thr
    130                 135                 140

Glu Val Thr Glu Val Val Glu Glu Ser Ser Gln Lys Ala Thr Thr Ile
145                 150                 155                 160

Ser Thr Thr Thr Ser Thr Thr Ala Ala Thr Thr Thr Gly Ala Pro Thr
                165                 170                 175
```

```
Met Ala Thr Ala Pro Ala Thr Ala Thr Ala Pro Ser Thr Pro
            180                 185                 190

Glu Ala Pro Pro Ala Thr Ala Thr Val Ala Asp Val Arg Thr Thr Gly
        195                 200                 205

Ile Gln Gly Met Leu Pro Leu Pro Leu Thr Thr Ala Ala Thr Ala Lys
    210                 215                 220

Ile Thr Thr Pro Ala Ala Pro Ser Pro Pro Thr Thr Val Ala Thr Leu
225                 230                 235                 240

Asp Thr Glu Ala Pro Thr Pro Arg Leu Val Asn Thr Ala Thr Ser Arg
                245                 250                 255

Pro Arg Ala Leu Pro Arg Pro Val Thr Thr Gln Glu Pro Asp Val Ala
            260                 265                 270

Glu Arg Ser Thr Leu Pro Leu Gly Thr Thr Ala Pro Gly Pro Thr Glu
        275                 280                 285

Met Ala Gln Thr Pro Thr Pro Glu Ser Leu Leu Thr Thr Ile Gln Asp
    290                 295                 300

Glu Pro Glu Val Pro Val Ser Gly Gly Pro Ser Gly Asp Phe Glu Leu
305                 310                 315                 320

Gln Glu Glu Thr Thr Gln Pro Asp Thr Ala Asn Glu Val Val Ala Val
                325                 330                 335

Glu Gly Ala Ala Ala Lys Pro Ser Pro Pro Leu Gly Thr Leu Pro Lys
            340                 345                 350

Gly Ala Arg Pro Gly Pro Gly Leu His Asp Asn Ala Ile Asp Ser Gly
        355                 360                 365

Ser Ser Ala Ala Gln Leu Pro Gln Lys Ser Ile Leu Glu Arg Lys Glu
    370                 375                 380

Val Leu Val Ala Val Ile Val Gly Gly Val Val Gly Ala Leu Phe Ala
385                 390                 395                 400

Ala Phe Leu Val Thr Leu Leu Ile Tyr Arg Met Lys Lys Lys Asp Glu
                405                 410                 415

Gly Ser Tyr Thr Leu Glu Glu Pro Lys Gln Ala Ser Val Thr Tyr Gln
            420                 425                 430

Lys Pro Asp Lys Gln Glu Glu Phe Tyr Ala
        435                 440

<210> SEQ ID NO 47
<211> LENGTH: 3669
<212> TYPE: DNA
<213> ORGANISM: Human

<400> SEQUENCE: 47
gcctgctgcc gcctgggccc cgccgagcgg agctagcgcc gcgcgcagag cacacgctcg      60
cgctccagct cccctcctgc gcggttcatg actgtgtccc ctgaccgcag cctctgcgag     120
cccccgccgc aggaccacgg cccgctcccc gccgccgcga gggcccccgag cgaaggaagg    180 aagggaggcg cgctgtgcgc cccgcggagc ccgcgaaccc cgctcgctgc cggctgccca    240
gcctggctgg caccatgctg cccgcgcgct gcgcccgcct gctcacgccc cacttgctgc    300
tggtgttggt gcagctgtcc cctgctcgcg gccaccgcac cacaggcccc aggtttctaa    360
taagtgaccg tgacccacag tgcaacctcc actgctccag gactcaaccc aaacccatct    420 gtcctctga tggcaggtcc tacgagtcca tgtgtgagta ccagcgagcc aagtgccgag    480
acccgaccct gggcgtggtg catcgaggta gatgcaaaga tgctggccag agcaagtgtc    540
gcctggagcg ggctcaagcc ctggagcaag ccaagaagcc tcaggaagct gtgtttgtcc    600
```

| | |
|---|---|
| cagagtgtgg cgaggatggc tcctttaccc aggtgcagtg ccatacttac actgggtact | 660 |
| gctggtgtgt cacccggat gggaagccca tcagtggctc ttctgtgcag aataaaactc | 720 |
| ctgtatgttc aggttcagtc accgacaagc ccttgagcca gggtaactca ggaaggaaag | 780 |
| atgacgggtc taagccgaca cccacgatgg agacccagcc ggtgttcgat ggagatgaaa | 840 |
| tcacagcccc aactctatgg attaaacact tggtgatcaa ggactccaaa ctgaacaaca | 900 |
| ccaacataag aaattcagag aaagtctatt cgtgtgacca ggagaggcag agtgccctgg | 960 |
| aagaggccca gcagaatccc cgtgagggta ttgtcatccc tgaatgtgcc cctgggggac | 1020 |
| tctataagcc agtgcaatgc caccagtcca ctggctactg ctggtgtgtg ctggtggaca | 1080 |
| cagggcgccc gctgcctggg acctccacac gctacgtgat gcccagttgt gagagcgacg | 1140 |
| ccagggccaa gactacagag gcggatgacc ccttcaagga cagggagcta ccaggctgtc | 1200 |
| cagaagggaa gaaaatggag tttatcacca gcctactgga tgctctcacc actgacatgg | 1260 |
| ttcaggccat taactcagca gcgcccactg gaggtgggag gttctcagag ccagacccca | 1320 |
| gccacaccct ggaggagcgg gtagtgcact ggtatttcag ccagctggac agcaatagca | 1380 |
| gcaacgacat taacaagcgg gagatgaagc cttcaagcg ctacgtgaag aagaaagcca | 1440 |
| agcccaagaa atgtgcccgg cgtttcaccg actactgtga cctgaacaaa gacaaggtca | 1500 |
| tttcactgcc tgagctgaag ggctgcctgg gtgttagcaa agaaggacgc ctcgtctaag | 1560 |
| gagcagaaaa cccaagggca ggtggagagt ccagggaggc aggatggatc accagacacc | 1620 |
| taaccttcag cgttgcccat ggccctgcca catcccgtgt aacataagtg gtgcccacca | 1680 |
| tgtttgcact tttaataact cttacttgcg tgttttgttt ttggtttcat tttaaaacac | 1740 |
| caatatctaa taccacagtg ggaaaaggaa agggaagaaa gactttattc tctctcttat | 1800 |
| tgtaagtttt tggatctgct actgacaact tttagagggt tttgggggg tgggggaggg | 1860 |
| tgttgttggg gcctgagaag aaagagattt atatgctgta tataaatata tatgtaaatt | 1920 |
| gtatagttct tttgtacagg cattggcatt gctgtttgtt tatttctctc cctctgcctg | 1980 |
| ctgtgggtgg tgggcactct ggacacatag tccagctttc taaaatccag gactctatcc | 2040 |
| tgggcctact aaacttctgt ttggagactg acccttgtgt ataaagacgg gagtcctgca | 2100 |
| attgtactgc ggactccacg agttcttttc tggtgggagg actatattgc cccatgccat | 2160 |
| tagttgtcaa aattgataag tcacttggct ctcggccttg tccagggagg ttgggctaag | 2220 |
| gagagatgga aactgccctg ggagaggaag ggagtccaga tcccatgaat agcccacaca | 2280 |
| ggtaccggct ctcagagggt ccgtgcattc ctgctctccg gaccccaaa gggcccagca | 2340 |
| tggtgggtg caccagtatc ttagtgaccc tcggagcaaa ttatccacaa aggatttgca | 2400 |
| ttacgtcact cgaaacgttt tcatccatgc ttagcatcta ctctgtataa cgcatgagag | 2460 |
| gggaggcaaa gaagaaaagg acacacggaa gggcctttaa aaaagtagat atttaatatc | 2520 |
| taagcagggg aggggacagg acagaaagcc tgcactgagg ggtgcggtgc aacagggaa | 2580 |
| actcttcacc tccctgcaaa cctaccagtg aggctcccag agacgcagct gtctcagtgc | 2640 |
| ccaggggcag attgggtgtg acctctccac tcctccatct cctgctgttg tcctagtggc | 2700 |
| tatcacaggc ctgggtgggt gggttggggg aagtgtcagt caccttgttg gtaacactaa | 2760 |
| agttgttttg ttggtttttt aaaaacccaa tactgaggtt cttcctgttc cctcaagttt | 2820 |
| tcttatgggc ttccaggctt taagctaatt ccagaagtaa aactgatctt gggtttccta | 2880 |
| ttctgcctcc cctagaaggg caggggtgat aacccagcta cagggaaatc ccggcccagc | 2940 |
| tttccacagg catcacaggc atcttccgcg gattctaggg tgggctgccc agccttctgg | 3000 |

```
tctgaggcgc agctccctct gcccaggtgc tgtgcctatt caagtggcct tcaggcagag    3060
cagcaagtgg cccttagcgc cccttcccat aagcagctgt ggtggcagtg agggaggttg    3120
ggtagccctg gactggtccc ctcctcagat caccccttgca aatctggcct catcttgtat    3180
tccaacccga catccctaaa agtacctcca cccgttccgg gtctggaagg cgttggcacc    3240
acaagcactg tccctgtggg aggagcacaa ccttctcggg acaggatctg atggggtctt    3300
gggctaaagg aggtccctgc tgtcctggag aaagtcctag aggttatctc aggaatgact    3360
ggtggccctg ccccaacgtg gaaaggtggg aaggaagcct tctcccatta gccccaatga    3420
gagaactcaa cgtgccggag ctgagtgggc cttgcacgag acactggccc cactttcagg    3480
cctggaggaa gcatgcacac atggagacgg cgcctgcctg tagatgtttg gatcttcgag    3540
atctccccag gcatcttgtc tcccacagga tcgtgtgtgt aggtggtgtt gtgtggtttt    3600
cctttgtgaa ggagagaggg aaactatttg tagcttgttt tataaaaaat aaaaaatggg    3660
taaatcttg                                                            3669
```

<210> SEQ ID NO 48
<211> LENGTH: 434
<212> TYPE: PRT
<213> ORGANISM: Human

<400> SEQUENCE: 48

```
Met Leu Pro Ala Arg Cys Ala Arg Leu Leu Thr Pro His Leu Leu Leu
1               5                   10                  15

Val Leu Val Gln Leu Ser Pro Ala Arg Gly His Arg Thr Thr Gly Pro
            20                  25                  30

Arg Phe Leu Ile Ser Asp Arg Asp Pro Gln Cys Asn Leu His Cys Ser
        35                  40                  45

Arg Thr Gln Pro Lys Pro Ile Cys Ala Ser Asp Gly Arg Ser Tyr Glu
    50                  55                  60

Ser Met Cys Glu Tyr Gln Arg Ala Lys Cys Arg Asp Pro Thr Leu Gly
65                  70                  75                  80

Val Val His Arg Gly Arg Cys Lys Asp Ala Gly Gln Ser Lys Cys Arg
                85                  90                  95

Leu Glu Arg Ala Gln Ala Leu Glu Gln Ala Lys Lys Pro Gln Glu Ala
            100                 105                 110

Val Phe Val Pro Glu Cys Gly Glu Asp Gly Ser Phe Thr Gln Val Gln
        115                 120                 125

Cys His Thr Tyr Thr Gly Tyr Cys Trp Cys Val Thr Pro Asp Gly Lys
    130                 135                 140

Pro Ile Ser Gly Ser Ser Val Gln Asn Lys Thr Pro Val Cys Ser Gly
145                 150                 155                 160

Ser Val Thr Asp Lys Pro Leu Ser Gln Gly Asn Ser Gly Arg Lys Asp
                165                 170                 175

Asp Gly Ser Lys Pro Thr Pro Thr Met Glu Thr Gln Pro Val Phe Asp
            180                 185                 190

Gly Asp Glu Ile Thr Ala Pro Thr Leu Trp Ile Lys His Leu Val Ile
        195                 200                 205

Lys Asp Ser Lys Leu Asn Asn Thr Asn Ile Arg Asn Ser Glu Lys Val
    210                 215                 220

Tyr Ser Cys Asp Gln Glu Arg Gln Ser Ala Leu Glu Glu Ala Gln Gln
225                 230                 235                 240

Asn Pro Arg Glu Gly Ile Val Ile Pro Glu Cys Ala Pro Gly Gly Leu
```

```
                   245                 250                 255
Tyr Lys Pro Val Gln Cys His Gln Ser Thr Gly Tyr Cys Trp Cys Val
            260                 265                 270

Leu Val Asp Thr Gly Arg Pro Leu Pro Gly Thr Ser Thr Arg Tyr Val
            275                 280                 285

Met Pro Ser Cys Glu Ser Asp Ala Arg Ala Lys Thr Thr Glu Ala Asp
        290                 295                 300

Asp Pro Phe Lys Asp Arg Glu Leu Pro Gly Cys Pro Glu Gly Lys Lys
305                 310                 315                 320

Met Glu Phe Ile Thr Ser Leu Leu Asp Ala Leu Thr Thr Asp Met Val
                325                 330                 335

Gln Ala Ile Asn Ser Ala Ala Pro Thr Gly Gly Gly Arg Phe Ser Glu
            340                 345                 350

Pro Asp Pro Ser His Thr Leu Glu Glu Arg Val Val His Trp Tyr Phe
        355                 360                 365

Ser Gln Leu Asp Ser Asn Ser Ser Asn Asp Ile Asn Lys Arg Glu Met
    370                 375                 380

Lys Pro Phe Lys Arg Tyr Val Lys Lys Ala Lys Pro Lys Lys Cys
385                 390                 395                 400

Ala Arg Arg Phe Thr Asp Tyr Cys Asp Leu Asn Lys Asp Lys Val Ile
                405                 410                 415

Ser Leu Pro Glu Leu Lys Gly Cys Leu Gly Val Ser Lys Glu Gly Arg
            420                 425                 430

Leu Val

<210> SEQ ID NO 49
<211> LENGTH: 5802
<212> TYPE: DNA
<213> ORGANISM: Human

<400> SEQUENCE: 49
cggacttctg caggcaatcg cgaagctgct atccagttct gccacggtct ctcccggcgc     60
accggcagtc tcagcgtctt caccggactc agcgtccttg tccttcactt cacctttgcc    120
acctctccgg gttactgagc cccggtgcac acaggctccg tgttgggcac aaaggctcca    180
ccatggagct cctgcgggga ctaggtgtcc tgttcctgtt gcatatgtgt ggaagcaacc    240
gcattccaga gtctggggga gataacggtg tgtttgacat ctttgaactc attggaggtg    300
cacgaagggg ccccggtcgc cgactggtga agggccaaga tctatccagc cccgccttcc    360
gcattgagaa tgccaacctg atccccgctg tgccggatga caagttccaa gacctactgg    420
acgctgtgtg ggccgacaaa ggcttcatct tcctggcttc cttgaggcag atgaagaaga    480
cccgggcac actcctggct gtggaacgga agacaacac tggccagatc ttcagtgtgg    540
tctccaacgg caaagctggc accctggacc tgagcctgag cctgccaggg aagcaacaag    600
tggtgtcagt ggaggaagct ctcctggcca ctggccagtg aagagcatc acgctgtttg    660
ttcaagagga ccgggctcaa ctctacatag actgtgataa gatggagagc gcggagctgg    720
atgtacccat ccagagcatc ttcaccaggg atctggccag cgttgccagg ctccgagttg    780
caaagggaga tgtcaatgac aattttcagg gggtgctgca gaatgtgagg tttgtctttg    840
gaaccacccc agaagacatt ctcaggaaca aaggctgctc cagctcagct accaacgtcc    900
ttcttaccct tgacaacaac gtggtgaacg gttccagccc tgctatccgc accaactaca    960
tcggccacaa aacaaaggac ctccaagcta tctgtggcct ctcctgtgat gaactatcca   1020
```

-continued

```
gcatggtcct ggaactgaag ggcctgcgca ccatcgtgac cactctgcag gacagcatcc      1080
gaaaagtgac ggaagagaac agagagctgg tcagtgagct gaagcggcct cccctctgct      1140
ttcacaatgg agtccagtac aagaacaacg aggagtggac tgtagacagt tgcacagagt      1200
gtcactgcca gaactcggtt accatctgca aaaggtgtc ctgtcccatc atgccctgct       1260
ccaacgccac agttcctgat ggtgaatgct gcccacggtg ctggcccagc gactctgctg      1320
acgatggctg gtctccctgg tctgagtgga cctcctgctc tgccacatgt ggcaatggaa      1380
ttcagcaacg tggtcgttcc tgtgacagcc tcaacaacag atgcgagggc tcttcggtac      1440
agacaaggac ctgccacatt caggagtgtg acaaaagatt taaacaggat ggtggctgga      1500
gtcactggtc tccatggtcg tcctgttctg tgacctgtgg tgacggtgtg atcacaagga      1560
tccggctctg caactccccc agccccagagat gaacgggaa gccctgtgaa ggtgaagccc      1620
gggagaccaa agcctgcaag aaagacgcct gcccaattaa tggaggctgg ggtccctggt      1680
caccatggga catctgctct gtcacctgtg gaggaggagt gcagagacgc agccgactct      1740
gtaacaaccc cacaccccag tttggaggca agactgtgt tggcgatgtg acagaaaatc      1800
aagtttgcaa caagcaggac tgcccaattg atggatgcct gtccaatccc tgctttgctg      1860
gtgccaagtg tactagctac cctgatggta gctggaaatg tggtgcgtgt cctcctggct      1920
acagtggaaa tggcatccag tgcaaagacg tcgatgagtg caaagaagtg cctgatgctt      1980
gcttcaatca caacgagaaa catcggtgca agaaacacaga tcctggctac aactgcctgc      2040
cctgcccacc acgattcact ggctcacagc ccttcggccg aggtgtcgaa catgccatgg      2100
ccaacaaaca ggtgtgcaaa ccgcgaaacc ctgcacgga cgggacgcat gactgcaaca      2160
agaacgctaa gtgcaactac ctgggtcact acagtgaccc catgtaccgc tgtgagtgca      2220
agcccggcta tgcaggcaat ggcatcatct gcggagagga cacagacctg gacggctggc      2280
ctaatgaaaa cctggtgtgt gtggccaacg caacctacca ctgcaaaaag gacaactgcc      2340
ccaaccttcc caactcgggg caggaagact atgacaagga cgggattggc gatgcctgcg      2400
atgatgacga tgacaacgac aagatccccg atgacaggga caactgtcca ttccattaca      2460
acccagccca gtatgactat gacagagatg atgtgggaga ccgctgtgac aactgccccct      2520 acaaccacaa ccctgaccaa gcagacacag acaaaaacgg ggagggcgat gcctgtgctg      2580
tggacatcga tggagatgga atcctcaatg aacgagacaa ctgccagtac gtttacaacg      2640
tggaccagag ggacacggac atggatgggg ttggagatca gtgtgacaac tgcccctgg      2700 aacacaatcc agaccagctg gactctgact cagacctcat aggggacact tgtgacaaca      2760
atcaggacat cgatgaggat ggccatcaga acaatctgga caactgtccc tatgtgccta      2820
atgccaacca ggccgaccat gataaagatg caaaggaga tgcctgtgac catgacgatg      2880
acaatgacgg catccctgat acagagaca actgcaggct ggtgcccaat cctgaccaga      2940
aggactctga tgtgatggc cgaggtacg cctgcaaaga cgactttgac catgacaatg      3000
tgccagatat tgatgacatc tgtcctgaga atttgacat cagtgaaacc gatttccgac      3060
aattccagat gattcctcta gatcccaaag gaacctccca aaatgaccct aactgggttg      3120
tccgccatca gggcaaagaa cttgtccaga ctgtaaactg tgaccctgga cttgctgtag      3180
gttatgatga gtttaatgct gtggacttca gcggtaccct cttcatcaac accgagagag      3240
atgatgacta cgctggctt gtttcgggct accagtccag cagccgcttc tacgttgtga      3300
tgtggaaaca agtcacccag tcctactggg acaccaaccc cacaagggct cagggatact      3360
caggcctgtc tgtaaaggtt gtgaactcca ccaccggccc tggcgagcac ctgcggaatg      3420
```

```
cactgtggca cacaggaaac acccctggcc aggtgcgcac cctgtggcat gaccctcgcc    3480
acatcggctg gaaagatttc actgcataca gatggcgtct cagccacagg ccaaagaccg    3540
gttatatcag agtggtgatg tatgaaggaa agaaaatcat ggctgactcg ggacccatct    3600
atgacaaaac ctacgccggc ggtagactag gcctgttcgt cttctctcag gaaatggtgt    3660
tcttctcaga catgaaatac gagtgtcgag attcctaatc atcagctgcc aatcataacc    3720
agcgctggca atgcaccttc taaaaacaag ggctagagaa accccccacc cctgccggga    3780
tcgcctttcc tcgccttcct tgcctctctt cttgcatagt gtggacttgt aaagcctgag    3840
acctgcctca agaaaatgca gttttcaaac ccagagtcag cactcggcct ttaacgaatg    3900
agaatgcatc ttccaagacc atgaagagtt ccttgggttt gcttttggga aagccaaagc    3960
gcctatttac ttcccactag gaaggtgccc gctccactct gccttactca cagagccaga    4020
acttcttcga ggccacctct gagcagcaca cacagaagca ttttcaggca tgtcaaagaa    4080
aggaaaaaat gactcactag aactcaccgc caaacaacct ctgacatagg tcctgagatg    4140
tggggaggca ggagccaaag ctctagggag ggcatgtacc caagagatga ctgtatgaaa    4200
atgtggagga gctgttcggt actaaatcat tttcagggga cagacagact tgctgcattt    4260
ctgcatgctg ctggtgagag ctgattgacc caatcttcca cacaggcact tgagcaagca    4320
gggaagggag ggagatcata gcttctggac tttctcccct tgggcacttc tcacctgcag    4380
tggccagggt aggggtcaga agtgtgggcc atgctggctg cccttgactg gtcacgctga    4440
aactgttagc ttattctgca tgtacaacat gcatatgtat aaggacagct agagaacctt    4500
accgtctcag tgagctctag ctgcctccgc aggaggggca gtgcgccttt actttatggt    4560
tagaaaggca caaatttcct atcaacctaa ctaaaacatt cctttctctt ctttctttct    4620
ttctttcttt cttccttttt ctctcagtta ccatggattt ttccaaatct cttttggttt    4680
ttgtttaaca aatgctttaa caatgtaata tatttatttt gttcccctat ctggagggt    4740 tcgtcggaag gattgttact gaaacaggaa gcgtgggact atctgaatca tcttcgtagt    4800
gagtctttat gactgtaaga ttgtaaatac agattattta ttaaccctgt tctacctgga    4860
attagactgc atatagcaaa tgtttgcaag caggtagctg aggcggatca gcaaatctct    4920
ccaaaaccag tgtgtggaaa ggcagcagag gcagctgctt ttcatctggg gctcacagtg    4980
aatgatttgg actcctttgg cttccccttt gttttctctg tagtttcaag tggaattagg    5040
tggcggccgc ttgcattcac tcctccttgt aatggaagcc aggagtactc taaggcccac    5100
accacccctt gtgcctattt ccagggagaa gaaagaaaac acaatcacct tttctttatt    5160 tcatttttc cccaaaagag acaaggtgg aacttctata caaatattac ctcatttgtt    5220
gtgtgactga gtaaagaatt ttggattaag aagaaagagt ttaagtgtca ataaacttaa    5280
aactactgtt gtgtctaaaa agtcggtgtt gtacatagca taaaaatcct ttgccgagga    5340
tgatcccaag aaagaaacag ctttgtaatg ttaagtacaa cttctcaaag ttctggtttt    5400
gttctatcat cttttacacc gttgctttta tttttataaa ttattttctc gttgccattg    5460
gaatagagat ctcagactat gtagatatgc tatttaaata atttatcagg aaatactgcc    5520
tgtagagtta gtatttctgg ttttttatatg ttgcacactg aattgaagaa atgttggttt    5580
ttcttgtttc gttttagttt gtttcttttgg ttttgttttt gttttttgctt tttacttccc    5640 agttttgact ctttgccaat acccttttc ctaggaacgt gcttttttttt ttattttgta    5700 cacatttta tccattttac attctaaagc agtgtaactt gtatattact gtttcttatg    5760
```
tacaaggaac aacaataaat catatggaag tttatattta ta                          5802

<210> SEQ ID NO 50
<211> LENGTH: 1171
<212> TYPE: PRT
<213> ORGANISM: Human

<400> SEQUENCE: 50

Met Glu Leu Leu Arg Gly Leu Gly Val Leu Phe Leu Leu His Met Cys
1               5                   10                  15

Gly Ser Asn Arg Ile Pro Glu Ser Gly Asp Asn Gly Val Phe Asp
            20                  25                  30

Ile Phe Glu Leu Ile Gly Gly Ala Arg Arg Gly Pro Gly Arg Arg Leu
        35                  40                  45

Val Lys Gly Gln Asp Leu Ser Ser Pro Ala Phe Arg Ile Glu Asn Ala
50                  55                  60

Asn Leu Ile Pro Ala Val Pro Asp Asp Lys Phe Gln Asp Leu Leu Asp
65                  70                  75                  80

Ala Val Trp Ala Asp Lys Gly Phe Ile Phe Leu Ala Ser Leu Arg Gln
                85                  90                  95

Met Lys Lys Thr Arg Gly Thr Leu Leu Ala Val Glu Lys Asp Asn
            100                 105                 110

Thr Gly Gln Ile Phe Ser Val Val Ser Asn Gly Lys Ala Gly Thr Leu
        115                 120                 125

Asp Leu Ser Leu Ser Leu Pro Gly Lys Gln Gln Val Val Ser Val Glu
130                 135                 140

Glu Ala Leu Leu Ala Thr Gly Gln Trp Lys Ser Ile Thr Leu Phe Val
145                 150                 155                 160

Gln Glu Asp Arg Ala Gln Leu Tyr Ile Asp Cys Asp Lys Met Glu Ser
                165                 170                 175

Ala Glu Leu Asp Val Pro Ile Gln Ser Ile Phe Thr Arg Asp Leu Ala
            180                 185                 190

Ser Val Ala Arg Leu Arg Val Ala Lys Gly Asp Val Asn Asp Asn Phe
        195                 200                 205

Gln Gly Val Leu Gln Asn Val Arg Phe Val Phe Gly Thr Thr Pro Glu
    210                 215                 220

Asp Ile Leu Arg Asn Lys Gly Cys Ser Ser Ala Thr Asn Val Leu
225                 230                 235                 240

Leu Thr Leu Asp Asn Asn Val Val Asn Gly Ser Ser Pro Ala Ile Arg
                245                 250                 255

Thr Asn Tyr Ile Gly His Lys Thr Lys Asp Leu Gln Ala Ile Cys Gly
            260                 265                 270

Leu Ser Cys Asp Glu Leu Ser Ser Met Val Leu Glu Leu Lys Gly Leu
        275                 280                 285

Arg Thr Ile Val Thr Thr Leu Gln Asp Ser Ile Arg Lys Val Thr Glu
    290                 295                 300

Glu Asn Arg Glu Leu Val Ser Glu Leu Lys Arg Pro Pro Leu Cys Phe
305                 310                 315                 320

His Asn Gly Val Gln Tyr Lys Asn Asn Glu Glu Trp Thr Val Asp Ser
                325                 330                 335

Cys Thr Glu Cys His Cys Gln Asn Ser Val Thr Ile Cys Lys Lys Val
            340                 345                 350

Ser Cys Pro Ile Met Pro Cys Ser Asn Ala Thr Val Pro Asp Gly Glu
        355                 360                 365

```
Cys Cys Pro Arg Cys Trp Pro Ser Asp Ser Ala Asp Asp Gly Trp Ser
    370             375                 380

Pro Trp Ser Glu Trp Thr Ser Cys Ser Ala Thr Cys Gly Asn Gly Ile
385             390                 395                 400

Gln Gln Arg Gly Arg Ser Cys Asp Ser Leu Asn Asn Arg Cys Glu Gly
                405                 410                 415

Ser Ser Val Gln Thr Arg Thr Cys His Ile Gln Glu Cys Asp Lys Arg
            420                 425                 430

Phe Lys Gln Asp Gly Gly Trp Ser His Trp Ser Pro Trp Ser Ser Cys
        435                 440                 445

Ser Val Thr Cys Gly Asp Gly Val Ile Thr Arg Ile Arg Leu Cys Asn
    450                 455                 460

Ser Pro Ser Pro Gln Met Asn Gly Lys Pro Cys Glu Gly Glu Ala Arg
465             470                 475                 480

Glu Thr Lys Ala Cys Lys Lys Asp Ala Cys Pro Ile Asn Gly Gly Trp
                485                 490                 495

Gly Pro Trp Ser Pro Trp Asp Ile Cys Ser Val Thr Cys Gly Gly Gly
            500                 505                 510

Val Gln Arg Arg Ser Arg Leu Cys Asn Asn Pro Thr Pro Gln Phe Gly
            515                 520                 525

Gly Lys Asp Cys Val Gly Asp Val Thr Glu Asn Gln Val Cys Asn Lys
        530                 535                 540

Gln Asp Cys Pro Ile Asp Gly Cys Leu Ser Asn Pro Cys Phe Ala Gly
545                 550                 555                 560

Ala Lys Cys Thr Ser Tyr Pro Asp Gly Ser Trp Lys Cys Gly Ala Cys
        565                 570                 575

Pro Pro Gly Tyr Ser Gly Asn Gly Ile Gln Cys Lys Asp Val Asp Glu
            580                 585                 590

Cys Lys Glu Val Pro Asp Ala Cys Phe Asn His Asn Gly Glu His Arg
    595                 600                 605

Cys Lys Asn Thr Asp Pro Gly Tyr Asn Cys Leu Pro Cys Pro Pro Arg
    610                 615                 620

Phe Thr Gly Ser Gln Pro Phe Gly Arg Gly Val Glu His Ala Met Ala
625             630                 635                 640

Asn Lys Gln Val Cys Lys Pro Arg Asn Pro Cys Thr Asp Gly Thr His
                645                 650                 655

Asp Cys Asn Lys Asn Ala Lys Cys Asn Tyr Leu Gly His Tyr Ser Asp
        660                 665                 670

Pro Met Tyr Arg Cys Glu Cys Lys Pro Gly Tyr Ala Gly Asn Gly Ile
        675                 680                 685

Ile Cys Gly Glu Asp Thr Asp Leu Asp Gly Trp Pro Asn Glu Asn Leu
    690                 695                 700

Val Cys Val Ala Asn Ala Thr Tyr His Cys Lys Lys Asp Asn Cys Pro
705             710                 715                 720

Asn Leu Pro Asn Ser Gly Gln Glu Asp Tyr Asp Lys Asp Gly Ile Gly
            725                 730                 735

Asp Ala Cys Asp Asp Asp Asp Asp Asn Asp Lys Ile Pro Asp Asp Arg
        740                 745                 750

Asp Asn Cys Pro Phe His Tyr Asn Pro Ala Gln Tyr Asp Tyr Asp Arg
        755                 760                 765

Asp Asp Val Gly Asp Arg Cys Asp Asn Cys Pro Tyr Asn His Asn Pro
770                 775                 780

Asp Gln Ala Asp Thr Asp Lys Asn Gly Glu Gly Asp Ala Cys Ala Val
```

```
                785                 790                 795                 800
Asp Ile Asp Gly Asp Gly Ile Leu Asn Glu Arg Asp Asn Cys Gln Tyr
                    805                 810                 815

Val Tyr Asn Val Asp Gln Arg Asp Thr Asp Met Asp Gly Val Gly Asp
                820                 825                 830

Gln Cys Asp Asn Cys Pro Leu Glu His Asn Pro Asp Gln Leu Asp Ser
                835                 840                 845

Asp Ser Asp Leu Ile Gly Asp Thr Cys Asp Asn Gln Asp Ile Asp
            850                 855                 860

Glu Asp Gly His Gln Asn Asn Leu Asp Asn Cys Pro Tyr Val Pro Asn
865                 870                 875                 880

Ala Asn Gln Ala Asp His Asp Lys Asp Gly Lys Gly Asp Ala Cys Asp
                    885                 890                 895

His Asp Asp Asn Asp Gly Ile Pro Asp Asp Arg Asp Asn Cys Arg
            900                 905                 910

Leu Val Pro Asn Pro Asp Gln Lys Asp Ser Asp Gly Asp Gly Arg Gly
                915                 920                 925

Asp Ala Cys Lys Asp Asp Phe Asp His Asp Asn Val Pro Asp Ile Asp
930                 935                 940

Asp Ile Cys Pro Glu Asn Phe Asp Ile Ser Glu Thr Asp Phe Arg Gln
945                 950                 955                 960

Phe Gln Met Ile Pro Leu Asp Pro Lys Gly Thr Ser Gln Asn Asp Pro
                965                 970                 975

Asn Trp Val Val Arg His Gln Gly Lys Glu Leu Val Gln Thr Val Asn
                    980                 985                 990

Cys Asp Pro Gly Leu Ala Val Gly  Tyr Asp Glu Phe Asn  Ala Val Asp
                995                 1000                1005

Phe Ser  Gly Thr Phe Phe Ile  Asn Thr Glu Arg Asp  Asp Asp Tyr
    1010                1015                1020

Ala Gly  Phe Val Phe Gly Tyr  Gln Ser Ser Ser Arg  Phe Tyr Val
    1025                1030                1035

Val Met  Trp Lys Gln Val Thr  Gln Ser Tyr Trp Asp  Thr Asn Pro
    1040                1045                1050

Thr Arg  Ala Gln Gly Tyr Ser  Gly Leu Ser Val Lys  Val Val Asn
    1055                1060                1065

Ser Thr  Thr Gly Pro Gly Glu  His Leu Arg Asn Ala  Leu Trp His
    1070                1075                1080

Thr Gly  Asn Thr Pro Gly Gln  Val Arg Thr Leu Trp  His Asp Pro
    1085                1090                1095

Arg His  Ile Gly Trp Lys Asp  Phe Thr Ala Tyr Arg  Trp Arg Leu
    1100                1105                1110

Ser His  Arg Pro Lys Thr Gly  Tyr Ile Arg Val Val  Met Tyr Glu
    1115                1120                1125

Gly Lys  Lys Ile Met Ala Asp  Ser Gly Pro Ile Tyr  Asp Lys Thr
    1130                1135                1140

Tyr Ala  Gly Gly Arg Leu Gly  Leu Phe Val Phe Ser  Gln Glu Met
    1145                1150                1155

Val Phe  Phe Ser Asp Met Lys  Tyr Glu Cys Arg Asp  Ser
    1160                1165                1170

<210> SEQ ID NO 51
<211> LENGTH: 2242
<212> TYPE: DNA
<213> ORGANISM: Human
```

<400> SEQUENCE: 51

```
agttcccgcg gttcctccct ctcgagtgtg ctcctctagc tgctggcgct gtgggacgtg      60
ctggcattgc cagctttgcc agcatcgtgt ctctgcgtcc ccctctccct ccagccccca     120
cctctttcta cgcggccgcg catccactcc ctccttgctc cctcctctcc agcactccca     180
ggctcactcg caacggagac tggagacttg cacgcccagt cgtttaagta ggaacagctc     240
cagccccgcc agctgcagcc aaggcgagaa cttcacaagc agcacaggtt gggtcgctgc     300
ggcaggagtt gcaccaccag cgagaaggtc ctgagcacca tggctcggag aagagccttc     360
cctgctttcg cgctccggct ctggagcatc ctaccttgcc tgctcctgct gcgagcggat     420
gcagggcagc cacctgagga gagcttgtac ctgtggatcg acgcccatca ggctagagtg     480
ctcataggat ttgaagaaga cattctgatt gtctcggagg ggaaaatggc cccctttaca     540
catgatttca ggaaagccca acaaagaatg ccagccattc ctgtcaatat ccactccatg     600
aattttacct ggcaagctgc ggggcaggca gaatacttct acgagttcct gtctctgcgc     660
tccctggata aaggcatcat ggcagatcca actgtcaatg tccctttgct gggaacagtg     720
cctcacaagg catcagttgt tcaagttggt ttcccgtgtc tcggcaaaca agacggggta     780
gcagcatttg aagtgaatgt gattgtcatg aattctgaag caacaccat ccttaggacc     840
cctcagaatg ccatcttctt taaaacatgt caacaagctg agtgtcccgg agggtgtcga     900
aatggaggct tttgtaacga aaggcgggtc tgcgagtgtc cggatgggtt ctacgggcct     960
cactgtgaga aagccctgtg catacccga tgtatgaacg gtggtctgtg tgtcactcct    1020
ggcttctgca tctgcccccc tggattctac ggtgtcaact gtgacaaagc aaactgctca    1080
accacctgct taatggagg gacctgcttt tacccgggaa aatgtatttg ccctcctgga    1140
ctcgagggag agcagtgtga actcagcaaa tgcccccaac cctgccgaaa tggaggtaaa    1200
tgcattggta aaagcaagtg taagtgcccg aaaggttacc aaggagacct gtgctctaag    1260
cccgtctgcg agcctggctg tggtgcccac ggaacctgcc acgaacccaa caagtgccag    1320
tgtcgagagg gctggcacgg cagacactgc aataagaggt atggagccag cctcatgcat    1380
gccccgaggc cagcaggcgc cgggctggag cgacacacgc cttcacttaa aaaggctgag    1440
gatagaaggg atccacctga atccaattac atctggtgaa cccctacccc accatctgaa    1500
acggttcaag ttcacccggg ttcacagcct ttgttaacct ttcgcgtgtt ggatgttcaa    1560
atgctgttca ttcactttta gaacgccggc ctgaattttta ttagcttcat tataaatcac    1620
tgggctgata tctactcttc cttttaggtt ttctaagcgt gtctagcatg atggtataga    1680
ttttcttcct tcagtccttt tgggacagat cttatattgt gtcagttgat caggttaaaa    1740
agaaaaaaaa tatctgtctt ttcagtgtgt agttgacaga tacttgcaaa atcacaacac    1800
atttgtggtc ttagaatggg gagtgttaga gaggttaaac tgggcagaga tgcataaatt    1860
acaaggtttc ggataaagcc aatagcagcg tttaagctac agtatttcca attttattgt    1920
caaatatttg gacatctgtc taattaatac ttcaattgcc cccccccca tcttgaatgc    1980
atacaatcta tttcacccctt gctgttactc tagacagttc agttttgatg gggcggggga    2040
caaagtttaa aaaaattaca ctgagttagc ggcatttaaa caatataata tattgtaaac    2100
acgacgagat aaggaatata atgtatgaag cctttgcatt ggatggaagc aatataatat    2160
attgtaaaca aaacacagct cttacatagt aaacgttta tactgtttgt atgtatgaaa    2220
taaaggtgac gctttcactt tc                                             2242
```

<210> SEQ ID NO 52
<211> LENGTH: 379
<212> TYPE: PRT
<213> ORGANISM: Human

<400> SEQUENCE: 52

```
Met Ala Arg Arg Arg Ala Phe Pro Ala Phe Ala Leu Arg Leu Trp Ser
1               5                   10                  15

Ile Leu Pro Cys Leu Leu Leu Leu Arg Ala Asp Ala Gly Gln Pro Pro
                20                  25                  30

Glu Glu Ser Leu Tyr Leu Trp Ile Asp Ala His Gln Ala Arg Val Leu
            35                  40                  45

Ile Gly Phe Glu Glu Asp Ile Leu Ile Val Ser Glu Gly Lys Met Ala
        50                  55                  60

Pro Phe Thr His Asp Phe Arg Lys Ala Gln Gln Arg Met Pro Ala Ile
65                  70                  75                  80

Pro Val Asn Ile His Ser Met Asn Phe Thr Trp Gln Ala Ala Gly Gln
                85                  90                  95

Ala Glu Tyr Phe Tyr Glu Phe Leu Ser Leu Arg Ser Leu Asp Lys Gly
            100                 105                 110

Ile Met Ala Asp Pro Thr Val Asn Val Pro Leu Leu Gly Thr Val Pro
        115                 120                 125

His Lys Ala Ser Val Val Gln Val Gly Phe Pro Cys Leu Gly Lys Gln
130                 135                 140

Asp Gly Val Ala Ala Phe Glu Val Asn Val Ile Val Met Asn Ser Glu
145                 150                 155                 160

Gly Asn Thr Ile Leu Arg Thr Pro Gln Asn Ala Ile Phe Phe Lys Thr
                165                 170                 175

Cys Gln Gln Ala Glu Cys Pro Gly Gly Cys Arg Asn Gly Gly Phe Cys
            180                 185                 190

Asn Glu Arg Arg Val Cys Glu Cys Pro Asp Gly Phe Tyr Gly Pro His
        195                 200                 205

Cys Glu Lys Ala Leu Cys Ile Pro Arg Cys Met Asn Gly Gly Leu Cys
    210                 215                 220

Val Thr Pro Gly Phe Cys Ile Cys Pro Pro Gly Phe Tyr Gly Val Asn
225                 230                 235                 240

Cys Asp Lys Ala Asn Cys Ser Thr Thr Cys Phe Asn Gly Gly Thr Cys
                245                 250                 255

Phe Tyr Pro Gly Lys Cys Ile Cys Pro Pro Gly Leu Glu Gly Glu Gln
            260                 265                 270

Cys Glu Leu Ser Lys Cys Pro Gln Pro Cys Arg Asn Gly Gly Lys Cys
        275                 280                 285

Ile Gly Lys Ser Lys Cys Lys Cys Pro Lys Gly Tyr Gln Gly Asp Leu
    290                 295                 300

Cys Ser Lys Pro Val Cys Glu Pro Gly Cys Gly Ala His Gly Thr Cys
305                 310                 315                 320

His Glu Pro Asn Lys Cys Gln Cys Arg Glu Gly Trp His Gly Arg His
                325                 330                 335

Cys Asn Lys Arg Tyr Gly Ala Ser Leu Met His Ala Pro Arg Pro Ala
            340                 345                 350

Gly Ala Gly Leu Glu Arg His Thr Pro Ser Leu Lys Lys Ala Glu Asp
        355                 360                 365

Arg Arg Asp Pro Pro Glu Ser Asn Tyr Ile Trp
    370                 375
```

<210> SEQ ID NO 53
<211> LENGTH: 264
<212> TYPE: PRT
<213> ORGANISM: Human

<400> SEQUENCE: 53

```
Met Pro Arg Ser Phe Leu Val Arg Lys Pro Ser Asp Pro Arg Lys
1               5                   10                  15

Pro Asn Tyr Ser Glu Leu Gln Asp Ala Cys Val Glu Phe Thr Phe Gln
            20                  25                  30

Gln Pro Tyr Asp Gln Ala His Leu Leu Ala Ala Ile Pro Pro Pro Glu
        35                  40                  45

Val Leu Asn Pro Ala Ala Ser Leu Pro Thr Leu Ile Trp Asp Ser Leu
50                  55                  60

Leu Val Pro Gln Val Arg Pro Val Ala Trp Ala Thr Leu Pro Leu Arg
65                  70                  75                  80

Glu Ser Pro Lys Ala Val Glu Leu Thr Ser Leu Ser Asp Glu Asp Ser
                85                  90                  95

Gly Lys Ser Ser Gln Pro Pro Ser Pro Pro Ser Pro Ala Pro Ser Ser
            100                 105                 110

Phe Ser Ser Thr Ser Ala Ser Ser Leu Glu Ala Glu Ala Phe Ile Ala
        115                 120                 125

Phe Pro Gly Leu Gly Gln Leu Pro Lys Gln Leu Ala Arg Leu Ser Val
    130                 135                 140

Ala Lys Asp Pro Gln Ser Arg Lys Ile Phe Asn Cys Lys Tyr Cys Asn
145                 150                 155                 160

Lys Glu Tyr Leu Ser Leu Gly Ala Leu Lys Met His Ile Arg Ser His
                165                 170                 175

Thr Leu Pro Cys Val Cys Thr Thr Cys Gly Lys Ala Phe Ser Arg Pro
            180                 185                 190

Trp Leu Leu Gln Gly His Val Arg Thr His Thr Gly Glu Lys Pro Phe
        195                 200                 205

Ser Cys Ser His Cys Asn Arg Ala Phe Ala Asp Arg Ser Asn Leu Arg
    210                 215                 220

Ala His Leu Gln Thr His Ser Asp Val Lys Arg Tyr Gln Cys Gln Ala
225                 230                 235                 240

Cys Ala Arg Thr Phe Ser Arg Met Ser Leu Leu His Lys His Gln Glu
                245                 250                 255

Ser Gly Cys Ser Gly Gly Pro Arg
            260
```

<210> SEQ ID NO 54
<211> LENGTH: 1613
<212> TYPE: DNA
<213> ORGANISM: Human

<400> SEQUENCE: 54

| | | | | | | |
|---|---|---|---|---|---|---|
| cggagttgac | taccgacctt | gcgcgacccg | gtgaccccga | ctacctaggt | cgctctggcc | 60 |
| aacatgccgc | gctccttcct | ggtcaggaag | ccgtccgacc | ccgccggaa | gcccaactat | 120 |
| agcgagctgc | aggacgcgtg | tgtggagttc | accttccagc | agccctacga | ccaggcccac | 180 |
| ctgctggccg | ccatccctcc | gcccgaggtc | ctcaacccg | ccgcttcgct | gccaccctc | 240 |
| atctgggact | ctctcctggt | accccaagtg | cggccggttg | cctgggccac | cctcccgctg | 300 |
| cgggagagcc | ccaaggccgt | agagctgacc | tcgctgtccg | atgaggacag | tggcaaaagc | 360 |

| | |
|---|---|
| tcccagccgc ccagcccgcc ctcgccggcg ccgtcgtcct tctcgtccac ctcggcctcg | 420 |
| tccctggagg ccgaggcctt catcgccttc cctggcttgg gccaacttcc caagcagctg | 480 |
| gccaggctct cggtggccaa ggaccccag tcgcggaaga tcttcaactg caaatattgt | 540 |
| aacaaggagt acctcagcct gggcgctctg aagatgcaca tccgaagcca cacgctgcct | 600 |
| tgtgtctgca cgacctgtgg aaaggccttc tctaggccct ggctgcttca gggccacgtc | 660 |
| cgcacccaca ctggtgagaa gccattctcc tgctcccact gcaaccgtgc ttttgctgac | 720 |
| cgctccaacc tgcgtgccca cctccaaacc cactcggatg tgaagagata ccagtgccag | 780 |
| gcctgtgccc gaaccttctc ccgcatgtcc ttgctccaca gcaccaaga gtctggctgc | 840 |
| tccggaggcc ctcgctgacc ctgctacctc cccatcctcg ctggcatctt cccggagctc | 900 |
| accctcctcc tcactgccag gactccttcc agccttggtc cggggacctg tggcgtccat | 960 |
| gtctggacct ggttcctgct tggctctctt ggtggccttt gccgcaggtg gctgatggag | 1020 |
| tgcctttgta cccgcccaga gcctcctacc cctcagtatt catgaggtgt agcctctgga | 1080 |
| cacagctgct tcgagccata gaactaaagc caacccactg gctgggaagc ttgaaccccg | 1140 |
| ctcaggggac cccacttccc tacctccctc aaggaccctt caggccacct tctttgaggt | 1200 |
| acaacagact atgcaatagt tcccctcccc cccacccgt ccagctgtaa ccatgcctca | 1260 |
| gcagggtggt tactgacac atgtccaggt gcccctgggc ctgggcaact gtttcagccc | 1320 |
| ccgcccccat ttgtcctggt gacacctgtt tcacagcagt ttaactgtct cagaagggac | 1380 |
| catgaataat ggccatcact tgttaggggc caagtggggt gcttcagcct ggccaatgtg | 1440 |
| tctcccagaa ctattttggg gcccaacagg tggccccggg agaaagatgt ttacatttta | 1500 |
| aaggtattta tattgtaagc agcatttgt atagttaata tgtacagttt attgatattc | 1560 |
| aataaaatgg ttaatttata tactaaaaaa aaaaaaaaa aaaaaaaaa aaa | 1613 |

<210> SEQ ID NO 55
<211> LENGTH: 2920
<212> TYPE: DNA
<213> ORGANISM: Human

<400> SEQUENCE: 55

| | |
|---|---|
| gctgacctcc tctgagctcc tctggccgct cgcaggatct tcccgaccct gcaggacttg | 60 |
| gcaaactccc acctccgctc ccattagtcc tcccaccccc accaaatctc ctccctcgga | 120 |
| ggtcccctat ccatctcact ttgcagaatt tatcgcttct tccaacacct ttttgcaaca | 180 |
| ccccagaact ccgagtccct taactgaatt tgactttgt ttttatttct ctctggcttc | 240 |
| ctcttctgcc ccctcatctg attgatgtgc taaggctgat gtctctgcca gagcgagagg | 300 |
| aataataga tgctgcctcg cctagaggct tagacgcttg ggaagagcag ccggcgcagc | 360 |
| gaggcaccgg gctccgccaa gctagtggac cggacctggg agcacttgga tccaagagaa | 420 |
| ctgtgattgt cccaggggtg ggggcagctc cccaggtcgt tgggatcacc cctcggaacc | 480 |
| gcagggggag acttcggaac gaaagtgtct cccgcgtccg tcgctcggct gcgccctgcc | 540 |
| ccatcctgct gggaccatgg tctgctgcgg cccgggacgg atgctgctag gatgggccgg | 600 |
| gttgctagtc ctggctgctc tctgcctgct ccaggtgccc ggagctcagg ctgcagcctg | 660 |
| tgagcctgtc cgcatcccgc tgtgcaagtc ccttcctgg aacatgacca agatgcccaa | 720 |
| ccacctgcac acagcaccc aggctaacgc catcctggcc atggaacagt tcgaagggct | 780 |
| gctgggcacc cactgcagcc cggatcttct cttcttcctc tgtgcaatgt acgcacccat | 840 |

```
ttgcaccatc gacttccagc acgagcccat caagccctgc aagtctgtgt gtgagcgcgc      900
ccgacagggc tgcgagccca ttctcatcaa gtaccgccac tcgtggccgg aaagcttggc      960
ctgcgacgag ctgccggtgt acgaccgcgg cgtgtgcatc tctcctgagg ccatcgtcac     1020
cgcggacgga gcggattttc ctatggattc aagtactgga cactgcagag gggcaagcag     1080
cgaacgttgc aaatgtaagc ctgtcagagc tacacagaag acctatttcc ggaacaatta     1140
caactatgtc atccgggcta aagttaaaga ggtaaagatg aaatgtcatg atgtgaccgc     1200
cgttgtggaa gtgaaggaaa ttctaaaggc atcactggta acattccaa gggacaccgt      1260
caatctttat accacctctg ctgcctctg tcctccactt actgtcaatg aggaatatgt      1320
catcatgggc tatgaagacg aggaacgttc caggttactc ttggtagaag gctctatagc     1380
tgagaagtgg aaggatcggc ttggtaagaa agtcaagcgc tgggatatga aactccgaca     1440
ccttggactg ggtaaaactg atgctagcga ttccactcag aatcagaagt ctggcaggaa     1500
ctctaatccc cggccagcac gcagctaaat cctgaaatgt aaaaggccac acccacggac     1560
tcccttctaa gactggcgct gctggactaa caaaggaaaa ccgcacagtt gtgctcgtga     1620
ccgattgttt accgcagaca ccgcgtggct accgaagtta cttccggtcc cctttctcct     1680
gcttcttaat ggcctggggt tagatccttt aaatatgttat atattctgtt tcatcaatca    1740
cgtggggact gttctttgc aaccagaata gtaaattaaa tatgttgatg ctaaggtttc      1800
tgtactggac tccctgggtt taatttggtg ttctgtaccc tgattgagaa tgcaatgttt     1860
catgtaaaga gagaatcctg gtcatatctc aagaactaga tattgctgta agacagcctc     1920
tgctgctgcg cttatagtct tgtgtttgta tgcctttggc catttccctc atgctgtgaa     1980
agttatacat gtttataaag gtagaacggc attttgaaat cagacactgc acaagcagag     2040
tagcccaaca ccaggaagca tttatgagga aacgccacac agcatgactt attttcaaga     2100
ttggcaggca gcaaaataaa tagtgttggg agccaagaaa gaatatttt gcctggttaa      2160
gggggcacact ggaatcagta gcccttgagc cattaacagc agtgttcttc tggcaacgtt    2220
tttgatttgt tcataaatgt attcacgagc attagagatg aacttataac tagacatctg    2280
ttgttatcac tatagctctg cttccttcta aatcaaaccc attgttggat gctccctctc     2340
cattcataaa taaatttggc ttgctgtatt ggccaggaaa agaaagtatt aaagtatgca     2400
tgcatgtgca ccagggtgtt atttaacaga ggtatgtaac tctataaaag actataattt     2460
acaggacacg gaaatgtgca catttgttta cttttttct tccttttgct ttgggcttgt      2520
gattttggtt tttggtgtgt ttatgtctgt attttggggg gtgggtaggt ttaagccatt     2580
gcacattcaa gttgaactag attagagtag actaggctca ttggcctaga cattatgatt    2640
tgaatttgtg ttgtttaatg ctccatcaag atgtctaata aaaggaatat ggttgtcaac     2700
agagacgaca acaacaacaa aaatgttttt cttatgtgtg ctgcactgag accccaacaa     2760
cccatgggtg gggggaacc cacgatgcct tttcttcctt ccctgcagca gggatgtgcc      2820
catcacctga aagtctcatt ccctgaaatt tacacatgtg gtagtagtag gtccagattc     2880
ctaagttaca gtgtgctgaa aaataaaaca ggtatgaagc                           2920
```

<210> SEQ ID NO 56
<211> LENGTH: 323
<212> TYPE: PRT
<213> ORGANISM: Human

<400> SEQUENCE: 56

Met Val Cys Cys Gly Pro Gly Arg Met Leu Leu Gly Trp Ala Gly Leu

```
                1               5                    10                   15
            Leu Val Leu Ala Ala Leu Cys Leu Leu Gln Val Pro Gly Ala Gln Ala
                                20                  25                  30

Ala Ala Cys Glu Pro Val Arg Ile Pro Leu Cys Lys Ser Leu Pro Trp
                            35                  40                  45

Asn Met Thr Lys Met Pro Asn His Leu His His Ser Thr Gln Ala Asn
                        50                  55                  60

Ala Ile Leu Ala Met Glu Gln Phe Glu Gly Leu Leu Gly Thr His Cys
            65                  70                  75                  80

Ser Pro Asp Leu Leu Phe Phe Leu Cys Ala Met Tyr Ala Pro Ile Cys
                                85                  90                  95

Thr Ile Asp Phe Gln His Glu Pro Ile Lys Pro Cys Lys Ser Val Cys
                            100                 105                 110

Glu Arg Ala Arg Gln Gly Cys Glu Pro Ile Leu Ile Lys Tyr Arg His
                        115                 120                 125

Ser Trp Pro Glu Ser Leu Ala Cys Asp Glu Leu Pro Val Tyr Asp Arg
                    130                 135                 140

Gly Val Cys Ile Ser Pro Glu Ala Ile Val Thr Ala Asp Gly Ala Asp
            145                 150                 155                 160

Phe Pro Met Asp Ser Ser Thr Gly His Cys Arg Gly Ala Ser Ser Glu
                                165                 170                 175

Arg Cys Lys Cys Lys Pro Val Arg Ala Thr Gln Lys Thr Tyr Phe Arg
                            180                 185                 190

Asn Asn Tyr Asn Tyr Val Ile Arg Ala Lys Val Lys Glu Val Lys Met
                        195                 200                 205

Lys Cys His Asp Val Thr Ala Val Val Glu Val Lys Glu Ile Leu Lys
                    210                 215                 220

Ala Ser Leu Val Asn Ile Pro Arg Asp Thr Val Asn Leu Tyr Thr Thr
            225                 230                 235                 240

Ser Gly Cys Leu Cys Pro Pro Leu Thr Val Asn Glu Glu Tyr Val Ile
                                245                 250                 255

Met Gly Tyr Glu Asp Glu Glu Arg Ser Arg Leu Leu Leu Val Glu Gly
                            260                 265                 270

Ser Ile Ala Glu Lys Trp Lys Asp Arg Leu Gly Lys Lys Val Lys Arg
                        275                 280                 285

Trp Asp Met Lys Leu Arg His Leu Gly Leu Gly Lys Thr Asp Ala Ser
                    290                 295                 300

Asp Ser Thr Gln Asn Gln Lys Ser Gly Arg Asn Ser Asn Pro Arg Pro
            305                 310                 315                 320

Ala Arg Ser

<210> SEQ ID NO 57
            <211> LENGTH: 221
            <212> TYPE: PRT
            <213> ORGANISM: Human

<400> SEQUENCE: 57

Met Val Leu Val Thr Leu Leu Gly Leu Ser Trp Phe Cys Ser Pro Leu
            1               5                   10                  15

Ala Ala Leu Val Leu Asp Phe Asn Asn Ile Lys Ser Ser Ala Asp Val
                                20                  25                  30

Gln Gly Ala Gly Lys Gly Ser Leu Cys Ala Ser Asp Arg Asp Cys Ser
                            35                  40                  45

Glu Gly Lys Phe Cys Leu Ala Phe His Asp Glu Arg Ser Phe Cys Ala
```

```
                50                  55                  60
Thr Cys Arg Arg Val Arg Arg Cys Gln Arg Ser Ala Val Cys Cys
 65                  70                  75                  80

Pro Gly Thr Val Cys Val Asn Asp Val Cys Thr Ala Val Glu Asp Thr
                 85                  90                  95

Arg Pro Val Met Asp Arg Asn Thr Asp Gly Gln Asp Gly Ala Tyr Ala
                100                 105                 110

Glu Gly Thr Thr Lys Trp Pro Ala Glu Glu Asn Arg Pro Gln Gly Lys
                115                 120                 125

Pro Ser Thr Lys Lys Ser Gln Ser Ser Lys Gly Gln Glu Gly Glu Ser
                130                 135                 140

Cys Leu Arg Thr Ser Asp Cys Gly Pro Gly Leu Cys Cys Ala Arg His
145                 150                 155                 160

Phe Trp Thr Lys Ile Cys Lys Pro Val Leu Arg Glu Gly Gln Val Cys
                165                 170                 175

Ser Arg Arg Gly His Lys Asp Thr Ala Gln Ala Pro Glu Ile Phe Gln
                180                 185                 190

Arg Cys Asp Cys Gly Pro Gly Leu Thr Cys Arg Ser Gln Val Thr Ser
                195                 200                 205

Asn Arg Gln His Ser Arg Leu Arg Val Cys Gln Arg Ile
                210                 215                 220

<210> SEQ ID NO 58
<211> LENGTH: 835
<212> TYPE: DNA
<213> ORGANISM: Human

<400> SEQUENCE: 58
cagacgacgt gctgagctgc cagcttagtg gaagctctgc tctgggtgga gagcagcctc      60
gctttggtga cgcacagtgc tgggaccctc caggagcccc gggattgaag gatggtggcg     120
gccgtcctgc tggggctgag ctggctctgc tctcccctgg gagctctggt cctggacttc     180
aacaacatca ggagctctgc tgacctgcat ggggcccgga agggctcaca gtgcctgtct     240
gacacggact gcaataccag aaagttctgc ctccagcccc gcgatgagaa gccgttctgt     300
gctacatgtc gtgggttgcg gaggaggtgc cagcgagatg ccatgtgctg ccctgggaca     360
ctctgtgtga cgatgtttg tactacgatg aagatgcaa ccccaatatt agaaaggcag     420
cttgatgagc aagatggcac acatgcagaa ggaacaactg ggcacccagt ccaggaaaac     480
caacccaaaa ggaagccaag tattaagaaa tcacaaggca ggaagggaca agagggagaa     540
agttgtctga aactttgta ctgtggccct ggactttgct gtgctcgtca tttttggacg     600
aaaatttgta agccagtcct tttggaggga caggtctgct ccagaagagg gcataaagac     660
actgctcaag ctccagaaat cttccagcgt tgcgactgtg gccctggact actgtgtcga     720
agccaattga ccagcaatcg gcagcatgct cgattaagag tatgccaaaa aatagaaaag     780
ctataaatat ttcaaaataa agaagaatcc acattgcaaa aaaaaaaaaa aaaaa          835

<210> SEQ ID NO 59
<211> LENGTH: 1315
<212> TYPE: PRT
<213> ORGANISM: Human

<400> SEQUENCE: 59

Ala Cys Ala Cys Ala Cys Cys Thr Thr Cys Cys Thr Thr Gly Gly Gly
 1               5                  10                  15
```

-continued

```
Cys Ala Gly Ala Gly Thr Cys Thr Cys Thr Cys Thr Thr Thr Cys Ala
            20                  25                  30

Gly Ala Ala Ala Ala Gly Gly Cys Cys Thr Cys Thr Gly Thr Gly Gly
        35                  40                  45

Gly Cys Gly Ala Cys Thr Thr Gly Cys Ala Gly Ala Thr Thr Gly Thr
    50                  55                  60

Ala Cys Cys Thr Ala Gly Gly Gly Cys Cys Ala Cys Thr Cys Ala Gly
65                  70                  75                  80
Cys Ala Gly Cys Gly Cys Ala Gly Cys Cys Thr Thr Cys Gly Ala Ala
                85                  90                  95

Gly Ala Cys Thr Cys Ala Ala Gly Gly Gly Gly Thr Ala Cys Thr Gly
            100                 105                 110

Gly Ala Gly Cys Thr Cys Cys Gly Ala Gly Ala Gly Ala Cys Cys Ala
        115                 120                 125

Gly Ala Gly Thr Gly Ala Cys Thr Gly Ala Gly Gly Ala Thr Gly Gly
    130                 135                 140

Thr Ala Cys Thr Gly Gly Thr Gly Ala Cys Cys Thr Thr Gly Cys Thr
145                 150                 155                 160

Thr Gly Gly Ala Cys Thr Cys Ala Gly Cys Thr Gly Gly Thr Thr Thr
                165                 170                 175

Thr Gly Thr Thr Cys Ala Cys Cys Cys Cys Thr Gly Gly Cys Ala Gly
            180                 185                 190

Cys Cys Cys Thr Gly Gly Thr Thr Cys Thr Gly Gly Ala Cys Thr Thr
        195                 200                 205

Thr Ala Ala Cys Ala Ala Cys Ala Thr Cys Ala Ala Gly Ala Gly Cys
    210                 215                 220

Thr Cys Cys Gly Cys Gly Gly Ala Thr Gly Thr Gly Cys Ala Ala Gly
225                 230                 235                 240

Gly Cys Gly Cys Gly Gly Gly Gly Ala Ala Gly Gly Gly Cys Thr Cys
                245                 250                 255

Gly Cys Thr Gly Thr Gly Thr Gly Cys Ala Thr Cys Ala Gly Ala Cys
            260                 265                 270

Ala Gly Gly Gly Ala Cys Thr Gly Cys Ala Gly Cys Gly Ala Ala Gly
        275                 280                 285

Gly Gly Ala Ala Ala Thr Thr Cys Thr Gly Cys Thr Thr Ala Gly Cys
    290                 295                 300

Gly Thr Thr Thr Cys Ala Cys Gly Ala Thr Gly Ala Ala Cys Gly Gly
305                 310                 315                 320

Thr Cys Cys Thr Thr Cys Thr Gly Thr Gly Cys Cys Ala Cys Gly Thr
                325                 330                 335

Gly Cys Cys Gly Thr Ala Gly Ala Gly Thr Thr Cys Gly Cys Ala Gly
            340                 345                 350

Gly Ala Gly Gly Thr Gly Thr Cys Ala Gly Ala Gly Gly Ala Gly Cys
        355                 360                 365

Gly Cys Cys Gly Thr Gly Thr Gly Cys Thr Gly Cys Cys Cys Ala Gly
    370                 375                 380

Gly Ala Ala Cys Gly Gly Thr Cys Thr Gly Thr Gly Thr Gly Ala Ala
385                 390                 395                 400

Thr Gly Ala Thr Gly Thr Thr Thr Gly Cys Ala Cys Thr Gly Cys Ala
                405                 410                 415

Gly Thr Gly Gly Ala Ala Gly Ala Cys Ala Cys Ala Ala Gly Gly Cys
            420                 425                 430

Cys Ala Gly Thr Gly Ala Thr Gly Gly Ala Cys Ala Gly Ala Ala Ala
```

-continued

```
            435                 440                 445
Cys Ala Cys Thr Gly Ala Cys Gly Gly Cys Cys Ala Ala Gly Ala Cys
            450                 455                 460
Gly Gly Cys Gly Cys Cys Thr Ala Thr Gly Cys Ala Gly Ala Ala Gly
465                 470                 475                 480
Gly Ala Ala Cys Cys Ala Cys Thr Ala Ala Thr Gly Gly Cys Cys
                    485                 490                 495
Ala Gly Cys Ala Gly Ala Gly Gly Ala Ala Ala Cys Ala Gly Ala
                500                 505                 510
Cys Cys Thr Cys Ala Gly Gly Gly Ala Ala Gly Cys Cys Cys Ala
                515                 520                 525
Gly Thr Ala Cys Gly Ala Ala Gly Ala Ala Thr Cys Ala Cys Ala
            530                 535                 540
Ala Ala Gly Cys Ala Gly Thr Ala Ala Gly Gly Ala Cys Ala Gly
545                 550                 555                 560
Gly Ala Gly Gly Gly Ala Gly Ala Ala Ala Gly Cys Thr Gly Thr Cys
                    565                 570                 575
Thr Thr Ala Gly Ala Ala Cys Cys Thr Cys Thr Gly Ala Cys Thr Gly
                580                 585                 590
Thr Gly Gly Cys Cys Cys Thr Gly Gly Ala Cys Thr Thr Gly Cys
            595                 600                 605
Thr Gly Thr Gly Cys Thr Cys Gly Cys Cys Ala Thr Thr Thr Thr
            610                 615                 620
Gly Gly Ala Cys Ala Ala Ala Ala Thr Thr Thr Gly Cys Ala Ala
625                 630                 635                 640
Gly Cys Cys Ala Gly Thr Thr Cys Thr Ala Cys Gly Ala Gly Ala Gly
                    645                 650                 655
Gly Gly Ala Cys Ala Ala Gly Thr Cys Thr Gly Cys Thr Cys Cys Ala
                660                 665                 670
Gly Gly Ala Gly Gly Gly Gly Cys Ala Cys Ala Ala Ala Gly Ala
                675                 680                 685
Cys Ala Cys Thr Gly Cys Cys Ala Ala Gly Cys Cys Cys Cys Ala
            690                 695                 700
Gly Ala Ala Ala Thr Cys Thr Thr Cys Cys Ala Gly Cys Gly Thr Thr
705                 710                 715                 720
Gly Cys Gly Ala Cys Thr Gly Cys Gly Gly Cys Cys Thr Gly Gly
                    725                 730                 735
Ala Cys Thr Ala Ala Cys Gly Thr Gly Cys Cys Gly Ala Ala Gly Thr
                740                 745                 750
Cys Ala Gly Gly Thr Gly Ala Cys Cys Ala Gly Thr Ala Ala Cys Ala
                755                 760                 765
Gly Ala Cys Ala Ala Cys Ala Thr Thr Cys Ala Gly Gly Cys Thr
            770                 775                 780
Ala Ala Gly Ala Gly Thr Ala Thr Gly Cys Cys Ala Ala Ala Gly Ala
785                 790                 795                 800
Ala Thr Ala Thr Ala Ala Gly Thr Thr Gly Thr Ala Ala Ala Ala
                    805                 810                 815
Cys Ala Cys Gly Gly Gly Ala Cys Thr Thr Gly Thr Thr Gly Thr Thr
                820                 825                 830
Gly Thr Gly Thr Thr Cys Ala Cys Ala Cys Ala Gly Ala Ala Thr Cys
                835                 840                 845
Ala Ala Thr Cys Cys Cys Thr Gly Gly Cys Ala Cys Thr Ala Ala Thr
            850                 855                 860
```

-continued

```
Thr Thr Thr Ala Thr Thr Ala Thr Ala Thr Thr Thr Gly Thr Thr Ala
865                 870                 875                 880

Thr Thr Thr Thr Gly Thr Thr Thr Thr Cys Thr Gly Ala Gly Ala Cys
                885                 890                 895

Ala Gly Gly Gly Ala Thr Cys Thr Cys Ala Cys Thr Gly Thr Gly Thr
            900                 905                 910

Ala Gly Cys Cys Cys Thr Gly Gly Cys Thr Gly Gly Cys Cys Thr Thr
            915                 920                 925

Gly Cys Ala Cys Thr Cys Ala Thr Thr Gly Ala Gly Ala Thr Cys Thr
            930                 935                 940

Gly Cys Cys Thr Gly Cys Cys Thr Cys Thr Ala Cys Cys Thr Cys Cys
945                 950                 955                 960

Thr Gly Gly Ala Thr Gly Cys Thr Thr Thr Thr Thr Thr Thr Thr Thr
                965                 970                 975

Thr Thr Thr Thr Gly Gly Gly Gly Gly Gly Gly Gly Gly Gly
                980                 985                 990

Cys Gly Gly Gly Gly Cys Gly Gly Gly Gly Gly Ala Gly Gly Ala
            995                 1000                1005

Gly Cys Thr Thr Thr Cys Thr Gly Ala Gly Ala Cys Ala Gly Gly
        1010                1015                1020

Gly Thr Cys Thr Cys Ala Ala Ala Gly Thr Ala Ala Gly Cys Thr
        1025                1030                1035

Ala Thr Gly Thr Ala Gly Gly Cys Cys Ala Gly Cys Ala Ala Ala
        1040                1045                1050

Cys Thr Cys Ala Thr Gly Gly Cys Cys Thr Cys Ala Ala Ala Cys
        1055                1060                1065

Gly Cys Ala Thr Gly Ala Thr Cys Cys Cys Thr Gly Ala Cys
        1070                1075                1080

Cys Thr Cys Ala Ala Gly Thr Gly Cys Gly Thr Cys Thr Thr Gly
        1085                1090                1095

Gly Gly Ala Thr Thr Ala Cys Ala Gly Gly Cys Gly Ala Gly Cys
        1100                1105                1110

Ala Thr Gly Thr Thr Ala Cys Ala Cys Thr Cys Ala Gly Cys Ala
        1115                1120                1125

Cys Ala Thr Ala Ala Ala Thr Ala Ala Ala Gly Cys Cys Cys Ala
        1130                1135                1140

Ala Thr Cys Thr Cys Cys Thr Ala Gly Cys Ala Ala Cys Thr Gly
        1145                1150                1155

Ala Gly Ala Cys Ala Gly Ala Cys Ala Gly Cys Ala Ala Gly Cys
        1160                1165                1170

Ala Gly Ala Thr Ala Cys Thr Gly Ala Gly Ala Thr Gly Cys Thr
        1175                1180                1185

Ala Thr Ala Cys Thr Cys Thr Gly Ala Thr Gly Ala Gly Cys Cys
        1190                1195                1200

Ala Gly Cys Gly Ala Cys Thr Thr Thr Gly Gly Cys Thr Thr
        1205                1210                1215

Thr Gly Cys Gly Thr Cys Thr Ala Cys Thr Ala Thr Cys Thr Ala
        1220                1225                1230

Cys Ala Gly Thr Ala Cys Thr Gly Ala Cys Ala Gly Gly Ala Cys
        1235                1240                1245

Thr Thr Thr Ala Cys Ala Ala Thr Ala Ala Ala Ala Cys Ala Gly
        1250                1255                1260
```

-continued

```
Cys Cys Cys Gly Gly Ala Cys Ala Cys Ala Gly Thr     Gly Ala Cys
    1265                1270                1275

Thr Cys Ala Ala Thr Cys Cys Gly Thr Thr Cys Ala     Ala Ala Thr
    1280                1285                1290

Ala Ala Ala Thr Cys Thr Thr Thr Thr Thr Ala Ala     Ala Ala
    1295                1300                1305

Ala Thr Thr Gly Ala Ala Ala
    1310                1315

<210> SEQ ID NO 60
<211> LENGTH: 232
<212> TYPE: PRT
<213> ORGANISM: Human

<400> SEQUENCE: 60

Met Glu Arg Cys Pro Ser Leu Gly Val Thr Leu Tyr Ala Leu Val Val
1               5                   10                  15

Val Leu Gly Leu Arg Ala Thr Pro Ala Gly Gly Gln His Tyr Leu His
                20                  25                  30

Ile Arg Pro Ala Pro Ser Asp Asn Leu Pro Leu Val Asp Leu Ile Glu
            35                  40                  45

His Pro Asp Pro Ile Phe Asp Pro Lys Glu Lys Asp Leu Asn Glu Thr
        50                  55                  60

Leu Leu Arg Ser Leu Leu Gly Gly His Tyr Asp Pro Gly Phe Met Ala
65                  70                  75                  80

Thr Ser Pro Pro Glu Asp Arg Pro Gly Gly Gly Gly Ala Ala Gly
                85                  90                  95

Gly Ala Glu Asp Leu Ala Glu Leu Asp Gln Leu Leu Arg Gln Arg Pro
                100                 105                 110

Ser Gly Ala Met Pro Ser Glu Ile Lys Gly Leu Glu Phe Ser Glu Gly
            115                 120                 125

Leu Ala Gln Gly Lys Lys Gln Arg Leu Ser Lys Lys Leu Arg Arg Lys
        130                 135                 140

Leu Gln Met Trp Leu Trp Ser Gln Thr Phe Cys Pro Val Leu Tyr Ala
145                 150                 155                 160

Trp Asn Asp Leu Gly Ser Arg Phe Trp Pro Arg Tyr Val Lys Val Gly
                165                 170                 175

Ser Cys Phe Ser Lys Arg Ser Cys Ser Val Pro Glu Gly Met Val Cys
            180                 185                 190

Lys Pro Ser Lys Ser Val His Leu Thr Val Leu Arg Trp Arg Cys Gln
        195                 200                 205

Arg Arg Gly Gly Gln Arg Cys Gly Trp Ile Pro Ile Gln Tyr Pro Ile
    210                 215                 220

Ile Ser Glu Cys Lys Cys Ser Cys
225                 230

<210> SEQ ID NO 61
<211> LENGTH: 1892
<212> TYPE: DNA
<213> ORGANISM: Human

<400> SEQUENCE: 61
aaaccggtgc caacgtgcgc ggacgccgcc gccgccgccg ccgctggagt ccgccgggca      60
gagccggccg cggagcccgg agcaggcgga gggaagtgcc cctagaacca gctcagccag     120
cggcgcttgc acagagcggc cggacgaaga gcagcgagag gaggagggga gagcggctcg     180
```

```
tccacgcgcc ctgcgccgcc gccggcccgg gaaggcagcg aggagccggc gcctcccgcg      240
ccccgcggtc gccctggagt aatttcggat gcccagccgc ggccgccttc cccagtagac      300
ccgggagagg agttgcggcc aacttgtgtg cctttcttcc gccccggtgg gagccggcgc      360
tgcgcgaagg gctctcccgg cggctcatgc tgccggccct gcgcctgccc agcctcgggt      420
gagccgcctc cggagagacg ggggagcgcg gcggcgccgc gggctcggcg tgctctcctc      480
cggggacgcg ggacgaagca gcagcccggg gcgcgcgcca gaggcatgga gcgctgcccc      540
agcctagggg tcaccctcta cgccctggtg gtggtcctgg ggctgcgggc gacaccggcc      600
ggcggccagc actatctcca catccgcccg gcacccagcg acaacctgcc cctggtggac      660
ctcatcgaac acccagaccc tatctttgac cccaaggaaa aggatctgaa cgagacgctg      720
ctgcgctcgc tgctcggggg ccactacgac ccaggcttca tggccacctc gcccccgag      780 gaccggcccg gcggggcgg gggtgcagct ggggcgcgg aggacctggc ggagctggac      840
cagctgctgc ggcagcggcc gtcgggggcc atgccgagcg agatcaaagg gctagagttc      900
tccgagggct tggcccaggg caagaagcag cgcctaagca agaagctgcg gaggaagtta      960
cagatgtggc tgtggtcgca gacattctgc cccgtgctgt acgcgtggaa cgacctgggc     1020
agccgctttt ggccgcgcta cgtgaaggtg ggcagctgct tcagtaagcg ctcgtgctcc     1080
gtgcccgagg gcatggtgtg caagccgtcc aagtccgtgc acctcacggt gctgcggtgg     1140
cgctgtcagc ggcgcggggg ccagcgctgc ggctggattc ccatccagta ccccatcatt     1200
tccgagtgca gtgctcgtg ctagaactcg ggggcccct gcccgcaccc ggacacttga     1260
tcgatcccca ccgacgcccc ctgcaccgcc tccaaccagt tccaccaccc tctagcgagg     1320
gttttcaatg aactttttt tttttttttt ttttttttc tgggctacag agacctagct     1380
ttctggttcc tgtaatgcac tgtttaactg tgtaggaatg tatatgtgtg tgtatatacg     1440
gtcccagttt taatttactt attaaaaggt cagtattata cgttaaaagt taccggcttc     1500
tactgtattt ttaaaaaaaa gtaagcaaaa gaaaaaaaaa agaacagaga aaagagagac     1560
ttattctggt tgttgctaat aatgttaacc tgctatttat attccagtgc ccttcgcatg     1620
gcgaagcagg ggggaaaagt tattttttc ttgaagtaca aagagacggg ggaacttttg     1680
tagaggactt tttaaaagct attttccatt cttcggaaag tgttttggtt ttccttggac     1740
ctcgaagaag ctatagagtt caatgttatt ttacagttat tgtaaatata gagaacaaat     1800
ggaatgacta atcattgtaa attaagagta tctgctattt attctttata atatcccgtg     1860
tagtaaatga gaaagaagtg cagagcagga tt                                   1892
```